US012778133B2

(12) United States Patent
Thompson et al.

(10) Patent No.: US 12,778,133 B2
(45) Date of Patent: Nov. 3, 2026

(54) METHODS FOR PROTECTING ANIMALS FROM PATHOGENS USING EXOSPORIUM FRAGMENTS

(71) Applicant: Spogen Biotech Inc., St. Louis, MO (US)

(72) Inventors: Brian M. Thompson, Creve Coeur, MO (US); Ashley Siegel, St. Louis, MO (US)

(73) Assignee: Spogen Biotech Inc., St. Louis, MO (US)

( * ) Notice: Subject to any disclaimer, the term of this patent is extended or adjusted under 35 U.S.C. 154(b) by 355 days.

(21) Appl. No.: 15/461,188

(22) Filed: Mar. 16, 2017

(65) Prior Publication Data

US 2017/0347664 A1 Dec. 7, 2017

Related U.S. Application Data

(60) Provisional application No. 62/309,259, filed on Mar. 16, 2016.

(51) Int. Cl.

| | |
|---|---|
| ***A01N 63/50*** | (2020.01) |
| ***A23K 10/18*** | (2016.01) |
| ***A61F 13/00*** | (2024.01) |
| ***A61K 39/00*** | (2006.01) |
| ***A61K 39/02*** | (2006.01) |
| ***A61K 39/07*** | (2006.01) |
| ***A61L 2/18*** | (2026.01) |
| ***C02F 3/34*** | (2023.01) |
| ***C07K 14/32*** | (2006.01) |
| ***C07K 14/325*** | (2006.01) |
| ***C12N 1/20*** | (2026.01) |
| ***C12N 15/75*** | (2006.01) |
| ***C12P 21/02*** | (2006.01) |
| *A61F 13/51* | (2006.01) |
| *C12N 3/00* | (2006.01) |

(52) U.S. Cl.

CPC .............. *A01N 63/50* (2020.01); *A23K 10/18* (2016.05); *A61F 13/00063* (2013.01); *A61K 39/00* (2013.01); *A61K 39/0208* (2013.01); *A61K 39/07* (2013.01); *A61L 2/18* (2013.01); *C02F 3/348* (2013.01); *C07K 14/32* (2013.01); *C07K 14/325* (2013.01); *C12N 1/20* (2013.01); *C12N 15/75* (2013.01); *C12P 21/02* (2013.01); *A61F 2013/51047* (2013.01); *A61K 2039/523* (2013.01); *A61K 2039/552* (2013.01); *C07K 2319/00* (2013.01); *C12N 3/00* (2013.01)

(58) Field of Classification Search

CPC .... A01N 63/02; A61K 39/07; A61K 39/0208; A61K 39/00; A61K 2039/523; A61K 2039/552; C07K 14/325; C07K 14/32; C07K 2319/00; C12P 21/02; C12N 15/75; C12N 1/20; C12N 3/00; C02F 3/348; A61L 2/18; A61F 13/00063; A61F 2013/51047; A23K 10/18

See application file for complete search history.

(56) References Cited

U.S. PATENT DOCUMENTS

| | | | | |
|---|---|---|---|---|
| 5,348,743 | A | 9/1994 | Ryals et al. | |
| 5,466,449 | A * | 11/1995 | Kiczka | A61K 38/47 424/94.61 |
| 5,631,007 | A | 5/1997 | Ryals et al. | |
| 5,766,914 | A | 6/1998 | Deits | |
| 5,858,962 | A * | 1/1999 | Blackburn | C12Y 304/24075 514/192 |
| 6,333,302 | B1 | 12/2001 | Beer et al. | |
| 8,030,064 | B2 | 10/2011 | Lee et al. | |
| 8,097,769 | B2 | 1/2012 | Sarria-Millan et al. | |
| 8,105,613 | B2 | 1/2012 | Flick-Smith et al. | |
| 8,383,366 | B2 | 2/2013 | Ferrari et al. | |
| 8,673,311 | B2 | 3/2014 | Cutting et al. | |
| 9,132,175 | B2 | 9/2015 | Stewart et al. | |
| 9,133,251 | B2 | 9/2015 | Stewart et al. | |

(Continued)

FOREIGN PATENT DOCUMENTS

| | | |
|---|---|---|
| CN | 101056536 | 10/2007 |
| EP | 0792363 A1 | 9/1997 |

(Continued)

OTHER PUBLICATIONS

Sousa et al., Microbiology 148(Pt5):1291-1303, 2002.*

(Continued)

*Primary Examiner* — Delia M Ramirez

(74) *Attorney, Agent, or Firm* — Dentons US LLP

(57) ABSTRACT

Fusion proteins, recombinant *Bacillus cereus* family members that express fusion proteins, and exosporium fragments derived from spores of the recombinant *Bacillus cereus* family members are provided. Compositions comprising the spores or exosporium fragments are also provided. Methods involving the use of spores of recombinant *Bacillus cereus* family members and exosporium fragments derived from spores of a recombinant *Bacillus cereus* family member in the fields of animal health and aquaculture are provided. In particular, methods are for provided for using such spores or exosporium fragments for protecting an animal or an aquatic organism from a pathogen. Methods are also provided for using exosporium fragments for producing an immunogenic response in an aquatic animal. Products for use in protecting animals from pathogens are also provided, including adhesive patches, wound dressings, insert trays for livestock footbaths, hoof bandages, feed, feed additives, and insect foggers.

13 Claims, 7 Drawing Sheets

Specification includes a Sequence Listing.

(56) References Cited

U.S. PATENT DOCUMENTS

| | | | |
|---|---|---|---|
| 9,573,980 B2 | 2/2017 | Thompson et al. | |
| 9,713,632 B2 * | 7/2017 | Van Der Weerden | A61K 31/4174 |
| 9,826,743 B2 | 11/2017 | Curtis et al. | |
| 9,845,342 B2 | 12/2017 | Thompson et al. | |
| 9,850,289 B2 | 12/2017 | Thompson et al. | |
| 11,134,681 B2 | 10/2021 | Thompson et al. | |
| 11,882,829 B2 | 1/2024 | Thompson et al. | |
| 11,905,315 B2 | 2/2024 | Thompson et al. | |
| 12,031,164 B2 | 7/2024 | Thompson et al. | |
| 12,391,729 B2 | 8/2025 | Thompson et al. | |
| 2005/0232947 A1 | 10/2005 | Cutting | |
| 2008/0233175 A1 | 9/2008 | Steer et al. | |
| 2010/0055244 A1 | 3/2010 | Henriques et al. | |
| 2010/0233124 A1 | 9/2010 | Stewart et al. | |
| 2010/0291100 A1 | 11/2010 | Macinga | |
| 2011/0281316 A1 | 11/2011 | Stewart et al. | |
| 2012/0259101 A1 | 10/2012 | Tan et al. | |
| 2013/0216653 A1 | 8/2013 | Perkins et al. | |
| 2013/0331548 A1 | 12/2013 | Nakaar et al. | |
| 2014/0274707 A1 | 9/2014 | Thompson et al. | |
| 2014/0294883 A1 | 10/2014 | Poobalane et al. | |
| 2015/0064219 A1 | 3/2015 | Blander et al. | |
| 2016/0031948 A1 | 2/2016 | Thompson et al. | |
| 2016/0051656 A1 | 2/2016 | Stewart et al. | |
| 2016/0053222 A1 | 2/2016 | Stewart et al. | |
| 2016/0108096 A1 | 4/2016 | Thompson et al. | |
| 2017/0135353 A1 | 5/2017 | Thompson et al. | |
| 2017/0283472 A1 | 10/2017 | Curtis et al. | |
| 2017/0290339 A1 | 10/2017 | Curtis et al. | |
| 2017/0295785 A1 | 10/2017 | Curtis et al. | |
| 2017/0295797 A1 | 10/2017 | Curtis et al. | |
| 2017/0295798 A1 | 10/2017 | Curtis et al. | |
| 2017/0318808 A1 | 11/2017 | Curtis et al. | |
| 2024/0199709 A1 | 6/2024 | Thompson et al. | |
| 2024/0206466 A1 | 6/2024 | Thompson et al. | |

FOREIGN PATENT DOCUMENTS

| | | |
|---|---|---|
| RU | 2160778 C1 | 12/2000 |
| RU | 2439148 C1 | 1/2012 |
| WO | 96/23063 A1 | 8/1996 |
| WO | 02/00232 A2 | 1/2002 |
| WO | 02/46388 A1 | 6/2002 |
| WO | 2005/028654 A1 | 3/2005 |
| WO | 2006/012366 A2 | 2/2006 |
| WO | 2007/078127 A1 | 7/2007 |
| WO | 2007/086898 A2 | 8/2007 |
| WO | 2008/017483 A2 | 2/2008 |
| WO | 2013/144579 A1 | 10/2013 |
| WO | 2014/145964 A1 | 9/2014 |
| WO | 2016/044529 | 3/2016 |
| WO | 2016/044548 | 3/2016 |
| WO | 2016/044575 | 3/2016 |
| WO | 2016/044661 A1 | 3/2016 |

OTHER PUBLICATIONS

Thallinger et al., Biotechnology Journal 8:97-109; 2013.*
Valbuzzi et al., Microbiology 145:3121-3137, 1999.*
Sloma et al., Journal of Bacteriology 173(21):6889-6895, 1991.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Frankel, A. E., et al., "Characterization of Diphtheria Fusion Proteins Targeted to the Human Interleukin-3 Receptor," Protein Engineering, 2000, pp. 575-581, vol. 13, No. 8.
Pakula, A. A., et al., "Genetic Analysis of Protein Stability and Function," Annual Review of Genetics, 1989, pp. 289-310, vol. 23 (Abstract Only).
Bergman, N. H., et al., "Transcriptional Profiling of the Bacillus anthracis Life Cycle In Vitro and an Implied Model for Regulation of Spore Formation," Journal of Bacteriology, Sep. 2006, pp. 6092-6100, vol. 188, No. 17.
Boydston, J. A., et al., "The ExsY Protein is Required for Complete Formation of the Exosporium of Bacillus anthracis," Journal of Bacteriology, Nov. 2006, pp. 7440-7448, vol. 188, No. 21.
Bressuire-Isoard, C., et al., "Sporulation Temperature Reveals a Requirement for CotE in the Assembly of both the Coat and Exosporium Layers of Bacillus cereus Spores," Applied and Environmental Microbiology, Jan. 2016, pp. 232-243, vol. 82 No. 1.
Ciabattini, A., et al., "Oral Priming of Mice by Recombinant Spores of Bacillus subtilis", Vaccine, Oct. 2004, pp. 4139-4143, vol. 22, Nos. 31-32.
Dong, Y.-H., et al., "Identification of Quorum-Quenching N-Acyl Homoserine Lactonases from *Bacillus* species," Applied and Environmental Microbiology, Apr. 2002, pp. 1754-1759, vol. 68, No. 4.
Duc, L. H., et al., "Bacterial Spores as Vaccine Vehicles," Infection and Immunity, May 2003, pp. 2810-2818, vol. 71, No. 5.
Duc, L. H., et al., "Immunization Against Anthrax Using Bacillus subtilis Spores Expressing the Anthrax Protective Antigen," Vaccine, Jan. 2007, pp. 346-355, vol. 25, Issue 2.
Feng, F. et al., "Display of Human Proinsulin on the Bacillus subtilis Spore Surface for Oral Administration," Current Microbiology, 2013, pp. 1-8, vol. 67, Issue 1.
Goldberg, L. J., et al., "A Bacterial Spore Demonstrating Rapid Larvicidal Activity Against Anopheles Sergentii, Uranotaenia Unguiculata, Culex Univitattus, Aedes Aegypti and Culex Pipiens," Mosquito News, Sep. 1977, pp. 355-358, vol. 37, No. 3.
Guerchicoff, A., et al., "Identification and Characterization of A Previously Undescribed cyt Gene in *Bacillus thuringiensis* subsp. *israelensis*," Applied and Environmental Microbiology, Jul. 1997, pp. 2716-2721, vol. 63, No. 7.
Hoelscher, B., et al., "Removal of Toxic Contaminants from Polluted Soil and Water via Enzyme-Linked Bacillus Spores," Poster presented at Missouri Life Sciences Week Research Poster Session, Apr. 14, 2010.
Hunter, R. L., et al., "Copolymer Adjuvants and Titermax(R)," The Theory and Practical Application of Adjuvants, 1995, Chapter Four, pp. 51-94, John Wiley & Sons Ltd.
International Search Report and Written Opinion issued for PCT/US2017/022801, dated Jul. 31, 2017, 12 pages.
Invitation to Pay Additional Fees and, Where Applicable, Protest Fee issued for PCT/US2017/022801, dated May 22, 2017, 2 pages.
Isticato, R., et al., "Surface Display of Recombinant Proteins on Bacillus subtilis Spores," Journal of Bacteriology, Nov. 2001, pp. 6294-6301, vol. 183, No. 21.
Iwanicki, A., et al., "A System of Vectors for Bacillus subtilis Spore Surface Display," Microbial Cell Factories, 2014, pp. 1-9, vol. 13, No. 30.
Johnson, M. J., et al., "Exs Y and CotY Are Required for the Correct Assembly of the Exosporium and Spore Coat of Bacillus cereus," Journal of Bacteriology, Nov. 2006, pp. 7905-7913, vol. 188, No. 22.
Kim, J. H., et al., "Bacterial Surface Display of GFP(uv) on Bacillus subtilis Spores," Journal of Microbiology and Biotechnology, Apr. 2007, pp. 677-680, vol. 17, No. 4.
Kim, J. H., et al., "Spore-Displayed Streptavidin: A Live Diagnostic Tool in Biotechnology," Biochemical and Biophysical Research Communications, May 2005, pp. 210-214, vol. 331, No. 1.
Lakshmi, B., et al., "Probiotics as Antiviral Agents in Shrimp Aquaculture," Journal of Pathogens, 2013, 13 pages, vol. 2013, Article ID 424123, Hindawi Publishing Corporation.
Leski, T. A., et al., "Identification and Classification of bcl Genes and Proteins of Bacillus cereus Group Organisms and Their Application in Bacillus anthracis Detection and Fingerprinting," Applied and Environmental Microbiology, Nov. 2009, pp. 7163-7172, vol. 75, No. 22.
Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I fimbriae B Subunit," Vaccine, 2008, pp. 3998-4005, vol. 26, No. 32.

(56) References Cited

OTHER PUBLICATIONS

Mauriello, E. M., et al., "Display of Heterologous Antigens on the Bacillus subtilis Spore Coat Using CotC as a Fusion Partner," Vaccine, Mar. 2004, pp. 1177-1187, vol. 22, Issues 9-10.
Negri, A., et al., "Expression and Display of Clostridium difficile Protein FliD on the Surface of Bacillus subtilis Spores," Journal of Medical Microbiology, 2013, pp. 1379-1385, vol. 62.
Nguyen, A. T. V., et al., "Bacillus subtilis Spores Expressing the VP28 Antigen: A Potential Oral Treatment to Protect Litopenaeus vannamei Against White Spot Syndrome," FEMS Microbiology Letters, Sep. 2014, pp. 202-208, vol. 358, Issue 2.
Paccez, J. D., et al., "Evaluation of Different Promoter Sequences and Antigen Sorting Signals on the Immunogenicity of Bacillus subtilis Vaccine Vehicles," Vaccine, 2007, pp. 4671-4680, vol. 25, Issue 24.
Paccez, J. D., et al., "Stable Episomal Expression System Under Control of a Stress Inducible Promoter Enhances the Immunogenicity of Bacillus subtilis as a Vector for Antigen Delivery," Vaccine, 2006, pp. 2935-2943, vol. 24, Issue 15.
Park, T. J., et al., "Spore Display Using Bacillus thuringiensis Exosporium Protein InhA," Journal of Microbiology and Biotechnology, May 2009, pp. 495-501, vol. 19, No. 5.
Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.
Rasco, et al., UniProt KB database entry Q738B1-Q7381_BACC1, Jul. 5, 2004, 6 pages (referencing Rasco, et al., "The Genome Sequence of Bacillus cereus ATCC 10987 Reveals Metabolic Adaptations and a Large Plasmid Related to Bacillus anthracis pX01.," Nucleic Acids Research, 2004, pp. 977-988, vol. 32).
Sequence Listing filed in WO 2007/078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.
Steichen, C. T., et al., "Non-Uniform Assembly of the Bacillus anthracis Exosporium and a Bottle Cap Model for Spore Germination and Outgrowth," Molecular Microbiology, Apr. 2007, pp. 359-367, vol. 64, Issue 2.
Tan, L., et al., "An Unusual Mechanism of Isopeptide Bond Formation Attaches the Collagenlike Glycoprotein BclA to the Exosporium of Bacillus anthracis," mBio, May-Jun. 2011, 20 pages, vol. 2, No. 3.
Tan, L., et al., "An Unusual Mechanism of Isopeptide Bond Formation Attaches the Collagenlike Glycoprotein BclA to the Exosporium of Bacillus anthracis," mBio, May-Jun. 2011, 20 pages, vol. 2, No. 3 (Retraction).
Tan, L., et al., "Sequence Motifs and Proteolytic Cleavage of the Collagen-Like Glycoprotein BclA Required for Its Attachment to the Exosporium of Bacillus anthracis," Journal of Bacteriology, Mar. 2010, pp. 1259-1268, vol. 192, No. 5.
Thompson, B. M., "Amino-Terminal Sequences of the Bacillus Anthracis Exosporium Proteins BclA and BclB Important for Localization and Attachment to the Spore Surface," A Thesis presented to the Faculty of the Graduate School at the University of Missouri, Columbia, Aug. 2008, 165 pages.
Thompson, B. M., "The Role of the Glycoprotein BclB in the Exosporium in the Exosporium of Bacillus Anthracis," Doctoral Dissertation presented to the Department of Diagnostic Medicine/Pathobiology, College of Veterinary Medicine, Kansas State University, 2002, 178 pages.
Thompson, B. M. et al., "A System of Efficient, Cost-Effective, and Customizable Vaccines for Use with Multiple Vaccine Candidates," Oct. 2010 poster presentation, 1 page.
Thompson, B. M., et al., "Assembly of the BclB Glycoprotein into the Exosporium and Evidence for its Role in the Formation of the Exosporium 'cap' Structure in Bacillus anthracis, " Molecular Microbiology, Dec. 2012, pp. 1073-1084, vol. 86, No. 5.
Thompson, B. M., et al., "Localization and Assembly of the Novel Exosporium Protein BetA of Bacillus anthracis," Journal of Bacteriology, 2011, pp. 5098-5104, vol. 193, No. 19.
Thompson, B. M., et al., "Targeting of the BclA and BclB Proteins to the Bacillus anthracis Spore Surface," Molecular Microbiology, 2008, pp. 421-434, vol. 70, No. 2.
Thompson, B. M., et al., "The BclB Glycoprotein of Bacillus anthracis is Involved in Exosporium Integrity," Journal of Bacteriology, 2007, pp. 6704-6713, vol. 189, No. 18.
Thompson, B. M., et al., "The Co-Dependence of BxpB/ExsFA and BclA for Proper Incorporation into the Exosporium of Bacillus anthracis," Molecular Microbiology, 2011, pp. 799-813, vol. 79, No. 3.
Todd, C. W., et al., "Development of an Adjuvant-Active Nonionic Block Copolymer for use in Oil-Free Subunit Vaccines Formulations," Vaccine, 1997, pp. 564-570, vol. 15, No. 5.
Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.
Zeigler, D. R., "Bacillus thuringiensis and Bacillus cereus," Bacillus Genetic Stock Center Catalog of Strains, 1999, Seventh Edition, vol. 2, 58 pages.
Zhou, Z., et al., "Immunogenicity of Recombinant Bacillus subtilis Spores Expressing Clonorchis sinensis Tegumental Protein," Parasitology Research, 2008, pp. 293-297, vol. 102, Issue 2.
Zhou, Z., et al., "Oral Administration of a Bacillus subtilis Spore-Based Vaccine Expressing Clonorchis sinensis Tegumental Protein 22.3 kDa Confers Protection Against Clonorchis sinensis," Vaccine, 2008, pp. 1817-1825, vol. 26, Issue 15.
Barbe, V., et al., "From a Consortium Sequence to a Unified Sequence: The Bacillus subtilis 168 Reference Genome a Decade Later," Microbiology, 2009, pp. 1758-1775, vol. 155.
Dunne, C., et al., "Overproduction of an Inducible Extracellular Serine Protease Improves Biological Control of Pythium ultimum by Stenotrophomonas maltophilia Strain W81," Microbiology, 2000, pp. 2069-2078, vol. 146, Part 8.
Jimenez, G., et al., "Description of *Bacillus toyonensis* Sp. Nov., a Novel Species of the Bacillus Cereus Group, and Pairwise Genome Comparisons of the Species of the Group by Means of ANI Calculations," Systematic and Applied Microbiology, 2013, pp. 383-391, vol. 36, No. 6.
Jung, M. Y., et al., "*Bacillus gaemokensis* Sp. Nov., Isolated From Foreshore Tidal Flat Sediment From the Yellow Sea," Journal of Microbiology, Dec. 2010, pp. 867-871, vol. 48, No. 6 (Abstract Only).
NCBI Reference Sequence NP389608.1, Alkaline Serine Protease [*Bacillus subtilis* subsp. *subtilis* str. 168], 2018, 3 pages.
Saman, S., et al., "Isolation of a Potential New Member of the Bacillus cereus Group from Snow Covered Soil," Life Sciences and Medicine Research, 2010, 8 pages, vol. 2010, LSMR-18.
Yen, Y.-H., et al., "An Antifungal Protease Produced by Pseudomonas aeruginosa M-1001 with Shrimp and Crab Shell Powder as a Carbon Source," Enzyme and Microbial Technology, 2006, pp. 311-317, vol. 39.
Bailey-Smith et al., The ExsA protein of Bacillus cereus is required for assembly of coat and exosporium onto the spore surface, J Bacteriol. 187(11): 3800-3806, 2005.
Henriques and Moran, Structure, assembly, and function of the spore surface layers, Annu. Rev. Microbiol. 61:555-88, 2007.
Database Accession No. A0A380XNG8, Intracellular Serine Protease, (Online) Nov. 7, 2018, 1 page.
Database Accession No. W7KRH1, Intracellular Serine Protease (Online) Apr. 16, 2014, 2 pages.
Geng C.E., et al., "A Novel Serine Protease, Sep1 from Bacillus Firmus DS-1 Has Nematicidal Activity and Degrades Multiple Intestinal-Associated Nematode Proteins", Apr. 27, 2016, Scientific Reports, vol. 6, Article 25012, 12 pages.
Haldenwang, W.G., "The Sigma Factors of Bacillus Subtilis", Mar. 1995, Microbiological Reviews, vol. 59, No. 1, pp. 1-30.
Peng, et al., The Regulation of Exosporium-Related Genes in Bacillus Thuringiensis, 2016, Scientific Reports, vol. 6, No. 1, 13 pages.

(56) References Cited

OTHER PUBLICATIONS

Priest, F.G., et al., "Population Structure and Evolution of the Bacillus Cereus Group", Journal of Bacteriology, Dec. 2004, vol. 186, pp. 7959-7970.
Crane et al., Bacterial Nitric Oxide Synthases, Annual Review in Biochemistry 79:445-470, 2010.
GenBank Accession No. P33378, dated Feb. 22, 2023.
Singh et al., Protein Engineering Approaches in the Post-Genomic Era, Current Protein and Peptide Science 18:1-11, 2017.
Zhang et al., Propagated Perturbations from a Peripheral Mutation Show Interaction Supporting WW Domain Thermostability, Structure 26:1474-1485, 2018.
Aakre, et al. Inhibition of Bacillus cereus phospholipase C by univalent anions. The Biochemical Journal 203, 799-801, (1982).
Goldfine, et al. "Nonspecific phospholipase C of Listeria monocytogenes: activity on phospholipids in Triton X-100-mixed micelles and in biological membranes". J Bacteriol 175, 4298-4306, (1993).
Huang, et al. "Recombinant broad-range phospholipase C from Listeria monocytogenes exhibits optimal activity at acidic pH". Biochimica et Biophysica Acta (BBA)—Proteins and Proteomics 1864(6), 697-705, (2016).
Monturiol-Gross, et al. "Bacterial phospholipases C with dual activity: phosphatidylcholinesterase and sphingomyelinase". FEBS Open Bio, vol. 11(12), pp. 3262-3275, (2021).
Otnaess. "The hydrolysis of sphingomyelin by phospholipase C from Bacillus cereus". FEBS Letters 114, 202-204, (1980).
Pomerantsev, et al. "Phosphatidylcholine-specific phospholipase C and sphingomyelinase activities in bacteria of the Bacillus cereus group". Infect Immun. (2003); 71(11): 6591-606.
Tan, et al. "Cloning, overexpression, refolding, and purification of the nonspecific phospholipase C from Bacillus cereus". Protein Expr Purif 10, 365-372, (1997).
Zuckert, et al. "Modulation of enzymatic activity and biological function of Listeria monocytogenes broad-range phospholipase C by amino acid substitutions and by replacement with the Bacillus cereus ortholog". Infect Immun 66, 4823-4831, (1998).
Giorno, et al., Morphogenesis of the Bacillus anthracis Spore, Journal of Bacteriology, 89(3):691-705, 2007.
Saile et al., Bacillus anthracis multiplication, persistence, and genetic exchange in the rhizosphere of grass plants, Appl. Environ. Microbiol., 72(5):3168-3174, 2006.
U.S. Appl. No. 18/680,688, filed May 31, 2024, Thompson, et al.
Wang, Y. et al.; "Two distinct manganese-containing superoxide dismutase genes in Bacillus cereus: their physiological characterizations and roles in surviving in wheat rhizosphere"; FEMS Microbiology Letters; vol. 272(2), pp. 206-213; 2007.
Inaoka, T. et al., "SodA and Manganese Are Essential for Resistance to Oxidative Stress in Growing and Sporulationg Cells of Bacillus subtilis"; Journal of Bacteriology, vol. 181, No. 6; pp. 1939-1943; 1999.
U.S. Appl. No. 18/392,771, filed Dec. 21, 2023, Thompson, et al.
U.S. Appl. No. 18/398,650, filed Dec. 28, 2023, Thompson, et al.
Stewart, The Exosporium Layer of Bacterial Spores: a Connection to the Environment and the Infected Host, Microbiol. Mol. Bol. Rev. 79(4):435-457, 2015.
Written Opinion regarding Brazilian App. No. BR112018068719-7, dated Jun. 10, 2024.
Mukhopadhyay et al., Identification of Bacillus anthracis spore component antigens conserved across diverse Bacillus cereus sensu lato strains, Mol. Cell Proteomics, vol. 8, pp. 1174-1191, 2009.
Canadian Office Action regarding Canadian App. No. 3,016,922, dated Mar. 24, 2026.
European Office Action regarding European App. No. 17767570.9, dated Feb. 4, 2025.
Matz et al., Chemical Composition of Exosporium from Spores of Bacillus cereus, Journal of Bacteriology 101 (1):196-201, 1970.
U.S. Appl. No. 19/253,154, filed Jun. 27, 2025, Brian Thompson, et al.

* cited by examiner

FIG. 1A

| | SEQ ID NO. | 20-35 %Identity | 25-35 %Identity |
|---|---|---|---|
| MSNNNYSNGLNPDESLSAS**AFDPNLVGPTLPPIPP**FTLPTG | 1 | 100% | 100% |
| MSEKYIILHGT**ALEPNLIGPTLPPIPP**FTFPNG | 3 | 81.3% | 90.9% |
| MVKVVEGNGGKSKIKSPLNSNF**KILSDLVGPTFPPVPT**GMTGIT | 5 | 50.0% | 72.7% |
| MKQNDKLWLDKG**IIGPENIGPTFPVLPP**IHIPTG | 7 | 43.8% | 54.5% |
| MDEFLSSA**ALNPGSVGPTLPPMQP**FQFRTG | 9 | 62.5% | 72.7% |
| MFDKNEIQKINGILQAN**ALNPNLIGPTLPPIPP**FTLPTG | 11 | 81.3% | 90.9% |
| MFDKNEMKKTNEVLQAN**ALDPNIIGPTLPPIPP**FTLPTG | 13 | 81.3% | 81.8% |
| MSRKDKFNRSRMSRKDRFNSPKIKSEI**SISPDLVGPTFPPIPS**FTLPTG | 15 | 62.5% | 81.8% |
| MNEEYSILHGP**ALEPNLIGPTLPSIPP**FTFPTG | 17 | 75.0% | 81.8% |
| MKNRDNNRKQNSLSSNF**RIPPELIGPTFPPVPT**GFTGIG | 19 | 50.0% | 63.6% |
| MSDKHQMKKISEVLQAH**ALDPNLIGPPLPPITP**FTFPTG | 21 | 75.0% | 72.7% |
| MDEFLSFA**ALNPGSIGPTLPPVPP**FQFPTG | 23 | 62.5% | 72.7% |
| MDEFLSST**ALNPCSIGPTLPPMQP**FQFPTG | 25 | 56.2% | 63.6% |
| MKERDRQNSLNSNF**RISPNLIGPTFPPVPT**GFTGIG | 27 | 56.2% | 63.6% |
| VFDKNEIQKINGILQAN**ALNPNLIGPTLPPIPP**FTLPTG | 29 | 81.3% | 90.9% |
| MDEFLYFA**ALNPGSIGPTLPPVQP**FQFPTG | 31 | 56.2% | 63.6% |
| **MDSKNIGPTFPPLPS**INFPTG | 33 | 43.8% | 54.5% |
| **MIGPENIGPTFPILPP**IYIPTG | 35 | 43.8% | 54.5% |
| MSNNNIPSPFFFN**NFNPELIGPTFPPIPP**LTLPTG | 43 | 68.8% | 81.8% |
| MFSEKKRKDLIPDNFLSAP**ALDPNLIGPTFPPIPS**FTLPTG | 45 | 75.0% | 72.7% |
| MTRKDKFNRSRISRRDRFNSPKIKSEI**LISPDLVGPTFPPIPS**FTLPTG | 47 | 62.5% | 81.8% |
| MSRKDRFNSPKIKSEI**SISPDLVGPTFPPIPS**FTLPTG | 49 | 62.5% | 81.8% |
| MKERDNKGKQHSLNSNF**RIPPELIGPTFPPVPT**GFTGIG | 51 | 50.0% | 63.6% |
| MRERDNKRQQHSLNPNF**RISPELIGPTFPPVPT**GFTGIG | 53 | 50.0% | 63.6% |
| MKNRDNKGKQQSNF**RIPPELIGPTFPPVPT**GFTGIG | 55 | 50.0% | 63.6% |
| MKFSKKSTVDSSIVGKRVVSKVNILRFYDARSCQDKDVDGFVDVGELFTIFRKLNMEGSVQFKAHNSI<br>GKTYYITINEVYVFVTVLLQYSTLIGGSYVFDKNEIQKINGILQAN**ALNPNLIGPTLPPIPP**FTLPTG | 57 | 81.3% | 90.9% |

FIG. 1B

| | SEQ ID NO. | 20-35 %Identity | 25-35 %Identity |
|---|---|---|---|
| MSNNNYSNGLNPDESLSAS**AFDPNLVGPTLPPIPP**FTLPTG | 1 | 100% | 100% |
| MKERDKQNSLNSNF**RISPNLIGPTFPPVPT**GFTGIG | 59 | 56.2% | 63.6% |
| MMENKKGSKHNEFLSAK**AFNPNLVGPTLPPVPS**FTLPTG | 61 | 81.3% | 81.8% |
| MSNNNYSDGLNPDEFLSAS**AFDPNLVGPTLPPIPP**FTLPTG | 63 | 100% | 100% |
| MDEFLSSA**AINPNLVGPTLPPVPP**FTLPTG | 65 | 81.3% | 90.9% |
| MFDKNKILQAN**AFNSNLIGPTLPPIPP**FTLPTG | 67 | 81.3% | 90.9% |
| MSDENEKKYSNELAQADFISAA**AFDPSLVGPTLPPTPP**FTLPTG | 69 | 87.5% | 90.9% |
| MSRKDRFNSPKIKSEI**SISPDLVGPTFPPIPS**FTLPTG | 71 | 62.5% | 81.8% |
| MDEFLSSA**ALNPGSVGPTLPPMQP**FQFSTG | 73 | 62.5% | 72.7% |
| MFLGGGYMERKNKWYGLNSNVNLSAS**SFDPNLVGPTLPPISP**ISVPTG | 75 | 87.5% | 90.9% |
| MDELLSST**LINPDLLGPTLPAIPP**FTLPTG | 77 | 62.5% | 81.8% |
| MKNRDNNRKQNSLSSNF**RIPPELIGPTFPPVPT**GFTGIG | 79 | 50.0% | 63.6% |
| MVKVVEGNSGKSKIKSSLNSNF**KLSSGLVGPTFPPVPT**GMTGIT | 81 | 50.0% | 72.7% |
| MEGNGGKSKIKSPLNSNF**KILSDLVGPTFPPVPT**GMTGIT | 83 | 50.0% | 72.7% |
| MKQNDKLWLDKG**IIGPENIGPTFPVLPP**IHIPTG | 85 | 43.8% | 54.5% |
| MNSNEKLSLNKG**MVRPENIGPTFPVLPP**IYIPTG | 87 | 43.8% | 54.5% |
| MKRNDNLSLNKG**MIGPENIGPTFPILPP**IYIPTG | 89 | 43.8% | 54.5% |
| MDSFVDVGEIFTIFRKLNMEGSLQFKVHNS<br>MGKTYYITINEVYVYVTVLLQYSTLIGGSYVFDKNEIQKINGILQAN**ALNPNLIGPTLPPIPP**FTLPTG | 91 | 81.3% | 90.9% |
| MKFSKKSTVDSSIVGKRVVSKVNILRFYDARSWQDKDVDGFVDVGELFTIFRKLNMEGSVQFKAHNSI<br>GKTYYITINEVYVFVTVLLQYSTLIGGSYVFDKNEIQKINGILQAN**ALNPNLIGPTLPPIPP**FTLPTG | 93 | 81.3% | 90.9% |

A B C

A BT013A Control

B BT013A ExsY K/O

C BT013A CotE K/O

METHODS FOR PROTECTING ANIMALS FROM PATHOGENS USING EXOSPORIUM FRAGMENTS

CROSS-REFERENCE TO RELATED APPLICATIONS

This application claims the benefit of U.S. Provisional Application Ser. No. 62/309,259, filed on Mar. 16, 2016, the entirety of which is herein incorporated by reference.

FIELD OF THE INVENTION

The present invention generally relates to fusion proteins, recombinant *Bacillus cereus* family members that express such fusion proteins, and exosporium fragments derived from spores of the recombinant *Bacillus cereus* family members. The present invention further relates to compositions containing spores of a recombinant *Bacillus cereus* family member or exosporium fragments derived from spores of a recombinant *Bacillus cereus* family member. Uses of spores of recombinant *Bacillus cereus* family members and exosporium fragments derived from spores of a recombinant *Bacillus cereus* family member in the fields of animal health and aquaculture are also provided. In particular, the invention relates to methods for using the spores or exosporium fragments for protecting an animal or an aquatic organism from a pathogen. The invention further relates to methods for using exosporium fragments and/or spores of a recombinant *Bacillus cereus* family member for producing an immunogenic response in an animal. Products for use in protecting animals from pathogens are also provided, including adhesive patches, wound dressings, insert trays for livestock footbaths, hoof bandages, feed, feed additives, and insect foggers.

BACKGROUND OF THE INVENTION

Colonization of an organism by a pathogen is the first step towards the occurrence of disease. Currently, no effective means for delivery of a peptide, enzyme, or other protein to an animal exists that allows the peptide, enzyme or other protein to remain active long enough to effectively disrupt bacteria, fungal, or protozoan colonization or infection. Thus, there is a need in the art for methods for stabilizing and delivering proteins or peptides that protect animals from pathogens through antibacterial, antifungal, antihelminthic, or insecticidal activity, or through suppression of pathogen reproduction. Previous attempts to introduce peptides, enzymes, and other proteins to animals has been hampered by quick degradation and limited absorption of enzymes, proteins, and peptides in or on the animal. Additionally, the prevalence of systemic proteases in animals; rapid metabolism; opsonization; conformational changes; dissociation of subunit proteins; non-covalent complex formation with blood products; and destruction of labile side-groups all are impairments in using protein, peptides, or enzymes as disease management in animals.

Aquaculture is the farming of aquatic organisms under controlled conditions for all or parts of their lifecycles. Interest in aquacultural production is on the rise because restrictions on the wild harvest of many seafood species may diminish wild harvest seafood supplies. Aquaculture growers can more easily maintain a steady supply of products. Farmed seafood is also likely to be more uniform in size and quantity, thus moderating price swings. Selective breeding can be used to enhance disease resistance, increase growth rates, or promote other desirable traits (e.g., better feed conversion). Despite the benefits of aquaculture, aquaculture also has some disadvantages as compared to wild harvest, such as waste disposal from intensive production sites (leading to eutrophication of nearby water ways), dangerous levels of cancer-causing chemicals due to feed sources, overuse of antibiotics and biological control agents, and the loss of product to disease outbreak among cultured fish. Thus, the aquaculture industry has been overwhelmed with its share of diseases and problems caused by viruses, bacteria, fungi, parasites and other undiagnosed and emerging pathogens. Current practices in aquaculture for disease management include use of chemical insecticides and pesticides as well as other common chemicals that are often toxic to the fish themselves. Bleach, iodophores, and benzalkonium chlorides are commonly used in aquaculture to reduce both disease and biofilm formation. Many of the microbial pathogens in aquaculture cause toxicity in fish and shrimp as a primary problem, and as a secondary problem also form biofilms making control of these pathogens critical to continue to see increased production from farmed fish. Thus, there is a need in the art for methods to control pathogens in aquaculture.

A biofilm forms when microorganisms adhere to the surface of some object in a moist environment and begin to reproduce. The microorganisms form an attachment to the surface of almost any object by secreting extracellular polymeric substances. Biofilms most often consist of mixtures of many microorganisms including species of bacteria, as well as fungi, algae, yeasts, and protozoa. It has been well demonstrated that bacteria within biofilms are hundreds to thousands of times more resistant to antibiotics and biocides than their free forms. In biofilms, poor antibiotic penetration, nutrient limitation and slow growth, adaptive stress responses, and formation of persister cells are hypothesized to constitute a multi-layered defense making them very difficult to eliminate. For these reasons biofilms present problems in animal health through formation on host tissue (e.g., chronic wounds, osteomyelitits, cystic fibrosis, otitis), surfaces in aquaculture systems (e.g., pipes, tanks, or even the gills of fish), medical devices (e.g., catheters, trancutaneous devices), and on medical equipment (e.g., hemodialysis machines, ventilators, shunts, hospital surfaces). Thus, there is a need in the art to prevent biofilm formation or to remove biofilms from surfaces once they have formed.

In methodologies for treating disease that is on the exterior of an animal (e.g., foot rot or mastitis) common practice is application of antibacterial solutions. The problem with this method is contamination to unaffected members of the herd or facility where milking or shearing is performed. Also, repeated applications are needed and antibiotic resistance or even ineffectiveness can occur. Mastitis is a disease that affects a large number of dairy cattle throughout the world and using antibiotics is not an ideal solution. Not only do they affect the milk being collected (withdrawal for days, contamination from antibiotic residues, problems associated with yogurt and cheese processing), antibiotics have not reduced the incidence of mastitis. Thus, there is a need in the art for improved methods for treating diseases such as foot rot and mastitis.

It is important to control insect vectors because the insect is the main transmitter of disease in animals. Vector-borne disease has significant negative impacts on animal health and dramatic economic implications. Without intervention by vector control dangerous disease would move quickly throughout the globe. Current methods of vector control include habitat control, reducing contact with vectors, biological control via predators, chemical control via insecticides or larvacides, bacterial toxins or botanical compounds. The current goals of finding long-lasting insecticides and finding new pesticides to combat resistant species is in effective for the global problem. Elimination of these insect vectors can alleviate disease spread and lower the mortality associated with the diseases they spread. Thus, there is also a need in the art for methods for protecting animals from pathogens by killing insect vectors.

SUMMARY OF THE INVENTION

A fusion protein is provided. The fusion protein comprises a targeting sequence, exosporium protein, or exosporium protein fragment that targets the fusion protein to the exosporium of a recombinant *Bacillus cereus* family member and at least one protein or peptide of interest. The protein or peptide of interest can comprise an antibody, an antibody fragment, a histone, a cecropin, a penaeidin, a bactenecin, a callinectin, a myticin, a tachyplesin, a clavanin, amisgurin, a pleurocidin, a parasin, an apyrase, an alginate lyase, a dispersin B, a DNAse, an endochitinase, an exochitinase, a proteinase K, a secreted insecticidal (Sip) protein, a mosquitocidal toxin, a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, a Cyt1Aa protein, an AiiA, a *Bacillus subtilis* serine protease, or a combination of any thereof.

Another fusion protein is provided. The fusion protein comprises a targeting sequence, exosporium protein, or exosporium protein fragment that targets the fusion protein to the exosporium of a recombinant *Bacillus cereus* family member and a LfcinB. The LfcinB comprises an amino acid sequence having at least 70%, at least 75%, at least 80%, at least 85%, at least 90%, at least 95%, at least 98%, at least 99%, or 100% sequence identity to SEQ ID NO: 212.

Yet another fusion protein is provided. The fusion protein comprises a targeting sequence, exosporium protein, or exosporium protein fragment that targets the fusion protein to the exosporium of a recombinant *Bacillus cereus* family member and a LysM. The LysM comprises an amino acid sequence having at least 70%, at least 75%, at least 80%, at least 85%, at least 90%, at least 95%, at least 98%, at least 99%, or 100% sequence identity to SEQ ID NO: 213.

Another fusion protein is provided. The fusion protein comprises a targeting sequence, exosporium protein, or exosporium protein fragment that targets the fusion protein to the exosporium of a recombinant *Bacillus cereus* family member and a β-1,3-glucanase. The β-1,3-glucanase comprises an amino acid sequence having at least 70%, at least 75%, at least 80%, at least 85%, at least 90%, at least 95%, at least 98%, at least 99%, or 100% sequence identity to SEQ ID NO: 214 or 216.

A further fusion protein is provided. The fusion protein comprises a targeting sequence, exosporium protein, or exosporium protein fragment that targets the fusion protein to the exosporium of a recombinant *Bacillus cereus* family member and a Cry21A protein. The Cry21A protein comprises an amino acid sequence having at least 70%, at least 75%, at least 80%, at least 85%, at least 90%, at least 95%, at least 98%, at least 99%, or 100% sequence identity to SEQ ID NO: 215.

A recombinant *Bacillus cereus* family member that expresses any of the fusion proteins is provided.

Exosporium fragments derived from spores of any of the recombinant *Bacillus cereus* family members are also provided.

Compositions comprising a carrier and spores of any of the recombinant *Bacillus cereus* family members described herein are provided.

Compositions comprising a carrier and exosporium fragments derived from spores of any of the recombinant *Bacillus cereus* family members described herein are also provided.

A pharmaceutical composition is provided. The pharmaceutical composition comprises a pharmaceutically acceptable carrier and exosporium fragments. The exosporium fragments are derived from spores of a recombinant *Bacillus cereus* family member and comprise a fusion protein. The fusion protein comprises at least one protein or peptide that protects an animal from a pathogen and a targeting sequence, exosporium protein, or exosporium protein fragment that targets the fusion protein to the exosporium of the recombinant *Bacillus cereus* family member.

A vaccine composition is provided. The composition comprises a pharmaceutically acceptable carrier. The vaccine composition also comprises exosporium fragments of a first type and exosporium fragments of a second type. The exosporium fragments of the second type are different from the exosporium fragments of the first type. The exosporium fragments of the first and second types are derived from spores of a recombinant *Bacillus cereus* family member that comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore. At least one of the exosporium fragments of the first type and the exosporium fragments of the second type comprise a fusion protein. The fusion protein comprises an antigen or an immunogen and a targeting sequence, exosporium protein, or exosporium protein fragment that targets the fusion protein to the exosporium of the recombinant *Bacillus cereus* family member.

Another vaccine composition is provided. The composition comprises a pharmaceutically acceptable carrier. The composition further comprises spores of a recombinant *Bacillus cereus* family member that expresses a first fusion protein. The first fusion protein comprising at least one antigen or immunogen and a targeting sequence, exosporium protein, or exosporium protein fragment that targets the first fusion protein to the exosporium of the recombinant *Bacillus cereus* family member. The composition also comprises exosporium fragments, wherein the exosporium fragments are derived from spores of a recombinant *Bacillus cereus* family member.

Yet another vaccine composition is provided. The composition comprises a pharmaceutically acceptable carrier. The composition also comprises a first immunogen or antigen. The composition further comprises exosporium fragments, wherein the exosporium fragments are derived from spores of a recombinant *Bacillus cereus* family member.

A method for producing an immunogenic response in an animal is provided. The method comprises administering any of the vaccine compositions to the animal.

A method for protecting an animal from a pathogen is provided. The method comprises administering spores of a recombinant *Bacillus cereus* family member that expresses a fusion protein to the animal, to the environment of the animal, or to the pathogen. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Another method for protecting an animal from a pathogen is provided. The method comprises administering exosporium fragments to the animal, to the environment of the animal, or to the pathogen. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

A composition is provided. The composition comprises a carrier acceptable for use in aquaculture and exosporium fragments. The exosporium fragments are derived from spores of a recombinant *Bacillus cereus* family member and comprise a fusion protein. The fusion protein comprises at least one protein or peptide that protects an aquatic organism from a pathogen and a targeting sequence, exosporium protein, or exosporium protein fragment that targets the fusion protein to the exosporium of the recombinant *Bacillus cereus* family member.

A method is provided for protecting an aquatic organism from a pathogen. The method comprises cultivating the aquatic organism in an aquaculture system. Spores of a recombinant *Bacillus cereus* family member that expresses a fusion protein are introduced into the aquaculture system. The fusion protein comprises at least one protein or peptide that protects the aquatic organism from a pathogen and a targeting sequence, exosporium protein, or exosporium protein fragment that targets the fusion protein to the exosporium of the recombinant *Bacillus cereus* family member. The aquatic organism is selected from fish, amphibians, reptiles, crustaceans, mollusks, worms, coral, sponges, red algae, brown algae, or combinations of any thereof.

Another method for protecting an aquatic organism from a pathogen is provided. The method comprises cultivating the aquatic organism in an aquaculture system. Exosporium fragments are introduced into the aquaculture system. The exosporium fragments are derived from spores of a recombinant *Bacillus cereus* family member and comprise a fusion protein. The fusion protein comprises at least one protein or peptide that protects the aquatic organism from a pathogen and a targeting sequence, exosporium protein, or exosporium protein fragment that targets the fusion protein to the exosporium of the recombinant *Bacillus cereus* family member. The aquatic organism is selected from fish, amphibians, reptiles, crustaceans, mollusks, worms, coral, sponges, red algae, brown algae, or combinations of any thereof.

Adhesive patches and wound dressings are provided. The adhesive patch or wound dressing comprising a pharmaceutical composition is provided. The pharmaceutical composition comprises a pharmaceutically acceptable carrier and spores of a recombinant *Bacillus cereus* family member that expresses a fusion protein. The fusion protein comprising at least one protein or peptide that protects an animal from a pathogen and a targeting sequence, exosporium protein, or exosporium protein fragment that targets the fusion protein to the exosporium of the recombinant *Bacillus cereus* family member.

Alternatively or in addition, the adhesive patch or wound dressing can comprise a pharmaceutical composition comprising a pharmaceutically acceptable carrier and exosporium fragments. The exosporium fragments are derived from spores of a recombinant *Bacillus cereus* family member and comprise a fusion protein. The fusion protein comprises at least one protein or peptide that protects an animal from a pathogen and a targeting sequence, exosporium protein, or exosporium protein fragment that targets the fusion protein to the exosporium of the recombinant *Bacillus cereus* family member.

An insert tray for a livestock footbath is provided. The insert tray comprises spores of a recombinant *Bacillus cereus* family member that expresses a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member. The spores are immobilized on an inner surface of the insert tray.

Alternatively or in addition, the insert tray comprises exosporium fragments. The exosporium fragments are derived from spores of a recombinant *Bacillus cereus* family member and comprise a fusion protein. The fusion protein comprising at least one protein or peptide that protects a hooved animal from a pathogen and a targeting sequence, exosporium protein, or exosporium protein fragment that targets the fusion protein to the exosporium of the recombinant *Bacillus cereus* family member. The exosporium fragments are immobilized on an inner surface of the insert tray.

A hoof bandage is provided. The hoof bandage comprises a pharmaceutical composition. The pharmaceutical composition comprises a pharmaceutically acceptable carrier and spores of a recombinant *Bacillus cereus* family member that expresses a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member.

Alternatively or in addition, the hoof bandage comprises a pharmaceutical composition comprising a pharmaceutically acceptable carrier and exosporium fragments. The exosporium fragments are derived from spores of a recombinant *Bacillus cereus* family member and comprise a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member.

Feed and feed additives are provided. The feed or feed additive comprises exosporium fragments, wherein the exosporium fragments are derived from spores of a recombinant *Bacillus cereus* family member and comprise a fusion protein, the fusion protein comprising at least one protein or peptide that protects an animal from a pathogen and a targeting sequence, exosporium protein, or exosporium protein fragment that targets the fusion protein to the exosporium of the recombinant *Bacillus cereus* family member.

A method for protecting an animal from a pathogen by killing an insect or arachnid vector of the pathogen is provided. The method comprises contacting the insect or arachnid vector or larvae of the insect or arachnid vector with spores of a recombinant *Bacillus cereus* family member. The recombinant *Bacillus cereus* family member expresses a fusion protein. The fusion protein comprises at least one protein or peptide that has insecticidal or acaricidal activity against an insect or arachnid vector of an animal pathogen or larvae of the insect or arachnid vector and a targeting sequence, exosporium protein, or exosporium protein fragment that targets the fusion protein to the exosporium of the recombinant *Bacillus cereus* family member.

Alternatively or in addition, the method for protecting an animal from a pathogen by killing an insect or arachnid vector of the pathogen comprises contacting the insect or arachnid vector or larvae of the insect or arachnid vector with exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae of the insect vector and a targeting sequence, exosporium protein, or exosporium protein fragment that targets the fusion protein to the exosporium of the recombinant *Bacillus cereus* family member.

An insecticidal or acaricidal composition is provided. The composition comprising a carrier and exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

An insect fogger is provided. The insect fogger comprises a carrier and spores of a recombinant *Bacillus cereus* family member that expresses a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

Alternatively or in addition, the insect fogger can comprise the carrier and exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

A method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The exosporium fragments are administered to the aquatic animal by immersing the aquatic animal in a solution comprising the exosporium fragments.

Alternatively or in addition, the method for producing an immunogenic response in an aquatic animal comprises administering spores to the aquatic animal. The spores are spores of a recombinant *Bacillus cereus* family member that expresses a fusion protein. The fusion protein comprises at least one antigen or immunogen and a targeting sequence, exosporium protein, or exosporium protein fragment that targets the fusion protein to the exosporium of the recombinant *Bacillus cereus* family member. The spores are administered to the aquatic animal by immersing the aquatic animal in a solution comprising the spores.

Another method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The aquatic animal is selected from fish, amphibians, crustaceans, mollusks, and combinations of any thereof.

Another method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The administration of the exosporium fragments to the aquatic animal results in vaccination of the aquatic animal against a pathogen selected from *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna, Icthyophous hoferi*, and combinations of any thereof.

Alternatively or in addition, the method for producing an immunogenic response in an aquatic animal comprises administering spores to the aquatic animal. The spores are spores of a recombinant *Bacillus cereus* family member that expresses a fusion protein. The fusion protein comprises at least one antigen or immunogen and a targeting sequence, exosporium protein, or exosporium protein fragment that targets the fusion protein to the exosporium of the recombinant *Bacillus cereus* family member. The administration of the spores to the aquatic animal results in vaccination of the aquatic animal against a pathogen selected from *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna, Icthyophous hoferi*, and combinations of any thereof.

Other objects and features will be in part apparent and in part pointed out hereinafter.

BRIEF DESCRIPTION OF THE DRAWINGS

FIGS. 1A and 1B show alignments of the amino acid sequence of an amino-terminal portion of *Bacillus anthracis* Sterne strain BclA and with the corresponding region from various exosporium proteins from *Bacillus cereus* family members.

Corresponding reference characters indicate corresponding parts throughout the drawings.

Definitions

Figure 2:
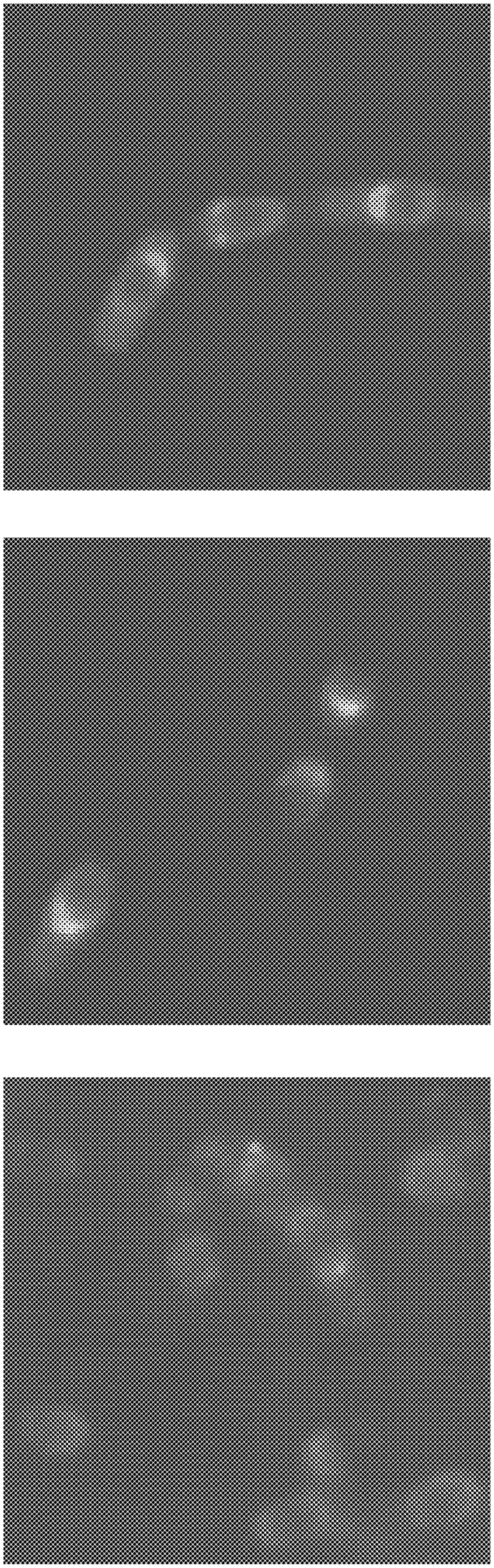
FIG. 2 shows exemplary fluorescent microscopy results for the expression of fusion proteins containing various exosporium proteins linked to an mCherry reporter on the exosporium of a recombinant *Bacillus cereus* family member.

When the articles "a," "an," "one," "the," and "said" are used herein, they mean "at least one" or "one or more" unless otherwise indicated.

The term "animal" encompasses any non-human animal as well as humans. For example, where the term "animal" is used herein, the animal can be a mammal (e.g., humans, monkeys, sheep, goats, cows, pigs, deer, alpacas, bison, camels, donkeys, horses, mules, yaks, reindeer, llamas, rabbits, dogs, cats, ferrets, gerbils, guinea pigs, hamsters, mice, rabbits, or rats), a bird (e.g., chickens, turkeys, ducks, geese, quail, doves, pigeons, ostriches, emus, or pheasants), a fish (e.g., hobby fish, salmon, trout, halibut, seabass, snapper, grouper, mullet, tilapia, tuna, catfish, carp, or sturgeon), an amphibian (e.g., frogs, toads, newts, or salamanders), a reptile (e.g., snakes, lizards, iguanas, crocodiles, alligators, turtles, or tortoises), a crustacean (e.g., a shrimp, prawn, krill, lobster, crab, or crayfish), a mollusk (e.g., mussels, clams, oysters, scallops, snails, slugs, squid, cuttlefish, or octopi), a worm (e.g., earthworms, nematodes, flatworms, roundworms, tapeworms, or flukes), an insect (e.g., bees, ladybugs, butterflies, silkworms, flies, beetles, or the larvae of any thereof), a coral, or a sponge.

The term "aquaculture" as used herein refers to the farming of aquatic organisms, and in particular fish, amphibians, reptiles, crustaceans, mollusks, worms, coral, sponges, red algae, brown algae. The term "aquaculture" as used herein does not encompass farming of aquatic plants.

The term "*Bacillus cereus* family member" as used herein refers to any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis*. *Bacillus cereus* family members are also referred to in the art as "*Bacillus cereus* senso lato."

The terms "comprising," "including," and "having" are intended to be inclusive and mean that there may be additional elements other than the listed elements.

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "hobby fish" as used herein refers to any fish that are kept in a private or public aquarium, garden pond, or other enclosure as pet fish, as ornamental fish, and/or for entertainment purposes (as opposed to fish that are farmed for food or for manufacture of a product).

The term "inactivate" or "inactivation" as used herein in reference to the inactivation of spores of a recombinant *Bacillus cereus* family member means that the spores are unable to germinate, or that the spores can germinate, but are damaged such that germination does not result in a living bacterium. The terms "partially inactivate" or "partial inactivation" mean that a percentage of the spores are inactivated, but that some spores retain the ability to germinate and return to a live, replicating state. The term "genetic inactivation" refers to inactivation of spores a recombinant *Bacillus cereus* family member by a mutation of the spore's DNA that results in complete or partial inactivation of the spore. The terms "physical inactivation" and "chemical inactivation refer to inactivation of spores using any physical or chemical means, e.g., by heat treatment, gamma irradiation, x-ray irradiation, UV-A irradiation, UV-B irradiation, or treatment with a solvent such as gluteraldehyde, formaldehyde, hydrogen peroxide, acetic acid, bleach, chloroform, or phenol, or any combination thereof.

The term "non-vaccine method" as used herein refers to a method that does not require the use of a vaccine, antigen, or immunogen. Instead the desired effect of protecting the animal from the pathogen is achieved without the use of a vaccine, antigen, or immunogen.

The terms "protein or peptide that protects an animal from a pathogen" and "protein or peptide that protects an aquatic organism from a pathogen" as used herein include any protein or peptide that prevents or treats an infection of the animal or aquatic organism with the pathogen. Proteins or peptides that protect an animal or aquatic organism from a pathogen can act directly or indirectly on the pathogen. Protective mechanisms for the proteins or peptides that protect an animal or an aquatic organism from a pathogen include, but are not limited to lysis of cell walls of the pathogen, prevention of establishment or colonization of the animal by the pathogen, blocking of cell-to-cell communication in the pathogen, activation of an immune response in the animal (but do not induce an antibody response), and/or increasing recognition of the pathogen by the animal. Proteins or peptides that protect animals or aquatic organisms from a pathogen also include proteins or peptide that prevent or inhibit the formation of biofilms or promote the dissolution of biofilms on the animal or aquatic organism or on a surface within the environment of the animal or aquatic organism.

The term "recombinant" as used in reference to the bacteria described herein encompasses bacteria having any genetic modification as compared to wild-type bacteria of the same type, including bacteria that have been modified to delete of a gene or a portion of a gene (e.g., bacteria that have a "knock-out" of a gene), as well as bacteria that have been modified to express an exogenous peptide or protein.

The term "targeting sequence" as used herein refers to a polypeptide sequence that, when present as part of a longer polypeptide or a protein, results in the localization of the longer polypeptide or the protein to a specific subcellular location. The targeting sequences described herein result in localization of proteins to the exosporium of a *Bacillus cereus* family member.

DESCRIPTION OF THE INVENTION

I. Fusion Proteins for Expression in *Bacillus Cereus* Family Members and Recombinant *Bacillus Cereus* Family Members Expressing Such Fusion Proteins The present invention relates to fusion proteins, recombinant *Bacillus cereus* family members that express such fusion proteins, and exosporium fragments derived from spores of the recombinant *Bacillus cereus* family members. The present invention further relates to compositions containing spores of a recombinant *Bacillus cereus* family member or exosporium fragments derived from spores of a recombinant *Bacillus cereus* family member, as well as uses of spores of recombinant *Bacillus cereus* family members and exosporium fragments derived from spores of a recombinant *Bacillus cereus* family member in the fields of animal health and aquaculture. Various products that contain the spores or exosporium fragments are also provided, including adhesive patches or wound dressings comprising the spores or exosporium fragments, insert trays for livestock footbaths comprising the spores or exosporium fragments, hoof bandages comprising the spores or exosporium fragments, feed and feed additives comprising the spores or exosporium fragments, and insect foggers containing the spores or exosporium fragments.

The spores express fusion proteins comprising a targeting sequence, an exosporium protein, or an exosporium protein fragment targets the fusion protein to the exosporium of a *Bacillus cereus* family member and at least one protein or peptide of interest (e.g., a protein or peptide that protects an animal from a pathogen, a protein or peptide that protects an aquatic organism from a pathogen, a protein or peptide that has insecticidal activity against an insect vector of an animal pathogen or larvae of the insect vector, or an antigen or immunogen). When expressed in *Bacillus cereus* family member bacteria, these fusion proteins are targeted to the exosporium layer of the spore and are physically oriented such that the protein or peptide of interest is displayed on the outside of the spore.

This *Bacillus* exosporium display (BEMD) system can be used to deliver peptides, enzymes, and other proteins to animals, aquatic organisms, or insect vectors of animal pathogens. In addition, as is described further hereinbelow, the BEMD system can be modified such that the exosporium of the recombinant *Bacillus cereus* family member can be removed from the spore, generating exosporium fragments containing the fusion proteins. The exosporium fragments can also be used to deliver peptides, enzymes, and other proteins to animals, aquatic organisms, or insect vectors of animal pathogens in a cell-free preparation.

A. Targeting Sequences, Exosporium Proteins, and Exosporium Protein Fragments for Targeting Proteins or Peptides of Interest to the Exosporium of a *Bacillus cereus* Family Member For ease of reference, descriptions of the amino acid sequences for the targeting sequences, exosporium proteins, and exosporium protein fragments that can be used for targeting of proteins or peptides of interest (e.g., proteins or peptides that protect an animal from a pathogen or proteins or peptides that protect an aquatic organism from a pathogen) to the exosporium of a *Bacillus cereus* family members, are provided in Table 1 together with their SEQ ID NOs.

TABLE 1

Peptide and protein sequences used for targeting of proteins or peptides of interest to the exosporium of *Bacillus cereus* family members

| Protein, protein fragment, or targeting sequence | SEQ ID NO. |
|---|---|
| AA 1-41 of BclA (*B. anthracis* Sterne) | 1* |
| Full length BclA (*B. anthracis* Sterne) | 2* |
| AA 1-33 of BetA/BAS3290 (*B. anthracis* Sterne) | 3 |
| Full length BetA/BAS3290 (*B. anthracis* Sterne) | 4 |
| Met + AA 2-43 of BAS4623 (*B. anthracis* Sterne) | 5 |
| Full length BAS4623 (*B. anthracis* Sterne) | 6 |
| AA 1-34 of BclB (*B. anthracis* Sterne) | 7 |
| Full length BclB (*B. anthracis* Sterne) | 8 |
| AA 1-30 of BAS1882 (*B. anthracis* Sterne) | 9 |
| Full length BAS1882 (*B. anthracis* Sterne) | 10 |
| AA 1-39 of gene 2280 (*B. weihenstephensis* KBAB4) | 11 |
| Full length KBAB4 gene 2280 (*B. weihenstephensis* KBAB4) | 12 |
| AA 1-39 of gene 3572 (*B. weihenstephensis* KBAB4) | 13 |
| Full Length KBAB4 gene 3572 (*B. weihenstephensis* KBAB4) | 14 |
| AA 1-49 of Exosporium Leader Peptide (*B. cereus* VD200) | 15 |
| Full Length Exosporium Leader Peptide (*B. cereus* VD200) | 16 |
| AA 1-33 of Exosporium Leader Peptide (*B. cereus* VD166) | 17 |
| Full Length Exosporium Leader Peptide (*B. cereus* VD166) | 18 |
| AA 1-39 of hypothetical protein IKG_04663 (*B. cereus* VD200) | 19 |
| Hypothetical protein IKG_04663, partial (*B. cereus* VD200) | 20 |
| AA 1-39 of YVTN β-propeller protein (*B. weihenstephensis* KBAB4) | 21 |
| Full length YVTN β-propeller protein KBAB4 (*B. weihenstephensis* KBAB4) | 22 |

TABLE 1-continued

Peptide and protein sequences used for targeting of proteins or peptides of interest to the exosporium of *Bacillus cereus* family members

| Protein, protein fragment, or targeting sequence | SEQ ID NO. |
|---|---|
| AA 1-30 of hypothetical protein bcerkbab4__2363 (*B. weihenstephensis* KBAB4) | 23 |
| Full length hypothetical protein bcerkbab4__2363 (*B. weihenstephensis* KBAB4) | 24 |
| AA 1-30 of hypothetical protein bcerkbab4__2131 (*B. weihenstephensis* KBAB4) | 25 |
| Full length hypothetical protein bcerkbab4__2131 (*B. weihenstephensis* KBAB4) | 26 |
| AA 1-36 of triple helix repeat containing collagen (*B. weihenstephensis* KBAB4) | 27 |
| Full length triple helix repeat-containing collagen KBAB4 (*B. weihenstephensis* KBAB4) | 28 |
| AA 1-39 of hypothetical protein bmyco0001__21660 (*B. mycoides* 2048) | 29 |
| Full length hypothetical protein bmyco0001__21660 (*B. mycoides* 2048) | 30 |
| AA 1-30 of hypothetical protein bmyc0001__22540 (*B. mycoides* 2048) | 31 |
| Full length hypothetical protein bmyc0001__22540 (*B. mycoides* 2048) | 32 |
| AA 1-21 of hypothetical protein bmyc0001__21510 (*B. mycoides* 2048) | 33 |
| Full length hypothetical protein bmyc0001__21510 (*B. mycoides* 2048) | 34 |
| AA 1-22 of collagen triple helix repeat protein (*B. thuringiensis* 35646) | 35 |
| Full length collagen triple helix repeat protein (*B. thuringiensis* 35646) | 36 |
| AA 1-35 of hypothetical protein WP__69652 (*B. cereus*) | 43 |
| Full length hypothetical protein WP__69652 (*B. cereus*) | 44 |
| AA 1-41 of exosporium leader WP016117717 (*B. cereus*) | 45 |
| Full length exosporium leader WP016117717 (*B. cereus*) | 46 |
| AA 1-49 of exosporium peptide WP002105192 (*B. cereus*) | 47 |
| Full length exosporium peptide WP002105192 (*B. cereus*) | 48 |
| AA 1-38 of hypothetical protein WP87353 (*B. cereus*) | 49 |
| Full length hypothetical protein WP87353 (*B. cereus*) | 50 |
| AA 1-39 of exosporium peptide 02112369 (*B. cereus*) | 51 |
| Full length exosporium peptide 02112369 (*B. cereus*) | 52 |
| AA 1-39 of exosporium protein WP016099770 (*B. cereus*) | 53 |
| Full length exosporium protein WP016099770 (*B. cereus*) | 54 |
| AA 1-36 of hypothetical protein YP006612525 (*B. thuringiensis*) | 55 |
| Full length hypothetical protein YP006612525 (*B. thuringiensis*) | 56 |
| AA 1-136 of hypothetical protein TIGR03720 (*B. mycoides*) | 57** |
| Full length hypothetical protein TIGR03720 (*B. mycoides*) (SEQ ID NO: 58)** | 58** |
| AA 1-36 of collagen triple helix repeat domain protein (*B. cereus* ATCC 10987) | 59 |
| Full length collagen triple helix repeat domain protein (*B. cereus* ATCC 10987) | 60 |
| AA 1-39 of collagen-like protein (*B. cereus* E33L) | 61 |
| Full length collagen-like protein (*B. cereus* E33L) | 62 |
| AA 1-41 of triple helix repeat-containing collagen (*B. weihenstephanensis* KBAB4) | 63 |
| Full length triple helix repeat-containing collagen (*B. weihenstephanensis* KBAB4) | 64 |
| AA 1-30 of hypothetical protein BALH__2230 (*B. thuringiensis* str. Al Hakam) | 65 |
| Full length hypothetical protein BALH__2230 (*B. thuringiensis* str. Al Hakam) | 66 |
| AA 1-33 of triple helix repeat-containing collagen (*B. cereus* ATCC 14579) | 67 |
| Full length triple helix repeat-containing collagen (*B. cereus* ATCC 14579) | 68 |
| AA 1-44 of collagen triple helix repeat (*B. cereus*) | 69 |
| Full length collagen triple helix repeat (*B. cereus*) | 70 |
| AA 1-38 of triple helix repeat-containing collagen (*B. cereus* ATCC 14579) | 71 |
| Full length triple helix repeat-containing collagen (*B. cereus* ATCC 14579) | 72 |
| AA 1-30 of hypothetical protein BCZK1835 (*B. cereus* E33L) | 73 |
| Full length hypothetical protein BCZK1835 (*B. cereus* E33L) | 74 |
| AA 1-48 of triple helix repeat-containing collagen (*B. weihenstephanensis* KBAB4) | 75 |
| Full length triple helix repeat-containing collagen (*B. weihenstephanensis* KBAB4) | 76 |
| AA 1-30 of triple helix repeat-containing collagen (*B. cereus* ATCC 14579) | 77 |
| Full length triple helix repeat-containing collagen (*B. cereus* ATCC 14579) | 78 |
| AA 1-39 of hypothetical protein BC4725 (*B. cereus* ATCC 14579) | 79 |
| Full length hypothetical protein BC4725 (*B. cereus* ATCC 14579) | 80 |
| AA 1-44 of hypothetical protein BCZK4476 (*B. cereus* E33L) | 81 |
| Full length hypothetical protein BCZK4476 (*B. cereus* E33L) | 82 |
| AA 1-40 of triple helix repeat-containing collagen (*B. anthracis* str. 'Ames Ancestor') | 83 |
| Full length triple helix repeat-containing collagen (*B. anthracis* str. 'Ames Ancestor') | 84 |
| AA 1-34 of BclA protein (*B. thuringiensis* serovar konkukian str. 97-27) | 85 |
| Full length BclA protein (*B. thuringiensis* serovar konkukian str. 97-27) | 86 |

TABLE 1-continued

| Peptide and protein sequences used for targeting of proteins or peptides of interest to the exosporium of *Bacillus cereus* family members | |
|---|---|
| Protein, protein fragment, or targeting sequence | SEQ ID NO. |
| AA 1-34 of conserved hypothetical protein (*B. cereus* ATCC 10987) | 87 |
| Full length conserved hypothetical protein (*B. cereus* ATCC 10987) | 88 |
| AA 1-34 of triple helix repeat-containing collagen (*B. cereus* ATCC 14579) | 89 |
| Full length triple helix repeat-containing collagen (*B. cereus* ATCC 14579) | 90 |
| AA 1-99 of exosporium leader peptide partial sequence (*B. cereus*) | 91 |
| Exosporium leader peptide partial sequence (*B. cereus*) | 92 |
| AA 1-136 of hypothetical protein ER45_27600, partial sequence (*B. weihenstephanensis*) | 93 |
| Hypothetical protein ER45_27600, partial sequence (*B. weihenstephanensis*) | 94 |
| AA 1-196 of BclA (*B. anthracis* Sterne) | 95* |
| Met + AA 20-35 of BclA (*B. anthracis* Sterne) | 96 |
| Met + AA 12-27 of BetA/BAS3290 (*B. anthracis* Sterne) | 97 |
| Met + AA 18-33 of gene 2280 (*B. weihenstephensis* KBAB4) | 98 |
| Met + AA 18-33 of gene 3572 (*B. weihenstephensis* KBAB4) | 99 |
| Met + AA 12-27 of Exosporium Leader Peptide (*B. cereus* VD166) | 100 |
| Met + AA 18-33 of YVTN β-propeller protein (*B. weihenstephensis* KBAB4) | 101 |
| Met + AA 9-24 of hypothetical protein bcerkbab4_2363 (*B. weihenstephensis* KBAB4) | 102 |
| Met + AA 9-24 of hypothetical protein bcerkbab4_2131 (*B. weihenstephensis* KBAB4) | 103 |
| Met + AA 9-24 of hypothetical protein bmyc0001_22540 (*B. mycoides* 2048) | 104 |
| Met + AA 9-24 of BAS1882 (*B. anthracis* Sterne) | 105 |
| Met + AA 20-35 of exosporium leader WP016117717 (*B. cereus*) | 106 |
| Met + AA 9-24 of hypothetical protein BALH_2230 (*B. thuringiensis* str. Al Hakam) | 107 |
| Full length InhA (*B. mycoides*) | 108 |
| Full length BAS1141 (ExsY) (*B. anthracis* Sterne) | 109 |
| Full length BAS1144 (BxpB/ExsFA) (*B. anthracis* Sterne) | 110 |
| Full length BAS1145 (CotY) (*B. anthracis* Sterne) | 111 |
| Full length BAS1140 (*B. anthracis* Sterne) | 112 |
| Full length ExsFB (*B. anthracis* H9401) | 113 |
| Full length InhA1 (*B. thuringiensis* HD74) | 114 |
| Full length ExsJ (*B. cereus* ATCC 10876) | 115 |
| Full length ExsH (*B. cereus*) | 116 |
| Full length YjcA (*B. anthracis* Ames) | 117 |
| Full length YjcB (*B. anthracis*) | 118 |
| Full length BclC (*B. anthracis* Sterne) | 119 |
| Full length acid phosphatase (*Bacillus thuringiensis* serovar konkukian str. 97-27) | 120 |
| Full length InhA2 (*B. thuringiensis* HD74) | 121 |
| Full length InhA3 (*B. mycoides*) | 122 |

AA = amino acids

**B. anthracis* Sterne strain BclA has 100% sequence identity with *B. thuringiensis* BclA. Thus, SEQ ID NOs: 1, 2, and 95 also represent amino acids 1-41 of *B. thuringiensis* BclA, full length *B. thuringiensis* BclA, and amino acids 1-196 of *B. thuringiensis* BclA, respectively. Likewise, SEQ ID NO: 96 also represents a methionine residue plus amino acids 20-35 of *B. Thuringiensis* BclA.

***B. mycoides* hypothetical protein TIGR03720 has 100% sequence identity with *B. Mycoides* hypothetical protein WP003189234. Thus, SEQ ID NOs: 57 and 58 also represent amino acids 1-136 of *B. mycoides* hypothetical protein WP003189234 and full length *B. Mycoides* hypothetical protein WP003189234, respectively.

*Bacillus* is a genus of rod-shaped bacteria. The *Bacillus cereus* family of bacteria includes any *Bacillus* species that is capable of producing an exosporium. Thus, the *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus weihenstephensis*, and *Bacillus toyoiensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members. BclA, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of BclA and BclB could be used to target a peptide or protein to the exosporium of a *Bacillus cereus* family member endospore (see U.S. Patent Application Publication Nos. 2010/0233124 and 2011/0281316, and Thompson et al., *Targeting of the BclA and BclB proteins to the Bacillus anthracis spore surface*, Molecular Microbiology 70(2):421-34 (2008)). It was also found that the BetA/BAS3290 protein of *Bacillus anthracis* localized to the exosporium. Further targeting sequences, as well as exosporium proteins and fragments of exosporium proteins, that can be incorporated into a fusion protein and used to target a peptide or protein of interest to the exosporium of a recombinant *Bacillus cereus* family member are described in U.S. Patent Application Publication No. 2016/0031948, which is incorporated by reference herein in its entirety.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIGS. 1A and 1B. As can be seen from FIGS. 1A and 1B, there is a region of high-homology among all of the proteins in the region corresponding to amino acids 20-41 of BclA. However, in these sequences, the amino acids corresponding to amino acids 36-41 of BclA contain secondary structure and are not necessary for fusion protein localization to the exosporium. The conserved targeting sequence region of BclA (amino acids 20-35 of SEQ ID NO: 1) is shown in bold in FIGS. 1A and 1B and corresponds to the minimal targeting sequence needed for localization to the exosporium. A more highly conserved region spanning amino acids 25-35 of BclA within the targeting sequence is underlined in the sequences in FIGS. 1A and 1B, and is the recognition sequence for ExsFA/BxpB/ExsFB and homologs, which direct and assemble the described proteins on the surface of the exosporium. The amino acid sequences of SEQ ID NOs. 3, 5, and 7 in FIG. 1A are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1A, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIGS. 1A and 1B, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of *Bacillus cereus* exosporium peptide 02112369, SEQ ID NO: 53 is amino acids 1-39 of *Bacillus cereus* exosporium protein WP016099770, SEQ ID NO: 55 is amino acids 1-36 of *Bacillus thuringiensis* hypothetical protein YP006612525, SEQ ID NO: 57 is amino acids 1-136 of *Bacillus mycoides* hypothetical protein TIGRO3720, SEQ ID NO: 59 is amino acids 1-36 of *B. cereus* ATCC 10987 collagen triple helix repeat domain protein, SEQ ID NO: 61 is amino acids 1-39 of *B. cereus* E33L collagen-like protein, SEQ ID NO: 63 is amino acids 1-41 of *B. weihenstephanensis* KBAB4 triple helix repeat-containing collagen, SEQ ID NO: 65 is amino acids 1-30 of *B. thuringiensis* str. Al Hakam hypothetical protein BALH_2230, SEQ ID NO: 67 is amino acids 1-33 of *B. cereus* ATCC 14579 triple helix repeat-containing collagen, SEQ ID NO: 69 is amino acids 1-44 of *B. cereus* collagen triple helix repeat, SEQ ID NO: 71 is amino acids 1-38 of *B. cereus* ATCC 14579 triple helix repeat-containing collagen, SEQ ID NO: 73 is amino acids 1-30 of *B. cereus* E33L hypothetical protein BCZK1835, SEQ ID NO: 75 is amino acids 1-48 of *B. weihenstephanensis* KBAB4 triple helix repeat-containing collagen, SEQ ID NO: 77 is amino acids 1-30 of *B. cereus* ATCC 14579 triple helix repeat-containing collagen, SEQ ID NO: 79 is amino acids 1-39 of *B. cereus* ATCC 14579 hypothetical protein BC4725, SEQ ID NO: 81 is amino acids 1-44 of *B. cereus* E33L hypothetical protein BCZK4476, SEQ ID NO: 83 is amino acids 1-40 of *B. anthracis* str. 'Ames Ancestor' triple helix repeat-containing collagen, SEQ ID NO: 85 is amino acids 1-34 of *B. thuringiensis* serovar konkukian str. 97-27 BclA protein, SEQ ID NO: 87 is amino acids 1-34 of *B. cereus* ATCC 10987 conserved hypothetical protein, SEQ ID NO: 89 is amino acids 1-34 of *B. cereus* ATCC 14579 triple helix repeat-containing collagen, SEQ ID NO: 91 is amino acids 1-99 of *B. cereus* exosporium leader peptide partial sequence, and SEQ ID NO: 93 is amino acids 1-136 of *B. weihenstephanensis* hypothetical protein ER45_27600. As shown in FIGS. 1A and 1B, each of the N-terminal regions of these proteins contains a region that is conserved with amino acids 20-35 of BclA (SEQ ID NO: 1), and a more highly conserved region corresponding to amino acids 25-35 of BclA.

Any portion of BclA which includes amino acids 20-35 can be used as to target a fusion protein to the exosporium. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2) or a midsized fragment of BclA that lacks the carboxy-terminus such as SEQ ID NO: 95 (amino acids 1-196 of BclA) can be used to target the fusion proteins to the exosporium. Midsized fragments such as the fragment of SEQ ID NO: 95 have less secondary structure than full length BclA and have been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 96 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663, *B. weihenstephensis* KBAB4 YVTN β-propeller protein, *B. weihenstephensis* KBAB4 hypothetical protein bcerkbab4_2363, *B. weihenstephensis* KBAB4 hypothetical protein bcerkbab4_2131, *B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, *B. thuringiensis* 35646 collagen triple helix repeat protein, *B. cereus* hypothetical protein WP_69652, *B. cereus* exosporium leader WP016117717, *B. cereus* exosporium peptide WP002105192, *B. cereus* hypothetical protein WP87353, *B. cereus* exosporium peptide 02112369, *B. cereus* exosporium protein WP016099770, *B. thuringiensis* hypothetical protein YP006612525, *B. mycoides* hypothetical protein TIGRO3720, *B. cereus* ATCC 10987 collagen triple helix repeat domain protein, *B. cereus* E33L collagen-like protein, *B. weihenstephanensis* KBAB4 triple helix repeat-containing collagen, *B. thuringiensis* str. Al Hakam hypothetical protein BALH_2230, *B. cereus* ATCC 14579 triple helix repeat-containing collagen, *B. cereus* collagen triple helix repeat, *B. cereus* ATCC 14579 triple helix repeat-containing collagen, *B. cereus* E33L hypothetical protein BCZK1835, *B. weihenstephanensis* KBAB4 triple helix repeat-containing collagen, *B. cereus* ATCC 14579 triple helix repeat-containing collagen, *B. cereus* ATCC 14579 hypothetical protein BC4725, *B. cereus* E33L hypothetical protein BCZK4476, *B. anthracis* str. 'Ames Ancestor' triple helix repeat-containing collagen, *B. thuringiensis* serovar konkukian str. 97-27 BclA protein, *B. cereus* ATCC 10987 conserved hypothetical protein, *B. cereus* ATCC 14579 triple helix repeat-containing collagen, *B. cereus* exosporium leader peptide partial sequence, or *B. weihenstephanensis* hypothetical protein ER45_27600 which includes the amino acids corresponding to amino acids 20-35 of BclA can serve as the targeting sequence.

As can be seen from FIG. 1A, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, amino acids 1-16 of *B. thuringiensis* 35646 collagen triple helix repeat protein, amino acids 14-29 of *B. cereus* hypothetical protein WP_69652, amino acids 20-35 of *B. cereus* exosporium leader WP016117717, amino acids 28-43 of *B. cereus* exosporium peptide WP002105192, amino acids 17-32 of *B. cereus* hypothetical protein WP87353, amino acids 18-33 of *B. cereus* exosporium peptide 02112369, amino acids 18-33 of *B. cereus* exosporium protein WP016099770, amino acids 15-30 of *B. thuringiensis* hypothetical protein YP006612525, and amino acids 115-130 of *B. mycoides* hypothetical protein TIGR03720 correspond to amino acids 20-35 of BclA. As can be seen from FIG. 1B, amino acids 15-30 of *B. cereus* ATCC 10987 collagen triple helix repeat domain protein, amino acids 18-33 of *B. cereus* E33L collagen-like protein, amino acids 20-35 of *B. weihenstephanensis* KBAB4 triple helix repeat-containing collagen, amino acids 9-24 of *B. thuringiensis* str. Al Hakam hypothetical protein BALH_2230, amino acids 12-27 of *B. cereus* ATCC 14579 triple helix repeat-containing collagen, amino acids 23-38 of *B. cereus* collagen triple helix repeat, amino acids 17-32 of *B. cereus* ATCC 14579 triple helix repeat-containing collagen, amino acids 9-24 of *B. cereus* E33L hypothetical protein BCZK1835, amino acids 27-42 of *B. weihenstephanensis* KBAB4 triple helix repeat-containing collagen, amino acids 9-24 of *B. cereus* ATCC 14579 triple helix repeat-containing collagen, amino acids 18-33 of *B. cereus* ATCC 14579 hypothetical protein BC4725, amino acids 23-38 of *B. cereus* E33L hypothetical protein BCZK4476, amino acids 19-34 *B. anthracis* str. 'Ames Ancestor' triple helix repeat-containing collagen, amino acids 13-28 of *B. thuringiensis* serovar konkukian str. 97-27 BclA protein, amino acids 13-28 of *B. cereus* ATCC 10987 conserved hypothetical protein, amino acids 13-28 of *B. cereus* ATCC 14579 triple helix repeat-containing collagen, amino acids 78-93 of *B. cereus* exosporium leader peptide partial sequence, and amino acids 115-130 of *B. weihenstephanensis* hypothetical protein ER45_27600 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids, can serve as the targeting sequence.

Thus, the targeting sequence can comprise amino acids 1-35 of SEQ ID NO: 1, amino acids 20-35 of SEQ ID NO: 1, SEQ ID NO: 1, SEQ ID NO: 96, amino acids 22-31 of SEQ ID NO: 1, amino acids 22-33 of SEQ ID NO: 1, or amino acids 20-31 of SEQ ID NO: 1. Alternatively, the targeting sequence consists of amino acids 1-35 of SEQ ID NO: 1, amino acids 20-35 of SEQ ID NO: 1, SEQ ID NO: 1, or SEQ ID NO: 96. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 59 (amino acids 1-196 of BclA). Alternatively, the exosporium protein fragment can consist of SEQ ID NO: 59.

The targeting sequence can comprise amino acids 2-35 of SEQ ID NO: 1; amino acids 5-35 of SEQ ID NO: 1; amino acids 8-35 of SEQ ID NO: 1; amino acids 10-35 of SEQ ID NO: 1; or amino acids 15-35 of SEQ ID NO: 1.

The targeting sequence can also comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 97. The targeting sequence can also comprise amino acids 14-23 of SEQ ID NO: 3, amino acids 14-25 of SEQ ID NO: 3, or amino acids 12-23 of SEQ ID NO: 3.

The targeting sequence can comprise amino acids 2-27 of SEQ ID NO: 3; amino acids 5-27 of SEQ ID NO: 3; amino acids 8-27 of SEQ ID NO: 3; or amino acids 10-27 of SEQ ID NO: 3.

The targeting sequence can also comprise amino acids 1-38 of SEQ ID NO: 5, amino acids 23-38 of SEQ ID NO: 5, or SEQ ID NO: 5, or the exosporium protein can comprise full length BAS4623 (SEQ ID NO: 6).

The targeting sequence can comprise amino acids 2-38 of SEQ ID NO: 5; amino acids 5-38 of SEQ ID NO: 5; amino acids 8-38 of SEQ ID NO: 5; amino acids 10-38 of SEQ ID NO: 5; amino acids 15-38 of SEQ ID NO: 5; or amino acids 20-38 of SEQ ID NO: 5.

Alternatively, the targeting sequence can comprise amino acids 1-28 of SEQ ID NO: 7, amino acids 13-28 of SEQ ID NO: 7, or SEQ ID NO: 7, or the exosporium protein can comprise full length BclB (SEQ ID NO:8).

The targeting sequence can comprise amino acids 2-28 of SEQ ID NO: 7; amino acids 5-28 of SEQ ID NO: 7; amino acids 8-28 of SEQ ID NO: 7; or amino acids 10-28 of SEQ ID NO: 7.

The targeting sequence can also comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can also be used as a targeting sequence. Thus, the targeting sequence can comprise SEQ ID NO: 105.

The targeting sequence can comprise amino acids 2-24 of SEQ ID NO: 9; amino acids 5-24 of SEQ ID NO: 9; or amino acids 8-24 of SEQ ID NO: 9.

The targeting sequence can also comprise amino acids 1-33 of SEQ ID NO:11, amino acids 18-33 of SEQ ID NO: 11, or SEQ ID NO: 11, or the exosporium protein can comprise the full length *B. weihenstephensis* KBAB4 2280 gene product (SEQ ID NO: 12). A methionine residue linked to amino acids 18-33 of the *B. weihenstephensis* KBAB4 2280 gene product can also be used as a targeting sequence. Thus, the targeting sequence can comprise SEQ ID NO: 98.

The targeting sequence can comprise amino acids 2-33 of SEQ ID NO: 11; amino acids 5-33 of SEQ ID NO: 11; amino acids 8-33 of SEQ ID NO: 11; amino acids 10-33 of SEQ ID NO: 11; or amino acids 15-33 of SEQ ID NO: 11.

The targeting sequence can also comprise amino acids 1-33 of SEQ ID NO: 13, amino acids 18-33 of SEQ ID NO: 13, or SEQ ID NO:13, or the exosporium protein can comprise the full length *B. weihenstephensis* KBAB4 3572 gene product (SEQ ID NO:14). A methionine residue linked to amino acids 18-33 of the *B. weihenstephensis* KBAB4 3572 gene product can also be used as a targeting sequence. Thus, the targeting sequence can comprise SEQ ID NO: 99.

The targeting sequence can comprise amino acids 2-33 of SEQ ID NO: 13; amino acids 5-33 of SEQ ID NO: 13; amino acids 8-33 of SEQ ID NO: 13; amino acids 10-33 of SEQ ID NO: 13; or amino acids 15-33 of SEQ ID NO: 13.

Alternatively, the targeting sequence can comprise amino acids 1-43 of SEQ ID NO: 15, amino acids 28-43 of SEQ ID NO: 15, or SEQ ID NO:15, or the exosporium protein can comprise full length *B. cereus* VD200 exosporium leader peptide (SEQ ID NO:16).

The targeting sequence can comprise amino acids 2-43 of SEQ ID NO: 15; amino acids 5-43 of SEQ ID NO: 15; amino acids 8-43 of SEQ ID NO: 15; amino acids 10-43 of SEQ ID NO: 15; amino acids 15-43 of SEQ ID NO: 15; amino acids 20-43 of SEQ ID NO: 15; or amino acids 25-43 of SEQ ID NO: 15.

The targeting sequence can also comprise amino acids 1-27 of SEQ ID NO: 17, amino acids 12-27 of SEQ ID NO: 17, or SEQ ID NO: 17, or the exosporium protein can comprise full-length *B. cereus* VD166 exosporium leader peptide (SEQ ID NO:18). A methionine residue linked to amino acids 12-27 of the *B. cereus* VD166 exosporium leader peptide can also be used as a targeting sequence. Thus, the targeting sequence can comprise SEQ ID NO: 100.

The targeting sequence can comprise amino acids 2-27 of SEQ ID NO: 17; amino acids 5-27 of SEQ ID NO: 17; amino acids 8-27 of SEQ ID NO: 17; or amino acids 10-27 of SEQ ID NO: 17.

The targeting sequence can also comprise amino acids 1-33 of SEQ ID NO: 19, amino acids 18-33 of SEQ ID NO: 19, or SEQ ID NO:19, or the exosporium protein can comprise full length *B. cereus* VD200 hypothetical protein IKG 04663 (SEQ ID NO:20).

The targeting sequence can comprise amino acids 2-33 of SEQ ID NO: 19; amino acids 5-33 of SEQ ID NO: 19; amino acids 8-33 of SEQ ID NO: 19; amino acids 10-33 of SEQ ID NO: 19; or amino acids 15-33 of SEQ ID NO: 19.

Alternatively, the targeting sequence comprises amino acids 1-33 of SEQ ID NO: 21, amino acids 18-33 of SEQ ID NO: 21, or SEQ ID NO:21, or the exosporium protein can comprise full length *B. weihenstephensis* KBAB4 YVTN β-propeller protein (SEQ ID NO:22). A methionine residue linked to amino acids 18-33 of the *B. weihenstephensis* KBAB4 YVTN β-propeller protein can also be used as a targeting sequence. Thus, the targeting sequence can comprise SEQ ID NO: 101.

The targeting sequence can comprise amino acids 2-33 of SEQ ID NO: 21; amino acids 5-33 of SEQ ID NO: 21; amino acids 8-33 of SEQ ID NO: 21; amino acids 10-33 of SEQ ID NO: 21; or amino acids 15-33 of SEQ ID NO: 21.

The targeting sequence can also comprise amino acids 1-24 of SEQ ID NO: 23, amino acids 9-24 of SEQ ID NO: 23, or SEQ ID NO:23, or the exosporium protein can comprise full length *B. weihenstephensis* KBAB4 hypothetical protein bcerkbab4_2363 (SEQ ID NO:24). A methionine residue linked to amino acids 9-24 of *B. weihenstephensis* KBAB4 hypothetical protein bcerkbab4_2363 can also be used as a targeting sequence. Thus, the targeting sequence can comprise SEQ ID NO: 102.

The targeting sequence can comprise amino acids 2-24 of SEQ ID NO:23; amino acids 5-24 of SEQ ID NO: 23; or amino acids 8-24 of SEQ ID NO: 23.

The targeting sequence comprise amino acids 1-24 of SEQ ID NO: 25, amino acids 9-24 of SEQ ID NO: 25, or SEQ ID NO: 25, or the exosporium protein can comprise full length *B. weihenstephensis* KBAB4 hypothetical protein bcerkbab4_2131 (SEQ ID NO:26). A methionine residue linked to amino acids 9-24 of *B. weihenstephensis* KBAB4 hypothetical protein bcerkbab4_2131 can also be used as a targeting sequence. Thus, the targeting sequence can comprise SEQ ID NO: 103.

The targeting sequence can comprise amino acids 2-24 of SEQ ID NO: 25; amino acids 5-24 of SEQ ID NO: 25; or amino acids 8-24 of SEQ ID NO: 25.

Alternatively, the targeting sequence comprises amino acids 1-30 of SEQ ID NO: 27, amino acids 15-30 of SEQ ID NO: 27, or SEQ ID NO:27, or the exosporium protein can comprise full length *B. weihenstephensis* KBAB4 triple helix repeat containing collagen (SEQ ID NO:28).

The targeting sequence can comprise amino acids 2-30 of SEQ ID NO: 27; amino acids 5-30 of SEQ ID NO: 27; amino acids 8-30 of SEQ ID NO: 27; or amino acids 10-30 of SEQ ID NO: 27.

The targeting sequence can also comprise amino acids 1-33 of SEQ ID NO: 29, amino acids 18-33 of SEQ ID NO: 29, or SEQ ID NO:29, or the exosporium protein can comprise full length *B. mycoides* 2048 hypothetical protein bmyco0001_21660 (SEQ ID NO:30).

The targeting sequence can comprise amino acids 2-33 of SEQ ID NO: 29; amino acids 5-33 of SEQ ID NO: 29; amino acids 8-33 of SEQ ID NO: 29; amino acids 10-33 of SEQ ID NO: 29; or amino acids 15-33 of SEQ ID NO: 29.

The targeting sequence can also comprise amino acids 1-24 of SEQ ID NO: 31, amino acids 9-24 of SEQ ID NO: 31, or SEQ ID NO:31, or the exosporium protein can comprise full length *B. mycoides* 2048 hypothetical protein bmyc0001_22540 (SEQ ID NO:32). A methionine residue linked to amino acids 9-24 of *B. mycoides* 2048 hypothetical protein bmyc0001_22540 can also be used as a targeting sequence. Thus, the targeting sequence can comprise SEQ ID NO: 104.

The targeting sequence can comprise amino acids 2-24 of SEQ ID NO: 31; amino acids 5-24 of SEQ ID NO: 31; or amino acids 8-24 of SEQ ID NO: 31.

Alternatively, the targeting sequence comprises amino acids 1-15 of SEQ ID NO: 33, SEQ ID NO:33, or the exosporium protein comprises full length *B. mycoides* 2048 hypothetical protein bmyc0001_21510 (SEQ ID NO:34).

The targeting sequence can also comprise amino acids 1-16 of SEQ ID NO: 35, SEQ ID NO:35, or the exosporium protein can comprise full length *B. thuringiensis* 35646 collagen triple helix repeat protein (SEQ ID NO:36).

The targeting sequence can comprise amino acids 1-29 of SEQ ID NO:43, amino acids 14-29 of SEQ ID NO: 43, or SEQ ID NO: 43, or the exosporium protein can comprise full length *B. cereus* hypothetical protein WP_69652 (SEQ ID NO: 44).

The targeting sequence can comprise amino acids 2-29 of SEQ ID NO: 43; amino acids 5-29 of SEQ ID NO: 43; amino acids 8-29 of SEQ ID NO: 43; or amino acids 10-29 of SEQ ID NO: 43.

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can also be used as a targeting sequence. Thus, the targeting sequence can comprise SEQ ID NO: 106.

The targeting sequence can comprise amino acids 2-35 of SEQ ID NO: 45; amino acids 5-35 of SEQ ID NO: 45; amino acids 8-35 of SEQ ID NO: 45; amino acids 10-35 of SEQ ID NO: 45; or amino acids 15-35 of SEQ ID NO: 45.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 2-43 of SEQ ID NO: 47; amino acids 5-43 of SEQ ID NO: 47; amino acids 8-43 of SEQ ID NO: 47; amino acids 10-43 of SEQ ID NO: 47; amino acids 15-43 of SEQ ID NO: 47; amino acids 20-43 of SEQ ID NO: 47; or amino acids 25-43 of SEQ ID NO: 47.

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

The targeting sequence can comprise amino acids 2-32 of SEQ ID NO: 49; amino acids 5-32 of SEQ ID NO: 49; amino acids 8-32 of SEQ ID NO: 49; amino acids 10-32 of SEQ ID NO: 49; or amino acids 15-32 of SEQ ID NO: 49.

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 2-33 of SEQ ID NO: 51; amino acids 5-33 of SEQ ID NO: 51; amino acids 8-33 of SEQ ID NO: 51; amino acids 10-33 of SEQ ID NO: 51; or amino acids 15-33 of SEQ ID NO: 51.

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

The targeting sequence can comprise amino acids 2-33 of SEQ ID NO: 53; amino acids 5-33 of SEQ ID NO: 53; amino acids 8-33 of SEQ ID NO: 53; amino acids 10-33 of SEQ ID NO: 53; or amino acids 15-33 of SEQ ID NO: 53.

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can comprise amino acids 2-30 of SEQ ID NO: 55; amino acids 5-30 of SEQ ID NO: 55; amino acids 8-30 of SEQ ID NO: 55; or amino acids 10-30 of SEQ ID NO: 55.

The targeting sequence can also comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGRO3720 (SEQ ID NO: 58).

The targeting sequence can comprise amino acids 2-130 of SEQ ID NO: 57; amino acids 5-130 of SEQ ID NO: 57; amino acids 10-130 of SEQ ID NO: 57; amino acids 20-130 of SEQ ID NO: 57; amino acids 30-130 of SEQ ID NO: 57; amino acids 40-130 of SEQ ID NO: 57; amino acids 50-130 of SEQ ID NO: 57; amino acids 60-130 of SEQ ID NO: 57; amino acids 70-130 of SEQ ID NO: 57; amino acids 80-130 of SEQ ID NO: 57; amino acids 90-130 of SEQ ID NO: 57; amino acids 100-130 of SEQ ID NO: 57; or amino acids 110-130 of SEQ ID NO: 57.

The targeting sequence can comprise amino acids 1-30 of SEQ ID NO: 59; or SEQ ID NO: 59; or the exosporium protein can comprise full length *B. cereus* ATCC 10987 collagen triple helix repeat domain protein (SEQ ID NO: 60).

The targeting sequence can comprise amino acids 2-30 of SEQ ID NO: 59; amino acids 4-30 of SEQ ID NO: 59; or amino acids 6-30 of SEQ ID NO: 59.

The targeting sequence can comprise amino acids 1-33 of SEQ ID NO: 61; amino acids 18-33 of SEQ ID NO: 61; or SEQ ID NO: 61; or the exosporium protein can comprise full length *B. cereus* E33L collagen-like protein (SEQ ID NO: 62).

The targeting sequence can comprise amino acids 2-33 of SEQ ID NO: 61; amino acids 5-33 of SEQ ID NO: 61; amino acids 10-33 of SEQ ID NO: 61; or amino acids 15-33 of SEQ ID NO: 61.

The targeting sequence can comprise amino acids 1-35 of SEQ ID NO: 63; or SEQ ID NO: 63; or the exosporium protein can comprise full length *B. weihenstephanensis* KBAB4 triple helix repeat-containing collagen (SEQ ID NO: 64).

The targeting sequence can comprise amino acids 2-35 of SEQ ID NO: 63; amino acids 5-35 of SEQ ID NO: 63; amino acids 8-35 of SEQ ID NO: 63; amino acids 10-35 of SEQ ID NO: 63; or amino acids 15-35 of SEQ ID NO: 63.

The targeting sequence can comprise amino acids 1-24 of SEQ ID NO: 65; acids 9-24 of SEQ ID NO: 65; SEQ ID NO: 65; or SEQ ID NO: 107; or the exosporium protein can comprise full length *B. thuringiensis* str. Al Hakam hypothetical protein BALH_2230 (SEQ ID NO: 66).

The targeting sequence can comprise amino acids 2-24 of SEQ ID NO: 65; or amino acids 5-24 of SEQ ID NO: 65.

The targeting sequence can comprise acids 1-27 of SEQ ID NO: 67; amino acids 12-27 of SEQ ID NO: 67; or SEQ ID NO: 67; or the exosporium protein can comprise full length *B. cereus* ATCC 14579 triple helix repeat-containing collagen (SEQ ID NO: 68).

The targeting sequence can comprise amino acids 2-27 of SEQ ID NO: 67; amino acids 5-27 of SEQ ID NO: 67; or amino acids 10-27 of SEQ ID NO: 67.

The targeting sequence can comprise amino acids 1-38 of SEQ ID NO: 69; amino acids 23-38 of SEQ ID NO: 69; or SEQ ID NO: 69; or the exosporium protein can comprise full length *B. cereus* collagen triple helix repeat (SEQ ID NO: 70).

The targeting sequence can comprise amino acids 2-38 of SEQ ID NO: 69; amino acids 5-38 of SEQ ID NO: 69; amino acids 10-38 of SEQ ID NO: 69; or amino acids 15-38 of SEQ ID NO: 69.

The exosporium protein can comprise full length *B. cereus* ATCC 14579 triple helix repeat-containing collagen (SEQ ID NO: 72).

The targeting sequence can comprise SEQ ID NO: 73, or the exosporium protein can comprise full length *B. cereus* E33L hypothetical protein BCZK1835 (SEQ ID NO: 74).

The targeting sequence can comprise amino acids 1-42 of SEQ ID NO: 75; amino acids 27-42 of SEQ ID NO: 75; or SEQ ID NO: 75; or the exosporium protein can comprise full length *B. weihenstephanensis* KBAB4 triple helix repeat-containing collagen (SEQ ID NO: 76).

The targeting sequence can comprise amino acids 2-42 of SEQ ID NO: 75; amino acids 5-42 of SEQ ID NO: 75; amino acids 10-42 of SEQ ID NO: 75; amino acids 15-42 of SEQ ID NO: 75; amino acids 20-42 of SEQ ID NO: 75; or amino acids 25-42 of SEQ ID NO: 75.

The targeting sequence can comprise amino acids 1-24 of SEQ ID NO: 77; amino acids 9-24 of SEQ ID NO: 77; or SEQ ID NO: 77; or the exosporium protein can comprise full length *B. cereus* ATCC 14579 triple helix repeat-containing collagen (SEQ ID NO: 78).

The targeting sequence can comprise amino acids 2-24 of SEQ ID NO: 77; or amino acids 5-24 of SEQ ID NO: 77;

The exosporium protein can comprise full length *B. cereus* ATCC 14579 hypothetical protein BC4725 (SEQ ID NO: 80).

The targeting sequence can comprise amino acids 1-38 of SEQ ID NO: 81; amino acids 23-38 of SEQ ID NO: 81; or SEQ ID NO: 81; or the exosporium protein can comprise full length *B. cereus* E33L hypothetical protein BCZK4476 (SEQ ID NO: 82).

The targeting sequence can comprise amino acids 2-38 of SEQ ID NO: 81; acids 5-38 of SEQ ID NO: 81; amino acids 10-38 of SEQ ID NO: 81; amino acids 15-38 of SEQ ID NO: 81; or amino acids 20-38 of SEQ ID NO: 81.

The targeting sequence can comprise amino acids 1-34 of SEQ ID NO: 83; or SEQ ID NO: 83; or the exosporium protein can comprise full length *B. anthracis* str. 'Ames Ancestor' triple helix repeat-containing collagen (SEQ ID NO: 84).

The exosporium protein can comprise full length *B. thuringiensis* serovar konkukian str. 97-27 BclA protein (SEQ ID NO: 86).

The targeting sequence can comprise amino acids 1-28 of SEQ ID NO: 87; amino acids 13-28 of SEQ ID NO: 87; or SEQ ID NO: 87; or the exosporium protein can comprise full length *B. cereus* ATCC 10987 conserved hypothetical protein (SEQ ID NO: 88).

The targeting sequence can comprise amino acids 2-28 of SEQ ID NO: 87; amino acids 5-28 of SEQ ID NO: 87; or amino acids 10-28 of SEQ ID NO: 87.

The targeting sequence can comprise amino acids 1-28 of SEQ ID NO: 89; or SEQ ID NO: 89; or the exosporium protein can comprise full length *B. cereus* ATCC 14579 triple helix repeat-containing collagen (SEQ ID NO: 90).

The targeting sequence can comprise amino acids 2-28 of SEQ ID NO: 89; amino acids 5-28 of SEQ ID NO: 89; or amino acids 10-28 of SEQ ID NO: 89

The targeting sequence can comprise amino acids 1-93 of SEQ ID NO: 91; or SEQ ID NO: 91; or the exosporium protein can comprise *B. cereus* exosporium leader peptide partial sequence (SEQ ID NO: 92).

The targeting sequence can comprise amino acids 2-93 of SEQ ID NO: 91; amino acids 10-93 of SEQ ID NO: 91; amino acids 20-93 of SEQ ID NO: 91; amino acids 30-93 of SEQ ID NO: 91; amino acids 40-93 of SEQ ID NO: 91; amino acids 50-93 of SEQ ID NO: 91; or amino acids 60-93 of SEQ ID NO: 91.

The targeting sequence can comprise amino acids 1-130 of SEQ ID NO: 93; or SEQ ID NO: 93; or the exosporium protein can comprise *B. weihenstephanensis*) hypothetical protein ER45_27600, partial sequence (SEQ ID NO: 94).

The targeting sequence can comprise amino acids 2-130 of SEQ ID NO: 93; amino acids 10-130 of SEQ ID NO: 93; amino acids 20-130 of SEQ ID NO: 93; or amino acids 30-130 of SEQ ID NO: 93.

Furthermore, as illustrated in the Examples provided hereinbelow, it has been found that sequences shorter than amino acids 20-35 of BclA can be used to target a fusion protein to the exosporium of a recombinant *Bacillus cereus* family member. In particular, amino acids 20-33 of BclA, amino acids 20-31 of BclA, amino acids 21-33 of BclA, or amino acids 23-31 of BclA can be used to target a fusion protein to the exosporium of a recombinant *Bacillus cereus* family member. Thus, the targeting sequence can consist of amino acids 20-33 of SEQ ID NO: 1, amino acids 20-31 of SEQ ID NO: 1, amino acids 21-33 of SEQ ID NO: 1, or amino acids 23-31 of SEQ ID NO: 1. The corresponding regions of any of the SEQ ID NOs. shown in FIGS. 1A and 1B can also be used to target a fusion protein to the exosporium of a recombinant *Bacillus cereus* family member. By "corresponding regions," it is meant that when the sequences are aligned with SEQ ID NO: 1, as shown in FIGS. 1A and 1B, the regions of the other amino acid sequences that align with the amino acids of SEQ ID NO: are the "corresponding regions" of those sequences. Thus, for example, amino acids 12-25 of SEQ ID NO: 3, amino acids 23-36 of SEQ ID NO: 5, amino acids 13-26 of SEQ ID NO: 7, etc. can be used to target a fusion protein to the exosporium of a recombinant *Bacillus cereus* family member, since these regions align with amino acids 20-33 of SEQ ID NO: 1 as shown in FIG. 1A.

Even shorter regions within amino acids 20-35 of BclA can also be used for targeting a fusion protein to the exosporium of a recombinant *Bacillus cereus* family member. In particular, any amino acid sequence that includes amino acids 25-30 of SEQ ID NO: 1 or the corresponding amino acids from any of the sequences shown in FIGS. 1A and 1B can be used. A skilled person will recognize that starting with amino acids 25-30 of SEQ ID NO: 1 or the corresponding region of any of the sequences shown in FIGS. 1A and 1B, additional amino acids can be added to the amino-terminus, the carboxy terminus, or both the amino- and carboxy termini to create a targeting sequence that will be effective for targeting a fusion protein to the exosporium of a recombinant *Bacillus cereus* family member.

In addition, it can readily be seen from the sequence alignment in FIGS. 1A and 1B that while amino acids 20-35 of BclA are conserved, and amino acids 25-35 are more conserved, some degree of variation can occur in this region without affecting the ability of the targeting sequence to target a protein to the exosporium. FIGS. 1A and 1B list the percent identity of each of corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIGS. 1A and 1B.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIGS. 1A and 1B.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence consisting of 16 amino acids and having at least about 62% identity with amino acids 20-35 of SEQ ID NO: 1, wherein the identity with amino acids 25-35 of SEQ ID NO:1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprises an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO:1 is at least about 81%.

The targeting sequence can also comprise an amino acid sequence having at least about 81% identity with amino acids 20-35 of SEQ ID NO:1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO:1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

Certain *Bacillus cereus* family exosporium proteins which lack regions having homology to amino acids 25-35 of BclA can also be used to target a peptide or protein to the exosporium of a *Bacillus cereus* family member. In particular, the fusion proteins can comprise an exosporium protein comprising SEQ ID NO: 108 (*B. mycoides* InhA), an exosporium protein comprising SEQ ID NO: 109 (*B. anthracis* Sterne BAS1141 (ExsY)), an exosporium protein comprising SEQ ID NO: 110 (*B. anthracis* Sterne BAS1144 (BxpB/ExsFA)), an exosporium protein comprising SEQ ID NO: 111 (*B. anthracis* Sterne BAS1145 (CotY)), an exosporium protein comprising SEQ ID NO: 112 (*B. anthracis* Sterne BAS1140), an exosporium protein comprising SEQ ID NO: 113 (*B. anthracis* H9401 ExsFB), an exosporium protein comprising SEQ ID NO: 114 (*B. thuringiensis* HD74 InhA1), an exosporium protein comprising SEQ ID NO: 115 (*B. cereus* ATCC 10876 ExsJ), an exosporium protein comprising SEQ ID NO: 116 (*B. cereus* ExsH), an exosporium protein comprising SEQ ID NO: 117 (*B. anthracis* Ames YjcA), an exosporium protein comprising SEQ ID NO: 118 (*B. anthracis* YjcB), an exosporium protein comprising SEQ ID NO: 119 (*B. anthracis* Sterne BclC), an exosporium protein comprising SEQ ID NO: 120 (*Bacillus thuringiensis* serovar konkukian str. 97-27 acid phosphatase), an exosporium protein comprising SEQ ID NO: 121 (*B. thuringiensis* HD74 InhA2), or an exosporium protein comprising SEQ ID NO: 122 (*B. mycoides* InhA3). Inclusion of an exosporium protein comprising any of SEQ ID NOs: 108-122 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein or exosporium protein fragment comprising an amino acid sequence having at least 85% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122. Alternatively, the fusion protein can comprise an exosporium protein having at least 90%, at least 95%, at least 98%, at least 99%, or 100% identity with any one of SEQ ID NOs: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

During sporulation of a recombinant *Bacillus cereus* family member expressing any of the fusion proteins described herein, the targeting motif, exosporium protein, or exosporium protein fragment is recognized by the spore exosporium assembly machinery and directed to the exosporium, resulting in display of the protein or peptide of interest portion of the fusion protein on the outside of the spore.

As illustrated further by the Examples provided hereinbelow, the use of different targeting sequences allows for control of the expression level of the fusion protein on the surface of the *Bacillus cereus* family member spore. Use of certain of the targeting sequences described herein will result in a higher level of expression of the fusion protein, whereas use of others of the targeting sequences will result in lower levels of expression of the fusion protein on the surface of the spore.

In any of the fusion proteins described herein, the targeting sequence, exosporium protein, or exosporium protein fragment can comprise the amino acid sequence GXT at its carboxy terminus, wherein X is any amino acid.

In any of the fusion proteins described herein, the targeting sequence, exosporium protein, or exosporium protein fragment, can comprise an alanine residue at the position of the targeting sequence that corresponds to amino acid 20 of SEQ ID NO: 1.

In any of the fusion proteins described herein, the targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

B. Fusion Proteins for Expression in Recombinant *Bacillus cereus* Family Members The present invention relates to fusion proteins comprising at least one protein or peptide of interest and a targeting sequence, exosporium protein fragment, or exosporium protein that targets the fusion protein to the exosporium of a recombinant *Bacillus cereus* family member. Recombinant *Bacillus cereus* family members that express such fusion proteins and exosporium fragments derived from spores of the recombinant *Bacillus cereus* family members are also provided. Compositions containing spores of a recombinant *Bacillus cereus* family member or exosporium fragments derived from spores of a recombinant *Bacillus cereus* family member are provided. In addition, the methods and products of the present invention involve the use of fusion proteins comprising at least one protein or peptide of interest (e.g., a protein or peptide that protects an animal from a pathogen, a protein or peptide that protects an aquatic organism from a pathogen, a protein or peptide that has insecticidal activity against an insect vector of an animal pathogen or larvae of the insect vector, or an antigen or immunogen) and a targeting sequence, exosporium protein fragment, or exosporium protein that targets the fusion protein to the exosporium of a recombinant *Bacillus cereus* family member.

In any of the fusion proteins, recombinant *Bacillus cereus* family members, compositions, methods, adhesive patches, wound dressings, insert trays, hoof bandages, feed, feed additives, or insect foggers described herein, the fusion protein can comprise: (1) a targeting sequence comprising an amino acid sequence having at least about 43% identity with amino acids 20-35 of SEQ ID NO: 1, wherein the identity with amino acids 25-35 is at least about 54%; (2) a targeting sequence comprising amino acids 1-35 of SEQ ID NO: 1; (3) a targeting sequence comprising amino acids 20-35 of SEQ ID NO: 1; (4) a targeting sequence comprising SEQ ID NO: 1; (5) an exosporium protein comprising an amino acid sequence having at least 85% identity with SEQ ID NO: 2; (6) a targeting sequence comprising amino acids 2-35 of SEQ ID NO: 1; (7) a targeting sequence comprising amino acids 5-35 of SEQ ID NO: 1; (8) a targeting sequence comprising amino acids 8-35 of SEQ ID NO: 1; (9) a targeting sequence comprising amino acids 10-35 of SEQ ID NO: 1; (10) a targeting sequence comprising amino acids 15-35 of SEQ ID NO: 1; (11) a targeting sequence comprising amino acids 1-27 of SEQ ID NO: 3; (12) a targeting sequence comprising amino acids 12-27 of SEQ ID NO: 3;

(13) a targeting sequence comprising SEQ ID NO: 3; (14) an exosporium protein comprising an amino acid sequence having at least 85% identity with SEQ ID NO: 4; (15) a targeting sequence comprising amino acids 2-27 of SEQ ID NO: 3; (16) a targeting sequence comprising amino acids 5-27 of SEQ ID NO: 3; (17) a targeting sequence comprising amino acids 8-27 of SEQ ID NO: 3; (18) a targeting sequence comprising amino acids 10-27 of SEQ ID NO: 3; (19) a targeting sequence comprising amino acids 1-38 of SEQ ID NO: 5; (20) a targeting sequence comprising amino acids 23-38 of SEQ ID NO: 5; (21) a targeting sequence comprising SEQ ID NO: 5; (22) an exosporium protein comprising an amino acid sequence having at least 85% identity with SEQ ID NO: 6; (23) a targeting sequence comprising amino acids 2-38 of SEQ ID NO: 5; (24) a targeting sequence comprising amino acids 5-38 of SEQ ID NO: 5; (25) a targeting sequence comprising amino acids 8-38 of SEQ ID NO: 5; (26) a targeting sequence comprising amino acids 10-38 of SEQ ID NO: 5; (27) a targeting sequence comprising amino acids 15-38 of SEQ ID NO: 5; (28) a targeting sequence comprising amino acids 20-38 of SEQ ID NO: 5; (29) a targeting sequence comprising amino acids 1-28 of SEQ ID NO: 7; (30) a targeting sequence comprising amino acids 13-28 of SEQ ID NO: 7; (31) a targeting sequence comprising SEQ ID NO: 7; (32) an exosporium protein comprising an amino acid sequence having at least 85% identity with SEQ ID NO: 8; (33) a targeting sequence comprising amino acids 2-28 of SEQ ID NO: 7; (34) a targeting sequence comprising amino acids 5-28 of SEQ ID NO: 7; (35) a targeting sequence comprising amino acids 8-28 of SEQ ID NO: 7; (36) a targeting sequence comprising amino acids 10-28 of SEQ ID NO: 7; (37) a targeting sequence comprising amino acids 1-24 of SEQ ID NO: 9; (38) a targeting sequence comprising amino acids 9-24 of SEQ ID NO: 9; (39) a targeting sequence comprising SEQ ID NO: 9; (40) an exosporium protein comprising an amino acid sequence having at least 85% identity with SEQ ID NO: 10; (41) a targeting sequence comprising amino acids 2-24 of SEQ ID NO: 9; (42) a targeting sequence comprising amino acids 5-24 of SEQ ID NO: 9; (43) a targeting sequence comprising amino acids 8-24 of SEQ ID NO: 9; (44) a targeting sequence comprising amino acids 1-33 of SEQ ID NO:11; (45) a targeting sequence comprising amino acids 18-33 of SEQ ID NO: 11; (46) a targeting sequence comprising SEQ ID NO: 11; (47) an exosporium protein comprising an amino acid sequence having at least 85% identity with SEQ ID NO: 12; (48) a targeting sequence comprising amino acids 2-33 of SEQ ID NO: 11; (49) a targeting sequence comprising amino acids 5-33 of SEQ ID NO: 11; (50) a targeting sequence comprising amino acids 8-33 of SEQ ID NO: 11; (51) a targeting sequence comprising amino acids 10-33 of SEQ ID NO: 11; (52) a targeting sequence comprising amino acids 15-33 of SEQ ID NO: 11; (53) a targeting sequence comprising amino acids 1-33 of SEQ ID NO: 13; (54) a targeting sequence comprising amino acids 18-33 of SEQ ID NO: 13; (55) a targeting sequence comprising SEQ ID NO:13; (56) an exosporium protein comprising an amino acid sequence having at least 85% identity with SEQ ID NO:14; (57) a targeting sequence comprising amino acids 2-33 of SEQ ID NO: 13; (58) a targeting sequence comprising amino acids 5-33 of SEQ ID NO: 13; (59) a targeting sequence comprising amino acids 8-33 of SEQ ID NO: 13; (60) a targeting sequence comprising amino acids 10-33 of SEQ ID NO: 13; (61) a targeting sequence comprising amino acids 15-33 of SEQ ID NO: 13; (62) a targeting sequence comprising amino acids 1-43 of SEQ ID NO: 15; (63) a targeting sequence comprising amino acids 28-43 of SEQ ID NO: 15; (64) a targeting sequence comprising SEQ ID NO:15; (65) an exosporium protein comprising an amino acid sequence having at least 85% identity with SEQ ID NO:16; (66) a targeting sequence comprising amino acids 2-43 of SEQ ID NO: 15; (67) a targeting sequence comprising amino acids 5-43 of SEQ ID NO: 15; (68) a targeting sequence comprising amino acids 8-43 of SEQ ID NO: 15; (69) a targeting sequence comprising amino acids 10-43 of SEQ ID NO: 15; (70) a targeting sequence comprising amino acids 15-43 of SEQ ID NO: 15; (71) a targeting sequence comprising amino acids 20-43 of SEQ ID NO: 15; (72) a targeting sequence comprising amino acids 25-43 of SEQ ID NO: 15; (73) a targeting sequence comprising amino acids 1-27 of SEQ ID NO: 17; (74) a targeting sequence comprising amino acids 12-27 of SEQ ID NO: 17; (75) a targeting sequence comprising SEQ ID NO:17; (76) an exosporium protein comprising an amino acid sequence having at least 85% identity with SEQ ID NO:18; (77) a targeting sequence comprising amino acids 2-27 of SEQ ID NO: 17; (78) a targeting sequence comprising amino acids 5-27 of SEQ ID NO: 17; (79) a targeting sequence comprising amino acids 8-27 of SEQ ID NO: 17; (80) a targeting sequence comprising amino acids 10-27 of SEQ ID NO: 17; (81) a targeting sequence comprising amino acids 1-33 of SEQ ID NO: 19; (82) a targeting sequence comprising amino acids 18-33 of SEQ ID NO: 19; (83) a targeting sequence comprising SEQ ID NO:19; (84) an exosporium protein comprising an amino acid sequence having at least 85% identity with SEQ ID NO:20; (85) a targeting sequence comprising amino acids 2-33 of SEQ ID NO: 19; (86) a targeting sequence comprising amino acids 5-33 of SEQ ID NO: 19; (87) a targeting sequence comprising amino acids 8-33 of SEQ ID NO: 19; (88) a targeting sequence comprising amino acids 10-33 of SEQ ID NO: 19; (89) a targeting sequence comprising amino acids 15-33 of SEQ ID NO: 19; (90) a targeting sequence comprising amino acids 1-33 of SEQ ID NO: 21; (91) a targeting sequence comprising amino acids 18-33 of SEQ ID NO: 21; (92) a targeting sequence comprising SEQ ID NO:21; (93) an exosporium protein comprising an amino acid sequence having at least 85% identity with SEQ ID NO:22; (94) a targeting sequence comprising amino acids 2-33 of SEQ ID NO: 21; (95) a targeting sequence comprising amino acids 5-33 of SEQ ID NO: 21; (96) a targeting sequence comprising amino acids 8-33 of SEQ ID NO: 21; (97) a targeting sequence comprising amino acids 10-33 of SEQ ID NO: 21; (98) a targeting sequence comprising amino acids 15-33 of SEQ ID NO: 21; (99) a targeting sequence comprising amino acids 1-24 of SEQ ID NO: 23; (100) a targeting sequence comprising amino acids 9-24 of SEQ ID NO: 23; (101) a targeting sequence comprising SEQ ID NO:23; (102) an exosporium protein comprising an amino acid sequence having at least 85% identity with SEQ ID NO:24; (103) a targeting sequence comprising amino acids 2-24 of SEQ ID NO:23; (104) a targeting sequence comprising amino acids 5-24 of SEQ ID NO: 23; (105) a targeting sequence comprising amino acids 8-24 of SEQ ID NO: 23; (106) a targeting sequence comprising amino acids 1-24 of SEQ ID NO: 25; (107) a targeting sequence comprising amino acids 9-24 of SEQ ID NO: 25; (108) a targeting sequence comprising SEQ ID NO:25; (109) an exosporium protein comprising an amino acid sequence having at least 85% identity with SEQ ID NO:26; (110) a targeting sequence comprising amino acids 2-24 of SEQ ID NO: 25; (111) a targeting sequence comprising amino acids 5-24 of SEQ ID NO: 25; (112) a targeting sequence comprising amino acids 8-24 of SEQ ID NO: 25; (113) a targeting sequence comprising amino acids 1-30 of SEQ ID NO: 27; (114) a targeting sequence comprising amino acids 15-30 of SEQ ID NO: 27; (115) a targeting sequence comprising SEQ ID NO:27; (116) an exosporium protein comprising an amino acid sequence having at least 85% identity with SEQ ID NO:28; (117) a targeting sequence comprising amino acids 2-30 of SEQ ID NO: 27; (118) a targeting sequence comprising amino acids 5-30 of SEQ ID NO: 27; (119) a targeting sequence comprising amino acids 8-30 of SEQ ID NO: 27; (120) a targeting sequence comprising amino acids 10-30 of SEQ ID NO: 27; (121) a targeting sequence comprising amino acids 1-33 of SEQ ID NO: 29; (122) a targeting sequence comprising amino acids 18-33 of SEQ ID NO: 29; (123) a targeting sequence comprising SEQ ID NO:29; (124) an exosporium protein comprising an amino acid sequence having at least 85% identity with SEQ ID NO:30; (125) a targeting sequence comprising amino acids 2-33 of SEQ ID NO: 29; (126) a targeting sequence comprising amino acids 5-33 of SEQ ID NO: 29; (127) a targeting sequence comprising amino acids 8-33 of SEQ ID NO: 29; (128) a targeting sequence comprising amino acids 10-33 of SEQ ID NO: 29; (129) a targeting sequence comprising amino acids 15-33 of SEQ ID NO: 29; (130) a targeting sequence comprising amino acids 1-24 of SEQ ID NO: 31; (131) a targeting sequence comprising amino acids 9-24 of SEQ ID NO: 31; (132) a targeting sequence comprising SEQ ID NO:31; (133) an exosporium protein comprising an amino acid sequence having at least 85% identity with SEQ ID NO:32; (134) a targeting sequence comprising amino acids 2-24 of SEQ ID NO: 31; (135) a targeting sequence comprising amino acids 5-24 of SEQ ID NO: 31; (136) a targeting sequence comprising amino acids 8-24 of SEQ ID NO: 31; (137) a targeting sequence comprising amino acids 1-15 of SEQ ID NO: 33; (138) a targeting sequence comprising SEQ ID NO:33; (139) an exosporium protein comprising an amino acid sequence having at least 85% identity with SEQ ID NO:34; (140) a targeting sequence comprising amino acids 1-16 of SEQ ID NO: 35; (141) a targeting sequence comprising SEQ ID NO:35; (142) an exosporium protein comprising an amino acid sequence having at least 85% identity with SEQ ID NO:36; (143) a targeting sequence comprising amino acids 1-29 of SEQ ID NO:43; (144) a targeting sequence comprising amino acids 14-29 of SEQ ID NO: 43; (145) a targeting sequence comprising SEQ ID NO: 43; (146) an exosporium protein comprising an amino acid sequence having at least 85% identity with SEQ ID NO: 44; (147) a targeting sequence comprising amino acids 2-29 of SEQ ID NO: 43; (148) a targeting sequence comprising amino acids 5-29 of SEQ ID NO: 43; (149) a targeting sequence comprising amino acids 8-29 of SEQ ID NO: 43; (150) a targeting sequence comprising amino acids 10-29 of SEQ ID NO: 43; (151) a targeting sequence comprising amino acids 1-35 of SEQ ID NO: 45; (152) a targeting sequence comprising amino acids 20-35 of SEQ ID NO: 45; (153) a targeting sequence comprising SEQ ID NO: 45; (154) an exosporium protein comprising an amino acid sequence having at least 85% identity with SEQ ID NO: 46; (155) a targeting sequence comprising amino acids 2-35 of SEQ ID NO: 45; (156) a targeting sequence comprising amino acids 5-35 of SEQ ID NO: 45; (157) a targeting sequence comprising amino acids 8-35 of SEQ ID NO: 45; (158) a targeting sequence comprising amino acids 10-35 of SEQ ID NO: 45; (159) a targeting sequence comprising amino acids 15-35 of SEQ ID NO: 45; (160) a targeting sequence comprising amino acids 1-43 of SEQ ID NO: 47; (161) a targeting sequence comprising amino acids 28-43 of SEQ ID NO: 47; (162) a targeting sequence comprising SEQ ID NO: 47; (163) an exosporium protein comprising an amino acid sequence having at least 85% identity with SEQ ID NO: 48; (164) a targeting sequence comprising amino acids 2-43 of SEQ ID NO: 47; (165) a targeting sequence comprising amino acids 5-43 of SEQ ID NO: 47; (166) a targeting sequence comprising amino acids 8-43 of SEQ ID NO: 47; (167) a targeting sequence comprising amino acids 10-43 of SEQ ID NO: 47; (168) a targeting sequence comprising amino acids 15-43 of SEQ ID NO: 47; (169) a targeting sequence comprising amino acids 20-43 of SEQ ID NO: 47; (170) a targeting sequence comprising amino acids 25-43 of SEQ ID NO: 47; (171) a targeting sequence comprising amino acids 1-32 of SEQ ID NO: 49; (172) a targeting sequence comprising amino acids 17-32 of SEQ ID NO: 49; (173) a targeting sequence comprising SEQ ID NO: 49; (174) an exosporium protein comprising an amino acid sequence having at least 85% identity with SEQ ID NO: 50; (175) a targeting sequence comprising amino acids 2-32 of SEQ ID NO: 49; (176) a targeting sequence comprising amino acids 5-32 of SEQ ID NO: 49; (177) a targeting sequence comprising amino acids 8-32 of SEQ ID NO: 49; (178) a targeting sequence comprising amino acids 10-32 of SEQ ID NO: 49; (179) a targeting sequence comprising amino acids 15-32 of SEQ ID NO: 49; (180) a targeting sequence comprising amino acids 1-33 of SEQ ID NO: 51; (181) a targeting sequence comprising amino acids 18-33 of SEQ ID NO: 51; (182) a targeting sequence comprising SEQ ID NO: 51; (183) an exosporium protein comprising an amino acid sequence having at least 85% identity with SEQ ID NO: 52; (184) a targeting sequence comprising amino acids 2-33 of SEQ ID NO: 51; (185) a targeting sequence comprising amino acids 5-33 of SEQ ID NO: 51; (186) a targeting sequence comprising amino acids 8-33 of SEQ ID NO: 51; (187) a targeting sequence comprising amino acids 10-33 of SEQ ID NO: 51; (188) a targeting sequence comprising amino acids 15-33 of SEQ ID NO: 51; (189) a targeting sequence comprising amino acids 1-33 of SEQ ID NO: 53; (190) a targeting sequence comprising amino acids 18-33 of SEQ ID NO: 53; (191) a targeting sequence comprising SEQ ID NO: 53; (192) an exosporium protein comprising an amino acid sequence having at least 85% identity with SEQ ID NO: 54; (193) a targeting sequence comprising amino acids 2-33 of SEQ ID NO: 53; (194) a targeting sequence comprising amino acids 5-33 of SEQ ID NO: 53; (195) a targeting sequence comprising amino acids 8-33 of SEQ ID NO: 53; (196) a targeting sequence comprising amino acids 10-33 of SEQ ID NO: 53; (197) a targeting sequence comprising amino acids 15-33 of SEQ ID NO: 53; (198) a targeting sequence comprising amino acids 1-30 of SEQ ID NO: 55; (199) a targeting sequence comprising amino acids 15-30 of SEQ ID NO: 55; (200) a targeting sequence comprising SEQ ID NO: 55; (201) an exosporium protein comprising an amino acid sequence having at least 85% identity with SEQ ID NO: 56; (202) a targeting sequence comprising amino acids 2-30 of SEQ ID NO: 55; (203) a targeting sequence comprising amino acids 5-30 of SEQ ID NO: 55; (204) a targeting sequence comprising amino acids 8-30 of SEQ ID NO: 55; (205) a targeting sequence comprising amino acids 10-30 of SEQ ID NO: 55; (206) a targeting sequence comprising amino acids 1-130 of SEQ ID NO: 57; (207) a targeting sequence comprising amino acids 115-130 of SEQ ID NO: 57; (208) a targeting sequence comprising SEQ ID NO: 57; (209) an exosporium protein comprising an amino acid sequence having at least 85% identity with SEQ ID NO: 58; (210) a targeting sequence comprising amino acids 2-130 of SEQ ID NO: 57; (211) a targeting sequence comprising amino acids 5-130 of SEQ ID NO: 57; (212) a targeting sequence comprising amino acids 10-130 of SEQ ID NO: 57; (213) a targeting sequence comprising amino acids 20-130 of SEQ ID NO: 57; (214) a targeting sequence comprising amino acids 30-130 of SEQ ID NO: 57; (215) a targeting sequence comprising amino acids 40-130 of SEQ ID NO: 57; (216) a targeting sequence comprising amino acids 50-130 of SEQ ID NO: 57; (217) a targeting sequence comprising amino acids 60-130 of SEQ ID NO: 57; (218) a targeting sequence comprising amino acids 70-130 of SEQ ID NO: 57; (219) a targeting sequence comprising amino acids 80-130 of SEQ ID NO: 57; (220) a targeting sequence comprising amino acids 90-130 of SEQ ID NO: 57; (221) a targeting sequence comprising amino acids 100-130 of SEQ ID NO: 57; (222) a targeting sequence comprising amino acids 110-130 of SEQ ID NO: 57; (223) an exosporium protein fragment comprising an amino acid sequence having at least 85% identity with SEQ ID NO: 95; (224) a targeting sequence comprising SEQ ID NO: 96; (225) a targeting sequence comprising SEQ ID NO: 97; (226) a targeting sequence comprising SEQ ID NO: 98; (227) a targeting sequence comprising SEQ ID NO: 99; (228) a targeting sequence comprising SEQ ID NO: 100; (229) a targeting sequence comprising SEQ ID NO: 101; (230) a targeting sequence comprising SEQ ID NO: 102; (231) a targeting sequence comprising SEQ ID NO: 103; (232) a targeting sequence comprising SEQ ID NO: 104; (233) a targeting sequence comprising SEQ ID NO: 105; (234) a targeting sequence comprising SEQ ID NO: 106; (235) an exosporium protein comprising an amino acid sequence having at least 85% identity with SEQ ID NO: 108; (236) an exosporium protein comprising an amino acid sequence having at least 85% identity with SEQ ID NO: 109; (237) an exosporium protein comprising an amino acid sequence having at least 85% identity with SEQ ID NO: 110; (238) an exosporium protein comprising an amino acid sequence having at least 85% identity with SEQ ID NO: 111; (239) an exosporium protein comprising an amino acid sequence having at least 85% identity with SEQ ID NO: 112; (240) an exosporium protein comprising an amino acid sequence having at least 85% identity with SEQ ID NO: 113; (241) an exosporium protein comprising an amino acid sequence having at least 85% identity with SEQ ID NO: 114; (242) an exosporium protein comprising an amino acid sequence having at least 85% identity with SEQ ID NO: 115; (243) an exosporium protein comprising an amino acid sequence having at least 85% identity with SEQ ID NO: 116; (244) an exosporium protein comprising an amino acid sequence having at least 85% identity with SEQ ID NO: 117; (245) an exosporium protein comprising an amino acid sequence having at least 85% identity with SEQ ID NO: 118; (246) an exosporium protein comprising an amino acid sequence having at least 85% identity with SEQ ID NO: 119; (247) an exosporium protein comprising an amino acid sequence having at least 85% identity with SEQ ID NO: 120; (248) an exosporium protein comprising an amino acid sequence having at least 85% identity with SEQ ID NO: 121; (249) a targeting sequence comprising amino acids 22-31 of SEQ ID NO: 1; (250) a targeting sequence comprising amino acids 22-33 of SEQ ID NO: 1; (251) a targeting sequence comprising amino acids 20-31 of SEQ ID NO: 1; (252) a targeting sequence comprising amino acids 14-23 of SEQ ID NO: 3; (253) a targeting sequence comprising amino acids 14-25 of SEQ ID NO: 3; (254) a targeting sequence comprising amino acids 12-23 of SEQ ID NO: 3; (255) a targeting sequence comprising amino acids 1-30 of SEQ ID NO: 59; (256) a targeting sequence comprising SEQ ID NO: 59; (257) an exosporium protein comprising an amino acid sequence having at least 85% identity with SEQ ID NO: 60; (258) a targeting sequence comprising amino acids 2-30 of SEQ ID NO: 59; (259) a targeting sequence comprising amino acids 4-30 of SEQ ID NO: 59; (260) a targeting sequence comprising amino acids 6-30 of SEQ ID NO: 59; (261) a targeting sequence comprising amino acids 1-33 of SEQ ID NO: 61; (262) a targeting sequence comprising amino acids 18-33 of SEQ ID NO: 61; (263) a targeting sequence comprising SEQ ID NO: 61; (264) an exosporium protein comprising an amino acid sequence having at least 85% sequence identity with SEQ ID NO: 62; (265) a targeting sequence comprising amino acids 2-33 of SEQ ID NO: 61; (266) a targeting sequence comprising amino acids 5-33 of SEQ ID NO: 61; (267) a targeting sequence comprising amino acids 10-33 of SEQ ID NO: 61; (268) a targeting sequence comprising amino acids 15-33 of SEQ ID NO: 61; (269) a targeting sequence comprising amino acids 1-35 of SEQ ID NO: 63; (270) a targeting sequence comprising SEQ ID NO: 63; (271) an exosporium protein comprising an amino acid sequence having at least 85% identity with SEQ ID NO: 64; (272) a targeting sequence comprising amino acids 2-35 of SEQ ID NO: 63; (273) a targeting sequence comprising amino acids 5-35 of SEQ ID NO: 63; (274) a targeting sequence comprising amino acids 8-35 of SEQ ID NO: 63; (275) a targeting sequence comprising amino acids 10-35 of SEQ ID NO: 63; (276) a targeting sequence comprising amino acids 15-35 of SEQ ID NO: 63; (277) a targeting sequence comprising amino acids 1-24 of SEQ ID NO: 65; (278) a targeting sequence comprising amino acids 9-24 of SEQ ID NO: 65; (279) a targeting sequence comprising SEQ ID NO: 65; (280) an exosporium protein comprising an amino acid sequence having at least 85% identity with SEQ ID NO: 66; (281) a targeting sequence comprising SEQ ID NO: 107; (282) a targeting sequence comprising amino acids 2-24 of SEQ ID NO: 65; (283) a targeting sequence comprising amino acids 5-24 of SEQ ID NO: 65; (284) a targeting sequence comprising amino acids 1-27 of SEQ ID NO: 67; (285) a targeting sequence comprising amino acids 12-27 of SEQ ID NO: 67; (286) a targeting sequence comprising SEQ ID NO: 67; (287) an exosporium protein comprising an amino acid sequence having at least 85% identity with SEQ ID NO: 68; (288) an targeting sequence comprising amino acids 2-27 of SEQ ID NO: 67; (289) a targeting sequence comprising amino acids 5-27 of SEQ ID NO: 67; (290) a targeting sequence comprising amino acids 10-27 of SEQ ID NO: 67; (291) a targeting sequence comprising amino acids 1-38 of SEQ ID NO: 69; (292) a targeting sequence comprising amino acids 23-38 of SEQ ID NO: 69; (293) a targeting sequence comprising SEQ ID NO: 69; (294) an exosporium protein comprising an amino acid sequence having at least 85% identity with SEQ ID NO: 70; (295) a targeting sequence comprising amino acids 2-38 of SEQ ID NO: 69; (296) a targeting sequence comprising amino acids 5-38 of SEQ ID NO: 69; (297) a targeting sequence comprising amino acids 10-38 of SEQ ID NO: 69; (298) a targeting sequence comprising amino acids 15-38 of SEQ ID NO: 69; (299) an exosporium protein comprising SEQ ID NO: 72; (300) a targeting sequence comprising SEQ ID NO: 73; (301) an exosporium protein comprising an amino acid sequence having at least 95% identity with SEQ ID NO: 74; (302) a targeting sequence comprising amino acids 1-42 of SEQ ID NO: 75; (303) a targeting sequence comprising amino acids 27-42 of SEQ ID NO: 75; (304) a targeting sequence comprising SEQ ID NO: 75; (305) an exosporium protein comprising an amino acid sequence having at least 85% identity with SEQ ID NO: 76; (306) a targeting sequence comprising amino acids 2-42 of SEQ ID NO: 75; (307) a targeting sequence comprising amino acids 5-42 of SEQ ID NO: 75; (308) a targeting sequence comprising amino acids 10-42 of SEQ ID NO: 75; (309) a targeting sequence comprising amino acids 15-42 of SEQ ID NO: 75; (310) a targeting sequence comprising amino acids 20-42 of SEQ ID NO: 75; (311) a targeting sequence comprising amino acids 25-42 of SEQ ID NO: 75; (312) a targeting sequence comprising amino acids 1-24 of SEQ ID NO: 77; (313) a targeting sequence comprising amino acids 9-24 of SEQ ID NO: 77; (314) a targeting sequence comprising SEQ ID NO: 77; (315) an exosporium protein comprising an amino acid sequence having at least 85% identity with SEQ ID NO: 78; (316) a targeting sequence comprising amino acids 2-24 of SEQ ID NO: 77; (317) a targeting sequence comprising amino acids 5-24 of SEQ ID NO: 77; (318) an exosporium protein comprising an amino acid sequence having at least 85% identity with SEQ ID NO: 80; (319) a targeting sequence comprising amino acids 1-38 of SEQ ID NO: 81; (320) a targeting sequence comprising amino acids 23-38 of SEQ ID NO: 81; (321) a targeting sequence comprising SEQ ID NO: 81; (322) an exosporium protein comprising an amino acid sequence having at least 85% identity with SEQ ID NO: 82; (323) a targeting sequence comprising amino acids 2-38 of SEQ ID NO: 81; (324) a targeting sequence comprising amino acids 5-38 of SEQ ID NO: 81; (325) a targeting sequence comprising amino acids 10-38 of SEQ ID NO: 81; (326) a targeting sequence comprising amino acids 15-38 of SEQ ID NO: 81; (327) a targeting sequence comprising amino acids 20-38 of SEQ ID NO: 81; (328) a targeting sequence comprising amino acids 1-34 of SEQ ID NO: 83; (329) a targeting sequence comprising SEQ ID NO: 83; (330) an exosporium protein comprising an amino acid sequence having at least 85% identity with SEQ ID NO: 84; (331) an exosporium protein comprising an amino acid sequence having at least 85% identity with SEQ ID NO: 86; (332) a targeting sequence comprising amino acids 1-28 of SEQ ID NO: 87; (333) a targeting sequence comprising amino acids 13-28 of SEQ ID NO: 87; (334) a targeting sequence comprising SEQ ID NO: 87; (335) an exosporium protein comprising an amino acid sequence having at least 85% identity with SEQ ID NO: 88; (336) a targeting sequence comprising amino acids 2-28 of SEQ ID NO: 87; (337) a targeting sequence comprising amino acids 5-28 of SEQ ID NO: 87; (338) a targeting sequence comprising amino acids 10-28 of SEQ ID NO: 87; (339) a targeting sequence comprising amino acids 1-28 of SEQ ID NO: 89; (340) a targeting sequence comprising SEQ ID NO: 89; (341) an exosporium protein comprising an amino acid sequence having at least 85% identity with SEQ ID NO: 90; (342) a targeting sequence comprising amino acids 2-28 of SEQ ID NO: 89; (343) a targeting sequence comprising amino acids 5-28 of SEQ ID NO: 89; (344) a targeting sequence comprising amino acids 10-28 of SEQ ID NO: 89; (345) a targeting sequence comprising amino acids 1-93 of SEQ ID NO: 91; (346) a targeting sequence comprising SEQ ID NO: 91; (347) an exosporium protein comprising an amino acid sequence having at least 85% identity with SEQ ID NO: 92; (348) a targeting sequence comprising amino acids 2-93 of SEQ ID NO: 91; (349) a targeting sequence comprising amino acids 10-93 of SEQ ID NO: 91; (350) a targeting sequence comprising amino acids 20-93 of SEQ ID NO: 91; (351) a targeting sequence comprising amino acids 30-93 of SEQ ID NO: 91; (352) a targeting sequence comprising amino acids 40-93 of SEQ ID NO: 91; (353) a targeting sequence comprising amino acids 50-93 of SEQ ID NO: 91; (354) a targeting sequence comprising amino acids 60-93 of SEQ ID NO: 91; (355) a targeting sequence comprising amino acids 1-130 of SEQ ID NO: 93; (356) a targeting sequence comprising SEQ ID NO: 93; (357) an exosporium protein comprising an amino acid sequence having at least 85% identity with SEQ ID NO: 94; (358) a targeting sequence comprising amino acids 2-130 of SEQ ID NO: 93; (359) a targeting sequence comprising amino acids 10-130 of SEQ ID NO: 93; (360) a targeting sequence comprising amino acids 20-130 of SEQ ID NO: 93; (361) a targeting sequence comprising amino acids 30-130 of SEQ ID NO: 93; (362) an exosporium protein comprising an amino acid sequence having at least 85% identity with SEQ ID NO: 122; (363) a targeting sequence consisting of amino acids 20-33 of SEQ ID NO: 1; (364) a targeting sequence consisting of amino acids 21-33 of SEQ ID NO: 1; (365) a targeting sequence consisting of amino acids 23-31 of SEQ ID NO: 1; (366) a targeting sequence consisting of amino acids 1-15 of SEQ ID NO: 96; (367) a targeting sequence consisting of amino acids 1-13 of SEQ ID NO: 96; (368) a targeting sequence consisting of amino acids 12-25 of SEQ ID NO: 3; (369) a targeting sequence consisting of amino acids 13-25 of SEQ ID NO: 3; (370) a targeting sequence consisting of amino acids 15-23 of SEQ ID NO: 3; (371) a targeting sequence consisting of amino acids 1-15 of SEQ ID NO: 97; (372) a targeting sequence consisting of amino acids 1-13 of SEQ ID NO: 98; (373) a targeting sequence consisting of amino acids 23-36 of SEQ ID NO: 5; (374) a targeting sequence consisting of amino acids 23-34 of SEQ ID NO: 5; (375) a targeting sequence consisting of amino acids 24-36 of SEQ ID NO: 5; (376) a targeting sequence consisting of amino acids 26-34 of SEQ ID NO: 5; (377) a targeting sequence consisting of amino acids 13-26 of SEQ ID NO: 7; (378) a targeting sequence consisting of amino acids 13-24 of SEQ ID NO: 7; (379) a targeting sequence consisting of amino acids 14-26 of SEQ ID NO: 7; (380) a targeting sequence consisting of amino acids 16-24 of SEQ ID NO: 7; (381) a targeting sequence consisting of amino acids 9-22 of SEQ ID NO: 9; (382) a targeting sequence consisting of amino acids 9-20 of SEQ ID NO: 9; (383) a targeting sequence consisting of amino acids 10-22 of SEQ ID NO: 9; (384) a targeting sequence consisting of amino acids 12-20 of SEQ ID NO: 9; (385) a targeting sequence consisting of amino acids 1-15 of SEQ ID NO: 105; (386) a targeting sequence consisting of amino acids 1-13 of SEQ ID NO: 105; (387) a targeting sequence consisting of amino acids 18-31 of SEQ ID NO: 11; (388) a targeting sequence consisting of amino acids 18-29 of SEQ ID NO: 11; (389) a targeting sequence consisting of amino acids 19-31 of SEQ ID NO: 11; (390) a targeting sequence consisting of amino acids 1-15 of SEQ ID NO: 98; (391) a targeting sequence consisting of amino acids 1-13 of SEQ ID NO: 98; (392) a targeting sequence consisting of amino acids 18-31 of SEQ ID NO: 13; (393) a targeting sequence consisting of amino acids 18-29 of SEQ ID NO: 13; (394) a targeting sequence consisting of amino acids 19-31 of SEQ ID NO: 13; (395) a targeting sequence consisting of amino acids 21-29 of SEQ ID NO: 13; (396) a targeting sequence consisting of amino acids 1-15 of SEQ ID NO: 99; (397) a targeting sequence consisting of amino acids 1-13 of SEQ ID NO: 99; (398) a targeting sequence consisting of amino acids 28-41 of SEQ ID NO: 15; (399) a targeting sequence consisting of amino acids 28-39 of SEQ ID NO: 15; (400) a targeting sequence consisting of amino acids 29-41 of SEQ ID NO: 15; (401) a targeting sequence consisting of amino acids 31-39 of SEQ ID NO: 15; (402) a targeting sequence consisting of amino acids 12-25 of SEQ ID NO: 17; (403) a targeting sequence consisting of amino acids 13-25 of SEQ ID NO: 17; (404) a targeting sequence consisting of amino acids 1-15 of SEQ ID NO: 100; (405) a targeting sequence consisting of amino acids 18-31 of SEQ ID NO: 19; (406) a targeting sequence consisting of amino acids 18-29 of SEQ ID NO: 19; (407) a targeting sequence consisting of amino acids 19-31 of SEQ ID NO: 19; (408) a targeting sequence consisting of amino acids 21-29 of SEQ ID NO: 19; (409) a targeting sequence consisting of amino acids 18-31 of SEQ ID NO: 21; (410) a targeting sequence consisting of amino acids 18-29 of SEQ ID NO: 21; (411) a targeting sequence consisting of amino acids 19-31 of SEQ ID NO: 21; (412) a targeting sequence consisting of amino acids 21-29 of SEQ ID NO: 21; (413) a targeting sequence consisting of amino acids 1-15 of SEQ ID NO: 101; (414) a targeting sequence consisting of amino acids 1-13 of SEQ ID NO: 101; (415) a targeting sequence consisting of amino acids 9-22 of SEQ ID NO: 23; (416) a targeting sequence consisting of amino acids 9-20 of SEQ ID NO: 23; (417) a targeting sequence consisting of amino acids 10-22 of SEQ ID NO: 23; (418) a targeting sequence consisting of amino acids 12-20 of SEQ ID NO: 23; (419) a targeting sequence consisting of amino acids 1-15 of SEQ ID NO: 102; (420) a targeting sequence consisting of amino acids 1-13 of SEQ ID NO: 102; (421) a targeting sequence consisting of amino acids 9-22 of SEQ ID NO: 25; (422) a targeting sequence consisting of amino acids 9-20 of SEQ ID NO: 25; (423) a targeting sequence consisting of amino acids 10-22 of SEQ ID NO: 25; (424) a targeting sequence consisting of amino acids 12-20 of SEQ ID NO: 25; (425) a targeting sequence consisting of amino acids 1-15 of SEQ ID NO: 103; (426) a targeting sequence consisting of amino acids 1-13 of SEQ ID NO: 103; (427) a targeting sequence consisting of amino acids 15-28 of SEQ ID NO: 27; (428) a targeting sequence consisting of amino acids 15-26 of SEQ ID NO: 27; (429) a targeting sequence consisting of amino acids 16-28 of SEQ ID NO: 27; (430) a targeting sequence consisting of amino acids 18-26 of SEQ ID NO: 27; (431) a targeting sequence consisting of amino acids 1-15 of SEQ ID NO: 104; (432) a targeting sequence consisting of amino acids 1-13 of SEQ ID NO: 104; (433) a targeting sequence consisting of amino acids 1-13 of SEQ ID NO: 33; (434) a targeting sequence consisting of amino acids 1-11 of SEQ ID NO: 33; (435) a targeting sequence consisting of amino acids 3-11 of SEQ ID NO: 33; (436) a targeting sequence consisting of amino acids 1-14 of SEQ ID NO: 35; (437) a targeting sequence consisting of amino acids 1-12 of SEQ ID NO: 35; (438) a targeting sequence consisting of amino acids 2-14 of SEQ ID NO: 35; (439) a targeting sequence consisting of amino acids 14-27 of SEQ ID NO: 43; (440) a targeting sequence consisting of amino acids 14-25 of SEQ ID NO: 43; (441) a targeting sequence consisting of amino acids 15-27 of SEQ ID NO: 43; (442) a targeting sequence consisting of amino acids 20-33 of SEQ ID NO: 45; (443) a targeting sequence consisting of amino acids 20-31 of SEQ ID NO: 45; (444) a targeting sequence consisting of amino acids 21-33 of SEQ ID NO: 45; (445) a targeting sequence consisting of amino acids 1-15 of SEQ ID NO: 106; (446) a targeting sequence consisting of amino acids 1-13 of SEQ ID NO: 106; (447) a targeting sequence consisting of amino acids 28-41 of SEQ ID NO: 47; (448) a targeting sequence consisting of amino acids 28-39 of SEQ ID NO: 47; (449) a targeting sequence consisting of amino acids 18-31 of SEQ ID NO: 53; (450) a targeting sequence consisting of amino acids 18-29 of SEQ ID NO: 53; (451) a targeting sequence consisting of amino acids 19-31 of SEQ ID NO: 53; (452) a targeting sequence comprising amino acids 18-31 of SEQ ID NO: 61; (453) a targeting sequence comprising amino acids 18-29 of SEQ ID NO: 61; (454) a targeting sequence comprising amino acids 19-31 of SEQ ID NO: 61; (455) a targeting sequence comprising amino acids 9-22 of SEQ ID NO: 65; (456) a targeting sequence comprising amino acids 9-20 of SEQ ID NO: 65; (457) a targeting sequence comprising amino acids 10-22 of SEQ ID NO: 65; (458) a targeting sequence comprising amino acids 1-15 of SEQ ID NO: 107; (459) a targeting sequence comprising amino acids 1-13 of SEQ ID NO: 107; (460) a targeting sequence comprising amino acids 12-25 of SEQ ID NO: 67; (461) a targeting sequence comprising amino acids 12-23 of SEQ ID NO: 67; (462) a targeting sequence comprising amino acids 13-25 of SEQ ID NO: 67; (463) a targeting sequence comprising amino acids 15-23 of SEQ ID NO: 67; (464) a targeting sequence comprising amino acids 23-36 of SEQ ID NO: 69; (465) a targeting sequence comprising amino acids 23-34 of SEQ ID NO: 69; (466) a targeting sequence comprising amino acids 24-36 of SEQ ID NO: 69; (467) a targeting sequence comprising amino acids 26-34 of SEQ ID NO: 69; (468) a targeting sequence comprising amino acids 27-40 of SEQ ID NO: 75; (469) a targeting sequence comprising amino acids 27-38 of SEQ ID NO: 75; (470) a targeting sequence comprising amino acids 9-22 of SEQ ID NO: 77; (471) a targeting sequence comprising amino acids 9-20 of SEQ ID NO: 77; (472) a targeting sequence comprising amino acids 10-22 of SEQ ID NO: 77; (473) a targeting sequence comprising amino acids 12-20 of SEQ ID NO: 77; (474) a targeting sequence comprising amino acids 23-36 of SEQ ID NO: 81; (475) a targeting sequence comprising amino acids 23-34 of SEQ ID NO: 81; (476) a targeting sequence comprising amino acids 24-36 of SEQ ID NO: 81; (477) a targeting sequence comprising amino acids 26-34 of SEQ ID NO: 81; (478) a targeting sequence comprising amino acids 13-26 of SEQ ID NO: 87; (479) a targeting sequence comprising amino acids 13-24 of SEQ ID NO: 87; or (480) a targeting sequence comprising amino acids 14-26 of SEQ ID NO: 87.

For example, the targeting sequence can comprise an amino acid sequence having at least about 50% identity with amino acids 20-35 of SEQ ID NO: 1, wherein the identity with amino acids 25-35 is at least about 63%.

For example, the targeting sequence can comprise an amino acid sequence having at least about 56% identity with amino acids 20-35 of SEQ ID NO: 1, wherein the identity with amino acids 25-35 is at least about 63%.

For example, the targeting sequence can comprise an amino acid sequence having at least about 50% identity with amino acids 20-35 of SEQ ID NO: 1, wherein the identity with amino acids 25-35 is at least about 72%.

For example, the targeting sequence can comprise an amino acid sequence having at least about 62% identity with amino acids 20-35 of SEQ ID NO: 1, wherein the identity with amino acids 25-35 is at least about 72%.

For example, the targeting sequence can comprise an amino acid sequence having at least about 75% identity with amino acids 20-35 of SEQ ID NO: 1, wherein the identity with amino acids 25-35 is at least about 72%.

For example, the targeting sequence can comprise an amino acid sequence having at least about 68% identity with amino acids 20-35 of SEQ ID NO: 1, wherein the identity with amino acids 25-35 is at least about 81%.

For example, the targeting sequence can comprise an amino acid sequence having at least about 75% identity with amino acids 20-35 of SEQ ID NO: 1, wherein the identity with amino acids 25-35 is at least about 81%.

For example, the targeting sequence can comprise an amino acid sequence having at least about 81% identity with amino acids 20-35 of SEQ ID NO: 1, wherein the identity with amino acids 25-35 is at least about 81%.

For example, the targeting sequence can comprise an amino acid sequence having at least about 81% identity with amino acids 20-35 of SEQ ID NO: 1, wherein the identity with amino acids 25-35 is at least about 90%.

For example, the targeting sequence can consist of: (a) an amino acid sequence consisting of 16 amino acids and having at least about 43% identity with amino acids 20-35 of SEQ ID NO: 1, wherein the identity with amino acids 25-35 is at least about 54%; (b) amino acids 1-35 of SEQ ID NO: 1; (c) amino acids 20-35 of SEQ ID NO: 1; (d) SEQ ID NO: 1; (e) SEQ ID NO: 96; or (f) SEQ ID NO: 120.

The targeting sequence can consist of the amino acid sequence as described in these examples.

The fusion protein can comprise an exosporium protein or an exosporium protein fragment comprising an amino acid sequence having at least 90% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 95% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 98% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having at least 99% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein or an exosporium protein fragment comprising an amino acid sequence having 100% identity with SEQ ID NO: 2, 4, 6, 8, 10, 12, 14, 16, 18, 20, 22, 24, 26, 28, 30, 32, 34, 36, 44, 46, 48, 50, 52, 54, 56, 58, 60, 62, 64, 66, 68, 70, 72, 74, 76, 78, 80, 82, 84, 86, 88, 90, 92, 94, 95, 108, 109, 110, 111, 112, 113, 114, 115, 116, 117, 118, 119, 120, 121, and 122.

The fusion protein can comprise an exosporium protein comprising an amino acid sequence having at least 90% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 95% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 98% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having at least 99% identity with SEQ ID NO: 60, 62, 64, 66, 68, 70, 76, 78, 80, 82, 84, 86, 88, 90, 92, 94 or 122.

The fusion protein can comprise an exosporium protein comprising an amino acid sequence having 100% identity with SEQ ID NO: 60, 62, 64, 66, 68, 70, 76, 78, 80, 82, 84, 86, 88, 90, 92, 94 or 122.

The targeting sequence, exosporium protein, or exosporium protein fragment of the fusion protein can comprise the amino acid sequence GXT at its carboxy terminus, wherein X is any amino acid.

The targeting sequence, exosporium protein, or exosporium protein fragment can comprise an alanine residue at the position of the targeting sequence that corresponds to amino acid 20 of SEQ ID NO: 1.

The targeting sequence, exosporium protein, or exosporium protein fragment can further comprise a methionine, serine, or threonine residue at the amino acid position immediately preceding the first amino acid of the targeting sequence, exosporium protein, or exosporium protein fragment or at the position of the targeting sequence that corresponds to amino acid 20 of SEQ ID NO: 1.

The protein or peptide of interest in the fusion protein described above can comprise a protein or peptide that protects an animal from a pathogen.

The protein or peptide of interest in the fusion protein described above can comprise a protein or peptide that protects an aquatic organism from a pathogen.

The protein or peptide of interest in the fusion protein described above can comprise a protein or peptide that has insecticidal activity against an insect vector of an animal pathogen or larvae of the insect vector.

The protein or peptide of interest in the fusion protein described above can comprise an antigen or an immunogen.

Fusion proteins are provided. In any of the fusion proteins, the targeting sequence, exosporium protein, or exosporium protein fragment can be any of the targeting sequences, exosporium proteins, or exosporium protein fragments described herein.

A fusion protein is provided. The fusion protein comprises a targeting sequence, exosporium protein, or exosporium protein fragment that targets the fusion protein to the exosporium of a recombinant *Bacillus cereus* family member and at least one protein or peptide of interest. The protein or peptide of interest can comprise an antibody, an antibody fragment, a histone, a cecropin, a penaeidin, a bactenecin, a callinectin, a myticin, a tachyplesin, a clavanin, amisgurin, a pleurocidin, a parasin, an apyrase, an alginate lyase, a dispersin B, a DNAse, an endochitinase, an exochitinase, a proteinase K, a secreted insecticidal (Sip) protein, a mosquitocidal toxin, a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, a Cyt1Aa protein, an AiiA, a *Bacillus subtilis* serine protease, or a combination of any thereof.

The DNAse can comprise DNAse I.

The endochitinase can comprise a chitinase C.

The exochitinase comprises a chitinase D.

The protein or peptide of interest can comprise an antibody, an antibody fragment, a histone, a cecropin, a penaeidin, a bactenecin, a callinectin, a myticin, a tachyplesin, a clavanin, amisgurin, a pleurocidin, a parasin, an apyrase, an alginate lyase, a dispersin B, a secreted insecticidal (Sip) protein, a mosquitocidal toxin, or a combination of any thereof.

For example, the protein or peptide of interest can comprise an apyrase.

Where the enzyme comprises an apyrase, the apyrase can comprise a *Solanum tuberosum* apyrase encoded by the Rrop1 gene. The amino acid sequence for this *Solanum tuberosum* apyrase is provided by SEQ ID NO: 204.

Alternatively, where the enzyme comprises an apyrase, the apyrase can comprise a *Bacillus subtilis* apyrase encoded by the YtkD gene. The amino acid sequence for this *Bacillus subtilis* apyrase is provided by SEQ ID NO: 205.

Where the protein or peptide of interest comprises an apyrase, the apyrase can comprise an amino acid having at least 70% sequence identity to SEQ ID NO: 204 or 205.

The apyrase can comprise an amino acid having at least 75% sequence identity to SEQ ID NO: 204 or 205.

The apyrase can comprise an amino acid having at least 80% sequence identity to SEQ ID NO: 204 or 205.

The apyrase can comprise an amino acid having at least 85% sequence identity to SEQ ID NO: 204 or 205.

The apyrase can comprise an amino acid having at least 90% sequence identity to SEQ ID NO: 204 or 205.

The apyrase can comprise an amino acid having at least 95% sequence identity to SEQ ID NO: 204 or 205.

The apyrase can comprise an amino acid having at least 98% sequence identity to SEQ ID NO: 204 or 205.

The apyrase can comprise an amino acid having at least 99% sequence identity to SEQ ID NO: 204 or 205.

The apyrase can comprise an amino acid having 100% sequence identity to SEQ ID NO: 204 or 205.

For example, the apyrase can comprise an amino acid having at least 70% sequence identity to SEQ ID NO: 205.

The apyrase can comprise an amino acid having at least 75% sequence identity to SEQ ID NO: 205.

The apyrase can comprise an amino acid having at least 80% sequence identity to SEQ ID NO: 205.

The apyrase can comprise an amino acid having at least 85% sequence identity to SEQ ID NO: 205.

The apyrase can comprise an amino acid having at least 90% sequence identity to SEQ ID NO: 205.

The apyrase can comprise an amino acid having at least 95% sequence identity to SEQ ID NO: 205.

The apyrase can comprise an amino acid having at least 98% sequence identity to SEQ ID NO: 205.

The apyrase can comprise an amino acid having at least 99% sequence identity to SEQ ID NO: 205.

The apyrase can comprise an amino acid having 100% sequence identity to SEQ ID NO: 205.

The protein or peptide of interest can comprise a dispersin B.

The protein or peptide of interest can comprise an endochitinase, an exochitinase, or a combination thereof.

For example, the endochitinase can comprise a *Bacillus thuringiensis* endochitinase having the amino acid sequence provided by SEQ ID NO: 206.

Where the protein or peptide of interest comprises an endochitinase, the endochitinase can comprise an amino acid sequence having at least 70% sequence identity to SEQ ID NO: 206.

The endochitinase can comprise an amino acid sequence having at least 75% sequence identity to SEQ ID NO: 206.

The endochitinase can comprise an amino acid sequence having at least 80% sequence identity to SEQ ID NO: 206.

The endochitinase can comprise an amino acid sequence having at least 85% sequence identity to SEQ ID NO: 206.

The endochitinase can comprise an amino acid sequence having at least 90% sequence identity to SEQ ID NO: 206.

The endochitinase can comprise an amino acid sequence having at least 95% sequence identity to SEQ ID NO: 206.

The endochitinase can comprise an amino acid sequence having at least 98% sequence identity to SEQ ID NO: 206.

The endochitinase can comprise an amino acid sequence having at least 99% sequence identity to SEQ ID NO: 206.

The endochitinase can comprise an amino acid sequence having 100% sequence identity to SEQ ID NO: 206.

The protein or peptide of interest can comprise an AiiA lactonase.

For example, the AiiA lactonase can comprise a *Bacillus thuringiensis* B184 AiiA or a *Bacillus pseudomycoides* B30 AiiA. An amino acid sequence for the *Bacillus thuringiensis* B184 AiiA is provided by SEQ ID NO: 207. An amino acid sequence for the *Bacillus pseudomycoides* B30 AiiA is provided by SEQ ID NO: 208.

Where the protein or peptide of interest comprises an AiiA lactonase, the AiiA lactonase can comprise an amino acid having at least 70% sequence identity to SEQ ID NO: 207 or 208.

The AiiA lactonase can comprise an amino acid having at least 75% sequence identity to SEQ ID NO: 207 or 208.

The AiiA lactonase can comprise an amino acid having at least 80% sequence identity to SEQ ID NO: 207 or 208.

The AiiA lactonase can comprise an amino acid having at least 85% sequence identity to SEQ ID NO: 207 or 208.

The AiiA lactonase can comprise an amino acid having at least 90% sequence identity to SEQ ID NO: 207 or 208.

The AiiA lactonase can comprise an amino acid having at least 95% sequence identity to SEQ ID NO: 207 or 208.

The AiiA lactonase can comprise an amino acid having at least 98% sequence identity to SEQ ID NO: 207 or 208.

The AiiA lactonase can comprise an amino acid having at least 99% sequence identity to SEQ ID NO: 207 or 208.

The AiiA lactonase can comprise an amino acid having 100% sequence identity to SEQ ID NO: 207 or 208.

The protein or peptide of interest can comprise a *Bacillus subtilis* serine protease. Illustrative amino acid sequences for *Bacillus subtilis* serine proteases are provided by SEQ ID NOs. 209 and 210.

Where the protein or peptide of interest comprises a *Bacillus subtilis* serine protease, the serine protease can comprise an amino acid sequence having at least 80% sequence identity to SEQ ID NO: 209.

The serine protease can comprise an amino acid sequence having at least 85% sequence identity to SEQ ID NO: 209.

The serine protease can comprise an amino acid sequence having at least 90% sequence identity to SEQ ID NO: 209.

The serine protease can comprise an amino acid sequence having at least 95% sequence identity to SEQ ID NO: 209.

The serine protease can comprise an amino acid sequence having at least 98% sequence identity to SEQ ID NO: 209.

The serine protease can comprise an amino acid sequence having at least 99% sequence identity to SEQ ID NO: 209.

The serine protease can comprise an amino acid sequence having 100% sequence identity to SEQ ID NO: 209.

Where the protein or peptide of interest comprises a *Bacillus subtilis* serine protease, the *Bacillus subtilis* serine protease can comprise an amino acid sequence having at least 80% sequence identity to SEQ ID NO: 210.

The serine protease can comprise an amino acid sequence having at least 85% sequence identity to SEQ ID NO: 210.

The serine protease can comprise an amino acid sequence having at least 90% sequence identity to SEQ ID NO: 210.

The serine protease can comprise an amino acid sequence having at least 95% sequence identity to SEQ ID NO: 210.

The serine protease can comprise an amino acid sequence having at least 98% sequence identity to SEQ ID NO: 210.

The serine protease can comprise an amino acid sequence having at least 99% sequence identity to SEQ ID NO: 210.

The serine protease can comprise an amino acid sequence having 100% sequence identity to SEQ ID NO: 210.

The protein or peptide of interest can comprise a mosquitocidal toxin.

For example, the mosquitocidal toxin can comprise an Mtx-like mosquitocidal toxin or a Bin-like mosquitocidal toxin.

The Mtx-like mosquitocidal toxin can comprise Mtx1.

For example, the Mtx1 can comprise a *Bacillus sphaericus* Mtx1. An amino acid sequence for a *Bacillus sphaericus* Mtx1 is provided by SEQ ID NO: 211.

Where the protein or peptide of interest comprises Mtx1, the Mtx1 can comprise an amino acid sequence having at least 70% identity to SEQ ID NO: 211.

The Mtx1 can comprise an amino acid sequence having at least 75% identity to SEQ ID NO: 211.

The Mtx1 can comprise an amino acid sequence having at least 80% identity to SEQ ID NO: 211.

The Mtx1 can comprise an amino acid sequence having at least 85% identity to SEQ ID NO: 211.

The Mtx1 can comprise an amino acid sequence having at least 90% identity to SEQ ID NO: 211.

The Mtx1 can comprise an amino acid sequence having at least 95% identity to SEQ ID NO: 211.

The Mtx1 can comprise an amino acid sequence having at least 98% identity to SEQ ID NO: 211.

The Mtx1 can comprise an amino acid sequence having at least 99% identity to SEQ ID NO: 211.

The Mtx1 can comprise an amino acid sequence having 100% identity to SEQ ID NO: 211.

Another fusion protein is provided. The fusion protein comprises a targeting sequence, exosporium protein, or exosporium protein fragment that targets the fusion protein to the exosporium of a recombinant *Bacillus cereus* family member and a LfcinB. The LfcinB comprises an amino acid sequence having at least 70% sequence identity to SEQ ID NO: 212.

For example, the LfcinB can comprise an amino acid sequence having at least 75% sequence identity to SEQ ID NO: 212.

The LfcinB can comprise an amino acid sequence having at least 80% sequence identity to SEQ ID NO: 212.

The LfcinB can comprise an amino acid sequence having at least 85% sequence identity to SEQ ID NO: 212.

The LfcinB can comprise an amino acid sequence having at least 90% sequence identity to SEQ ID NO: 212.

The LfcinB can comprise an amino acid sequence having at least 95% sequence identity to SEQ ID NO: 212.

The LfcinB can comprise an amino acid sequence having at least 98% sequence identity to SEQ ID NO: 212.

The LfcinB can comprise an amino acid sequence having at least 99% sequence identity to SEQ ID NO: 212.

The LfcinB can comprise an amino acid sequence having 100% sequence identity to SEQ ID NO: 212.

Yet another fusion protein is provided. The fusion protein comprises a targeting sequence, exosporium protein, or exosporium protein fragment that targets the fusion protein to the exosporium of a recombinant *Bacillus cereus* family member and a LysM. The LysM comprises an amino acid sequence having at least 70% identity to SEQ ID NO: 213.

For example, the LysM can comprise an amino acid sequence having at least 75% sequence identity to SEQ ID NO: 213.

The LysM can comprise an amino acid sequence having at least 80% sequence identity to SEQ ID NO: 213.

The LysM can comprise an amino acid sequence having at least 85% sequence identity to SEQ ID NO: 213.

The LysM can comprise an amino acid sequence having at least 90% sequence identity to SEQ ID NO: 213.

The LysM can comprise an amino acid sequence having at least 95% sequence identity to SEQ ID NO: 213.

The LysM can comprise an amino acid sequence having at least 98% sequence identity to SEQ ID NO: 213.

The LysM can comprise an amino acid sequence having at least 99% sequence identity to SEQ ID NO: 213.

The LysM can comprise an amino acid sequence having 100% sequence identity to SEQ ID NO: 213.

Another fusion protein is provided. The fusion protein comprises a targeting sequence, exosporium protein, or exosporium protein fragment that targets the fusion protein to the exosporium of a recombinant *Bacillus cereus* family member and a β-1,3-glucanase. The β-1,3-glucanase comprises an amino acid sequence having at least 70% identity to SEQ ID NO: 214 or 216.

For example, the β-1,3-glucanase can comprise an amino acid sequence having at least 75% sequence identity to SEQ ID NO: 214 or 216.

The β-1,3-glucanase can comprise an amino acid sequence having at least 80% sequence identity to SEQ ID NO: 214 or 216.

The β-1,3-glucanase can comprise an amino acid sequence having at least 85% sequence identity to SEQ ID NO: 214 or 216.

The β-1,3-glucanase can comprise an amino acid sequence having at least 90% sequence identity to SEQ ID NO: 214 or 216.

The β-1,3-glucanase can comprise an amino acid sequence having at least 95% sequence identity to SEQ ID NO: 214 or 216.

The β-1,3-glucanase can comprise an amino acid sequence having at least 98% sequence identity to SEQ ID NO: 214 or 216.

The β-1,3-glucanase can comprise an amino acid sequence having at least 99% sequence identity to SEQ ID NO: 214 or 216.

The β-1,3-glucanase can comprise an amino acid sequence having 100% sequence identity to SEQ ID NO: 214 or 216.

A further fusion protein is provided. The fusion protein comprises a targeting sequence, exosporium protein, or exosporium protein fragment that targets the fusion protein to the exosporium of a recombinant *Bacillus cereus* family member and a Cry21A protein. The Cry21A protein comprises an amino acid sequence having at least 70% sequence identity to SEQ ID NO: 215.

For example, the Cry21A protein can comprise an amino acid sequence having at least 75% sequence identity to SEQ ID NO: 215.

The Cry21A protein can comprise an amino acid sequence having at least 80% sequence identity to SEQ ID NO: 215.

The Cry21A protein can comprise an amino acid sequence having at least 85% sequence identity to SEQ ID NO: 215.

The Cry21A protein can comprise an amino acid sequence having at least 90% sequence identity to SEQ ID NO: 215.

The Cry21A protein can comprise an amino acid sequence having at least 95% sequence identity to SEQ ID NO: 215.

The Cry21A protein can comprise an amino acid sequence having at least 98% sequence identity to SEQ ID NO: 215.

The Cry21A protein can comprise an amino acid sequence having at least 99% sequence identity to SEQ ID NO: 215.

The Cry21A protein can comprise an amino acid sequence having 100% sequence identity to SEQ ID NO: 215.

C. Methods for Making the Fusion Proteins

Any of the fusion proteins described herein can be made using standard cloning and molecular biology methods known in the art. For example, a gene encoding a protein or peptide of interest (e.g., a gene encoding a protein or peptide that protects an animal from a pathogen) can be amplified by polymerase chain reaction (PCR) and ligated to DNA coding for any of the above-described targeting sequences, exosporium proteins, or exosporium protein fragments, to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. Alternatively, DNA coding for the fusion protein can be integrated into the chromosomal DNA of the *B. cereus* family member or spore-forming bacterium host.

D. Tags, Markers, and Linkers that can be Included in the Fusion Proteins

Any of the fusion proteins described herein can also comprise additional polypeptide sequences that are not part of the targeting sequence, exosporium protein, exosporium protein fragment, or the protein or peptide of interest. For example, the fusion protein can include tags or markers to facilitate purification or visualization of the fusion protein (e.g., a polyhistidine tag or a fluorescent protein such as GFP or YFP) or visualization of recombinant *Bacillus cereus* family member spores expressing the fusion protein.

Expression of fusion proteins on the exosporium of a *Bacillus cereus* family member using the targeting sequences, exosporium proteins, and exosporium protein fragments described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, spore coat protein, and the protein or peptide of interest.

Thus, any of the fusion proteins described herein can comprise an amino acid linker between the targeting sequence, the exosporium protein, or the exosporium protein fragment and the protein or peptide of interest.

The linker can comprise a polyalanine linker or a polyglycine linker. A linker comprising a mixture of both alanine and glycine residues can also be used.

For example, in a fusion protein where the targeting sequence comprises SEQ ID NO: 1, a fusion protein can have one of the following structures:

No linker: SEQ ID NO: 1-POI

Alanine Linker: SEQ ID NO: 1-$A_n$-POI

Glycine Linker: SEQ ID NO: 1-$G_n$-POI

Mixed Alanine and Glycine Linker: SEQ ID NO: 1-$(A/G)_n$-POI where $A_n$, $G_n$, and $(A/G)_n$ are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "POI" represents the protein or peptide of interest.

Alternatively or in addition, the linker can comprise a protease recognition site. Inclusion of a protease recognition site allows for targeted removal, upon exposure to a protease that recognizes the protease recognition site, of the protein or peptide of interest.

E. Recombinant *Bacillus cereus* Family Members Hosts for Expression of the Fusion Proteins A recombinant *Bacillus cereus* family member that expresses a fusion protein is provided. The fusion protein can be any of the fusion proteins described above in Section I.B.

Exosporium fragments derived from spores of the recombinant *Bacillus cereus* family members are also provided. The exosporium fragments can comprise any of the fusion proteins described above in Section I.B. Mutations that allow for collection of exosporium fragments and methods for preparation of exosporium fragments are described below in Section III.

In addition, the compositions, methods, and products of the present invention involve the use of spores of recombinant *Bacillus cereus* family members that express a fusion protein, or exosporium fragments derived from such spores that comprise a fusion protein. The fusion protein can be any of the fusion proteins described herein.

Any *Bacillus cereus* family member can serve as a host for expression of fusion proteins comprising a targeting sequence, an exosporium protein, or an exosporium protein fragment that targets the fusion protein to the exosporium of the *Bacillus cereus* family member.

The recombinant *Bacillus cereus* family member can comprise any *Bacillus* species that is capable of producing an exosporium. For example, the recombinant *Bacillus cereus* family member can comprise *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis*, or a combination thereof. In particular, the recombinant *Bacillus cereus* family member can comprise *Bacillus thuringiensis* or *Bacillus mycoides.*

The recombinant *Bacillus cereus* family member can coexpress two or more of any of the fusion proteins discussed above. For example, the recombinant *Bacillus cereus* family member can coexpress two or more fusion proteins comprising proteins or peptides that protect an animal from a pathogen. The two or more proteins that protect an animal from a pathogen can protect the animal from the same pathogen. Alternatively, the two or more proteins that protect an animal from a pathogen can protect the animal from two different pathogens. For example, a recombinant *Bacillus cereus* family member could express a first fusion protein comprising an antibacterial protein or peptide and a second fusion protein comprising an antifungal protein or peptide.

To generate a recombinant *Bacillus cereus* family member expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant *Bacillus cereus* family member can then exposed to conditions which will induce sporulation. Suitable conditions for inducing sporulation are known in the art. For example, the recombinant *Bacillus cereus* family member can be plated onto agar plates, and incubated at a temperature of about 30° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family member spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Many *Bacillus cereus* family member strains have inherent attributes that would be of benefit in the methods described herein. For example, some strains have insecticidal, fungicidal, nematicidal, or bacteriocidal compounds. Thus, the recombinant *Bacillus cereus* family member that expresses the fusion protein can comprise a strain of bacteria that produces an insecticidal toxin (e.g., a Cry toxin), produces a fungicidal compound (e.g., a β-1,3-glucanase, a chitosanase, a lyticase, or a combination thereof), produces a nematocidal compound (e.g., a Cry toxin), or produces a bacteriocidal compound, is resistant to one or more antibiotics, or comprises one or more freely replicating plasmids.

The recombinant *Bacillus cereus* family member can comprise an inactivating mutation in its BclA gene, its CotE gene, or its CotO gene (e.g., a knock-out of the BclA gene, CotE gene, or CotO gene). For example, the recombinant *Bacillus cereus* family member can comprise an inactivating mutation in its BclA gene (e.g., a knock-out of the BclA gene). It has been found that expression of fusion proteins in a recombinant *Bacillus cereus* family member having such a mutation results in increased expression levels of the fusion protein.

F. Proteins and Peptides of Interest

Proteins or peptides of interest that can be included in the fusion proteins are described further hereinbelow in connection with each of the methods, compositions, and related products. The protein or peptide of interest can comprise: (a) a protein or peptide that protects an animal from a pathogen; (b) a protein or peptide that protects an aquatic organism from a pathogen; (c) a protein or peptide that has insecticidal activity against an insect vector of an animal pathogen or larvae of the insect vector; or (d) or an antigen or immunogen.

II. Promoters for Expression of Fusion Proteins in Recombinant *Bacillus cereus* Family Members The DNA encoding the fusion proteins used in the recombinant *Bacillus cereus* family members, compositions, methods, adhesive patches, wound dressings, insert trays, hoof bandages, feed, feed additives, and insect foggers described herein is suitably under the control of a sporulation promoter which will cause expression of the fusion protein on the exosporium of a *B. cereus* family member endospore (e.g., a native bclA promoter from a *B. cereus* family member).

Thus, any of the fusion proteins described above in Section I.B can be expressed in the recombinant *Bacillus cereus* family member under the control of a sporulation promoter that is native to the targeting sequence, exosporium protein, or exosporium protein fragment of the fusion protein, or a portion of such a promoter.

Any of the fusion proteins s can be expressed under the control of a high-expression sporulation promoter.

The high-expression sporulation promoter can comprise a sigma-K sporulation-specific polymerase promoter sequence.

For ease of reference, exemplary nucleotide sequences for promoters that can be used to express any of the fusion proteins in a recombinant *Bacillus cereus* family member are provided in Table 2 below, together with their SEQ ID NOs. Table 2 also provides exemplary minimal promoter sequences for many of the promoters. In Table 2, sigma-K sporulation-specific polymerase promoter sequences in the promoters are indicated by bold and underlined text. Several of the sequences have multiple sigma K sequences that overlap with one another. The overlaps are indicated by double underlining in the table. The promoter sequences are immediately upstream of the start codon for each of the indicated genes. In other words, in the sequences shown in Table 2 below, the last nucleotide of the promoter sequence immediately precedes the first nucleotide of the start codon for the coding region of the gene encoding the indicated protein.

TABLE 2

Promoter Sequences for Expression of Fusion Proteins in Recombinant *Bacillus cereus* family members

| Promoter (SEQ ID NO) | Promoter Sequence |
|---|---|
| ExsY promoter (*B. cereus* F837/76) (SEQ ID NO: 37) | TTTCTTAATCCTTTACCCTTTACTTTTGTAAAAGTTGATACACTT<br>CCATCCGGCTCTGTAATTTCTAATTCATCAATAAATGGTCTTCG<br>CAAAAAGCCTGTAATTTTATCATAAACAATTAAACGAGTGAGC<br>CTAAAAGCAGCTAACGCGAAAATAAAAAATAAAAGCCAGCTT<br>GTAAACAGCATAATTCCACCTTCCCTTATCCTCTTTCGCCTATT<br>TAAAAAAAGGTCTTGAGATTGTGACCAAATCTCCTCAACTCC**A**<br>**ATATCTTA**TTAATGTAAATACAAACAAGAAGATAAGGA |
| ExsY minimal promoter (*B. cereus* F837/76) (SEQ ID NO: 38) | ACCAAATCTCCTCAACTCC**AATATCTTA**TTAATGTAAATACAA<br>ACAAGAAGATAAGGA |
| ExsFA/BxpB promoter (*B. anthracis* Sterne) (SEQ ID NO: 39) | ACCACCTACCGACGATCCAATCTGTACATTCCTAGCTGTACCA<br>AATGCAAGATTAATATCGACTAACACTTGTCTTACTGTTGATTT<br>AAGTTGCTTCTGTGCGATTCAATGCTTGCGTGATGTTACGATTT<br>AAAACTAAATAATGAGCTAAG**CATGGATTG**GGTGGCAGAATT<br>ATCTGCCACCCAATCCATGCTTAACGAGTATTATTATGTAAATT |

TABLE 2-continued

Promoter Sequences for Expression of Fusion Proteins in Recombinant *Bacillus cereus* family members

| Promoter (SEQ ID NO) | Promoter Sequence |
| --- | --- |
| | TCTTAAAATTGGGAACTTGTCTAGAACATAGAACCTGTCCTTTT<br>**CATTAACTG**AAAGTAGAAACAGATAAAGGAGTGAAAAAC |
| ExsFA/BxpB minimal promoter (*B. anthracis* Sterne) (SEQ ID NO: 40) | ACATAGAACCTGTCCTTTT**CATTAACTG**AAAGTAGAAACAGAT<br>AAAGGAGTGAAAAAC |
| CotY/CotZ promoter (*B. anthracis* Sterne) (SEQ ID NO: 41) | TAGAAGAAGAACGCCGACTACTTTATGTCGCAATTACACGGGC<br>GAAAGAAGAACTTTACATTTCCTCTCCGCAATTTTTTAGAGGA<br>AAAAAATTAGATATATCTCGTTTTTTATACACTGTGCGAAAAG<br>ATTTACCTGAAAAGACATCCACTAAATAAGGATGTCTTTTTTTA<br>TATTGTATTATGTACATCCCTACTATATAAATTCCCTGCTTTTAT<br>CGTAAGAATTAACGTAATATCAACCATATCCCGTT**CATATTGT**<br>**A**GTAGTGTATGTCAGAACTCACGAGAAGGAGTGAACATA |
| CotY/CotZ minimal promoter (*B. anthracis* Sterne) (SEQ ID NO: 42) | TCAACCATATCCCGTT**CATATTGTA**GTAGTGTATGTCAGAACT<br>CACGAGAAGGAGTGAACATA |
| CotO promoter (*B. cereus*) (SEQ ID NO: 123) | TAACTCAATCTTAAGAGAAATTGAGGAGCGCGCACCACTTCGT<br>CGTACAACAACGCAAGAAGAAGTTGGGGATACAGCAGTATTCT<br>TATTCAGTGATTTAGCACGCGGCGTAACAGGAGAAAACATTCA<br>CGTTGATTCAGGGTAT**CATATCTTA**GGATA**AATATAATA**TTAA<br>TTTTAAAGGACAATCTCTACATGTTGAGATTGTCCTTTTTATTT<br>GTTCTTAGAAAGAACGATTTTTAACGAAAGTTCTTACCACGTTA<br>TGAATATAAGTATAATAGTACACGATTTATTCAGCTACGT |
| CotO minimal promoter (*B. cereus*) (SEQ ID NO: 124) | ACGTTGATTCAGGGTAT**CATATCTTA**GGATA**AATATAATA**TTA<br>ATTTTAAAGGACAATCTCTACATGTTGAGATTGTCCTTTTTATT<br>TGTTCTTAGAAAGAACGATTTTTAACGAAAGTTCTTACCACGTT<br>ATGAATATAAGTATAATAGTACACGATTTATTCAGCTACGT |
| ExsFB promoter (*B. cereus* F837/76) (SEQ ID NO: 125) | CATAAAAATCTACTTTTCTTGTCAAAGAGTATGCTTATATGCGT<br>GCTCTTTTTATTTGGTTTTCTTTCATTTCTAAATAACATTTTCAA<br>CTCTATTCATACTATTCTTTCAACTTTAGGTTACAAACTATTTCT<br>GTAAGCGTAGTGTTTCTTTTGTACTATAGGCAGTTAGTTTTATC<br>CATAACAGTACACCTCTGCACTATTCACTATAAATTTT**CATATA**<br>**TTA**TATTGTGCTTGTCCAAAACATGTGGTTATTACTCACGCGAT<br>CTAAATGAAAGAAAGGAGTGAAAAT |
| ExsFB minimal promoter (*B. cereus* F837/76) (SEQ ID NO: 126) | ACTATTCACTATAAATTTT**CATATATTA**TATTGTGCTTGTCCAA<br>AACATGTGGTTATTACTCACGCGATCTAAATGAAAGAAAGGAG<br>TGAAAAT |
| InhA1 promoter (*B. thuringiensis* serovar kurstaki str. HD-1) (SEQ ID NO: 127) | AATACATGATAATGAAATCCGATTTTGTGTTTTATATAGTGAAT<br>TATCAAATATTGTGTAGATGAAACAAAGATAAAATCCCCATTA<br>AACTCCCTCTATGGAAATTATAAATTGTTCGATAAAAACTTTCA<br>ATATTTTCAGAAAACATTGTTGAATTGTGATATATTCGTATGCT<br>AACTATGAAATTTTTACAAATATATTAAAAACATTA**CATAATA**<br>**TG**ACTAAATATTGAAAAAATATTGAATTTTTAATAAAATTTAA<br>TTTGTAATA**CATATTATT**TATTAGGGGAGGAAATAAGGG |
| InhA1 minimal promoter (*B. thuringiensis* serovar kurstaki str. HD-1) (SEQ ID NO: 128) | AAAATTTAATTTGTAATA**CATATTATT**TATTAGGGGAGGAAAT<br>AAGGG |
| InhA2 promoter (*B. mycoides* strain 219298) (SEQ ID NO: 129) | AATTGTGCATATTGTCTTTTAAATTTTCTATCTAAGTTATTTAAT<br>ATATAATAAATAACTCTTTTTTGTGAGTTTTTTTGATACGAGGT<br>AAATAATCAGTACAGGGTCTGACCAGAGGACTGGAGGGCATG<br>ATTCTATAAGGGAATATTTACTATTCCATGATTATAGAACTATG<br>TCTTTTTTATTGTATATAGAAGGGGGGATAGGTC**TATATTATA**<br>GAACTTATATATATTGTGCATTC**CATATTATC**AATTATCTAAAT<br>TTTAAGTCTTGTTACAATTAATAAGGGAGGAAATAGTA |
| InhA2 minimal promoter (*B. mycoides* strain 219298) (SEQ ID NO: 130) | ACTTATATATATTGTGCATTC**CATATTATC**AATTATCTAAATTT<br>TAAGTCTTGTTACAATTAATAAGGGAGGAAATAGTA |

TABLE 2-continued

Promoter Sequences for Expression of Fusion Proteins in Recombinant *Bacillus cereus* family members

| Promoter (SEQ ID NO) | Promoter Sequence |
|---|---|
| ExsJ promoter (*B. thuringiensis* serovar kurstaki) (SEQ ID NO: 131) | AATGACGTTTTCAAGTTTGATTATCATTCATGTTTCCTATTTTAA GAGAAACATATAACTCAACTACTTTTTTCAATGG**CATCTTTTA** TAGTACTTAGAATAGGAAAACACTCAACTATAAGAAAAGTAA GGAGGAAATAA |
| ExsJ minimal promoter (*B. thuringiensis* serovar kurstaki) (SEQ ID NO: 132) | ACTACTTTTTTCAATGG**CATCTTTTA**TAGTACTTAGAATAGGA AAACACTCAACTATAAGAAAAGTAAGGAGGAAATAA |
| ExsH promoter (*B. cereus* F837/76) (SEQ ID NO: 133) | ATATGCTAATGCTTAGTTTTTATACTCAAGTTAAAATGTGCTTT TGGACCTAAGAGATAAACGTGGAAA**AATAAAATA**AACTCTTA AGTTTAGGTGTTTAATCTAAGCAGTCAATTATTAAAAA**CATAT AATT**AATATGTGAGTCATGAA**CATAATTAA**ATAATGTTTTCAA GTTTAATTATCGTTCATGTTTCCTATTTTAAGCAGAACAAATAA CTCAATTACTTTTTTCGATTGGATCTTTTTTAACTCTTATAATAG GAAAACACTCAACTATAAAAATAAGTAAGGAGGAAATAA |
| ExsH minimal promoter (*B. cereus* F837/76) (SEQ ID NO: 134) | AATATGTGAGTCATGAA**CATAATTA**AATAATGTTTTCAAGTTT AATTATCGTTCATGTTTCCTATTTTAAGCAGAACAAATAACTCA ATTACTTTTTTCGATTGGATCTTTTTTAACTCTTATAATAGGAA AACACTCAACTATAAAAATAAGTAAGGAGGAAATAA |
| YjcA promoter (*B. thuringiensis* serovar kurstaki str. HD73) (SEQ ID NO: 135) | TATAAAATAAAAGGGCGTGTATTTGCTACTGATGCAGTATTGT GTGCGCCTAAAAATGGAATTTCACAACCAGATCCACATGTTGT TGTAGAACAATCTTGTAATTCATTGATGAATTTTACAACGTCAA CTACACAATGAGAAGAGCCATGGTGTTTATTTTCGTTACAACTC ATTAATGTCACTCCTTATCTTCTTGTTTGTATTTACATT**AATAA GATA**TTGGAGTTGAGGAGATTTGGTCACAATCTCAAGACCTTT TTTTTAAATAGGCGAAAGAGGATAAGGGAAGGTGGAATT |
| YjcA minimal promoter (*B. thuringiensis* serovar kurstaki str. HD73) (SEQ ID NO: 136) | TCTTGTTTGTATTTACATT**AATAAGATA**TTGGAGTTGAGGAGAT TTGGTCACAATCTCAAGACCTTTTTTTTAAATAGGCGAAAGAG GATAAGGGAAGGTGGAATT |
| YjcB promoter (*B. thuringiensis* serovar kurstaki str. HD73) (SEQ ID NO: 137) | ATCAACTTTTACAAAAGTAAAGGGTAAAGGATTAAGAAAGTG GATTGGCGAATTATTAAGCTGTTATTGGTGTACAGGTGTATGG GTTAGTGCTTTTTTATTAGTTTTATATAATTGGATTCCGATCGTT GCAGAGCCGTTACTTGCATTATTAGCTATTGCAGGAGCAGCAG CAATCATTGAAACGATTACAG**GATATTTTA**TGGGAG**AATAAT ATA**TTTTCATAATACGAGAAAAAGCGGAGTTTAAAAGAATGAG GGAACGGAAATAAAGAGTTGTT**CATATAGTA**AATAGACAGAA |
| YjcB minimal promoter (*B. thuringiensis* serovar kurstaki str. HD73) (SEQ ID NO: 138) | ACGGAAATAAAGAGTTGTT**CATATAGTA**AATAGACAGAA |
| BclC promoter (*B. anthracis* Sterne) (SEQ ID NO: 139) | TGAAGTATCTAGAGCTAATTTACGCAAAGGAATCTCAGGACAA CACTTTCGCAACACC**TATATTTTA**AATTTAATAAAAAAAGAGA CTCCGGAGTCAGAAATTATAAAGCTAGCTGGGTTCAAATCAAA AATTTCACTAAAACGATATTATCAATACGCAGAAAATGGAAAA AACGCCTTATCATAAGGCGTTTTTTCCATTTTTTCTTCAAACAA ACGATTTTACTATGACCATTTAACTAATTTTTG**CATCTACTA**TG ATGAGTTTCATTCACATTCTCATTAGAAAGGAGAGATTTA |
| BclC minimal promoter (*B. anthracis* Sterne) (SEQ ID NO: 140) | ACCATTTAACTAATTTTTG**CATCTACTA**TGATGAGTTTCATTCA CATTCTCATTAGAAAGGAGAGATTTA |
| AcpC promoter (*B. cereus* F837/76) (SEQ ID NO: 141) | GACTATGTTTATTCAG**GATAAAATA**TAGCACTACACTCTCTCCT CTTATTATGTAGCATCTCTCTAATCCATCATTTGTTTCATTTAGT TAAAATTGTAAATAAAATCACATGATTTGTCAATTATAATTGTC ATTTCGACAATTAAACTTGTCAAAATAATTCTCATCATTTTTTC TCATCTTTCTAATATAGGACATACTACTATATATACAAAAGAC AATATGCAAATGTT**CATACAAAA**AATATTATTTTTCGA**TATAT AATA**TTAACTGATTTTCTAACATCAAGGAGGGTACAT |
| AcpC minimal promoter (*B. cereus* F837/76) (SEQ ID NO: 142) | AGACAATATGCAAATGTT**CATACAAAA**AATATTATTTTTCGA**T ATATAATA**TTAACTGATTTTCTAACATCAAGGAGGGTACAT |

TABLE 2-continued

Promoter Sequences for Expression of Fusion Proteins in Recombinant *Bacillus cereus* family members

| Promoter (SEQ ID NO) | Promoter Sequence |
| --- | --- |
| InhA3 promoter (*B. thuringiensis* serovar kurstaki str. HD73) (SEQ ID NO: 143) | ATAGTGAGTAATATGGTAATC**CATAGATTAAATAGTATA**GAA<br>AATATTTAATTCTTATTTTTATTAAAAAAGCATGAATCCCAGAT<br>TTACTGGGTTTTGATTGTAACTAAGAA**CATATAAAA**GTTCACT<br>GTTATTTATAGGAGAGTCTGTTTGTTTT**TATATCTTA**TGTATTT<br>CACCCTG**CATAAAAAA**ATATTTCTCAACATTTTATTTGTTGAAA<br>AATATTGAATATTCGTATTATAACGAATATTATGTTGTTATCGG<br>CAAAAAACGATAATTTGCAGACACTGGGGAGGAAATACA |
| InhA3 minimal promoter (**B**. *thuringiensis* serovar kurstaki str. HD73) (SEQ ID NO: 144) | TCTTATGTATTTCACCCTG**CATAAAAAA**ATATTTCTCAACATTT<br>TATTTGTTGAAAAATATTGAATATTCGTATTATAACGAATATTA<br>TGTTGTTATCGGCAAAAAACGATAATTTGCAGACACTGGGGAG<br>GAAATACA |
| Alanine racemase 1 promoter (*B. cereus* F837/76) (SEQ ID NO: 145) | CTTCGTCAGCAATAAGTGTGAGCGGAGAATTGGTTGATCTTGG<br>CTTTACAATTGGAGCATTGACGAAAGACTCTTTAACGTGGTCG<br>**CATAACGGA**GTAGAATATATGCTCGTGTCTAAAGGTTTAGAGC<br>CGAAGGAGCTATTAATGGTTGCTCGTTCAGTTACAGAGAAGCA<br>AGTGAAGTAAACTTCTTAGACGTGGTGATATATGTGCACCACG<br>TCTTTTCTTAGTTTGAAGGGTGGATTT**CATAAAAGA**AG**CATAT**<br>**AAAA**GAATAAGCTTCG**CATATCGTG**TATAAGGAAGTGTATTT |
| Alanine racemase 1 minimal promoter (*B. cereus* F837/76) (SEQ ID NO: 146) | ATAAAAGAATAAGCTTCG**CATATCGTG**TATAAGGAAGTGTAT<br>TT |
| Alanine racemase 2 promoter (*B. thuringiensis* serovar kurstaki str. HD73) (SEQ ID NO: 147) | CATTTCAAATAATGAACGCTTCGATTGAATCGGAGCTATTTTCA<br>AATCAATTTCAGTATATTGATCCAGCATTTGAATAGAAGTATC<br>AACAGCAACTTTAAGTTGATGCAATGCAGATTGTACAAACATT<br>GTAATTCTCCTCTTCTCCGTA**TATAATA**GTTTCTTGAGGGTATT<br>ATATCATGCTCAAAATTCCGAAAATTCTAGTAGTTTGACTAG**C**<br>**ATATTGAA**AAGTAT**TATATTGTA**AAAGGT**CATATGAAA**CGTG<br>AAATAGAATGGAATGCAATTATTGAGTTAGGAGTTAGACCA |
| Alanine racemase 2 minimal promoter (*B. thuringiensis* serovar kurstaki str. HD73) (SEQ ID NO: 148) | T**TATATTGTA**AAAGGT**CATATGAAA**CGTGAAATAGAATGGAA<br>TGCAATTATTGAGTTAGGAGTTAGACCA |
| BclA promoter (*B. cereus* F837/76) (SEQ ID NO: 149) | ATCGATGGAACCTGTATCAACCACTATAATTTCATCCACAATTT<br>TTTCAACTGAGTCTAAACAACGGGCTATTGTCTTCTCCTCATCT<br>CGAACAAT**CATACATAAACTA**ATTGTAATTCCTTGCTTGTTCA<br>ACATAATCACCCTCTTCCAAATCAAT**CATATGTTA**TA**CATATA**<br>**CTA**AACTTTCCATTTTTTTAAATTGTTCAAGTAGTTTAAGATTT<br>CTTTTCAATAATTCAAATGTCCGTGTCATTTTCTTTCGGTTTTG**C**<br>**ATCTACTA**TATAATGAACGCTTTATGGAGGTGAATTT |
| BclA minimal promoter (*B. cereus* F837/76) (SEQ ID NO: 150) | AATCAAT**CATATGTTA**TA**CATATACTA**AACTTTCCATTTTTTT<br>AAATTGTTCAAGTAGTTTAAGATTTCTTTTCAATAATTCAAATG<br>TCCGTGTCATTTTCTTTCGGTTTTG**CATCTACTA**TATAATGAAC<br>GCTTTATGGAGGTGAATTT |
| BclB promoter (*B. thuringiensis* serovar konkukian str. 97-27) (SEQ ID NO: 151) | GACCTGTAAGTCTGTAGGGAAGAATAATTTCAAGAGCCAGTGA<br>TAATAGATTTTTTTGTTTTTTCATTCTTATCTTGAATATAAATCA<br>CCT**CATCTTTTA**ATTAGAACGTAACCAATTTAGTATTTTGAAA<br>TAGAGCTAT**CATTTTATA**ATATGAATACTACTAGTTATAGAAA<br>CGGCAAAAAGTTTAATATATGTAAAAATCATTTGGATATGAAA<br>AAAGTAGC**CATAGATTT**TTTCGAAATGATAAATGTTTTATTTT<br>GTTAATTAGGAAACAAAAAATGTGGAATGAGGGGGATTTAA |
| BclB minimal promoter (*B. thuringiensis* serovar konkukian str. 97-27) (SEQ ID NO: 152) | ATATGAAAAAAGTAGC**CATAGATTT**TTTCGAAATGATAAATGT<br>TTTATTTTGTTAATTAGGAAACAAAAAATGTGGAATGAGGGGGA<br>TTTAA |
| BxpA promoter (*B. anthracis* str. Sterne) (SEQ ID NO: 153) | TTTT**CATCTGCTA**CATCGTGAAGTAATGCTGCCATTTCAATTAT<br>AAAACGATTTCCTCCTTCTTGCTCGGATAAAGAAATCGCCAGTT<br>TATGTACACGCTC**AATATGATA**CCAATCATGCCCACTGGCATC<br>TTTTTCTAAAATATGTTTTACAAAAGTAATTGTTTTTTCTATCTT<br>TTCTTGTTTTGTCATTTTTATCTTCACCCAGTTACTTATTGTAACA<br>CGCCCGCATTTTTT**CATCACATATTTTC**TTGTCCGCCC**CATACA**<br>**CTA**GGTGGTAGGCATCATCATGAAGGAGGAATAGAT |

TABLE 2-continued

Promoter Sequences for Expression of Fusion Proteins in Recombinant *Bacillus cereus* family members

| Promoter (SEQ ID NO) | Promoter Sequence |
|---|---|
| BxpA minimal promoter (*B. anthracis* str. Sterne) (SEQ ID NO: 154) | **ACATATTTTC**TTGTCCGCC**CATACACTA**GGTGGTAGGCATCAT<br>CATGAAGGAGGAATAGAT |
| BclE promoter (*B. anthracis* ΔSterne) (SEQ ID NO: 155) | GGTGACGACAA**CATATACAA**GAGGCACTCCTGCTGGTACTGTA<br>ACAGGAACAAATATGGGGCAAAGTGTAAATA**CATCGGGTA**TA<br>GCACAAGCTGTCCCGAATACA**GATAATATG**GATTCAACGGCG<br>GGACTCCCTTAAGAAATTAGGGGAGTCTTTATTTGGAAAAAGA<br>GCTTATGTTACATAAAAACAGGAGTAATTGTTTTAAAAGTAGT<br>ATTGGTGACGTTGTTAGAAAATACAATTTAAGTAGAAGGTGCG<br>TTTTTATATGA**AATATATTT**TATAGCTGTACTTTACCTTTCAAG |
| BclE minimal promoter (*B. anthracis* ΔSterne) (SEQ ID NO: 156) | ACAAGCTGTCCCGAATACA**GATAATATG**GATTCAACGGCGGG<br>ACTCCCTTAAGAAATTAGGGGAGTCTTTATTTGGAAAAAGAGC<br>TTATGTTACATAAAAACAGGAGTAATTGTTTTAAAAGTAGTAT<br>TGGTGACGTTGTTAGAAAATACAATTTAAGTAGAAGGTGCGTT<br>TTTATATGA**AATATATTT**TATAGCTGTACTTTACCTTTCAAG |
| BetA promoter (*B. anthracis* Sterne) (SEQ ID NO: 157) | ATTTATTTCATTCAATTTTTCCTATTTAGTACCTACCGCACTCAC<br>AAAAAGCACCTCTCATTAATTTATATTATAGTCATTGAAATCTA<br>ATTTAATGAAATCAT**CATACTATA**TGTTTTATAAGAAGTAAAG<br>GTAC**CATACTTAA**TTAATACATATCTATACACTTCAATATCAC<br>AGCATGCAGTTGAATTATATCCAACTTTCATTTCAAATTAAATA<br>AGTGCCTCCGCTATTGTGAATGTCATTTACTCTCCCTACTA**CAT**<br>**TTAATA**ATTATGACAAGCAATCATAGGAGGTTACTAC |
| BetA minimal promoter (*B. anthracis* Sterne) (SEQ ID NO: 158) | TAAGAAGTAAAGGTAC**CATACTTAA**TTAATACATATCTATACA<br>CTTCAATATCACAGCATGCAGTTGAATTATATCCAACTTTCATT<br>TCAAATTAAATAAGTGCCTCCGCTATTGTGAATGTCATTTACTC<br>TCCCTACTA**CATTTAATA**ATTATGACAAGCAATCATAGGAGGT<br>TACTAC |
| CotE promoter (*B. cereus* AH820) (SEQ ID NO: 159) | AGTTGTACAAGAATTTAAATCTTCACAAA**CATATGTAA**ATGAC<br>TTACTACAGCTAGTTGCAAGTACGATTTCTAACAACGTAACAG<br>ATGAAATATTAATTTCAACTAATGGCGATGTATTGAAGGGTGA<br>AACGGGCGCAGCGGTAGAAAGTAAAAAAGGAAATTGTGGTTG<br>TTAAAGAGATGTCGAAATGACATCTCTTTTTTTAGTGGATTAAA<br>CGTAAGTTCTTCTCAAAAAAAGAATGACACATTCCGCTATTGT<br>CACG**CATATGATT**AAGTGAATAGTGATTGAGGAGGGTTACGA |
| CotE minimal promoter (*B. cereus* AH820) (SEQ ID NO: 160) | ACATTCCGCTATTGTCACG**CATATGATT**AAGTGAATAGTGATT<br>GAGGAGGGTTACGA |
| ExsA promoter (*B. cereus* strain ATCC 10876) (SEQ ID NO: 161) | AACGTTATTAGCGTAGACAAACAAGTAACGGCAGAAGCAGTTC<br>TTG**CATTAAATC**GTATGTTAGAGCGTGTGTAAAGCAACGGTAT<br>TCCCGTTGCTTTTTTTCATA**CATATAATC**ATAACGAGAACGAA<br>ATGGG**CATACATTG**TTTTGAAGAAATCATTGTGGTTCTTTATG<br>CTTATTCCACTTCGAATGATATTGAAAATCGAAGAAGTGATAA<br>AAGTAAAAAGAAGTTAATGTTATTTAGAAAGAGTTACTTCATG<br>AGATTTGTTACTTATA**GATAAGTTA**TACAGGAGGGGGAAAAT |
| ExsA minimal promoter (*B. cereus* strain ATCC 10876) (SEQ ID NO: 162) | TCATGAGATTTGTTACTTATA**GATAAGTTA**TACAGGAGGGGGA<br>AAAT |
| ExsK promoter (*B. thuringiensis* serovar konkukian str. 97-27) (SEQ ID NO: 163) | AAGCCGCGGTCAATGCTGTATATGCA**AATAAGATT**GCAGCTTT<br>ACCTGAAGAAGAGCGT**GATAGCTTC**ATTGCTGAAAAACGAGA<br>AGAGTATAAGAAAGATATTGATATTTACCATTTAGCATCAGAG<br>ATGGTCATTGATGGTATTGTTCATCCAAACAATTTAAGAGAAG<br>AGTTAAAAGGACGATTCGAAATGTATATGAGTAAATATCAAGT<br>ATTTACGGATCGTAAA**CATCCTGTT**TATCCAGTTTAAAAGCCC<br>TATTTAGGGCTTTCTTGCTCAAAAAGTTAAGGAGGGGAAAACA |
| ExsK minimal promoter (*B. thuringiensis* serovar konkukian str. 97-27) (SEQ ID NO: 164) | TCAAGTATTTACGGATCGTAAA**CATCCTGTT**TATCCAGTTTAA<br>AAGCCCTATTTAGGGCTTTCTTGCTCAAAAAGTTAAGGAGGGG<br>AAAACA |
| ExsB promoter (*B. cereus* F837/76) (SEQ ID NO: 165) | AGGATTTCAGTGGGACGCCTCCTCTCTTCTTACATTAAATTAAT<br>**CATACTATA**AAATGAAAGAAATGAAATGAAAAATAGCGGAAA<br>AATCAGAAATTTTTTCTGGTAG**TATACAATATGTTA**CAATAAG<br>CTTTGTCAATGAAAGAAGGAATTCCGTGCAATGCACGGGAGAG<br>GTTCGCGAACTCCCTCTATAAAAAACTATGGAAACAAC**AATAT** |

TABLE 2-continued

| Promoter Sequences for Expression of Fusion Proteins in Recombinant *Bacillus cereus* family members | |
|---|---|
| Promoter (SEQ ID NO) | Promoter Sequence |
| | **CTTT**AGGTATTGTTTTGTTTTTTTATTGTGACAGTTCAAGAACG<br>TTCTTTCTTCTTATTCGTAGTAGAGAAGGAGAATGAGTGAA |
| ExsB minimal promoter (*B. cereus* F837/76) (SEQ ID NO: 166) | ACTATGGAAACAAC**AATATCTTT**AGGTATTGTTTTGTTTTTTTA<br>TTGTGACAGTTCAAGAACGTTCTTTCTTCTTATTCGTAGTAGAG<br>AAGGAGAATGAGTGAA |
| YabG promoter (*B. cereus* AH820) (SEQ ID NO: 167) | TTTTGCACAACGCCGTAAAACTTTAATG**AATAATTTA**TCA**AAT**<br>**AATTTA**AATGGTTTCCCGAAAGATAAAGAGCTGTTGGATCGAA<br>TTTTAACAGAAGTAGGAATTGATCCAAAACGAAGAGGCGAAA<br>CGCTATCTATCGAAGAGTTTGCGACATTAAGTAATGCATTAGTT<br>CTT**CATAAGTTA**TCATAAGAATACAAAAGGGACAGTTCAATTT<br>GAACTGTCCCTTTTGTCACCTTTCTCCTCCTAAATT**CATACTTT**<br>**A**AAAACAGGTAAGATGGCCTAACGAGTTTGGAGGTAGGAGA |
| YabG minimal promoter (*B. cereus* AH820) (SEQ ID NO: 168) | TCTCCTCCTAAATT**CATACTTTA**AAAACAGGTAAGATGGCCTA<br>ACGAGTTTGGAGGTAGGAGA |
| Tgl promoter (*B. thuringiensis* serovar konkukian str. 97-27) (SEQ ID NO: 169) | GGAAACAGAAGTCATCCCATTTGAAAATGCAGCAGGTCGTATT<br>ATAGCTGATTTCGTTATGGTTTATCCGCCAGGGATTCCAATCTT<br>TACTCCGGGGGAAATTATTACACAAGACAACTTAGAGTATATT<br>CGTAAAAACTTAGAAGCAGGTTTACCTGTACAAGGTCCTGAAG<br>ATATGACATTACAAACATTACGCGTGATCAAAGAGTACAAGCC<br>TATCAGTTGATAGGCTTTTTTTCACCCTTTTTCCCTTTTCT**CATA**<br>**CGATA**TTATGTAATGTAACGTATAGGTGGGGATACTACT |
| Tgl minimal promoter (*B. thuringiensis* serovar konkukian str. 97-27) (SEQ ID NO: 170) | ACCCTTTTTCCCTTTTCT**CATACGATA**TTATGTAATGTAACGTA<br>TAGGTGGGGATACTACT |
| Superoxide dismutase (SODA1) promoter (*B. cereus* F837/76) (SEQ ID NO: 171) | ATTGTGGACCCTTAGCTCAGCTGGTTAGAGCAGACGGCTCATA<br>ACCGTCCGGTCGTAGGTTCGAGTCCTACAGGGTCCATATCCATT<br>TCACATGTTTATTATGTCGGCAGGAAGCTTCCTTGTAGAAGGG<br>AGCTTTTTTTATGAAATATATGAGCATTTTAATTGAAATGAAGT<br>GGGAATTTTGCTACTTTAATGATAGCAAGACAATGTGATTTATT<br>TGTTTGCACCCTATGGCAATTAGGGTAGAATGAAGTTGTATGT<br>CACTTAAGTGGCAATA**CATAAACTG**GGAGGAATATAACA |
| Superoxide dismutase (SODA1) minimal promoter (*B. cereus* F837/76) (SEQ ID NO: 172) | ACTTAAGTGGCAATA**CATAAACTG**GGAGGAATATAACA |
| Superoxide dismutase (SODA2) promoter (*B. cereus* AH820) (SEQ ID NO: 173) | AATATAACAGAAAATTCTGATGTTTTTTCAAATCCTATAATAAG<br>GAGTGTTCCGTATGATGCCTT**TATATTTTC**CGGAAGATAAAAC<br>AG**AATATATTA**TTCCAGGGATTGTTTGTGTTCTATTTATCATCG<br>GTGCGATTGCTACGTGGCGTATGTTCATTCGTGTATCAAAACG<br>AGAAGCAGAGCGATTACAGAAAGTTGAAGAAAAGCTGTTAGC<br>TGAAAAGAAACAGTAACTCATTTTTGTATGTTTCCCTCTATGCT<br>CGGACAATCTAAGGGCAGAATGTATTTTGGAGGGAATGAA |
| Superoxide dismutase (SODA2) minimal promoter (*B. cereus* AH820) (SEQ ID NO: 174) | TCCGGAAGATAAAACAG**AATATATTA**TTCCAGGGATTGTTTGT<br>GTTCTATTTATCATCGGTGCGATTGCTACGTGGCGTATGTTCAT<br>TCGTGTATCAAAACGAGAAGCAGAGCGATTACAGAAAGTTGA<br>AGAAAAGCTGTTAGCTGAAAAGAAACAGTAACTCATTTTTGTA<br>TGTTTCCCTCTATGCTCGGACAATCTAAGGGCAGAATGTATTTT<br>GGAGGGAATGAA |
| BclA promoter (*B. anthracis* Sterne) (SEQ ID NO: 175) | TAATCACCCTCTTCCAAATCAAT**CATATGTTA**TA**CATATACTA**<br>AACTTTCCATTTTTTTAAATTGTTCAAGTAGTTTAAGATTTCTT<br>TTCAATAATTCAAATGTCCGTGTCATTTTCTTTCGGTTTTG**CAT**<br>**CTACTA**TATAATGAACGCTTTATGGAGGTGAATTT |
| BAS1882 promoter (*B. anthracis* Sterne) (SEQ ID NO: 176) | AATTACATAACAAGAACTACATTAGGGAGCAAGCAGTCTAGCG<br>AAAGCTAACTGCTTTTTTATTAAATAACTATTTTATTAAATTTC<br>ATATATACAATCGCTTGTCCATTTCATTTGGCTCTACCCACG**CA**<br>**TTTACTA**TTAGTAATATGAATTTTTCAGAGGTGGATTTTATT |
| Gene 3572 promoter (*B. weihenstephensis* KBAB 4) (SEQ ID NO: 177) | CTATGATTTAAGATACACAATAGCAAAAGAGAAA**CATATTAT**<br>**A**TAACGATAAATGAAACTTATGTATATGTATGGTAACTGTATA<br>TATTACTACAATACAGTATACTCATAGGAGGTAGGT |

TABLE 2-continued

Promoter Sequences for Expression of Fusion Proteins in Recombinant *Bacillus cereus* family members

| Promoter (SEQ ID NO) | Promoter Sequence |
|---|---|
| YVTN β-propeller protein promoter (*B. weihenstephensis* KBAB 4) (SEQ ID NO: 178) | GGTAGGTAGATTTGAAATATGATGAAGAAAAGGAATAACTAA<br>AAGGAGTCGATATCCGACTCCTTTTAGTTATAAATAATGTGGA<br>ATTAGAGTATAATTTTATATAGGTATATTGTATTAGATGAACGC<br>TTTATCCTTTAATTGTGATTAATGATGGATTGTAAGAGAAGGG<br>GCTTACAGTCCTTTTTTTATGGTGTTCTATAAGCCTTTTTAAAA<br>GGGGTACCACCCCACACCCAAAAACAGGGGGGGTTATAACTA<br>CATATTGGATGTTTTGTAACGTACAAGAATCGGTATTAATTACC<br>CTGTAAATAAGTTATGTGTATATAAGGTAACTT**TATATATTC**T<br>CCTACAATAAAATAAAGGAGGTAATAAA |
| Cry1A promoter (*B. thuringiensis* HD-73) (SEQ ID NO: 179) | AACCCTTAATGCATTGGTTAAACATTGTAAAGTCTAAAGCATG<br>GATAATGGGCGAGAAGTAAGTAGATTGTTAACACCCTGGGTCA<br>AAAATTGATATTTAGTAAAATTAGTTGCACTTTGTGCATTTTTT<br>**CATAAGATG**AGT**CATATGTTT**TAAATTGTAGTAATGAAAAAC<br>AGTAT**TATATCATAATGAA**TTGGTATCTTAATAAAAGAGATGG<br>AGGTAACTTA |
| ExsY promoter (*B. thuringiensis* serovar konkukian str. 97-27) (SEQ ID NO: 180) | TAATTCCACCTTCCCTTATCCTCTTTCGCCTATTTAAAAAAAGG<br>TCTTGAGATTGTGACCAAATCTCCTCAACTCC**AATATCTTA**TTA<br>ATGTAAATACAAACAAGAAGATAAGGA |
| CotY promoter (*B. thuringiensis* Al Hakam) (SEQ ID NO: 181) | AGGATGTCTTTTTTTATATTGTATTATGTACATCCCTACTATATA<br>AATTCCCTGCTTTTATCGTAAGAATTAACGTAATATCAACCATA<br>TCCCGTT**CATATTGTA**GTAGTGTATGTCAGAACTCACGAGAAG<br>GAGTGAACATAA |
| YjcA promoter (*B. thuringiensis* serovar kurstaki str. HD73) (SEQ ID NO: 182) | TTAATGTCACTCCTTATCTTCTTGTTTGTATTTACATT**AATAAG**<br>**ATA**TTGGAGTTGAGGAGATTTGGTCACAATCTCAAGACCTTTTT<br>TTTAAATAGGCGAAAGAGGATAAGGGAAGGTGGAATT |
| YjcB promoter (*B. thuringiensis* serovar kurstaki str. HD73) (SEQ ID NO: 183) | ATATATTTTCATAATACGAGAAAAAGCGGAGTTTAAAAGAATG<br>AGGGAACGGAAATAAAGAGTTGTT**CATATAGTA**AATAGACAG<br>AA |
| ExsFA/BxpB promoter (*B. thuringiensis* Al Hakam) (SEQ ID NO: 184) | AAACTAAATAATGAGCTAAGCATGGATTGGGTGGCAGAATTAT<br>CTGCCACCCAATC**CATGCTTAA**CGAGTATTATTATGTAAATTT<br>CTTAAAATTGGGAACTTGTCTAGAACATAGAACCTGTCCTTTT**C**<br>**ATTAACTG**AAAGTAGAAACAGATAAAGGAGTGAAAAAC |
| Rhamnose promoter (*B. thuringiensis* Al Hakam) (SEQ ID NO: 185) | ATTCACTACAACGGGGATGAGTTTGATGCGGATA**CATATGAG**<br>**A**AGTACCGGAAAGTGTTTGTAGAA**CATTACAA**AGATATATTAT<br>CTCCATCATAAAGGAGAGATGCAAAG |
| CotO promoter (*B. anthracis* Sterne) (SEQ ID NO: 186) | CGCGCACCACTTCGTCGTACAACAACGCAAGAAGAAGTTGGGG<br>ATACAGCAGTATTCTTATTCAGTGATTTAGCACGCGGCGTAAC<br>AGGAGAAAACATTCACGTTGATTCAGGGTAT**CATATCTTA**GGA<br>TAAATATAATATTAATTTTAAAGGACAATCTCTACATGTTGAG<br>ATTGTCCTTTTTATTTGTTCTTAGAAAGAACGATTTTTAACGAA<br>AGTTCTTACCACGTTATGAATATAAGTATAATAGTACACGATTT<br>ATTCAGCTACGTA |
| Sigma K promoter (*B. anthracis* Sterne) (SEQ ID NO: 187) | TATATCATATGTAAAATTAGTTCTTATTCCCA**CATATCATA**TAG<br>AATCGC**CATATTATA**CATGCAGAAAACTAAGTATGGTATTATT<br>CTTAAATTGTTTAGCACCTTCTAATATTACAGATAGAATCCGTC<br>ATTTTCAACAGTGAACATGGATTTCTTCTGAACACAACTCTTTT<br>TCTTTCCTTATTTCCAAAAAGAAAAGCAGCCCATTTTAAAATAC<br>GGCTGCTTGTAATGTACATTA |
| InhA1 promoter (*B. thuringiensis* Al Hakam) (SEQ ID NO: 188) | TATCACATAACTCTTTATTTTTAATATTTCGA**CATAAAGTG**AAA<br>CTTTAATCAGTGGGGGCTTTGTTCATCCCCCCACTGATTATTAA<br>TTGAACCAAGGGATAAAAAGATAGAGGGTCTGACCAGAAAAC<br>TGGAGGGCATGATTCTATAACAAAAAGCTTAATGTTTATAGAA<br>TTATGTCTTTTTATATAGGGAGGGTAGTAAACAGAGATTTGGA<br>CAAAAATGCACCGATTTATCTGAATTTTAAGTTTTATAAAGGG<br>GAGAAATG |

TABLE 2-continued

Promoter Sequences for Expression of Fusion Proteins in Recombinant *Bacillus cereus* family members

| Promoter (SEQ ID NO) | Promoter Sequence |
|---|---|
| BclA cluster glycosyl transferase operon 1 (*B. thuringiensis* serovar konkukian str. 97-27) (SEQ ID NO: 189) | ATTTTTTACTTAGCAGTAAAACTGATATCAGTTTTACTGCTTTTT CATTTTTAAATTCAATCATTAAATCTTCCTTTTCTACATAGT**CA TAATGTT**GTATGACATTCCGTAGGAGGCACTTATA |
| BclA cluster glycosyl transferase operon 2 (*B. thuringiensis* serovar kurstaki str. HD73) (SEQ ID NO: 190) | ACATAAATTCACCTCCATAAAGCGTTCATTATATAGTAGATGC AAAACCGAAAGAAAATGACACGGACATTTGAATTATTGAAAA GAAATCTTAAACTACTTGAACAATTTAAAAAAATGGAAAGTTT AGTATATGTATAA**CATATGATT**GATTTGGAAGAGGGTGATTA |
| Glycosyl transferase promoter (*B. thuringiensis* Al Hakam) (SEQ ID NO: 191) | TTCTATTTTCCAA**CATAACATG**CTACGATTAAATGGTTTTTGC AAATGCCTTCTTGGGAAGAAGGATTAGAGCGTTTTTTTATAGA AACCAAAAGTCATTAACAATTTTAAGTTAATGACTTTTTTGTTT GCCTTTAAGAGGTTTTATGTTACTATAATTATAGTATCAGGTAC TAATAACAAGTATAAGTATTTCTGGGAGGATATATCA |

The sigma-K sporulation-specific polymerase promoter sequences in the promoter sequences shown in Table 2 result in high expression levels of the fusion protein during late sporulation. The consensus sequence for the sigma-K sporulation-specific polymerase promoter sequence is CATANNNTN; however, this sequence can comprise up to two mutations and still be functional. The sigma-K sporulation-specific polymerase promoter sequence is generally found upstream of the ribosome binding site (RBS).

Promoters having a high degree of sequence identity to any of the sequences shown above in Table 2 can also be used to express the fusion proteins.

For example, the fusion protein can be expressed under the control of a promoter comprising a nucleic acid sequence having at least 80% identity with a nucleic acid sequence of any one of SEQ ID NOs: 37-42 and 123-191.

The fusion protein can be expressed under the control of a promoter comprising a nucleic acid sequence having at least 90% identity with a nucleic acid sequence of any one of SEQ ID NOs: 37-42 and 123-191.

The fusion protein can be expressed under the control of a promoter comprising a nucleic acid sequence having at least 95% identity with a nucleic acid sequence of any one of SEQ ID NOs: 37-42 and 123-191.

The fusion protein can be expressed under the control of a promoter comprising a nucleic acid sequence having at least 98% identity with a nucleic acid sequence of any one of SEQ ID NOs: 37-42 and 123-191.

The fusion protein can be expressed under the control of a promoter comprising a nucleic acid sequence having at least 99% identity with a nucleic acid sequence of any one of SEQ ID NOs: 37-42 and 123-191.

The fusion protein can be expressed under the control of a promoter comprising a nucleic acid sequence having 100% identity with a nucleic acid sequence of any one of SEQ ID NOs: 37-42 and 123-191.

For example, fusion protein can be expressed under the control of a BclA promoter (e.g., SEQ ID NO: 149, 150, 175, 189 or 190), a CotY promoter (e.g., SEQ ID NO: 41, 41 or 181), an ExsY promoter (e.g., SEQ ID NO: 37, 38, or 180), or a rhamnose promoter (e.g., SEQ ID NO: 185). For example, the fusion protein can be expressed under the control of a promoter comprising a nucleic acid sequence having at least 80% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 85% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 90% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 95% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 98% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having at least 99% identity with a nucleic acid sequence of any one of SEQ ID NOs: 37, 38, 41, 42, 149, 150, 175, 180, 181, 185, 189, or 190.

The fusion protein can be expressed under the control of a promoter comprising a nucleic acid sequence having 100% identity with a nucleic acid sequence of any one of SEQ ID NOs: 37, 38, 41, 42, 149, 150, 175, 180, 181, 185, 189, or 190.

The fusion protein can be expressed under the control of a promoter comprising a sigma-K sporulation specific polymerase promoter sequence, wherein the sigma-K sporulation-specific polymerase promoter sequence or sequences have 100% identity with the corresponding nucleotides of any of SEQ ID NOs: 37-42 and 123-191.

The fusion proteins can be expressed under the control of a promoter that is native to the targeting sequence, exosporium protein, or exosporium protein fragment of the fusion protein. Thus, for example, where the targeting sequence is derived from BclA, the fusion protein can be expressed under the control of a native BclA promoter (e.g., SEQ ID NO: 149, 150, 175, 189 or 190).

Table 2 also provides exemplary minimal promoter sequences. The fusion proteins can be expressed under any of these minimal promoter sequences.

Furthermore, the fusion protein can be expressed under a portion of any of the promoters listed above in Table 2, so long as the portion of the promoter includes a sigma-K sporulation-specific polymerase promoter sequence. For example, the fusion protein can be expressed under a promoter region that comprises the first 25, 50, 100, 150, 200, 250, or 300 nucleotides upstream of the start codon, so long as that region comprises a sigma-K sporulation-specific polymerase promoter sequence.

III. Mutations and Other Genetic Alterations to Recombinant *Bacillus cereus* Family Members that Allow for Collection of Free Exosporium As is described further hereinbelow, the recombinant *Bacillus cereus* family members that express fusion proteins comprising a protein or peptide of interest and a targeting sequence, an exosporium protein, or an exosporium protein fragment that targets the fusion protein to the exosporium of the recombinant *Bacillus cereus* family member can be used for various purposes, including delivering proteins or peptides of interest to animals, aquatic organisms, or an insect vector of an animal pathogen. However, in some cases, the presence of the living microorganisms may not be desirable, and instead, it would be desirable to separate the living spore from the fusion proteins in the exosporium on the outside surface of the spore. For example, in some applications it will be desirable to increase enzyme activity without concern for spore integrity. In such situations, the exosporium fragments may be preferred over living microorganisms having the enzyme on their exosporium.

In addition, for some uses, it may be desirable to reduce the density of the product. In such instances, it would be desirable to separate the dense spore from the exosporium (containing the fusion proteins). In the field of vaccines, it may be desirable to separate the spore from the exosporium (containing fusion proteins that comprise an antigen) in order to remove potential antigens present on the spore itself from the vaccine preparation. Furthermore, under some circumstances the presence of live spores would lead to potential for bacterial growth in a product, which would be undesirable for some applications (e.g., wound dressings).

Mutations or other genetic alterations (e.g., overexpression of a protein) can be introduced into the recombinant *Bacillus cereus* family members that allow free exosporium to be separated from spores of the recombinant *Bacillus cereus* family member. This separation process yields exosporium fragments that contain the fusion proteins but that are substantially free of the spores themselves. By "substantially free of spores" it is meant that once the free exosporium is separated from the spores, a preparation is obtained that contains less than 5% by volume of spores, preferably less than 3% by volume of spores, even more preferably less than 1% by volume of spores, and most preferably contains no spores or if spores are present, they are undetectable. These exosporium fragments can be used in place of the recombinant *Bacillus cereus* family members themselves and can be in any of the compositions, methods, adhesive patches, wound dressings, insert trays, hoof bandages, or insect foggers described herein.

Exosporium fragments derived from spores of a recombinant *Bacillus cereus* family member can be used in any of the compositions, methods, adhesive patches, wound dressings, insert trays, hoof bandages, feed or feed additives, insect foggers described herein. The recombinant *Bacillus cereus* family member expresses a fusion protein comprising at least one protein or peptide of interest and a targeting sequence, exosporium protein, or exosporium protein fragment that targets the fusion protein to the exosporium of the recombinant *Bacillus cereus* family member. The recombinant *Bacillus cereus* family member comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore.

As further described below in Section IV, for vaccine compositions that comprise exosporium fragments, the exosporium fragments need not comprise a fusion protein. Such exosporium fragments can be derived from spores of a recombinant *Bacillus cereus* family member that does not express a fusion protein. The recombinant *Bacillus cereus* family member comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore. As explained further in Section IV, the exosporium fragments can act as an adjuvant in the vaccine composition.

The recombinant *Bacillus cereus* family member: (i) can comprise a mutation in a CotE gene; (ii) can express an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein; (iii) can express a BclB protein, wherein the expression of the BclB protein is increased as compared to the expression of the BclB protein in a wild-type *Bacillus cereus* family member under the same conditions; (iv) can express a YjcB protein, wherein the expression of the YjcB protein is increased as compared to the expression of the YjcB protein in a wild-type *Bacillus cereus* family member under the same conditions; (v) can comprise a mutation in an ExsY gene; (vi) can comprise a mutation in a CotY gene; (vii) can comprise a mutation in an ExsA gene; or (viii) can comprise a mutation in a CotO gene.

The recombinant *Bacillus cereus* family member can comprise a mutation in the CotE gene, such as a knock-out of the CotE gene or a dominant negative form of the CotE gene. The mutation in the CotE gene can partially or completely inhibit the ability of CotE to attach the exosporium to the spore.

The recombinant *Bacillus cereus* family member can express an ExsY protein. The ExsY protein comprises a carboxy-terminal tag comprising a globular protein (e.g., a green fluorescent protein (GFP) or a variant thereof), and the expression of the ExsY protein is increased as compared to the expression of the ExsY protein in a wild-type *Bacillus cereus* family member under the same conditions. The globular protein can have a molecular weight of between 25 kDa and 100 kDa. Expression of the ExsY protein comprising the carboxy-terminal tag comprising a globular protein can inhibit binding of the ExsY protein to its targets in the exosporium.

The recombinant *Bacillus cereus* family member can express a BclB protein. Expression of the BclB protein can result in the formation of a fragile exosporium. The expression of the BclB protein can be increased as compared to the expression of the BclB protein in a wild-type *Bacillus cereus* family member under the same conditions.

The recombinant *Bacillus cereus* family member can express a YjcB protein. Expression of the YjcB protein can cause the exosporium to form in pieces rather than in a complete structure. The expression of the YjcB protein can be increased as compared to the expression of the YjcB protein in a wild-type *Bacillus cereus* family member under the same conditions.

The recombinant *Bacillus cereus* family member can comprise a mutation an ExsY gene, such as a knock-out of the ExsY gene. The mutation in the ExsY gene can partially or completely inhibit the ability of ExsY to complete the formation of the exosporium or attach the exosporium to the spore.

The recombinant *Bacillus cereus* family member can comprise a mutation a CotY gene, such as a knock-out of the CotY gene. The mutation in the CotY gene can result in the formation of a fragile exosporium.

The recombinant *Bacillus cereus* family member can comprise a mutation an ExsA gene, such as a knock-out of the ExsA gene. The mutation in the ExsA gene can result in the formation of a fragile exosporium.

The recombinant *Bacillus cereus* family member can comprise a mutation a CotO gene, such as a knock-out of the CotO gene or a dominant negative form of the CotO gene. The mutation in the CotO gene can cause the exosporium to form in strips.

For ease of reference, descriptions of exemplary sequences for CotE, ExsY, BclB, YjcB, CotY, ExsA, and CotO are provided in Table 3 below.

TABLE 3

Sequences of Proteins that Can be Mutated or Otherwise Genetically Altered to Allow for Collection of Free Exosporium

| Protein | SEQ ID NO. for Amino Acid Sequence |
|---|---|
| CotE, *Bacillus cereus* group | 192 |
| ExsY, *Bacillus thuringiensis* | 193 |
| BclB, variant 1, *Bacillus anthracis* Sterne | 194 |
| BclB, variant 2 *Bacillus anthracis* Sterne | 195 |
| YjcB, Variant 1, *Bacillus cereus* | 196 |
| YjcB, Variant 2, *Bacillus cereus* | 197 |
| CotY, *Bacillus cereus* | 198 |
| CotO, *Bacillus anthracis* | 199 |

Exosporium fragments can be prepared from any of these recombinant *Bacillus cereus* family members and used for various purposes as described further hereinbelow. Where the recombinant *Bacillus cereus* family member expresses a fusion protein, the exosporium fragments will comprise the fusion proteins. Upon purification of the exosporium fragments that contain the fusion proteins from the spores, a cell-free protein preparation is obtained in which the fusion proteins are stabilized and supported through covalent bonds to the exosporium fragments.

To remove the exosporium from spores of the recombinant *Bacillus cereus* family member that have mutations or other genetic alterations that allow for collection of free exosporium, a suspension of the spores can be subjected to centrifugation or filtration to produce fragments of exosporium that are separated from the spores. Where the recombinant *Bacillus cereus* family member expresses a fusion protein, the exosporium fragments will comprise the fusion protein.

A suspension comprising the spores can be subjected to centrifugation, followed by collection of the supernatant. The supernatant comprises the fragments of the exosporium and is substantially free of spores.

Alternatively, a suspension comprising the spores can be subjected to filtration, followed by collection of the filtrate. The filtrate comprises the fragments of the exosporium and is substantially free of spores.

The suspension of spores can be agitated or mechanically disrupted prior to centrifugation or filtration.

The exosporium fragments can also be separated from the spores by gradient centrifugation, affinity purification, or by allowing the spores to settle out of the suspension.

Due to the strong covalent bonds between the fusion proteins and the exosporium fragments, the fusion proteins become resistant to heat. The heat resistance of the fusion proteins bound to the exosporium fragments allows them to be used for applications that require heat-resistant proteins or enzymes (e.g., in feed additives).

IV. Compositions

Compositions comprising a carrier and spores of any of the recombinant *Bacillus cereus* family members described herein are provided.

Compositions comprising a carrier and exosporium fragments derived from spores of any of the recombinant *Bacillus cereus* family members described herein are also provided.

The compositions can comprise spores of any of the recombinant *Bacillus cereus* family members described above in Section I.E or exosporium fragments derived from such spores.

A. Pharmaceutical, Insecticidal, Acaricidal, Helminthicidal, and Nematicidal Compositions The composition can be a pharmaceutical composition. Where the composition comprises a pharmaceutical composition, the carrier comprises a pharmaceutically acceptable carrier.

The composition can be an insecticidal composition.

The composition can be an acaricidal composition.

Where the composition is an insecticidal or acaricidal composition, the protein of interest can comprise a secreted insecticidal (Sip) protein, a mosquitocidal toxin, an endochitinase, an exochitinase, a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, a Cyt1Aa protein, or a combination of any thereof.

The mosquitocidal toxin can comprise a Mtx-like mosquitocidal toxin (e.g., Mtx1) or a Bin-like mosquitocidal toxin. Where the mosquitocidal toxin comprises Mtx1, the Mtx1 can be any of the Mtx1 proteins described herein.

The composition can be a helminthicidal composition

The composition can be a nematicidal composition.

Where the composition is a helminthicidal or nematicidal composition, the protein or peptide of interest can comprise a chitinase C, a chitinase D, or a combination thereof.

A pharmaceutical composition is provided. The pharmaceutical composition comprises a pharmaceutically acceptable carrier and exosporium fragments. The exosporium fragments are derived from spores of a recombinant *Bacillus cereus* family member and comprise a fusion protein. The fusion protein comprises at least one protein or peptide that protects an animal from a pathogen and a targeting sequence, exosporium protein, or exosporium protein fragment that targets the fusion protein to the exosporium of the recombinant *Bacillus cereus* family member.

Where the composition comprises a pharmaceutical composition, the composition can be suitable for topical, oral, intravenous, intra-arterial, intraperitoneal, intramuscular, subcutaneous, intrapleural, intranasal, intradermal, inhalation, rectal, transdermal, transepithelial administration, administration to an aquatic animal by immersion of the animal in the pharmaceutical composition, or a combination of any thereof.

For example, the pharmaceutical composition can be suitable for topical administration.

The pharmaceutical composition can be in the form of a topical spray composition.

The pharmaceutical composition can be suitable for oral administration.

For example, the pharmaceutical composition can be formulated as a feed additive.

In any of the pharmaceutical compositions other than the vaccine compositions, the protein or peptide that protects the animal from a pathogen preferably does not comprise an antigen or an immunogen.

In any of the pharmaceutical compositions, the protein or peptide that protects the animal from a pathogen preferably does not comprise a nucleic acid binding protein or peptide.

For any of the pharmaceutical compositions, the protein or peptide that protects an animal from a pathogen can protect any of the animals discussed herein.

For any of the pharmaceutical compositions, the protein or peptide that protects an animal from a pathogen can protect the animal from any of the pathogens discussed herein.

In any of the compositions described herein, the protein or peptide that protects the animal from a pathogen can have antibacterial activity, antifungal activity, antihelminthic activity, nematicidal activity, insecticidal activity, acaricidal activity, can suppress insect or worm reproduction, or a combination of any thereof.

For example, the protein or peptide that protects the animal from a pathogen can have antibacterial activity, antifungal activity, or a combination thereof The protein or peptide that protects the animal from a pathogen can comprise a bacteriocin, an avidin, a streptavidin, an antimicrobial peptide, a conalbumin, an albumin, a lactoferrin, a lactoferrin peptide, a lysozyme peptide, TasA, a defensin, an antibody, an antibody fragment, an enzyme, a histone, or a combination of any thereof.

The lactoferrin peptide can comprise LfcinB.

The LfcinB can comprise a *Bos taurus* lactoferrin. The amino acid sequence for a *Bos taurus* lactoferrin is provided by SEQ ID NO: 212.

The LfcinB can comprise any of the LfcinB peptides described above in Section I.B. Thus the LfcinB can comprise an amino acid sequence having at least 70%, at least 75%, at least 80%, at least 85%, at least 90%, at least 95%, at least 98%, at least 99%, or 100% sequence identity to SEQ ID NO: 212.

The lysozyme peptide can comprise a LysM peptide. The LysM can comprise a *Gallus gallus* LysM. The amino acid sequence for a *Gallus gallus* LysM is provided by SEQ ID NO: 213.

The LysM can comprise any of the LysM peptides described above in Section I.B. Thus, the LysM can comprise an amino acid sequence having at least 70%, at least 75%, at least 80%, at least 85%, at least 90%, at least 95%, at least 98%, at least 99%, or 100% sequence identity to SEQ ID NO: 213.

The ovalbumin can comprise an ovalbumin.

The antimicrobial peptide can comprise a non-ribosomal antibacterial peptide, a non-ribosomal antifungal peptide, a cecropin, a penaeidin, a bactenecin, a callinectin, a myticin, a tachyplesin, a clavanin, amisgurin, a pleurocidin, a parasin, or a combination of any thereof.

The enzyme can comprise a nuclease, a protease, a lactonase, an apyrase, a glycoside hydrolase, an alginate lyase, a glucanase, a chitosanase, a chitinase, a chitosanase-like enzyme, a lyticase, a mutanolysin, or a stapholysin, or a combination of any thereof.

Where the enzyme comprises an apyrase, the apyrase can comprise any of the apyrases described above in Section I.B. Thus, the apyrase can comprise a *Solanum tuberosum* apyrase encoded by the Rrop1 gene. The amino acid sequence for this *Solanum tuberosum* apyrase is provided by SEQ ID NO: 204.

Alternatively, the apyrase can comprise a *Bacillus subtilis* apyrase encoded by the YtkD gene. The amino acid sequence for this *Bacillus subtilis* apyrase is provided by SEQ ID NO: 205.

The apyrase can comprise an amino acid sequence having at least 70%, at least 75%, at least 80%, at least 85%, at least 90%, at least 95%, at least 98%, at least 99%, or 100% sequence identity to SEQ ID NO: 204 or 205.

Where the enzyme comprises a glycoside hydrolase, the glycoside hydrolase can comprise a lysozyme, a dispersin B, or a combination of any thereof.

Where the enzyme comprises a nuclease, the nuclease can comprise a DNase (e.g., DNaseI).

The lactonase can comprise any of the lactonases described above in Section I.B. Thus, the lactonase can comprise an amino acid sequence having at least 70%, at least 75%, at least 80%, at least 85%, at least 90%, at least 95%, at least 98%, at least 99%, or 100% sequence identity to SEQ ID NO: 207 or 208.

Where the enzyme comprises a chitinase, the chitinase can comprise an endochitinase (e.g., a chitinase C) or an exochitinase (e.g., a chitinase D).

Where the chitinase comprises an endochitinase, the endochitinase can comprise a *Bacillus thuringiensis* endochitinase. An amino acid sequence for a *Bacillus thuringiensis* endochitinase is provided by SEQ ID NO: 206.

The endochitinase can comprise any of the endochitinases described above in Section I.B. Thus, the endochitinase can comprise an amino acid sequence having at least 70%, at least 75%, at least 80%, at least 85%, at least 90%, at least 95%, at least 98%, at least 99%, or 100% sequence identity to SEQ ID NO: 206.

The enzyme can comprise an enzyme that is specific for a bacterial signaling molecule. For example, the enzyme can comprise a protease or a lactonase. The protease can comprise any of the proteases described herein. The lactonase can comprise any of the lactonases described herein.

The lactonase can comprise a lactonase that is specific for a bacterial lactone homoserine signaling molecule.

Where the enzyme comprises a lactonase, the lactonase can comprise a 1,4-lactonase, a 2-pyrone-4,6-dicarboxylate lactonase, a 3-oxoadipate enol-lactonase, an actinomycin lactonase, a deoxylimonate A-ring-lactonase, a gluconolactonase L-rhamnono-1,4-lactonase, a limonin-D-ring-lactonase, a steroid-lactonase, a triacetate-lactonase, a xylono-1,4-lactonase, or a combination of any thereof.

The lactonase can comprise an AiiA lactonase.

For example, the lactonase can comprise a *Bacillus thuringiensis* B184 AiiA or a *Bacillus pseudomycoides* B30 AiiA. An amino acid sequence for the *Bacillus thuringiensis*

B184 AiiA is provided by SEQ ID NO: 207. An amino acid sequence for the *Bacillus pseudomycoides* B30 AiiA is provided by SEQ ID NO: 208.

The enzyme can comprise an enzyme specific for a cellular or extracellular component of a bacterium or fungus. For example, the enzyme can comprise a glucanase, a chitosanase, a chitinase, a chitosanase-like enzyme, a lyticase, a protease, a mutanolysin, a stapholysin, a lysozyme, or a combination of any thereof.

Where the enzyme comprises a glucanase, the glucanase can comprise a cellulase, β-1,3-glucanase, a β-1,4-glucanase, a β-1,6-glucanase, or a combination thereof.

Where the enzyme comprises a β-1,3-glucanase, the β-1,3-glucanase can comprise a *Bacillus circulans* β-1,3-glucanase encoded by the BglH gene. An amino acid sequence for this β-1,3-glucanase is provided by SEQ ID NO: 216.

Alternatively, the β-1,3-glucanase can comprise a *Hordeum vulgare* β-1,3-glucanase encoded by the HvGII gene. An amino acid sequence for this β-1,3-glucanase is provided by SEQ ID NO: 214.

The β-1,3-glucanase can comprise any of the β-1,3-glucanases described above in Section I.B. Thus, the β-1,3-glucanase can comprises an amino acid sequence having at least 70%, at least 75%, at least 80%, at least 85%, at least 90%, at least 95%, at least 98%, at least 99%, or 100% sequence identity to SEQ ID NO: 214 or 216.

Where the enzyme comprises a protease, the protease can comprise a peptidase (e.g., an endopeptidase or an exopeptidase), a proteinase (e.g., proteinase K), or a combination thereof.

The protease can comprise an alkaline protease, an acid protease, or a neutral protease.

The protease can comprise a *Bacillus subtilis* serine protease.

For example, the *Bacillus subtilis* serine protease can comprise any of the *Bacillus subtilis* serine proteases described above in Section I.B. Thus, the *Bacillus subtilis* serine protease can comprise an amino acid sequence having at least 80%, at least 85%, at least 90%, at least 95%, at least 98%, at least 99%, or 100% sequence identity to SEQ ID NO: 209.

The *Bacillus subtilis* serine protease can comprise an amino acid sequence having at least 80%, at least 85%, at least 90%, at least 95%, at least 98%, at least 99%, or 100% sequence identity to SEQ ID NO: 210.

The protein or peptide that protects the animal from a pathogen can have antihelminthic activity, nematicidal activity, insecticidal activity, acaricidal activity, can suppress insect or worm reproduction, or a combination of any thereof.

The protein or peptide that protects the animal from a pathogen can comprise an insecticidal bacterial toxin (e.g., a VIP insecticidal protein), an acaricidal bacterial toxin, an endotoxin (e.g., a delta endotoxin), a Cry toxin, a protease inhibitor protein or peptide (e.g., a trypsin inhibitor or an arrowhead protease inhibitor), a secreted insecticidal (Sip) protein, a mosquitocidal toxin (e.g., an Mtx1-like mosquitocidal toxin, a Bin-like mosquitocidal toxin, or a combination thereof), a cysteine protease, a *Bacillus subtilis* serine protease, a chitinase, or a combination of any thereof.

The chitinase can comprise any of the chitinases described herein (e.g., any of the endochitinases described herein).

The *Bacillus subtilis* serine protease can comprise any of the *Bacillus subtilis* serine proteases described herein.

The Mtx1-like mosquitocidal toxin can comprise Mtx1.

The Mtx1 can comprise any of the Mtx1 toxins described above in Section I.B. Thus, for example, the Mtx1 can comprise a *Bacillus sphaericus* Mtx1. An amino acid sequence for a *Bacillus sphaericus* Mtx1 is provided by SEQ ID NO: 211.

The Mtx1 can comprise an amino acid sequence having at least 70%, at least 75%, at least 80%, at least 85%, at least 90%, at least 95%, at least 98%, at least 99%, or 100% sequence identity to SEQ ID NO: 211.

The Cry toxin can comprise a Cry toxin from *Bacillus thuringiensis.*

The Cry toxin can comprise a Cry5B protein, a Cry21A protein, a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, a Cyt1Aa protein, or a combination of any thereof.

For example, the Cry toxin can comprise a Cry21A protein.

The Cry21A protein can comprise a *Bacillus thuringiensis* Cry21A protein. An amino acid sequence for a *Bacillus thuringiensis* Cry21A protein is provided by SEQ ID NO: 215.

The Cry21A protein can comprise any of the Cry21A proteins described above in Section I.B. Thus, the Cry21A protein can comprise an amino acid sequence having at least 70%, at least 75%, at least 80%, at least 85%, at least 90%, at least 95%, at least 98%, at least 99%, or 100% sequence identity to SEQ ID NO: 215.

Additional compositions (e.g., vaccine compositions and compositions for use in aquaculture) are described hereinbelow.

B. Vaccine Compositions

In any of the pharmaceutical compositions, the protein or peptide that protects an animal from a pathogen can comprise an antigen or an immunogen. Such pharmaceutical compositions are referred to herein as "vaccine compositions" and are suitable for use in connection with the methods for producing an immunogenic response described in Section VI below.

1. Vaccine Compositions Suitable for Use to Produce an Immunogenic Response in an Aquatic Animal Pharmaceutical compositions that are suitable for use to provide an immunogenic response in an aquatic animal are provided. The aquatic animal can be any of the aquatic animals listed in Section VI.

In the pharmaceutical compositions wherein the protein or peptide that protects an animal from a pathogen comprises an antigen or an immunogen, the antigen or immunogen can comprise an antigen or immunogen derived from a pathogen of an aquatic animal (e.g., *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna*, or *Icthyophous hoferi*). Such compositions are suitable for use in methods for producing an immunogenic response in an aquatic animal, including the methods described in Section VI below.

The pharmaceutical composition can be in the form of a powder or liquid concentrate. Such compositions are particularly suitable for use in methods for producing an immunogenic response in an aquatic animal, including the methods described in Section VI below.

2. Vaccine Compositions Containing Exosporium Fragments as Adjuvants and/or Stability Enhancers The exosporium fragments can act as an adjuvant when included in a vaccine composition. In addition, different types of exosporium fragments (e.g., exosporium fragments derived from different species of bacteria or exosporium fragments derived from recombinant *Bacillus* family members having different mutations that allow for the collection of free exosporium) can have different adjuvant properties or effects.

In addition, where exosporium fragments are used in a vaccine composition the antigen or immunogen is covalently bound to the exosporium fragment. Without being bound to any particular theory, it is thought that this increases the long-term stability of the vaccine composition and thereby allow for longer term storage of the vaccine composition, while maintaining the ability of the antigen or immunogen to elicit an immune response in an animal.

As described in greater detail below, various vaccine compositions are provided herein that contain exosporium fragments. The exosporium fragments can be derived from spores of a recombinant *Bacillus cereus* family member that expresses a fusion protein, wherein the fusion protein comprises an antigen or an immunogen. In such a case, the exosporium fragments can both act as a carrier of the antigen or immunogen in the vaccine composition and exert their adjuvant effects. In other compositions, the exosporium fragments are derived from spores of a recombinant *Bacillus cereus* family that does not express a fusion protein comprising an antigen or an immunogen. Such exosporium fragments do not carry an antigen or immunogen, but can be used as an adjuvant in vaccine compositions that contain: (1) an antigen or immunogen; (2) exosporium fragments derived from spores of a recombinant *Bacillus cereus* family member that expresses a fusion protein comprising an antigen or an immunogen; or (3) spores of a recombinant *Bacillus cereus* family member that expresses a fusion protein comprising an antigen or immunogen.

The mutations and other genetic alterations that allow for collection of free exosporium are described in Section III. Any of these mutations or other genetic alterations can be used to generate the exosporium fragments that can be included in the vaccine compositions.

a. Vaccine Compositions Containing Exosporium Fragments of a First Type and Exosporium Fragments of a Second Type A vaccine composition is provided. The composition comprises a pharmaceutically acceptable carrier. The vaccine composition also comprises exosporium fragments of a first type and exosporium fragments of a second type. The exosporium fragments of the second type are different from the exosporium fragments of the first type. The exosporium fragments of the first and second types are derived from spores of a recombinant *Bacillus cereus* family member that comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore. At least one of the exosporium fragments of the first type and the exosporium fragments of the second type comprise a fusion protein. The fusion protein comprises an antigen or an immunogen and a targeting sequence, exosporium protein, or exosporium protein fragment that targets the fusion protein to the exosporium of the recombinant *Bacillus cereus* family member.

Both the exosporium fragments of the first type and the exosporium fragments of the second type cam comprise a fusion protein. The fusion protein comprises an antigen or an immunogen and a targeting sequence, exosporium protein, or exosporium protein fragment that targets the fusion protein to the exosporium of the recombinant *Bacillus cereus* family member.

Where both the exosporium fragments of the first type and the exosporium fragments of the second type comprise a fusion protein, the exosporium fragments of the first type and the exosporium fragments of the second type can comprise fusion proteins that are identical to one another.

Alternatively, the exosporium fragments of the first type and the exosporium fragments of the second type can comprise fusion proteins that are different from one another.

For example the exosporium fragments of the first type can comprise a fusion protein comprising a first antigen or immunogen and the exosporium fragments of the second type can comprise a fusion protein comprising a second antigen or immunogen, where the first antigen or immunogen is different from the second antigen or immunogen.

Alternatively or in addition, where the exosporium fragments of the first type and the exosporium fragments of the second type comprise fusion proteins that are different from one another, the exosporium fragments of the first type can comprise a fusion protein comprising a first targeting sequence, exosporium protein, or exosporium protein fragment. The exosporium fragments of the second type comprise a fusion protein comprising a second targeting sequence, exosporium protein, or exosporium protein fragment. The first targeting sequence, exosporium protein, or exosporium protein fragment is different from the second targeting sequence, exosporium protein, or exosporium protein fragment.

In any of the vaccine compositions comprising exosporium fragments of a first type and exosporium fragments of a second type, the exosporium fragments of the first type can be derived from spores of a first species of bacteria within the *Bacillus cereus* family, and the exosporium fragments of the second type can be derived from spores of a second species of bacteria within the *Bacillus cereus* family. The second species of bacteria is different from the first species of bacteria. For example, the first species of bacteria can comprise *Bacillus thuringiensis* and the second species of bacteria can comprise *Bacillus pseudomycoides.*

In any of the vaccine compositions comprising exosporium fragments of a first type and exosporium fragments of a second type, the exosporium fragments of the first type can be derived from a spores of a recombinant *Bacillus cereus* family member that comprises a first mutation. The first mutation results in *Bacillus cereus* family member spores having an exosporium that is easier to remove from the spore as compared to the exosporium of a wild-type spore. The exosporium fragments of the second type are derived from spores of a recombinant *Bacillus cereus* family member that comprises a second mutation. The second mutation results in *Bacillus cereus* family member spores having an exosporium that is easier to remove from the spore as compared to the exosporium of a wild-type spore. The first mutation is different from the second mutation.

The first mutation and the second mutation can be independently selected from: (i) a mutation in a CotE gene; (ii) a mutation in an ExsY gene; (iii) a mutation in a CotY gene; (iv) a mutation in an ExsA gene; and (v) a mutation in a CotO gene. For example, the first mutation can comprise a knock-out of the CotE gene and the second mutation can comprise a knockout of the ExsY gene.

In any of the vaccine compositions comprising exosporium fragments of a first type and exosporium fragments of a second type, the exosporium fragments of the first type can be derived from spores of a recombinant *Bacillus cereus* family member that expresses a first protein, wherein the expression of the first protein is increased as compared to the expression of the first protein in a wild-type *Bacillus cereus* family member under the same conditions. The increased expression of the first protein results in *Bacillus cereus* family member spores having an exosporium that is easier to remove from the spore as compared to the exosporium of a wild-type spore. The exosporium fragments of the second type are derived from spores of a recombinant *Bacillus cereus* family member that expresses a second protein, wherein the expression of the second protein is increased as compared to the expression of the second protein in a wild-type *Bacillus cereus* family member under the same conditions. The increased expression of the second protein results in *Bacillus cereus* family member spores having an exosporium that is easier to remove from the spore as compared to the exosporium of a wild-type spore. The first protein is different from the second protein.

For example, the first protein and the second protein can be independently selected from: (i) an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein; (ii) a BclB protein, wherein the expression of the BclB protein is increased as compared to the expression of the BclB protein in a wild-type *Bacillus cereus* family member under the same conditions; and (iii) a YjcB protein, wherein the expression of the YjcB protein is increased as compared to the expression of the YjcB protein in a wild-type *Bacillus cereus* family member under the same conditions.

In any of the vaccine compositions comprising exosporium fragments of a first type and exosporium fragments of a second type, the exosporium fragments of the first type can be derived from spores of a recombinant *Bacillus cereus* family member that comprises a mutation, wherein the mutation results in *Bacillus cereus* family member spores having an exosporium that is easier to remove from the spore as compared to the exosporium of a wild-type spore. The exosporium fragments of the second type are derived from spores of a recombinant *Bacillus cereus* family member that expresses a protein, wherein the expression of the protein is increased as compared to the expression of the protein in a wild-type *Bacillus cereus* family member under the same conditions. The increased expression of the protein results in *Bacillus cereus* family member spores having an exosporium that is easier to remove from the spore as compared to the exosporium of a wild-type spore.

For example, the mutation can be selected from: (i) a mutation in a CotE gene; (ii) a mutation in an ExsY gene; (iii) a mutation in a CotY gene; (iv) a mutation in an ExsA gene; and (v) a mutation in a CotO gene. The protein can be selected from: (i) an ExsY protein, wherein the expression of the ExsY protein is increased as compared to the expression of the ExsY protein in a wild-type *Bacillus cereus* family member under the same conditions, and wherein the ExsY protein comprises a carboxy-terminal tag comprising a globular protein; (ii) a BclB protein, wherein the expression of the BclB protein is increased as compared to the expression of the BclB protein in a wild-type *Bacillus cereus* family member under the same conditions; and (iii) a YjcB protein, wherein the expression of the YjcB protein is increased as compared to the expression of the YjcB protein in a wild-type *Bacillus cereus* family member under the same conditions.

b. Vaccine Compositions Comprising Spores of a Recombinant *Bacillus cereus* Family Member and Exosporium Fragments Another vaccine composition is provided. The composition comprises a pharmaceutically acceptable carrier. The composition further comprises spores of a recombinant *Bacillus cereus* family member that expresses a first fusion protein. The first fusion protein comprising at least one antigen or immunogen and a targeting sequence, exosporium protein, or exosporium protein fragment that targets the first fusion protein to the exosporium of the recombinant *Bacillus cereus* family member. The composition also comprises exosporium fragments, wherein the exosporium fragments are derived from spores of a recombinant *Bacillus cereus* family member.

The exosporium fragments can be derived from a recombinant *Bacillus cereus* family member that comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore.

The exosporium fragments can be derived from spores of a recombinant *Bacillus cereus* family member that expresses a second fusion protein. The second fusion protein comprises at least one antigen or immunogen and a targeting sequence, exosporium protein, or exosporium protein fragment that targets the second fusion protein to the exosporium of the recombinant *Bacillus cereus* family member.

The first fusion protein and the second fusion protein can be identical to one another. Alternatively, the first fusion protein and the second fusion protein can be different from one another.

For example, the first fusion protein can comprise a first antigen or immunogen and the second fusion protein can comprise a second antigen or immunogen. The first antigen or immunogen is different from the second antigen or immunogen.

Alternatively or in addition, the first fusion can comprise a first targeting sequence, exosporium protein, or exosporium protein fragment. The second fusion protein comprises a second targeting sequence, exosporium protein, or exosporium protein fragment. The first targeting sequence, exosporium protein, or exosporium protein fragment is different from the second targeting sequence, exosporium protein, or exosporium protein fragment.

For vaccine compositions that comprise spores of a recombinant *Bacillus cereus* family member, the spores are preferably inactivated. Methods for inactivating spores of *Bacillus cereus* family members are described above in Section I.E and below in Section VIII.

c. Vaccine Compositions Comprising an Immunogen or Antigen and Exosporium Fragments Yet another vaccine composition is provided. The composition comprises a pharmaceutically acceptable carrier. The composition also comprises a first immunogen or antigen. The composition further comprises exosporium fragments, wherein the exosporium fragments are derived from spores of a recombinant *Bacillus cereus* family member.

The exosporium fragments can be derived from a recombinant *Bacillus cereus* family member that comprises a mutation or expresses a protein, wherein the expression of the protein is increased as compared to the expression of the protein in a wild-type *Bacillus cereus* family member under the same conditions. The mutation or the increased expression of the protein results in *Bacillus cereus* family member spores having an exosporium that is easier to remove from the spore as compared to the exosporium of a wild-type spore.

The exosporium fragments can be derived from spores of a recombinant *Bacillus cereus* family member that expresses a fusion protein. The fusion protein comprises a second antigen or immunogen and a targeting sequence, exosporium protein, or exosporium protein fragment that targets the fusion protein to the exosporium of the recombinant *Bacillus cereus* family member.

The first antigen or immunogen and the second antigen or immunogen can be the same the same.

Alternatively, the first antigen or immunogen and the second antigen or immunogen can be different from one another.

The immunogen or antigen preferably comprises a free antigen or free immunogen. The terms "free antigen" and "free immunogen" as used herein include partially purified, substantially purified, or purified antigen or immunogen.

Free antigens or immunogens can optionally be immobilized on a chemical matrix or support to allow for controlled release of the antigen or immunogen. The matrix or support can comprise charcoal, biochar, nanocarbon, agarose, an alginate, cellulose, a cellulose derivative, silica, plastic, stainless steel, glass, polystyrene, a ceramic, dolomite, a clay, diatomaceous earth, talc, a polymer, a gum, a water-dispersible material, or a combination of any thereof. Immobilization of the antigen or immunogen on the matrix or support preferably results in a slower release of the antigen or immunogen as compared to the release rate for the same non-immobilized antigen or immunogen, under the same conditions.

In addition, free antigens or immunogens can be part of a fusion protein. However, free antigens or free immunogens preferably do not include antigens or immunogens that are bound to exosporium of a *Bacillus cereus* family member. Free antigens or immunogens also preferably do not include enzymes bound to the exosporium of an intact *Bacillus cereus* family member spore.

The antigen or immunogen can be in the form of a DNA encoding the antigen or immunogen. The DNA encoding the antigen or immunogen can be administered to the animal. The antigen or immunogen is then expressed in vivo by the animal.

The term "partially purified" as used herein in reference to the antigens and immunogens means that a crude preparation of the antigen or immunogen (e.g., a cell lysate) has been subjected to procedures that remove at least some non-antigen or non-immunogen components (e.g., waste proteins, dead cell material, excess water, and/or unwanted cell debris). In a partially purified antigen or immunogen preparation, the antigen or immunogen preferably comprises at least 1% of the total protein content in the preparation, more preferably at least 2.5% of the total protein content in the preparation, and even more preferably greater than 5% of the total protein content in the preparation.

The term "substantially purified" as used herein in connection with free antigens and free immunogens means that the antigen or immunogen preparation has been subjected to procedures that remove a substantial amount of non-antigen or non-immunogen components (e.g., waste proteins, dead cell material, excess water, and/or unwanted cell debris). In a substantially purified antigen or immunogen preparation, the antigen or immunogen preferably comprises greater than 30% of the total protein content in the preparation, more preferably greater than about 40% of the total protein content in the preparation, and even more preferably greater than 50% of the total protein content in the preparation.

3. Adjuvants

In any of the vaccine compositions described herein, the vaccine can also comprise an adjuvant.

Where the vaccine composition comprises exosporium fragments, the adjuvant can provide further adjuvant effects in addition to those provided by the exosporium fragments.

For example the adjuvant can comprise Freund's complete adjuvant (FCA), Freund's incomplete adjuvant (FIA), aluminum (e.g., an aluminum salt such as aluminum hydroxide, aluminum phosphate, or aluminum sulfate), monophosphoryl lipid A, squalene, an oil-based adjuvant, a saponin, a non-metabolizable oil (e.g., a mineral oil, a plant oil, or an animal oil), polymers, carbomers, surfactants, natural organic compounds, plant extracts, carbohydrates, water-in-oil or oil-in-water emulsions, or combinations of any thereof. Suitable saponin adjuvants include the QUIL-A (Invivogen), QS-21 (Cambridge Biotech, Inc., a purified plant extract from *Quillaja saponaria* containing water-soluble triterpene glucoside compounds), and GPI-0100 (Galenica Pharmaceuticals, Inc., a semi-synthetic triterpene glycoside, derived from the naturally occurring saponins) products. Suitable emulsions include those comprising light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri-(caprylate/caprate) or propylene glycol dioleate; or esters of branched fatty acids or alcohols, in particular isostearic acid esters. The oil is used in combination with emulsifiers to form the emulsion. The emulsifiers are preferably nonionic surfactants, in particular esters of sorbitan, mannide (e.g. anhydromannitol oleate), glycol, polyglycerol, propylene glycol, and oleic, isostearic, ricinoleic or hydroxystearic acid, which are optionally ethoxylated, and polyoxypropylene-polyoxyethylene copolymer blocks, in particular the Pluronic products, especially L121. (See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997)).

Where the vaccine composition is for use to produce an immunogenic response in an aquatic animal, suitable adjuvants include, but are not limited to a yeast extract such as LIEBER beta-S (high-purity 1,3/1,6-beta-D-glucan molecules from the cell wall of *Saccharomyces cerevisiae*), NUPRO *S. cerevisiae* (nucleotide-rich *Saccharomyces cerevisiae* yeast protein), or MACROGARD (highly purified, exposed, and preserved beta 1,3/1,6 glucans produced from a strain of the yeast *Saccharomyces*; levamisole; dimer lysozyme; beta-hydroxy-methylbutyrate (HMB); and BIO-IMMUNO (a mixture of glucans and methisoprinol).

V. Non-Vaccine Methods for Protecting Animals or Aquatic Organisms from Pathogens, and Non-Vaccine Compositions and Products for Use in Protecting Animals or Aquatic Organisms from Pathogens Methods for protecting an animal from a pathogen are provided. These methods are preferably non-vaccine methods, in that the methods do not require the use of a vaccine, antigen, or immunogen. Instead the desired effect of protecting the animal from the pathogen is achieved without the use of a vaccine, antigen, or immunogen.

Spores of the recombinant *Bacillus cereus* family members expressing a fusion protein described herein or exosporium fragments derived from such spores can be used to display proteins or peptides (e.g., enzymes) that protect animals from a pathogen through antibacterial activity, antifungal activity, antibiofilm activity and/or other protective activities. The proteins or peptides that protect animals from a pathogen can exert direct antimicrobial action on their targets (e.g., bacteriocins, albumin, conalbumin, lysozymes, and lactoferrin) and/or can bind to and sequester essential nutrients that pathogens require for virulence (e.g., avidins and streptavidins). For example, LfcinB or lactoferrin can be used to lyse bacterial cells. The proteins or peptides that protect animals from a pathogen can have specific action on select microbes, and can selectively target a group of pathogens without obstructing all microbes.

A method for protecting an animal from a pathogen is provided. The method comprises administering spores of a recombinant *Bacillus cereus* family member that expresses a fusion protein to the animal, to the environment of the animal, or to the pathogen. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises administering exosporium fragments to the animal, to the environment of the animal, or to the pathogen. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The method can comprise administering the spores, the exosporium fragments, or a combination thereof to the animal.

The method preferably comprises administering the exosporium fragments.

The protein or peptide that protects the animal from a pathogen preferably does not comprise an antigen or an immunogen.

The protein or peptide that protects the animal from a pathogen preferably does not comprise a nucleic acid binding protein or peptide.

The animal can comprise a mammal, a bird, a fish, an amphibian, a reptile, a crustacean, a mollusk, a worm, an insect, a coral, or a sponge.

Where the animal comprises the mammal, the mammal can comprise a human, a monkey, a sheep, a goat, a cow, a pig, a deer, an alpaca, a bison, a camel, a donkey, a horse, a mule, a yak, a reindeer, a llama, a rabbit, a dog, a cat, a ferret, a gerbil, a guinea pig, a hamster, a mouse, a rabbit, or a rat.

Where the animal comprises the bird, the bird can comprise a chicken, a turkey, a duck, a goose, a quail, a dove, a pigeon, an ostrich, an emu, or a pheasant.

Where the animal comprises the fish, the fish can comprise a hobby fish, a salmon, a trout, a halibut, a seabass, a snapper, a grouper, a mullet, a tilapia, a tuna, a catfish, a carp, or a sturgeon.

Where the animal comprises the amphibian, the amphibian can comprise a frog, a toad, a newt, or a salamander.

Where the animal comprises the reptile, the reptile can comprise a snake, a lizards, an iguana, a crocodile, an alligator, a turtle, or a tortoise.

Where the animal comprises the crustacean, the crustacean can comprise a shrimp, a prawn, a krill, a lobster, a crab, or a crayfish.

Where the animal comprises a bird, a fish, an amphibian, a reptile, or a crustacean, the method for protecting an animal from a pathogen can comprise protecting the animal's eggs from the pathogen.

Where the animal comprises a bird, a fish, an amphibian, a reptile, or a crustacean, the method for protecting an animal from a pathogen can comprise administering the exosporium fragments or spores to the animal's eggs.

Where the animal comprises the mollusk, the mollusk can comprise a mussel, a clam, an oyster, a scallop, a snail, a slug, a squid, a cuttlefish, or an octopus.

Where the animal comprises the worm, the worm can comprise an earthworm, a nematode, a flatworm, a roundworm, a tapeworm, or a fluke.

Where the animal comprises the insect, the insect can comprise a bee, a ladybug, a butterfly, a silkworm, a fly, a beetle, or the larvae of any thereof.

The protein or peptide that protects the animal from a pathogen can have antibacterial activity, antifungal activity, antihelminthic activity, nematicidal activity, insecticidal activity, acaricidal activity, can suppress insect or worm reproduction, or a combination of any thereof.

For example, the protein or peptide that protects the animal from a pathogen can have antibacterial activity, antifungal activity, or a combination thereof The protein or peptide that protects the animal from a pathogen can comprise a bacteriocin, an avidin, a streptavidin, an antimicrobial peptide, a conalbumin, an albumin, a lactoferrin, a lactoferrin peptide, TasA, a defensin, an antibody, an antibody fragment, an enzyme, a histone, or a combination of any thereof.

The lactoferrin peptide can comprise LfcinB.

The LfcinB can comprise a *Bos taurus* lactoferrin. The amino acid sequence for a *Bos taurus* lactoferrin is provided by SEQ ID NO: 212.

The LfcinB can comprise any of the LfcinB peptides described above in Section I.B. Thus the LfcinB can comprise an amino acid sequence having at least 70%, at least 75%, at least 80%, at least 85%, at least 90%, at least 95%, at least 98%, at least 99%, or 100% sequence identity to SEQ ID NO: 212.

The ovalbumin can comprise an ovalbumin.

The antimicrobial peptide can comprise a non-ribosomal antibacterial peptide, a non-ribosomal antifungal peptide, a cecropin, a penaeidin, a bactenecin, a callinectin, a myticin, a tachyplesin, a clavanin, amisgurin, a pleurocidin, a parasin, or a combination of any thereof.

The enzyme can comprise a nuclease, a protease, a lactonase, an apyrase, a glycoside hydrolase, an alginate lyase, a glucanase, a chitosanase, a chitinase, a chitosanase-like enzyme, a lyticase, a mutanolysin, or a stapholysin, or a combination of any thereof.

Where the enzyme comprises an apyrase, the apyrase can comprise any of the apyrases described above in Section I.B. Thus, the apyrase can comprise a *Solanum tuberosum* apyrase encoded by the Rrop1 gene. The amino acid sequence for this *Solanum tuberosum* apyrase is provided by SEQ ID NO: 204.

Alternatively, the apyrase can comprise a *Bacillus subtilis* apyrase encoded by the YtkD gene. The amino acid sequence for this *Bacillus subtilis* apyrase is provided by SEQ ID NO: 205.

The apyrase can comprise an amino acid sequence having at least 70%, at least 75%, at least 80%, at least 85%, at least 90%, at least 95%, at least 98%, at least 99%, or 100% sequence identity to SEQ ID NO: 204 or 205.

Where the enzyme comprises a glycoside hydrolase, the glycoside hydrolase can comprise a lysozyme (e.g., LysM) a lysozyme peptide, dispersin B, or a combination of any thereof.

Where the glycoside hydrolase comprises LysM, the LysM can comprise a *Gallus gallus* LysM. The amino acid sequence for a *Gallus gallus* LysM is provided by SEQ ID NO: 213.

The LysM can comprise any of the LysM peptides described above in Section I.B. Thus, the LysM can comprise an amino acid sequence having at least 70%, at least 75%, at least 80%, at least 85%, at least 90%, at least 95%, at least 98%, at least 99%, or 100% sequence identity to SEQ ID NO: 213.

Where the enzyme comprises a nuclease, the nuclease can comprise a DNase (e.g., DNAseI).

The lactonase can comprise any of the lactonases described above in Section I.B. Thus, the lactonase can comprise an amino acid sequence having at least 70%, at least 75%, at least 80%, at least 85%, at least 90%, at least 95%, at least 98%, at least 99%, or 100% sequence identity to SEQ ID NO: 207 or 208.

Where the enzyme comprises a chitinase, the chitinase can comprise an endochitinase (e.g., a chitinase C) or an exochitinase (e.g., a chitinase D).

Where the chitinase comprises an endochitinase, the endochitinase can comprise a *Bacillus thuringiensis* endochitinase. An amino acid sequence for a *Bacillus thuringiensis* endochitinase is provided by SEQ ID NO: 206

The endochitinase can comprise any of the endochitinases described above in Section I.B. Thus, the endochitinase can comprise an amino acid sequence having at least 70%, at least 75%, at least 80%, at least 85%, at least 90%, at least 95%, at least 98%, at least 99%, or 100% sequence identity to SEQ ID NO: 206.

The enzyme can comprise an enzyme that is specific for a bacterial signaling molecule. For example, the enzyme can comprise a protease or a lactonase. The protease can comprise any of the proteases described herein. The lactonase can comprise any of the lactonases described herein.

The lactonase can comprise a lactonase that is specific for a bacterial lactone homoserine signaling molecule.

Where the enzyme comprises a lactonase, the lactonase can comprise a 1,4-lactonase, a 2-pyrone-4,6-dicarboxylate lactonase, a 3-oxoadipate enol-lactonase, an actinomycin lactonase, a deoxylimonate A-ring-lactonase, a gluconolactonase L-rhamnono-1,4-lactonase, a limonin-D-ring-lactonase, a steroid-lactonase, a triacetate-lactonase, a xylono-1,4-lactonase, or a combination of any thereof.

The lactonase can comprise an AiiA lactonase.

For example, the lactonase can comprise a *Bacillus thuringiensis* B184 AiiA or a *Bacillus pseudomycoides* B30 AiiA. An amino acid sequence for the *Bacillus thuringiensis* B184 AiiA is provided by SEQ ID NO: 207. An amino acid sequence for the *Bacillus pseudomycoides* B30 AiiA is provided by SEQ ID NO: 208.

The enzyme can comprise an enzyme specific for a cellular or extracellular component of a bacterium or fungus. For example, the enzyme can comprise a glucanase, a chitosanase, a chitinase, a chitosanase-like enzyme, a lyticase, a protease, a mutanolysin, a stapholysin, a lysozyme, or a combination of any thereof.

Where the enzyme comprises a glucanase, the glucanase can comprise a cellulase, β-1,3-glucanase, a β-1,4-glucanase, a β-1,6-glucanase, or a combination thereof.

Where the enzyme comprises a β-1,3-glucanase, the β-1,3-glucanase can comprise a *Bacillus circulans* β-1,3-glucanase encoded by the BglH gene. An amino acid sequence for this β-1,3-glucanase is provided by SEQ ID NO: 216.

Alternatively, the β-1,3-glucanase can comprise a *Hordeum vulgare* β-1,3-glucanase encoded by the HvGII gene. An amino acid sequence for this β-1,3-glucanase is provided by SEQ ID NO: 214.

The β-1,3-glucanase can comprise any of the β-1,3-glucanases described above in Section I.B. Thus, the β-1,3-glucanase can comprises an amino acid sequence having at least 70%, at least 75%, at least 80%, at least 85%, at least 90%, at least 95%, at least 98%, at least 99%, or 100% sequence identity to SEQ ID NO: 214 or 216.

Where the enzyme comprises a protease, the protease can comprise a peptidase (e.g., an endopeptidase or an exopeptidase), a proteinase (e.g., proteinase K), or a combination thereof.

The protease can comprise an alkaline protease, an acid protease, or a neutral protease.

The protease can comprise a serine protease.

For example, the serine protease can comprise a *Bacillus subtilis* serine protease. The *Bacillus subtilis* serine protease can comprise any of the *Bacillus subtilis* serine proteases described above in Section I.B. Thus, the *Bacillus subtilis* serine protease can comprise an amino acid sequence having at least 80%, at least 85%, at least 90%, at least 95%, at least 98%, at least 99%, or 100% sequence identity to SEQ ID NO: 209.

The *Bacillus subtilis* serine protease can comprise an amino acid sequence having at least 80%, at least 85%, at least 90%, at least 95%, at least 98%, at least 99%, or 100% sequence identity to SEQ ID NO: 210.

The protein or peptide that protects the animal from a pathogen can have antihelminthic activity, nematicidal activity, insecticidal activity, acaricidal activity, can suppress insect or worm reproduction, or a combination of any thereof.

The protein or peptide that protects the animal from a pathogen can comprise an insecticidal bacterial toxin (e.g., a VIP insecticidal protein), an acaricidal bacterial toxin, an endotoxin (e.g., a delta endotoxin), a Cry toxin, a protease inhibitor protein or peptide (e.g., a trypsin inhibitor or an arrowhead protease inhibitor), a secreted insecticidal (Sip) protein, a mosquitocidal toxin (e.g., an Mtx1-like mosquitocidal toxin, a Bin-like mosquitocidal toxin, or a combination thereof), a cysteine protease, a *Bacillus subtilis* serine protease, a chitinase, or a combination of any thereof.

The chitinase can comprise any of the chitinases described herein (e.g., any of the endochitinases described herein).

The *Bacillus subtilis* serine protease can comprise any of the *Bacillus subtilis* serine proteases described herein.

The Mtx1-like mosquitocidal toxin can comprise Mtx1.

The Mtx1 can comprise any of the Mtx1 toxins described above in Section I.B. Thus, for example, the Mtx1 can comprise a *Bacillus sphaericus* Mtx1. An amino acid sequence for a *Bacillus sphaericus* Mtx1 is provided by SEQ ID NO: 211.

The Mtx1 can comprise an amino acid sequence having at least 70%, at least 75%, at least 80%, at least 85%, at least 90%, at least 95%, at least 98%, at least 99%, or 100% sequence identity to SEQ ID NO: 211.

The Cry toxin can comprise a Cry toxin from *Bacillus thuringiensis*.

The Cry toxin can comprise a Cry5B protein, a Cry21A protein, a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, a Cyt1Aa protein, or a combination of any thereof.

For example, the Cry toxin can comprise a Cry21A protein.

The Cry21A protein can comprise a *Bacillus thuringiensis* Cry21A protein. An amino acid sequence for a *Bacillus thuringiensis* Cry21A protein is provided by SEQ ID NO: 215.

The Cry21A protein can comprise any of the Cry21A proteins described above in Section I.B. Thus, the Cry21A protein can comprise an amino acid sequence having at least 70%, at least 75%, at least 80%, at least 85%, at least 90%, at least 95%, at least 98%, at least 99%, or 100% sequence identity to SEQ ID NO: 215.

The pathogen can comprise a bacterial pathogen, a fungal pathogen, a pathogenic worm, a pathogenic insect, a pathogenic arachnid, a pathogenic protist, or a combination of any thereof.

The bacterial pathogen can comprise a bacterial pathogen of the genus *Staphylococcus*, a bacterial pathogen of the genus *Hemophilus*, a bacterial pathogen of the genus *Pseudomonas*, a bacterial pathogen of the genus *Streptococcus*, a bacterial pathogen of the genus *Mycobacterium*, a bacterial pathogen of the genus *Clostridium*, a bacterial pathogen of the genus Enterobacteriaceae, a bacterial pathogen of the genus *Enterococcus*, a bacterial pathogen of the genus *Aeromonas*, a bacterial pathogen of the genus *Acinetobacter*, a bacterial pathogen of the genus *Fusobacterium*, a bacterial pathogen of the genus *Prevotella*, a bacterial pathogen of the genus *Flavobacterium*, a bacterial pathogen of the genus *Edwardsiella*, a bacterial pathogen of the genus *Anaplasm*, a bacterial pathogen of the genus *Bacillus*, a bacterial pathogen of the genus *Bartonella*, a bacterial pathogen of the genus *Bordetella*, a bacterial pathogen of the genus *Borrelia*, a bacterial pathogen of the genus *Brucella*, a bacterial pathogen of the genus *Burkolderia*, a bacterial pathogen of the genus *Chlamydophilia*, a bacterial pathogen of the genus *Coxiella*, a bacterial pathogen of the genus *Ehrlichia*, a bacterial pathogen of the genus *Helicobacter*, a bacterial pathogen of the genus *Klebsiella*, a bacterial pathogen of the genus *Lasonia*, a bacterial pathogen of the genus *Leptospira*, a bacterial pathogen of the genus *Mycoplasma*, a bacterial pathogen of the genus *Neorickettsia*, a bacterial pathogen of the genus *Pasteurella*, a bacterial pathogen of the genus *Rickettsia*, a bacterial pathogen of the genus *Salmonella*, or a combination of any thereof.

For example, the bacterial pathogen can comprise *Acinetobacter baumannii, Aeromonas hydrophila, Anaplasma phagocytophila, Anaplasma phagocytophilum, Anaplasma platys, Bacillus anthracis, Bartonella henselae, Bartonella rochalimae, Bartonella vinsonii subspecies berkhoffii, Bordetella bronchiseptica, Borrelia theileri, Borrelia burgdorferi, Brucella abortus, Brucella melitensis, Brucella suis, Burkholderia mallei, Burkholderia pseudomallei, Chlamydophila abortus, Chlamydophila felis, Chlamydophila psittaci, Clostridium botulinum, Clostridium difficile, Clostridium perfringens, Clostridium piliforme, Clostridium tetani, Coxiella burnetti, Edwardsiella ictaluri, Ehrlichia canis, Ehrlichia chaffeensis, Ehrlichia ewingii, Ehrlichia ruminantium, Enterococcus faecalis, Erysipelothrix rhusiopathiae, Flavobacterium columnare, Fusobacterium necrophorum, Hemophilus influenzae, Haemobartonella felis, Helicobacter hepaticus, Klebsiella pneumoniae, Lawsonia intracellularis, Leprospira Pomona, Leptospira autumnalis, Leptospira ballum, Leptospira canicola, Leptospira grippotyphosa, Leptospira icterohaemorrhagiae, Leptospira interrogans sensu lato, Mycobacterium avium* group, *Mycobacterium bovis, Mycobacterium fortuitum, Mycobacterium microti, Mycobacterium paratuberculosis, Mycobacterium tuberculosis, Mycoplasma agalactiae, Mycoplasma capricolum capricolum, Mycoplasma capricolum* subspecies *capripneumoniae, Mycoplasma felis, Mycoplasma mycoides* Capri, *Mycoplasma mycoides* subspecies *mycoides, Mycoplasma putrefasciens, Neorickettsia elokominica, Neorickettsia helminthoeca, Neorickettsia risticii, Pasteurella multocida, Pseudomonas aeruginosa, Prevotella melaninogenicus, Rickettsia prowazekii, Rickettsia typhi, Spiroplasma mirum, Staphylococcus aureus, Staphylococcus epidermidis, Staphylococcus pseudintermedius, Streptococcus pneumoniae, Streptococcus pyogenes, Streptococcus bovis, Streptococcus* Group A, *Streptococcus* Group B, *Streptococcus* Group C, *Streptococcus* Group D, *Streptococcus* Group G, *Streptococcus equi* subspecies equi, *Streptococcus equi* subspecies *zooepidemicus, Taylorella equigenitalis*, or a combination of any thereof.

The fungal pathogen can comprise a fungal pathogen of the genus *Aspergillus*, a fungal pathogen of the genus *Microsporum*, a fungal pathogen of the genus *Cryptococcus*, a fungal pathogen of the genus *Chrysosporium*, a fungal pathogen of the genus *Encephalitozoon*, a fungal pathogen of the genus *Enterocytozoon*, a fungal pathogen of the genus *Fusarium*, a fungal pathogen of the genus *Lichtheimia*, a fungal pathogen of the genus *Malassezia*, a fungal pathogen of the genus *Trichophyton*, a fungal pathogen of the genus *Mortierella*, a fungal pathogen of the genus *Mycor*, a fungal pathogen of the genus *Absidia*, a fungal pathogen of the genus *Rhizopus*, a fungal pathogen of the genus *Cladosporium*, a fungal pathogen of the genus *Scopulariopsis*, a fungal pathogen of the genus *Prototheca*, a fungal pathogen of the genus *Pythium*, a fungal pathogen of the genus *Rhodotorula*, a fungal pathogen of the genus *Stachybotrys*, a fungal pathogen of the genus *Lagenidium*, a fungal pathogen of the genus *Sirolpidium*, a fungal pathogen of the genus *Candida*, or a combination of any thereof.

The fungal pathogen can comprise an opportunistic dematiaceous fungal pathogen.

The fungal pathogen can comprise *Chrysosporium parvum, Encephalitozoon cuniculi, Lichtheimia corymbifera, Lagenidium myophilum, Mortierella wolfii, Stachybotrys chartarum, Cryptococcus neoformans, Candida albicans, Trichophyton verrucosum, Trichophyton equinum, Trichophyton mentagrophytes*, or a combination of any thereof.

The pathogenic worm can comprise a nematode, a helminth, a roundworm, a pinworm, a whipworm, a threadworm, a cecal worm, a stomach worm, a hairworm, a threadnecked worm, a fluke, a tapeworm, or a of any combination thereof.

For example, the pathogenic worm can comprise *Ascaris suum, Trichinella spiralis, Trichuris suis, Ascaris lumbricoides, Ascaris* spp., *Trichinella* sp., *Ostertagia ostertagi, Haemonchus placei, Cooperia oncophora, Dictyocaulus viviparus, Fasciola hepatica, Haemonchus contortus, Nematodirus battus, Strongyloides* sp., *Ancylostoma caninum, Toxocara canis, Toxocara cati, Taenia taeniaeformis*, or a combination of any thereof.

The pathogenic insect can comprise an endoparasite, an ectoparasite, or a combination thereof.

The ectoparasite can be selected from fleas, ticks, lice, mites, flies, mosquitoes, the larvae of any thereof, and combinations of any thereof.

The endoparasite can be selected from heel flies, bomb flies, bot flies, *Gasterophilus* sp., the larvae of any thereof, and combinations of any thereof.

The pathogenic protist can comprise a protist of the genus *Babesia*, a protist of the genus *Neospora*, a protist of the genus *Sarcocystis*, a protist of the genus *Theileria*, a protist of the genus *Trypanosoma*, a protist of the genus *Entamoeba*, a protist of the genus *Giardis*, a protist of the genus *Cryptosporidium*, a protist of the genus *Trichomonas*, a protist of the genus *Toxoplasma*, a protist of the genus *Plasmodium*, a protist of the genus *Coccidia*, a protist of the genus *Leishmania*, a protist of the genus *Cryptosporidia*, a protist of the genus *Cyclospora*, a protist of the genus *Eimeria*, a protist of the genus *Naeglaria*, a protist of the genus *Sarcocystis*, a protist of the genus *Neosporia*, a protist of the genus *Blastocystis*, a protist of the genus *Microsporidia*, or a combination of any thereof.

For example, the pathogenic protist can comprise *Entamoeba histolytica, Babesia bovis, Babesia bigemina, Babesia canis, Eimeria maxima, Eimeria tenella, Giardia duodenalis, Leishmania donovani, Neospora caninum, Sarcocystis neurona, Theileria parva, Theileria annulata, Theileria hirci, Toxoplasma gondii*, or a combination of any thereof.

A. Aquaculture Compositions and Methods

Compositions for use in aquaculture and methods for protecting aquatic organisms from pathogens are provided herein. Many pathogens are problematic in aquaculture. Bacterial and fungal pathogens can directly infect aquatic organisms in an aquaculture system. In addition, biofilms often form in aquaculture systems. Biofilms can form on the organisms in the aquaculture system themselves (e.g., on the gills of fish) or on surfaces within the aquaculture system (e.g., pipes, tanks, pumps, or filters). Thus, there is a need for methods to protect aquatic organisms in aquaculture systems from pathogens.

A composition is provided. The composition comprises a carrier acceptable for use in aquaculture and exosporium fragments. The exosporium fragments are derived from spores of a recombinant *Bacillus cereus* family member and comprise a fusion protein. The fusion protein comprises at least one protein or peptide that protects an aquatic organism from a pathogen and a targeting sequence, exosporium protein, or exosporium protein fragment that targets the fusion protein to the exosporium of the recombinant *Bacillus cereus* family member.

The carrier can comprise a hydrophobic polymer. Use of a hydrophobic polymer can aid the composition in adhering to surfaces within an aquaculture system.

The composition can be in the form of a dry powder or a water-dispersible granule.

In any of the compositions for use in aquaculture, the protein or peptide that protects an aquatic organism from a pathogen comprises an apyrase, a dispersin B, or a combination thereof. The apyrase can be any of the apyrases discussed herein, including any of the apyrases discussed above in Section I.B.

A method is provided for protecting an aquatic organism from a pathogen. The method comprises cultivating the aquatic organism in an aquaculture system. Spores of a recombinant *Bacillus cereus* family member that expresses a fusion protein are introduced into the aquaculture system. The fusion protein comprises at least one protein or peptide that protects the aquatic organism from a pathogen and a targeting sequence, exosporium protein, or exosporium protein fragment that targets the fusion protein to the exosporium of the recombinant *Bacillus cereus* family member. The aquatic organism is selected from fish, amphibians, reptiles, crustaceans, mollusks, worms, coral, sponges, red algae, brown algae, or combinations of any thereof.

Alternatively or in addition, the method comprises cultivating the aquatic organism in an aquaculture system. Exosporium fragments are introduced into the aquaculture system. The exosporium fragments are derived from spores of a recombinant *Bacillus cereus* family member and comprise a fusion protein. The fusion protein comprises at least one protein or peptide that protects the aquatic organism from a pathogen and a targeting sequence, exosporium protein, or exosporium protein fragment that targets the fusion protein to the exosporium of the recombinant *Bacillus cereus* family member. The aquatic organism is selected from fish, amphibians, reptiles, crustaceans, mollusks, worms, coral, sponges, red algae, brown algae, or combinations of any thereof.

In any of the aquaculture compositions or methods, the protein or peptide that protects the aquatic organism from a pathogen preferably does not comprise an antigen or an immunogen.

The aquatic organism can comprise red algae, brown algae, or a combination thereof.

The brown algae can comprise seaweed (e.g., nori, kelp, or a combination thereof).

A method for protecting an aquatic animal from a pathogen is provided. The method comprises cultivating the aquatic animal in an aquaculture system and administering spores or exosporium fragments to the aquatic animal by introducing the spores or exosporium fragments into the aquaculture system. The spores are spores of a recombinant *Bacillus cereus* family member that expresses a fusion protein, wherein the fusion protein comprises at least one protein or peptide that protects the animal from a pathogen and a targeting sequence, exosporium protein, or exosporium protein fragment that targets the fusion protein to the exosporium of the recombinant *Bacillus cereus* family member and the protein or peptide that protects the animal from a pathogen does not comprise an antigen or an immunogen. The exosporium fragments are derived from spores of a recombinant *Bacillus cereus* family member and comprise a fusion protein, wherein the fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

In any of the methods involving the use of an aquaculture system, the method preferably comprises introducing the exosporium fragments into the aquaculture system.

For any of the compositions for use in aquaculture or any of the methods involving the use of an aquaculture system, the aquatic organism or the aquatic animal can comprise a fish, an amphibian, a reptile, a crustacean, a mollusk, a worm, a coral, a sponge, or a combination of any thereof.

Where the aquatic organism or the aquatic animal comprises the fish, the fish can comprise a salmon, a trout, a halibut, a seabass, a snapper, a grouper, a mullet, a tilapia, a tuna, a catfish, a carp, a sturgeon, or a combination of any thereof.

Where the aquatic organism or the aquatic animal comprises the amphibian, the amphibian can comprise a frog, a toad, a newt, a salamander, or a combination of any thereof.

Where the aquatic organism or the aquatic animal comprises the reptile, the reptile can comprise a snake, a lizard, a crocodile, an alligator, a turtle, a tortoise, or a combination of any thereof.

The aquatic organism the or aquatic animal can comprise a frog, a toad, an alligator, a turtle, or a combination of any thereof.

Where the aquatic organism or the aquatic animal comprises a crustacean, the crustacean can comprise a shrimp, a prawn, a krill, a lobster, a crab, a crayfish, or a combination of any thereof.

Where the aquatic organism or the aquatic animal comprises a mollusk, the mollusk can comprise a mussel, a clam, an oyster, a scallop, a snail, a slug, a squid, a cuttlefish, or octopus, or a combination of any thereof.

In any of the methods involving the use of an aquaculture system, the method can prevent or treat a disease of the aquatic organism or the aquatic animal caused by the pathogen.

In any of the methods involving the use of an aquaculture system, the method can prevent or inhibit biofilm formation or promotes dissolution of a biofilm on a surface within the aquaculture system (e.g., a surface of a pipe, a tank, a pump, a filter, or a combination of any thereof).

In any of the methods involving the use of an aquaculture system, introducing the exosporium fragments or spores into the aquaculture system can comprise adding the exosporium fragments or spores to water in the aquaculture system.

In any of the methods involving the use of an aquaculture system, introducing the exosporium fragments or spores into the aquaculture system can comprise applying the exosporium fragments or spores to a surface within the aquaculture system (e.g., a surface of a pipe, a tank, a pump, a filter, or a combination of any thereof).

In any of the methods involving the use of an aquaculture system, introducing the exosporium fragments or spores into the aquaculture system can comprise dipping the aquatic organism or the aquatic animal into a solution comprising the exosporium fragments or spores.

The aquaculture system can be a freshwater aquaculture system.

The aquaculture system can be a saltwater aquaculture system.

The aquaculture system can be a brackish water aquaculture system.

The exosporium fragments or spores can be introduced into the aquaculture system in a composition comprising the exosporium fragments or spores and a carrier.

Examples of proteins or peptides that protect the animal or the aquatic animal from a pathogen that can be used in any of aquaculture compositions or in any of the methods involving the use of an aquaculture system include, but are not limited, to apyrases, proteases (e.g., a *Bacillus subtilis* serine protease), chitinases, glucanases (e.g., β-1,3-glucanase), antimicrobial proteins or peptides (e.g., a lactoferrin peptide), and lactonases. Combinations of any of these proteins or peptides can also be used.

Where the protein or peptide comprises an apyrase, the apyrase can comprise any of the apyrases described herein, including any of the apyrases described in Section I.B.

The protease can comprise a *Bacillus subtilis* serine protease. Where the protease comprises a *Bacillus subtilis* serine protease, the *Bacillus subtilis* serine protease can comprise any of the *Bacillus subtilis* serine proteases described herein, including the *Bacillus subtilis* serine proteases described in Section I.B. For example, the *Bacillus subtilis* serine protease can comprise an amino acid sequence having at least 80%, at least 85%, at least 90%, at least 95%, at least 98%, at least 99%, or 100% sequence identity to SEQ ID NO: 209 or 210.

Where the protein or peptide comprises a chitinase, the chitinase can comprise any of the chitinases described herein, including any of the endochitinases described in Section I.B.

Where the protein or peptide comprises a glucanase, the glucanase can comprise any of the glucanases described herein, including any of the β-1,3-glucanases described in Section I.B.

Where the protein or peptide comprises a lactonase, the lactonase can comprise any of the lactonases described herein, including any of the AiiA lactonases described in Section I.B.

Where the antimicrobial protein or peptide comprises a lactoferrin peptide, the lactoferrin peptide can comprise a LfcinB. The LfcinB can comprise any of the lactoferrin peptides described herein, including any of the LfcinB peptides described in Section I.B.

For any of the aquaculture compositions or for any of the methods involving the use of an aquaculture system, the pathogen can comprise a fungal pathogen of the genus *Lagenidium*, a fungal pathogen of the genus *Sirolpidium, Aeromonas hydrophila*, or a combination of any thereof.

B. Methods for the Treatment or Prevention an Infection in a Wound, Adhesive Patches, Wound Dressings, and Compositions for Use in Connection with the Methods, Adhesive Patches, and Wound Dressings Methods for protecting an animal from a pathogen by preventing or treating an infection of a wound in an animal are provided.

A method of protecting an animal from a pathogen is provided. The method comprises administering spores to the animal by applying the spores to a wound of the animal. The spores are spores of a recombinant *Bacillus cereus* family member that expresses a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises administering exosporium fragments to the animal by applying the exosporium fragments to a wound of the animal. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The method preferably comprises applying the exosporium fragments to the wound of the animal.

The method can prevent or treat an infection of the wound.

The method can prevent or inhibit biofilm formation in the wound or promote dissolution of a biofilm within the wound.

The method can comprise applying the exosporium fragments or spores to the wound in a pharmaceutical composition comprising the exosporium fragments or spores and a pharmaceutically acceptable carrier.

The composition can comprise a solution, a lotion, a cream, an ointment, a gel, a foam, a spray, a dip, or a bath.

Any of the pharmaceutical compositions described herein can comprise a solution, a lotion, a cream, an ointment, a gel, a foam, a spray, a dip, or a bath. Such compositions are suitable for application to a wound of an animal.

Any of the pharmaceutical compositions described herein can be provided in an adhesive patch or a wound dressing.

An adhesive patch or wound dressing comprising a pharmaceutical composition is provided. The pharmaceutical composition comprises a pharmaceutically acceptable carrier and spores of a recombinant *Bacillus cereus* family member that expresses a fusion protein. The fusion protein comprising at least one protein or peptide that protects an animal from a pathogen and a targeting sequence, exosporium protein, or exosporium protein fragment that targets the fusion protein to the exosporium of the recombinant *Bacillus cereus* family member.

Alternatively or in addition, the adhesive patch or wound dressing can comprise a pharmaceutical composition comprising a pharmaceutically acceptable carrier and exosporium fragments. The exosporium fragments are derived from spores of a recombinant *Bacillus cereus* family member and comprise a fusion protein. The fusion protein comprises at least one protein or peptide that protects an animal from a pathogen and a targeting sequence, exosporium protein, or exosporium protein fragment that targets the fusion protein to the exosporium of the recombinant *Bacillus cereus* family member.

In any of the methods involving application of exosporium fragments or spores to a wound of an animal, in any of the compositions suitable for application to a wound of an animal, or in any of the adhesive patches or wound dressings, the protein or peptide that protects the animal from a pathogen can comprise, for example, an enzyme an antibacterial peptide, an endotoxin (e.g., a delta endotoxin), a Cry protein, an antifungal peptide or protein, or a combination of any thereof.

The enzyme can comprise an apyrase, a lactonase, a protease, a glucanase, a chitinase, or a combination of any thereof.

Where the enzyme comprises an apyrase, the apyrase can comprise any of the apyrases described herein, including any of the apyrases described in Section I.B.

Where the enzyme comprises a lactonase, the lactonase can comprise any of the lactonases described herein, including any of the AiiA lactonases described in Section I.B.

Where the enzyme comprises an antibacterial peptide, the enzyme can comprise any of the antibacterial peptides described herein, including any of the LfcinB or LysM peptides described in Section I.B.

In any of the methods involving application of exosporium fragments or spores to a wound of an animal, in any of the compositions suitable for application to a wound of an animal, or in any of the adhesive patches or wound dressings, the pathogen can comprises a bacterial pathogen of the genus *Streptococcus*, a bacterial pathogen of the genus *Staphylococcus*, a bacterial pathogen of the genus *Pseudomonas*, a bacterial pathogen of the genus *Enterococcus*, or a combination of any thereof. Alternatively or in addition, the pathogen can comprise *Acinetobacter baumannii.*

C. Methods for the Prevention or Treatment of Hoof Infections, Insert Trays for Livestock Footbaths, and Hoof Bandages Methods for protecting an animal from a pathogen by preventing or treating hoof infections in a hooved animal are provided. Such methods can be used, for example, for treating infectious pododermatitis (also known as hoof rot or foot rot) or Leptospirosis.

A method for protecting a hooved animal from a pathogen is provided. The method comprises applying spores to one or more hooves of the animal. The spores are spores of a recombinant *Bacillus cereus* family member that expresses a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises applying exosporium fragments to one or more hooves of the hooved animal. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The method preferably comprises applying the exosporium fragments to the one or more hooves of the animal.

The method can prevent or treat an infectious disease that affects the hooves of the animal.

The infectious disease can comprise infectious pododermatitis or Leptospirosis, thrush, white line disease, an infection caused by a bacterial pathogen of the genus *Treponema*, an infection caused by a bacterial pathogen of the genus *Dichelobacter*, an infection caused by a bacterial pathogen of the genus *Fusobacterium*, an infection caused by a bacterial pathogen of the genus *Actinomyces*, or a combination of any thereof.

The hooved animal can comprise a cow, a sheep, a bison, a buffalo, a deer, a horse, a mule, a camel, a pig, or a goat.

Applying the exosporium fragments or spores to the one or more hooves of the animal can comprise the use of a footbath. For example, the method can comprise walking the animal through a footbath containing a composition comprising the exosporium fragments or spores and a carrier. The composition can be present in the footbath at a depth that is sufficient for the composition to make contact with an infected area of the animal's hoof as the animal walks through the footbath. The composition can comprise a liquid, a semisolid, a water-dispersible granule, a dissolvable powder, a foam, a lotion, or a gel. For example, the composition can comprise a liquid concentrate or powder for use in a footbath.

Moreover, any of the pharmaceutical compositions described herein can comprise a liquid, a semisolid, a water-dispersible granule, a dissolvable powder, a foam, a lotion, or a gel. For example, any of the pharmaceutical compositions described herein can comprise a liquid concentrate or powder for use in a footbath. Such compositions are suitable for use in connection with the methods that comprise applying spores or exosporium fragments to one or more hooves of a hooved animal.

An insert tray for a livestock footbath is provided. The insert tray comprises spores of a recombinant *Bacillus cereus* family member that expresses a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member. The spores are immobilized on an inner surface of the insert tray.

Alternatively or in addition, the insert tray comprises exosporium fragments. The exosporium fragments are derived from spores of a recombinant *Bacillus cereus* family member and comprise a fusion protein. The fusion protein comprising at least one protein or peptide that protects a hooved animal from a pathogen and a targeting sequence, exosporium protein, or exosporium protein fragment that targets the fusion protein to the exosporium of the recombinant *Bacillus cereus* family member. The exosporium fragments are immobilized on an inner surface of the insert tray.

The insert tray can be inserted into a livestock footbath. The term "inner surface" as used herein in reference to the insert tray means the surface of the insert tray that would come into contact with the hoof of a hooved animal when the hooved animal steps into the footbath.

The spores or exosporium fragments can be immobilized on the inner surface of the insert tray by spray drying the spores or exosporium fragments onto the surface. The spores or exosporium fragments would then be released from the surface of the insert tray upon addition of water to the insert tray by the end user.

The insert tray preferably comprises the exosporium fragments.

When footbaths are used and the hooved animals are dairy animals, the application methods and dosage regimens will generally depend in part on the frequency of milking, since the footbath units are generally accessible to the animals as they make their way from the milking parlor back to their stalls, corrals, barns, or pastures.

Footbath applications typically comprise a tank filled with at least about 4 to 6 inches of composition, or enough to cover any abscess, sole bruise, interdigital skin, interdigital cleft, or any area where there is foot rot, hairy foot warts or laminitis on the hoof. The composition should be deep enough so as to make contact with any infected area of the hoof.

Foam applications are effective where the foam composition can be applied directly to the hoof in order to insure the hoof is thoroughly coated with the foam.

Gel applications can be used in a footbath system as a replacement for a liquid dip composition. The main advantage of gels are their thickness, which allows the for a longer contact period between the composition and the hoof.

In any of the methods that comprise applying exosporium fragments or spores to one or more hooves of a hooved animal, the exosporium fragments or spores can be applied to the one or more hooves of the animal using a hoof bandage. The hoof bandage can comprise a composition comprising the exosporium fragments or spores and a carrier.

A hoof bandage is provided. The hoof bandage comprises a pharmaceutical composition. The pharmaceutical composition comprises a pharmaceutically acceptable carrier and spores of a recombinant *Bacillus cereus* family member that expresses a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member.

Alternatively or in addition, the hoof bandage comprises a pharmaceutical composition comprising a pharmaceutically acceptable carrier and exosporium fragments. The exosporium fragments are derived from spores of a recombinant *Bacillus cereus* family member and comprise a fusion protein. The fusion protein comprises at least one protein or peptide that protects a hooved animal from a pathogen and a targeting sequence, exosporium protein, or exosporium protein fragment that targets the fusion protein to the exosporium of the recombinant *Bacillus cereus* family member.

The spores or exosporium fragments can be immobilized on a surface of the bandage that contacts the hoof of a hooved animal.

The pharmaceutical composition in the hoof bandage preferably comprises the exosporium fragments.

The surface of the hoof bandage that contacts the hoof of a hooved animal can comprise a fabric or a foam, and immobilizing the spores or exosporium fragments on the surface of the hoof bandage can comprise soaking the fabric or foam in a solution comprising the spores or exosporium fragments. Alternatively or in addition, the spores or exosporium fragments can be suspended in an oil, an emulsion, a polymer, or a gel. The hoof bandage can then be impregnated with the oil, emulsion, polymer, or gel. The exosporium fragments or spores would then be released from the bandage when the bandage is applied to the hoof of the hooved animal by the end user.

Hoof bandages allow the infected hoof to be kept free of water and prolong contact of the composition with the infected hoof.

In any of the methods that comprise applying exosporium fragments or spores to one or more hooves of a hooved animal, in any of the compositions that are suitable for use in such methods, in any of the insert trays, or in any of the hoof bandages, the protein or peptide that protects the animal from a pathogen can comprise a lactoferrin or lactoferrin peptide (e.g., LfcinB), a lysozyme or lysozyme peptide (e.g., LysM), a protease, a glucanase, an antimicrobial peptide or protein, an apyrase, a lactonase, or a combination of any thereof.

The LfcinB can comprise any of the LfcinB peptides described herein, including any of the LfcinB peptides described in Section I.B.

The LysM can comprise any of the LysM peptides described herein, including any of the LysM peptides described in Section I.B.

The protease can comprise any of the proteases described herein, including any of the *Bacillus subtilis* serine proteases described in Section I.B.

The glucanase can comprise any of the glucanases described herein, including any of the β-1,3-glucanases described in Section I.B.

The apyrase can comprise any of the apyrases described herein, including any of the apyrases described in Section I.B.

The lactonase can comprise any of the lactonases described herein, including any of the AiiA lactonases described in Section I.B.

For any of the methods that comprise applying exosporium fragments or spores to one or more hooves of a hooved animal, for any of the compositions that are suitable for use in such methods, for any of the insert trays, or for any of the hoof bandages, the pathogen can comprise *Fusobacterium necrophorum, Prevotella melaninogenicus, Chrysosporium parvum*, a bacterial pathogen of the genus *Leptospira*, a bacterial pathogen of the genus *Actinomyces*, a bacterial pathogen of the genus *Treponema, Dichelobacter nodosus*, a bacterial pathogen of the genus *Fusobacterium*, or a combination of any thereof.

The pathogen can comprise a mixture of two or more pathogens.

D. Methods for Preventing or Treating Bloat in Ruminants, Feed, and Feed Additives Methods for preventing or treating bloat in ruminants are provided. Feedlot bloat (ruminal acidosis) occurs when large amounts of starch are added to the diet. Under these conditions, the growth of certain bacteria such as *Streptococcus bovis* is no longer restricted by a lack of this energy source and the bacterial population of *S. bovis* grows faster than other species of rumen bacteria. *S. bovis* produces lactic acid, an acid ten times stronger than acetic, propionic or butyric acid, the accumulation of which eventually exceeds the buffering capacity of rumen fluid resulting in disease.

A method for protecting a ruminant animal from a pathogen is provided. The method comprises orally administering spores to the ruminant. The spores are spores of a recombinant *Bacillus cereus* family member that expresses a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises orally administering exosporium fragments to the ruminant. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The method preferably comprises orally administering the exosporium fragment to the ruminant.

For example, the spores or the exosporium fragments can be orally administered to the ruminant by feeding the spores or the exosporium fragments to the ruminant.

The ruminant can comprise a cow, a sheep, a bison, a goat, a deer, or a horse.

The method can treat or prevent bloat in the ruminant.

Feed and feed additives are provided. The feed or feed additive comprises exosporium fragments, wherein the exosporium fragments are derived from spores of a recombinant *Bacillus cereus* family member and comprise a fusion protein, the fusion protein comprising at least one protein or peptide that protects an animal from a pathogen and a targeting sequence, exosporium protein, or exosporium protein fragment that targets the fusion protein to the exosporium of the recombinant *Bacillus cereus* family member.

In any of the methods for protecting a ruminant animal from a pathogen or in any of the feed or feed additives, the protein or peptide that protects the animal from a pathogen can comprise a lactoferrin or lactoferrin peptide (e.g., LfcinB), a lysozyme or lysozyme peptide (e.g., LysM), an antimicrobial protein or peptide, an enzyme (e.g., apyrase, a protease, a glucanase, a lactonase, or a combination of any thereof), or a combination of any thereof.

The LfcinB can comprise any of the LfcinB peptides described herein, including any of the LfcinB peptides described in Section I.B.

The LysM can comprise any of the LysM peptides described herein, including any of the LysM peptides described in Section I.B.

The apyrase can be any of the apyrases described herein, including any of the apyrases described in Section I.B.

The protease can comprise any of the proteases described herein, including any of the *Bacillus subtilis* serine proteases described in Section I.B.

The glucanase can comprise any of the glucanases described herein, including any of the β-1,3-glucanases described in Section I.B.

The lactonase can comprise any of the lactonases described herein, including any of the AiiA lactonases described in Section I.B.

The pathogen can comprise *Streptococcus bovis, Fusobacterium necrophorum*, or a combination thereof.

E. Methods and Compositions for Preventing or Treating Mastitis in Animals

Methods for preventing or treating mastitis in animals are provided.

A method for protecting an animal from a pathogen is provided. The method comprises administering spores to an animal for prevention or treatment of mastitis. The spores are spores of a recombinant *Bacillus cereus* family member that expresses a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises administering exosporium fragments to the animal for prevention or treatment of mastitis. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The method preferably comprises administering the exosporium fragments.

The animal can comprise a dairy animal

The animal can comprise a goat, a cow, a sheep, a buffalo, a camel, a yak, a horse, a reindeer, a human, a dog, a cat, or a donkey.

The method can comprise administering the exosporium fragments or spores in a composition comprising the exosporium fragments or spores and a pharmaceutically acceptable carrier.

The composition can be applied topically to the udder or teat of the animal.

The topical administration can comprise dipping the udder or teat of the animal into the composition, spraying the composition onto the udder or teat of the animal, or a composition thereof.

The mastitis can comprise fungal mastitis (e.g., fungal mastitis caused by *Cryptococcus neoformans, Candida albicans*, a fungal pathogen of the genus *Prototheca*, or a combination thereof).

The mastitis can comprise bacterial mastitis (e.g., bacterial mastitis caused by a bacterial pathogen of the genus *Staphylococcus*, a bacterial pathogen of the genus *Escherichia*, or a combination thereof).

Where the mastitis comprises bacterial mastitis, the method can further comprise coadministration of an antibiotic.

Any of the pharmaceutical compositions described herein can be in the form of a teat dip composition. Such compositions are suitable for use in the methods for prevention or treatment of mastitis.

The composition can further comprise an antibiotic.

However, one of the advantages of the compositions and methods for preventing or treating mastitis described herein is that they can avoid the overuse of antibiotics. Thus, the method preferably does not further comprise co-administration of an antibiotic. Likewise, the composition preferably does not further comprise an antibiotic.

In methods or compositions where an antibiotic is used, the antibiotic can comprise a β-lactam (e.g., amoxicillin, ceftiofur, cephapirin, cloxicillin, hetacillin, penicillin, or a combination of any thereof), a lincosamide (e.g., pirlimycin), or a combination thereof.

In any of the methods for prevention or treatment of mastitis or in any of the compositions suitable for use in methods for prevention or treatment of mastitis, the protein or peptide that protects the animal from a pathogen can comprise a glucanase (e.g., β-1,3-glucanase), a lyticase, a chitinase, a apyrase, an antimicrobial peptide or protein, a protease, a lactoferrin or lactoferrin peptide (e.g., LfcinB), a lysozyme or lysozyme peptide (e.g., LysM), a lactonase, or a combination of any thereof.

The LfcinB can comprise any of the LfcinB peptides described herein, including any of the LfcinB peptides described in Section I.B.

The LysM can comprise any of the LysM peptides described herein, including any of the LysM peptides described in Section I.B.

The apyrase can be any of the apyrases described herein, including any of the apyrases described in Section I.B.

The protease can comprise any of the proteases described herein, including any of the *Bacillus subtilis* serine proteases described in Section I.B.

The glucanase can comprise any of the glucanases described herein, including any of the β-1,3-glucanases described in Section I.B.

The lactonase can comprise any of the lactonases described herein, including any of the AiiA lactonases described in Section I.B.

The chitinase can be any of the chitinases described herein, including any of the endochitinases described in Section I.B.

F. Methods and Compositions for Preventing or Treating Insect, Arachnid, or Nematode Infections or Infestations in Animals Methods for preventing or treating insect or worm infections in animals are provided.

A method for protecting an animal from a pathogen by preventing or treating an insect, arachnid, or nematode infection or infestation is provided. The method comprises administering spores to the animal or to the insect, arachnid, or nematode. The spores are spores of a recombinant *Bacillus cereus* family member that expresses a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member. The protein or peptide that protects the animal from a pathogen does not comprise an antigen or an immunogen.

Alternatively or in addition, the method comprises administering exosporium fragments to the animal or to the insect, arachnid, or nematode. The exosporium fragments are derived from spores of a recombinant *Bacillus cereus* family member and comprise a fusion protein. The fusion protein comprises at least one protein or peptide that protects the animal from a pathogen and a targeting sequence, exosporium protein, or exosporium protein fragment that targets the fusion protein to the exosporium of the recombinant *Bacillus cereus* family member.

The animal can comprise a livestock animal, a human, or a companion animal.

The animal can comprise a cow, a horse, a sheep, a goat, a pig, a bison, a camel, a donkey, a mule, a yak, a reindeer, a llama, a rabbit, a dog, a cat, a ferret, a gerbil, a guinea pig, a hamster, a mouse, a rabbit, a rat, a turkey, a chicken, a goose, or a duck.

The method can prevent or treat a fly or fly larvae infestation (e.g., a fly or fly larvae infestation in a horse or a cow).

The method can prevent or treat an arachnid infestation (e.g., an arachnid infestation in a human).

The method can comprise topically administering the exosporium fragments or the spores to the animal.

For example, the method can comprise administering the exosporium fragments or spores via a topical spray, a topical lotion, a topical cream, a topical gel, or a combination of any thereof.

The pharmaceutical compositions described herein, and in particular the topical pharmaceutical compositions described herein, can be used in connection with the methods for preventing or treating an insect. arachnid, or nematode infection or infestation.

In any of the pharmaceutical compositions or in any of the methods for preventing or treating an insect. arachnid, or nematode infection or infestation, the protein or peptide that protects the animal from the pathogen can comprise Mtx1, a delta endotoxin, a Cry toxin, chitinase, a secreted insecticidal (Sip) protein, or a combination of any thereof.

The Mtx1 can comprise any of the Mtx1 proteins described herein, including any of the Mtx proteins described in Section I.B.

The method can comprise preventing or treating a nematode infection.

The method can comprise feeding the exosporium fragments or spores to the nematode.

The protein or peptide that protects the animal from a pathogen can comprise a nematicidal protein or peptide.

A nematicidal composition is provided. The composition comprises a carrier and exosporium fragments. The exosporium fragments are derived from spores of a recombinant *Bacillus cereus* family member and comprise a fusion protein. The fusion protein comprises at least one nematicidal protein or peptide and a targeting sequence, exosporium protein, or exosporium protein fragment that targets the fusion protein to the exosporium of the recombinant *Bacillus cereus* family member.

In any of the methods for preventing or treating a nematode infection or in any of the nematicidal compositions, the nematicidal protein or peptide can comprise a chitinase, a Cry protein, a delta endotoxin, or a combination of any thereof.

The chitinase can comprise any of the chitinases described herein, including the endochitinases described in Section I.B.

The chitinase can comprise chitinase C, chitinase D, or a combination thereof.

The Cry protein can comprise a Cry5B protein, a Cry21A protein, or a combination of any thereof.

The Cry21A protein can comprise any of the Cry21A proteins described herein, including the Cry21A proteins described in Section I.B.

In any of the methods for preventing or treating a nematode infection or in any of the nematicidal compositions, the exosporium fragments can comprise exosporium fragments derived from a *Bacillus cereus* family member that naturally expresses a Cry toxin, a nematicidal toxin, a chitinase, a protease inhibitor protein, or a combination of any thereof.

In any of the methods for preventing or treating a nematode infection, the method can further comprise administering exosporium fragments derived from a *Bacillus cereus* family member that naturally expresses a Cry toxin, a nematicidal toxin, a chitinase, a protease inhibitor protein, or a combination thereof.

In any of the nematicidal compositions, the composition can further comprise exosporium fragments derived from a *Bacillus cereus* family member that naturally expresses a Cry toxin, a nematicidal toxin, a chitinase, a protease inhibitor protein, or a combination thereof.

In any of the methods for preventing or treating a nematode infection, the method can further comprise administering a Cry protein or spores of a recombinant *Bacillus cereus* family member that expresses a fusion protein. The fusion protein comprising at least one Cry protein and a targeting sequence, exosporium protein, or exosporium protein fragment that targets the fusion protein to the exosporium of the recombinant *Bacillus cereus* family member.

In any of the nematicidal compositions, the composition can further comprise a Cry protein or spores of a recombinant *Bacillus cereus* family member that expresses a fusion protein. The fusion protein comprising at least one Cry protein and a targeting sequence, exosporium protein, or exosporium protein fragment that targets the fusion protein to the exosporium of the recombinant *Bacillus cereus* family member.

G. Methods for Protecting Animals from Pathogens by Killing Insect Vectors of the Pathogen, Insecticidal and Acaricidal Compositions, and Insect Foggers Methods for protecting animals from pathogens by killing insect vectors of the pathogen are provided.

A method for protecting an animal from a pathogen by killing an insect or arachnid vector of the pathogen is provided. The method comprises contacting the insect or arachnid vector or larvae of the insect or arachnid vector with spores of a recombinant *Bacillus cereus* family member. The recombinant *Bacillus cereus* family member expresses a fusion protein. The fusion protein comprises at least one protein or peptide that has insecticidal or acaricidal activity against an insect or arachnid vector of an animal pathogen or larvae of the insect or arachnid vector and a targeting sequence, exosporium protein, or exosporium protein fragment that targets the fusion protein to the exosporium of the recombinant *Bacillus cereus* family member.

Alternatively or in addition, the method comprises contacting the insect or arachnid vector or larvae of the insect or arachnid vector with exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae of the insect vector and a targeting sequence, exosporium protein, or exosporium protein fragment that targets the fusion protein to the exosporium of the recombinant *Bacillus cereus* family member.

The method preferably comprises contacting the insect or arachnid or larvae or instars thereof with the exosporium fragments.

An insecticidal or acaricidal composition is provided. The composition comprising a carrier and exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

The composition can be suitable for topical administration. For example, the can be in the form of a lotion, gel, cream, or lotion.

The composition can be in the form of a dry powder, a cake, or a water dispersible granule.

Any of the insecticidal or acaricidal compositions described herein, including both those described in the present Section and those described above in Section IV, can be suitable for use in an insect fogger An insect fogger is provided. The insect fogger comprises a carrier and spores of a recombinant *Bacillus cereus* family member that expresses a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

Alternatively or in addition, the insect fogger can comprise the carrier and exosporium fragments. The exosporium fragments are derived from spores of a recombinant *Bacillus cereus* family member and comprise a fusion protein. The fusion protein comprises at least one protein or peptide that has insecticidal or acaricidal activity against an insect or arachnid vector of an animal pathogen or larvae or instars of the insect or arachnid vector. The fusion protein further comprises a targeting sequence, exosporium protein, or exosporium protein fragment that targets the fusion protein to the exosporium of the recombinant *Bacillus cereus* family member.

In any of the methods that involve killing an insect or arachnid vector of a pathogen, in any of the insecticidal or acaricidal compositions, or in any of the insect foggers, the protein or peptide that has insecticidal or acaricidal activity preferably does not comprise a nucleic acid binding protein or peptide.

In any of the methods that involve killing an insect or arachnid vector of a pathogen, in any of the insecticidal or acaricidal compositions, or in any of the insect foggers, the protein or peptide that has insecticidal or acaricidal activity can comprise an insecticidal bacterial toxin (e.g., a VIP insecticidal protein), an acaricidal bacterial toxin, an endotoxin (e.g., a delta endotoxin), a Cry toxin, a protease inhibitor protein or peptide (e.g., a trypsin inhibitor or an arrowhead protease inhibitor), a secreted insecticidal (Sip) protein, a mosquitocidal toxin (e.g., a Mtx-like mosquitocidal toxin, a Bin-like mosquitocidal toxin, or a combination thereof), a cysteine protease, a *Bacillus subtilis* serine protease, a chitinase, or a combination of any thereof.

The Mtx1-like mosquitocidal toxin can comprise a Mtx1 protein. The Mtx1 protein can comprise any of the Mtx1 proteins described herein, including any of the Mtx1 proteins described in Section I.B.

The Cry toxin can comprise a Cry toxin from *Bacillus thuringiensis*.

The Cry toxin can comprise a Cry1Aa protein, a Cry1Ab protein, a Cry1Ac protein, a Cry1Ca protein, a Cry1Da protein, a Cry2Aa protein, a Cry3Aa protein, a Cry3Bb protein, a Cry4Aa protein, a Cry4Ab protein, a Cry11Aa protein, or a Cyt1Aa protein.

The serine protease can comprise any of the *Bacillus subtilis* serine proteases described herein, including any of the *Bacillus subtilis* serine proteases described in Section I.B.

The chitinase can comprise any of the chitinases described herein, including any of the endochitinases described in Section I.B For any of the methods that involve killing an insect or arachnid vector of a pathogen, for any of the insecticidal or acaricidal compositions, or for any of the insect foggers, the insect or arachnid vector can comprise a flea, a fly (e.g., a sandfly or blackfly), a tick, a mite, a mosquito, an assassin bug, or a combination of any thereof.

The larvae or instar of the insect or arachnid vector can comprise larvae of a flea, a fly (e.g., e.g., larvae of a sandfly or a blackfly), a tick, a mite, a mosquito, an assassin bug, or a combination of any thereof.

For any of the methods that involve killing an insect or arachnid vector of a pathogen, for any of the insecticidal or acaricidal compositions, or for any of the insect foggers, the pathogen can comprise a yellow fever virus, dengue virus, a bacterial pathogen of the genus *Yersinia*, a pathogenic worm of the genus *Onchocerca*, a Zika virus, a bacterial pathogen of the genus Ehlichia, a bacterial pathogen of the genus *Anaplasma*, a bacterial pathogen of the genus *Borrelia*, a pathogen of the genus *Babesia*, a pathogenic protist of the genus *Leishmania*, a pathogenic protist of the genus *Trypanosoma*, a pathogenic protist of the genus *Schistosoma*, a West Nile virus, a pathogenic protist of the genus *Plasmodium*, a bacterial pathogen of the genus *Rickettsia*, a Kawaskai virus, a chikungunya virus, a pathogenic worm of the genus *Dirofilaria*, an Eastern equine encephalitis virus, a Saint Louis encephalitis virus, a LaCrosse encephalits virus, a Western Equine Encephalitis virus, a Pappataci virus, or a combination of any thereof.

In any of the methods that involve killing an insect or arachnid vector of a pathogen, in any of the insecticidal or acaricidal compositions, or in any of the insect foggers, the exosporium fragments can comprise exosporium fragments derived from a *Bacillus cereus* family member that naturally expresses an insecticidal toxin (e.g., a Cry protein), an acaricidal toxin, or a combination thereof.

For any of the methods that involve killing an insect or arachnid vector of a pathogen, the method can further comprise administering exosporium fragments derived from a *Bacillus cereus* family member that naturally expresses an insecticidal toxin (e.g., a Cry protein), an acaricidal toxin, or a combination thereof.

In any of the insecticidal or acaricidal compositions, or in any of the insect foggers, the composition or insect fogger can further comprise exosporium fragments derived from a *Bacillus cereus* family member that naturally expresses an insecticidal toxin (e.g., a Cry protein), an acaricidal toxin, or a combination thereof.

In any of the methods that involve killing an insect or arachnid vector of a pathogen, the method can further comprise administering an insecticidal toxin (e.g., a Cry protein), an acaricidal toxin, or a combination thereof or spores of a recombinant *Bacillus cereus* family member that expresses a fusion protein. The fusion protein comprises at least one insecticidal toxin (e.g., a Cry protein) or acaricidal toxin and a targeting sequence, exosporium protein, or exosporium protein fragment that targets the fusion protein to the exosporium of the recombinant *Bacillus cereus* family member.

In any of the insecticidal or acaricidal compositions, or in any of the insect foggers, the composition or insect fogger can further comprise an insecticidal toxin (e.g., a Cry protein), an acaricidal toxin, or a combination thereof or spores of a recombinant *Bacillus cereus* family member that expresses a fusion protein. The fusion protein comprises at least one insecticidal toxin (e.g., a Cry protein) or acaricidal toxin and a targeting sequence, exosporium protein, or exosporium protein fragment that targets the fusion protein to the exosporium of the recombinant *Bacillus cereus* family member.

In any of the methods that involve killing an insect or arachnid vector of a pathogen, the method can comprise contacting the insect or arachnid vector or larvae of the insect vector with the exosporium fragments or spores comprising spraying a composition comprising the exosporium fragments or spores into the environment of the insects or larvae, applying a composition comprising the exosporium fragments or spores to a body of water or insect breeding grounds, applying the exosporium fragments or spores to a host of the pathogen, or a combination of any thereof.

Spraying the composition comprising the exosporium fragments or spores into the environment can comprise use of a fogger.

In any of the methods that involve killing an insect or arachnid vector of a pathogen, the method can comprise applying the exosporium fragments or spores to a host of the pathogen by spraying the host with a composition comprising the exosporium fragments or spores, immersing the host in a composition comprising the exosporium fragments or spores, or a combination thereof.

VI. Methods for Producing an Immunogenic Response in an Animal

A method for producing an immunogenic response in an animal is provided.

The method comprises administering any of the vaccine compositions described above in Section IV.B to the animal.

Methods for producing immunogenic responses in aquatic animals are also provided.

A method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The exosporium fragments are administered to the aquatic animal by immersing the aquatic animal in a solution comprising the exosporium fragments.

Alternatively or in addition, the method comprises administering spores to the aquatic animal. The spores are spores of a recombinant *Bacillus cereus* family member that expresses a fusion protein. The fusion protein comprises at least one antigen or immunogen and a targeting sequence, exosporium protein, or exosporium protein fragment that targets the fusion protein to the exosporium of the recombinant *Bacillus cereus* family member. The spores are administered to the aquatic animal by immersing the aquatic animal in a solution comprising the spores.

Another method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The aquatic animal is selected from fish, amphibians, crustaceans, mollusks, and combinations of any thereof.

In any of the methods for producing an immunogenic response in an aquatic animal, administration of the exosporium fragments to the aquatic animal can result in vaccination of the aquatic animal against a pathogen selected from *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna, Icthyophous hoferi*, and combinations thereof.

Another method for producing an immunogenic response in an aquatic animal is provided. The method comprises administering exosporium fragments to the aquatic animal. The exosporium fragments are derived from spores of a recombinant *Bacillus cereus* family member and comprise a fusion protein. The fusion protein comprises at least one antigen or immunogen and a targeting sequence, exosporium protein, or exosporium protein fragment that targets the fusion protein to the exosporium of the recombinant *Bacillus cereus* family member. The administration of the exosporium fragments to the aquatic animal results in vaccination of the aquatic animal against a pathogen selected from *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna, Icthyophous hoferi*, and combinations of any thereof.

Alternatively or in addition, the method comprises administering spores to the aquatic animal. The spores are spores of a recombinant *Bacillus cereus* family member that expresses a fusion protein. The fusion protein comprises at least one antigen or immunogen and a targeting sequence, exosporium protein, or exosporium protein fragment that targets the fusion protein to the exosporium of the recombinant *Bacillus cereus* family member. The administration of the spores to the aquatic animal results in vaccination of the aquatic animal against a pathogen selected from *Renibacterium salmoninarum, Yersinia ruckeri, Edwarsdiella ictaluri, Flavobacterium columnare, Aerococcus viridans, Aeromonas salmonicida, Aeromonas hydrophila, Leucothrix mucor, Vibrio vulnificus, Vibrio parahaemolyticus, Vibrio alginolyticus*, a bacterial pathogen of the genus *Shewanella* spp., *Xenohaliotis californiensis, Piscirickettsia salmonis*, a pathogenic protist of the genus *Saprolengia, Branchiomyces sanguinis, Branchiomyces demigrna, Icthyophous hoferi*, and combinations of any thereof.

In any of the methods for producing an immunogenic response in an aquatic animal, the method preferably comprises administering the exosporium fragments.

When the protein or peptide of interest is an antigen or immunogen, display of the antigen or immunogen on the outside of the spore or on an exosporium fragment provides an immune system response to achieve vaccination against various pathogens or diseases. Suitable antigens or small molecules are those that are known or expected to illicit a desired immune response that is sufficient to yield a therapeutic or protective effect when expressed on the exterior of a *Bacillus cereus* family member spore or displayed on an exosporium fragment. Suitability in large part will be determined by the folding in the three-dimensional structure once the recombinant antigen is incorporated into the exosporium, i.e. the antigenic portion(s) of the recombinant molecule must be available for detection by the immune system.

The antigen or immunogen can comprise a heat shock protein, a coat protein, a capsule protein, an outer membrane protein, a cell wall protein, a flagellar protein, a fimbrial protein, a pilus protein, a ciliar protein, a protein toxin, an i-antigen, or a combination of any thereof.

The exosporium fragments or spores can be administered to the aquatic animal by immersing the aquatic animal in a solution comprising the exosporium fragments or spores, by feeding the exosporium fragments or spores to the aquatic animal, by injecting the exosporium fragments or spores into the aquatic animal, or a combination of any thereof.

The injection can comprise intramuscular injection.

The exosporium fragments or spores can be administered to the aquatic animal by immersing the aquatic animal in a solution comprising the exosporium fragments, spores, or a combination thereof.

The exosporium fragments or spores can be administered in a composition comprising a carrier and the exosporium fragments, the spores, or a combination thereof.

The composition can further comprise an adjuvant. Suitable adjuvants for use in connection with producing an immunogenic response in an aquatic animal are described above in Section IV.B.3.

The aquatic animal can be selected from a fish, an amphibian, a reptile, a crustacean, a mollusk, or combinations of any thereof.

For example, the aquatic animal can be selected from a fish, a crustacean, or a combination thereof.

When the aquatic animal comprises a fish, the fish can comprise a hobby fish, a salmon, a trout, a halibut, a seabass, a snapper, a grouper, a mullet, a tilapia, a tuna, a catfish, a carp, a sturgeon, or a combination of any thereof.

When the aquatic animal comprises a crustacean, the crustacean can comprise a shrimp, a prawn, a krill, a lobster, a crab, a crayfish, or a combination of any thereof.

When the aquatic animal comprises a mollusk, the mollusk can comprise a mussel, a clam, an oyster, a scallop, a snail, a slug, a squid, a cuttlefish, an octopus, or a combination of any thereof.

The method can comprise administering the exosporium fragments to eggs of the aquatic animal.

VII. Routes of Administration

In any of the methods described herein wherein a composition, exosporium fragments, or spores are administered to an animal, the exosporium fragments or spores can be administered to the animal by topical, oral, intraperitoneal, intra-arterial, intravenous, intramuscular, subcutaneous, intrapleural, intranasal, rectal, intradermal, inhalation, transdermal, or transepithelial administration, or by immersing the animal into a solution comprising the exosporium fragments or spores.

Combinations of any of these routes of administration can also be used.

Where the administration comprises oral administration, the composition, exosporium fragments, or spores can be added to food or water, wherein the food or water is then consumed by the animal.

VIII. Inactivation of Spores Prior to Use

In any of the methods described herein that comprise the use of spores of a recombinant *Bacillus cereus* family member, the method can further comprise inactivating the spores prior to use in the method.

Thus, the method can comprise inactivating the spores of the recombinant *Bacillus cereus* family member prior to administering the vaccine composition to the animal, prior to administering the spores to the animal, prior to administering the spores to the environment of the animal, prior to administering the spores to the pathogen, prior to introducing the spores into the aquaculture system, prior to contacting the insect or arachnid vector or larvae of the insect or arachnid vector with the spores, or prior to administering the spores to the aquatic animal.

Any of the recombinant *Bacillus cereus* family members described herein can be in the form of a spore, wherein the spore is inactivated.

In any of the compositions, adhesive patches, wound dressings, insert trays, hoof bandages, or insect foggers that comprise spores, the spores can be inactivated.

For example, the spores can be physically or chemically inactivated, e.g., by heat treatment, gamma irradiation, x-ray irradiation, UV-A irradiation, UV-B irradiation, or treatment with a solvent such as gluteraldehyde, formaldehyde, hydrogen peroxide, acetic acid, bleach, chloroform, or phenol, or any combination thereof. Alternatively, the spores can be genetically inactivated by introducing a mutation that results in complete or partial inactivation of the spore.

Having described the invention in detail, it will be apparent that modifications and variations are possible without departing from the scope of the invention defined in the appended claims.

EXAMPLES

The following non-limiting examples are provided to further illustrate the present invention.

Example 1: Use of Various Targeting Sequences to Express Lipase on the Surface of *Bacillus thuringiensis*

A wide variety of targeting sequences that that have a high degree of homology with amino acids 20-35 of BclA (amino acids 20-35 of SEQ ID NO: 1) can be used to display enzymes, proteins, and peptides on the surface of *Bacillus cereus* family members. Several targeting sequences were compared by making fusion proteins containing the targeting sequences linked to *Bacillus subtilis* lipase. Fusion constructs were synthesized using the promoters native to the targeting sequence, cloned into the replicating plasmid pMK4, and introduced into *Bacillus thuringiensis* BT013A. *Bacillus thuringiensis* BT013A was deposited with the United States Department of Agriculture (USDA) Agricultural Research Service (ARS), having the address 1815 North University Street, Peoria, Illinois 61604 U.S.A., on Mar. 10, 2014, and assigned NRRL deposit number B-50924. *Bacillus thuringiensis* BT013A is also known as *Bacillus thuringiensis* 4Q7.

Strains were taken into sporulation by incubation at 30° C. on nutrient agar plates containing chloramphenicol 10 μg/ml for 3 days. Spores were collected, washed, and resuspended in PBS at a rate of $1\times10^8$/ml. $1\times10^5$ spores for each fusion construct spores were suspended in 400 μl $dH_2O$. The reactions were warmed with the reaction components to the desired reaction temperature (40° C.). 200 μl working buffer was added (9:1 Solution A: Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores, and absorbance at 420 nm was recorded. The results are shown in Table 4 below. Activity was normalized to a control fusion protein comprising amino acids 1-35 of SEQ ID NO: 1 fused to *Bacillus subtilis* lipase.

TABLE 4

| Strain | Targeting sequence | Enzyme | Relative activity |
|---|---|---|---|
| *B. thuringiensis* BT013A | Amino acids 1-35 of SEQ ID NO: 1 | Lipase | 100% |
| *B. thuringiensis* BT013A | Amino acids 1-27 of SEQ ID NO: 3 | Lipase | 92.5% |
| *B. thuringiensis* BT013A | Amino acids 1-28 of SEQ ID NO: 7 | Lipase | 13.5% |
| *B. thuringiensis* BT013A | Amino acid 1-24 of SEQ ID NO: 9 | Lipase | 24.8% |
| *B. thuringiensis* BT013A | Amino acid 1-33 of SEQ ID NO: 13 | Lipase | 98.5% |
| *B. thuringiensis* BT013A | Amino acid 1-33 of SEQ ID NO: 21 | Lipase | 107.8% |
| *B. thuringiensis* BT013A | SEQ ID NO: 96 | Lipase | 137.1% |
| *B. thuringiensis* BT013A | SEQ ID NO: 98 | Lipase | 146.3% |
| *B. thuringiensis* BT013A | SEQ ID NO: 100 | Lipase | 115.7% |
| *B. thuringiensis* BT013A | SEQ ID NO: 104 | Lipase | 81.5% |

Several targeting sequences linked to lipase result in higher expression levels and activity of enzyme on the surface of spores. In particular, SEQ ID NOs. 96, 98, and 100, each containing a shorter targeting sequence, resulted in enhanced fusion expression on the surface of the BEMD spores. All the fusion proteins containing targeting sequences tested resulted in surface display of lipase.

Example 2: Use of Various Exosporium Sequences to Express Lipase on the Surface of *Bacillus thuringiensis* and Demonstration of Fusion Protein Localization to the Exosporium Surface A wide variety of exosporium proteins can be used to display enzymes, proteins, and peptides on the surface of *Bacillus cereus* family members. Several different exosporium proteins were compared by making fusion proteins containing the exosporium proteins linked to *Bacillus subtilis* lipase as described in Example 1. Fusion constructs were synthesized using the promoter native to the exosporium protein indicated in Table 5 below, cloned into the replicating plasmid pMK4, and introduced into *Bacillus thuringiensis* BT013A. Spores displaying the various exosporium protein-*Bacillus subtilis* 168 lipase fusions were made by growing the transformed bacteria in brain heart infusion broth with selective pressure from 10 μg/ml chloramphenicol, plating onto nutrient agar plates, and incubating at 30° C. for 3 days. After 3 days, the spores were washed off the plates, purified by centrifugation, and resuspended in PBS at $1\times10^8$ CFU/ml.

$1\times10^5$ spores for each fusion construct were resuspended in 400 μl $dH_2O$. The reactions were warmed with the reaction components to the desired reaction temperature (40° C.). 200 μl of working buffer was added (9:1 Solution A:Solution B). Solution A was 50 mM Tris pH 10 and 13.6 mM deoxycholic acid and Solution B was 3 mg/ml p-nitrophenyl palmitate in isopropanol. The reaction was incubated at 40° C. for 10 minutes and placed on ice, centrifuged to remove spores and absorbance at 420 nm was recorded. Results are shown in Table 5 below. Activity was normalized to SEQ ID NO: 109 linked to lipase.

TABLE 5

| Strain | Exosporium protein | Enzyme | Relative activity |
|---|---|---|---|
| *B. thuringiensis* BT013A | SEQ ID NO: 109 | Lipase | 100% |
| *B. thuringiensis* BT013A | SEQ ID NO: 110 | Lipase | 134.5% |
| *B. thuringiensis* BT013A | SEQ ID NO: 113 | Lipase | 17.8% |
| *B. thuringiensis* BT013A | SEQ ID NO: 117 | Lipase | 19.8% |
| *B. thuringiensis* BT013A | SEQ ID NO: 118 | Lipase | 8.2% |

Use of the exosporium proteins of SEQ ID NOs. 109 and 110 resulted in the highest enzyme activity on the spore. All the fusion proteins containing exosporium proteins resulted in surface display of active *Bacillus subtilis* 168 lipase, albeit at different levels.

Additional exosporium proteins were demonstrated to result in targeting of fusion proteins to the exosporium using the fluorescent reporter mCherry. Fusion constructs were created that contained the exosporium proteins of SEQ ID NOs. 111, 120, and 110 linked to the mCherry reporter. Spores were grown for 1.5 days, collected, and resuspended as described above. 7 μl of fluorescent spores were put under a Nikon E1000 microscope and imaged during late sporulation. Circular localization in a ring is indicative of outer spore layer localization, and the appearance matches that of an exosporium protein. Fluorescent microscopy results are shown in FIG. 2. Panels A, B, and C of FIG. 2 are fluorescent microscopy images of spores expressing fusion proteins comprising the exosporium proteins of SEQ ID NOs. 111, 120, and 110, respectively, and the mCherry reporter. All three fusions demonstrated high levels of fluorescence and exosporium localization, demonstrating their potential utility for the expression of foreign proteins on the surface of the exosporium.

Example 3: Use of Various Targeting Sequences to Express Endoglucanase on the Surface of *Bacillus cereus* Family Member Spores The pSUPER plasmid (described in Example 8 below) was modified by cloning of a PCR generated fragment through homologous recombination that fused the BclA promoter, start codon, and amino acids 20-35 of BclA (amino acids 20-35 of SEQ ID NO: 1) in frame with *Bacillus subtilis* 168 endoglucanase (pSUPER-BclA 20-35-Endo). PCR fragments were generated that contained the BclA promoter (SEQ ID NO: 149), start codon, and amino acids 20-35 of BclA fused in frame to *Bacillus subtilis* 168 endoglucanase. These PCR fragments were digested with XhoI and ligated into the SalI site of the pSUPER plasmid to generate the plasmid pSUPER-BclA 20-35-Endoglucanase. This plasmid was then subjected to inverse PCR to amplify the entire plasmid backbone, but leaving out the sequence corresponding to amino acids 20-35 of BclA. This inverse PCR product was combined with a PCR product that amplified the equivalent region from each of SEQ ID NOs. 5, 15, 25, 81, 85, 87, or amino acids 20-33 of SEQ ID NO: 1. Thus, constructs were created that contained each of the following targeting sequences fused in frame with *Bacillus subtilis* 168 endoglucanase: (1) amino acids 20-35 of SEQ ID NO: 1; (2) amino acids 23-38 of SEQ ID NO: 5; (3) amino acids 28-43 of SEQ ID NO: 15; (4) amino acids 9-24 of SEQ ID NO: 25; (5) amino acids 23-38 of SEQ ID NO: 81; (6) amino acids 13-28 of SEQ ID NO: 85; (7) amino acids 13-28 of SEQ ID NO: 87; and (8) amino acids 20-33 of SEQ ID NO: 1. Each construct contained the wildtype BclA promoter and a methionine at the start codon, followed by the targeting sequence fused in frame to the *Bacillus subtilis* endoglucanase gene. Each of these constructs was transformed into *E. coli* and plated to obtain single colonies on Luria plates plus ampicillin (100 μg/ml). Plasmids from each single colony were grown up in overnight cultures in Luria broth plus ampicillin, and purified using a WIZARD SV miniprep kit, and sequences were verified by Sanger sequencing. DNA was also quantified via spectrophotometry, and the DNA was introduced into *Bacillus thuringiensis* BT013A. In addition, the pSUPER-BclA-20-35 Endo construct was introduced into *Bacillus thuringiensis* BT013A which had the native BclA protein removed from its genome through homologous recombination (BclA knockout, "BclA KO"). Correct colonies were screened by plating on nutrient broth plate containing antibiotic (tetracycline at 10 μg/ml). Each positive colony was grown up in brain heart infusion broth at 30° C. overnight at 300 rpm, with antibiotic, and genomic DNA was purified and re-sequenced to verify genetic purity. Verified colonies were grown overnight in brain heart infusion broth with 10 μg/ml tetracycline, and induced to sporulate through sporulation in a yeast extract-based media.

Each of the production runs in the yeast extract-based media were collected at 48 hours post production of spores, and subjected to enzyme comparison of the resultant spores. The assay for endoglucanase activity was performed by determining cellulase activity using a carboxymethylcellulose (CMC) substrate and a dinitrosalicylic acid (DNS reagent). A commercial source of cellulase enzyme was used to prepare standards in 50 mM citrate buffer, pH 4.8. 1% CMC (carboxymethylcellulose sodium salt) was prepared in 50 mM citrate buffer, pH 4.8, to serve as the substrate for the reaction. 250 μl of spore preparation was pelleted and the spores were resuspended in 150 μL of 50 mM citrate buffer, pH 4.8. The reaction was carried out with a reagent composed of 1% DNS, 1% NaOH, 0.05% $Na_2SO_4$, 0.2% phenol, and 18.2% Rochelle salts. 150 μl of the sample was mixed with 250 μl of the 1% CMC substrate and incubated in a water bath at 50° C. for 15 minutes. 300 μl of DNS reagent was added and the samples boiled at 100° C. for 10 minutes and then cooled on ice. The solution was centrifuged for 5 minutes at 14,000×g to remove the spores from the absorbance reading. The absorbance was determined at 540 nm using an IMPLEN nanospectrophotometer model P330. Samples were performed in triplicate with a blank for each reaction. The results from the enzyme readings are shown in Table 6.

TABLE 6

| Enzyme levels | | | |
|---|---|---|---|
| Targeting Sequence | Endo Enzyme Levels (mU/ml) | Sequence Identity to AA 20-35 of BclA | Sequence Identity to AA 25-35 of BclA |
| Control ($H_2O$) | 0 mU/ml | N/A | N/A |
| AA 20-35 of BclA (SEQ ID NO: 1) | 38.2 | 100% | 100% |
| AA 23-38 of SEQ ID NO: 5 | 33.5 | 50.0% | 72.7% |
| AA 28-43 of SEQ ID NO: 15 | 16.7 | 68.8% | 81.8% |
| AA 9-24 of SEQ ID NO: 25 | 25.7 | 56.3% | 63.6% |
| AA 23-38 of SEQ ID NO: 81 | 21.5 | 50.0% | 72.7% |
| AA 13-28 of SEQ ID NO: 85 | 38.3 | 43.8% | 54.5% |
| AA 13-28 of SEQ ID NO: 87 | 14.4 | 43.8% | 54.5% |
| AA 20-33 of SEQ ID NO: 1 | 30.5 | N/A | 100% |
| AA 20-35 of SEQ ID NO: 1 in BT013A BclA KO | 100.8 | 100% | 100% |

AA = amino acids
ND = not determined

The above data show that the use of different targeting sequences allows for control of the expression level of the enzyme on the outside of the spore. Use of amino acids 20-35 of SEQ ID NO: 1 or AA 13-28 of SEQ ID NO: 85 as the targeting sequence resulted in the highest levels of enzyme production. This is surprising considering the low degree of identity between these targeting sequences (43.8% identity over the entire length of the targeting sequence). Expression of the fusion protein containing amino acids 20-25 of SEQ ID NO: 1 as the targeting sequence in the BT013A BclA KO host led to very large (263.8%) increase in the amount of enzyme activity on the surface of the spores as compared to expression of the same fusion protein in the wild-type strain.

Example 4: Use of Various Targeting Sequences and Exosporium Proteins to Express Phospholipase, Lipase, and Endoglucanase on the Surface of *Bacillus cereus* Family Member Spores The pSUPER plasmid was modified by cloning of a PCR generated fragment (XhoI digestion and ligation) that fused the BclA promoter, start codon, and amino acids 20-35 of BclA (amino acids 20-35 of SEQ ID NO: 1) followed by a six alanine linker sequence in frame with either *Bacillus thuringiensis* phosphatidylcholine-specific phospholipase C gene (PC-PLC) (pSUPER-BclA 20-35-PL) or *Bacillus subtilis* lipase LipA (pSUPER-BclA-20-35-Lipase), or *Bacillus subtilis* endoglucanase eglS (pSUPER-BclA-20-35-Endo) as described above in Example 3. These plasmids were then subjected to inverse PCR to amplify the entire plasmid backbone, but without the sequence corresponding to amino acids 20-35 of BclA. This inverse PCR product was combined with a PCR product that amplified the equivalent region from each of SEQ ID NOs. 5 (i.e., amino acids 23-38 of SEQ ID NO: 5), 15 (i.e., amino acids 28-43 of SEQ ID NO: 15), and 25 (i.e., amino acids 9-24 of SEQ ID NO: 25); the full-length exosporium proteins of SEQ ID NOs. 120, 111, 121, 108, and 114; or amino acids 20-33, 20-31, 21-33, 23-33, or 23-31 of SEQ ID NO: 1. Each of these constructs contained the wild-type BclA promoter, a methionine at the start codon, followed by the targeting sequence or exosporium protein fused in frame to the *Bacillus cereus* phosphatidylcholine-specific phospholipase C, *Bacillus subtilis* 168 Lipase LipA, or *Bacillus subtilis* 168 eglS endoglucanase gene. Each of these constructs was screened for correct transformants as described in Example 3 above.

Each of the production runs in the yeast extract-based media were collected at 48 hours post production of spores, and subjected to enzyme comparison of the resultant spores. Determination of enzyme data for endoglucanase was performed as described above in Example 3. For the phospholipase C enzyme assay, 1 ml of recombinant spores was pelleted at 10,000×g for 3 minutes, and supernatant removed and discarded. The spore pellet was then resuspended in 500 μl reaction buffer (0.25 mM Tris-HCL, 60% glycerol, 20 mM o-nitrophenyl phosphorylcholine, pH 7.2). A negative control for enzyme assays contained BT013A spores with no enzyme expression. Each sample was incubated at 37° C. for 18 hours, centrifuged again to remove the spores, diluted 1:1 in water, and the Abs540 read using a spectrophotometer. This was compared to a standard curve against commercially purchased phospholipase and lipase controls to establish the U/ml of activity. The results from the enzyme readings are shown in Tables 7 and 8.

TABLE 7

| Endoglucanase Enzyme Levels | |
|---|---|
| | Endoglucanase Levels (mU/ml) |
| Targeting Sequence, Experiment #1 | |
| Control ($H_2O$) | 0 mU/ml |
| AA 20-3 5 SEQ ID NO: 1 | 38.2 |
| SEQ ID NO: 120 | 25.7 |
| SEQ ID NO: 111 | 29.7 |
| SEQ ID NO: 121 | 24.4 |
| SEQ ID NO: 108 | 24.0 |
| SEQ ID NO: 114 | 11.0 |
| AA 20-33 of SEQ ID NO: 1 | 30.5 |
| Targeting Sequence, Experiment #2 | |
| AA 20-31 of SEQ ID NO: 1 | 48.22 |
| AA 21-33 of SEQ ID NO: 1 | 60.86 |
| AA 23-33 of SEQ ID NO: 1 | 19.93 |
| AA 23-31 of SEQ ID NO: 1 | 45.31 |
| AA 20-35 of SEQ ID NO: 1 | 54.1 |

AA = Amino acids

Many of the targeting sequences and exosporium proteins were able to display a large amount of active enzymes on the surface of the spores, including SEQ ID NOs. 108, 111, 114, 120, and 121. Amino acids 20-31, 21-33, and 23-31 of SEQ ID NO: 1 provided similar enzyme expression levels to amino acids 20-35 of SEQ ID NO: 1, indicating that smaller fragments are adequate for the display of enzymes on the surface of the spores. Only amino acids 23-33 of SEQ ID NO: 1 exhibited a diminished enzyme display level on the spores.

TABLE 8

| Phospholipase Enzyme levels | | |
|---|---|---|
| Targeting Sequence | PC-PLC Enzyme Levels (relative to $H_2O$ control) | Lipase Enzyme Levels (relative to $H_2O$ control) |
| Control ($H_2O$) | 0.0 | 0.0 |
| AA 20-35 SEQ ID NO: 1 | .787 | .436 |
| AA 23-38 of SEQ ID NO: 5 | .688 | .602 |
| AA 28-43 of SEQ ID NO: 15 | .372 | .228 |
| AA 9-24 of SEQ ID NO: 25 | .247 | .359 |

TABLE 8-continued

| Phospholipase Enzyme levels | | |
|---|---|---|
| Targeting Sequence | PC-PLC Enzyme Levels (relative to $H_2O$ control) | Lipase Enzyme Levels (relative to $H_2O$ control) |
| SEQ ID NO: 114 | .446 | .798 |
| SEQ ID NO: 120 | 3.612 | .753 |
| SEQ ID NO: 111 | .738 | .329 |

AA = Amino acids

Similar to the results shown above in Table 7, the highest levels of phospholipase or lipase on the spore surface were observed when amino acids 20-35 of SEQ ID NO: 1, amino acids 23-38 of SEQ ID NO: 5, or the exosporium protein sequence of SEQ ID NO: 120 were used.

Example 5: Enhanced Expression of Fusion Constructs on the BEMD System by Use of Enhanced or Alternative Promoter Elements The BEMD system can display a wide range of proteins, peptides, and enzymes using one or more of the targeting sequences described herein. Some of these targeting sequences have a high affinity for the exosporium which would be beneficial for fusion protein expression, but their low fusion protein expression level limits their use on the BEMD system. For such fusion proteins and sequences, alternative high-expression sporulation promoters can be used instead of the native promoters.

For example, SEQ ID NO: 13 (amino acids 1-39 of *B. weihenstephensis* KBAB4 gene 3572) provides a very effective N-terminal sequence for the delivery of proteins to the exosporium of *Bacillus cereus* family members, as shown in Table 9 below. All genes were synthesized in their complete form (including promoter regions and regions coding for fusion proteins) as described herein. When the native promoter elements for *B. weihenstephensis* KBAB4 gene 3572 (SEQ ID NO: 177) were used to express a fusion protein comprising the targeting sequence of SEQ ID NO: 13 fused to a β-galactosidase enzyme (from *E. coli*), a low level of fusion protein was expressed, leading to a reduction in enzyme activity on the surface of the spore. Enzyme activity was measure by the conversion of 0.5M o-nitrophenylgalactoside in solution over 10 minutes. Enzyme conversion was measured with a spectrophotometer at $ABS_{540}$. Replacement of the native promoter elements of the *B. weihenstephensis* KBAB4 gene 3572 with the high-expression promoters of SEQ ID NO: 157 (*B. anthracis* BetA/BAS3290) or SEQ ID NO: 178 (*B. weihenstephensis* KBAB4 YVTN β-propeller protein) led to a dramatic increase in the enzymatic activity of the spores. On the other hand, replacement of the native promoter elements for *B. weihenstephensis* KBAB4 gene 3572 with the promoter native to *B. anthracis* Sterne BAS1882 (SEQ ID NO: 176) led to a decrease in the enzymatic activity of the spores. The expression level of the targeting sequence of SEQ ID NO: 13 fused to β-galactosidase was much lower (0.38×) when driven by the promoter of BAS1882 (SEQ ID NO: 176), and was greatly improved when driven from the BetA promoter (SEQ ID NO: 197) or YVTN protein promoter (SEQ ID NO: 178).

TABLE 9

| Promoter | Fusion Protein | β-galactosidase activity on BEMD system, normalized | Fold Change |
|---|---|---|---|
| SEQ ID NO: 177 | SEQ ID NO: 13 - β-galactosidase | 100% | |
| SEQ ID NO: 157 | SEQ ID NO: 13 - β-galactosidase | 213.4% | 2.13X |
| SEQ ID NO: 178 | SEQ ID NO: 13 - β-galactosidase | 220.7% | 2.21X |
| SEQ NO: ID 176 | SEQ ID NO: 13 - β-galactosidase | 38.1% | 0.38X |

Example 6: Expression Levels of Fusion Proteins Using Various Sigma-K Containing Promoters As shown in Example 5 above, replacing the native promoter of a targeting sequence, exosporium protein, or exosporium protein fragment can greatly affect the level of fusion protein expressed on the exosporium of a *Bacillus cereus* family spore. For example, replacing the native BclA promoter with the BclB promoter greatly reduces the level of fusion protein on the surface of *Bacillus cereus* family member spores. Alternatively, replacement of native BclB promoter with the BclA promoter increases fusion protein levels on the exosporium dramatically.

Relative promoter expression levels for various exosporium proteins under the control of their native sporulation promoters were obtained from microarray data from Bergman et al., 2008. The relative expression levels were determined during late sporulation timing (300 minutes after the start of the experiment), when sigma K promoters are most active. Sigma K promoters are key promoters for expression of exosporium localized genes and associated proteins. Relative expression is the increase in a gene's expression level when compared to the average of all other genes of the chromosome at all given times. Table 10 below shows the relative expression levels of a variety of sigma K driven genes in *Bacillus cereus* family members.

TABLE 10

| Protein (Promoter SEQ ID NO.) | Relative Expression (Fold increase in mRNA) |
|---|---|
| CotO (SEQ ID NO: 186) | 79.21 |
| Rhamnose (SEQ ID NO: 185) | 75.69 |
| BclC (SEQ ID NO: 139) | 14.44 |
| Sigma K (SEQ ID NO: 187) | 64 |
| BclA adjacent US Glycosyl transferase promoter 1 (SEQ ID NO: 189) | 72.25 |
| BclA adjacent DS Glycosyl transferase promoter 2 (SEQ ID NO: 190) | 73.96 |
| BclA (SEQ ID NO: 175) | 77.44 |
| ExsY (SEQ ID NO: 180) | 32.49 |
| YjcA (SEQ ID NO: 182) | 64 |
| YjcB (SEQ ID NO: 183) | 70.56 |
| BxpB/ExsFA (SEQ ID NO: 184) | 30.25 |
| InhA (SEQ ID NO: 188) | 34.25 |

Example 7: Preparation of Exosporium Fragments from Recombinant *Bacillus cereus* Family Members Comprising a Knockout of the CotE Gene The plasmid pUCpE was constructed that contained the pUC19 backbone, which is able to replicate in *E. coli*, as well as the origin of replication erythromycin resistance cassette from pE194. This construct is able to replicate in both *E. coli* and *Bacillus* spp. A 1 kb DNA region corresponding to the upstream region of the CotE gene and a 1 kb region corresponding to the downstream region of the gene CotE were PCR amplified from *Bacillus anthracis* ΔSterne. The two 1 kb regions were then spliced together using splicing by overlapping extension via 15 bp homologous overhangs that corresponded to the opposing PCR amplicons. This 2 kb fragment was digested with XhoI (in external primers) and ligated into the SalI site of pUCpE. This plasmid construct was verified by digestion and DNA sequencing. A Gram-positive omega-kanamycin resistance gene was digested with BamHI and placed between the two 1-kb regions. The final construct was again PCR verified and sequenced, and the final plasmid was introduced into *Bacillus anthracis* ΔSterne. Correct clones were screened by looking for both erythromycin resistance and kanamycin resistance.

Clones were passaged under high temperature (40° C.) in brain heart infusion broth in the presence of kanamycin (25 μg/ml) and were routinely struck for isolation onto LB agar plates containing kanamycin and grown at 30° C. Individual colonies were toothpicked onto LB agar plates containing erythromycin 5 μg/ml and grown at 30° C. Clones that maintained kanamycin resistance but lost erythromycin resistance (signifying loss of the plasmid but recombination and removal of the CotE gene) were grown in brain heart infusion broth plus kanamycin, and chromosomal DNA was isolated using a Qiagen Chromosomal DNA isolation kit. Proper deletion of the CotE gene was determined by PCR amplification of the CotE gene region and loss of CotE, and gain of the kanamycin resistance cassette.

A construct was generated (pHP13-AcpC-eGFP) that encoded the exosporium protein AcpC (acid phosphatase) fused in frame to the fluorescent reporter protein eGFP (enhanced green fluorescent protein). The pHP13-AcpC-eGFP construct included the native AcpC promoter, ribosomal binding site, and coding sequence for AcpC (from *B. anthracis* ΔSterne), fused in frame to eGFP (from pGFPuv). This construct was generated by PCR amplification of the individual AcpC and eGFP genes with corresponding primers that contained a 15 bp overlapping region corresponding to the alternate amplicons. The two PCR amplicons were then purified, and combined into a second PCR reaction using external primers that contained XhoI sites. The two amplicons prime each other with their compatible ends, and create a fusion PCR amplicons, that were purified and digested with XhoI for 1 hour at 37° C. The spliced PCR product was cloned into the SalI site of pHP13, and correct clones were sequence verified and transformed into SCS110 *E. coli*. The plasmid DNA was subsequently isolated from the *E. coli* and introduced into *B. anthracis* ΔSterne CotE::Kan, generated as described above, which was grown in brain heart infusion broth containing 10 μg/ml chloramphenicol overnight at 30° C. One milliliter of this culture was inoculated into nutrient broth (50 ml) in a baffled flask and grown at 30° C. for 3 days. Spores were collected via centrifugation at 10,000×g for 5 minutes, and the supernatant (containing the broken exosporium fragments) was filtered through a 100,000 Da membrane filter to obtain purified exosporium fragments containing the fusion proteins.

Figure 3:
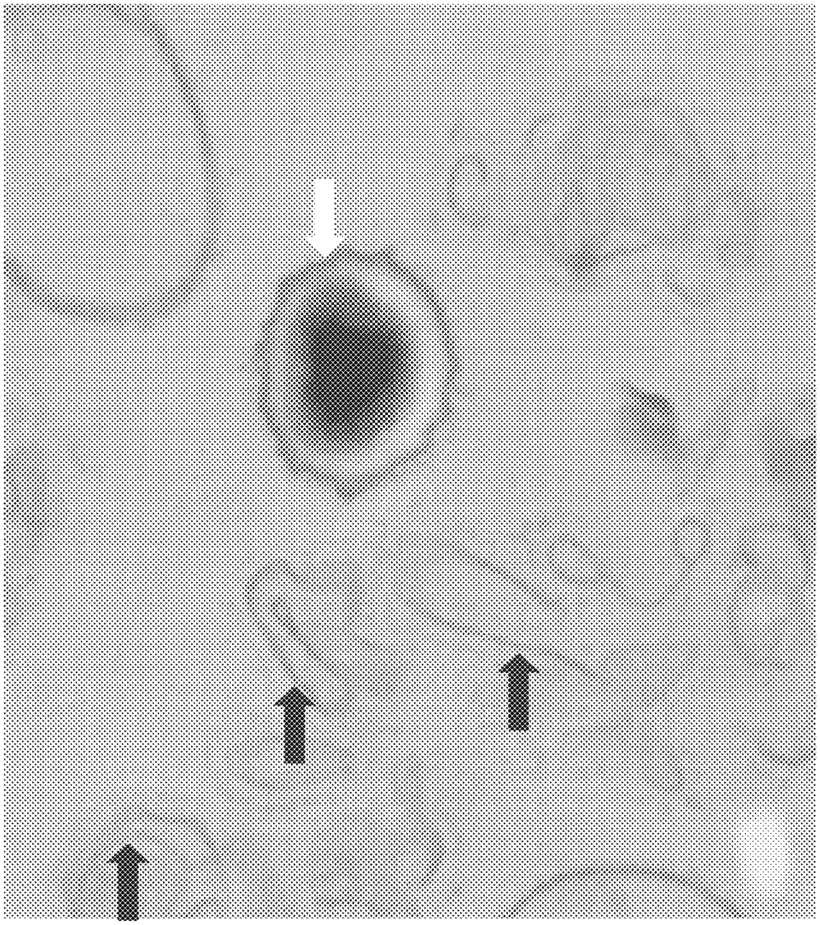
FIG. 3 is a transmission electron micrograph showing exosporium fragments and a *Bacillus cereus* family member spore from which the exosporium has been lost, generated using a recombinant *Bacillus cereus* family member having a knock-out mutation of its CotE gene.

A transmission electron micrograph showing the CotE knockout spores is provided in FIG. 3. The closed arrows indicate fragments of exosporium that have been separated from the spores, and the open arrow indicates a spore from which the exosporium has been removed.

Figure 4:
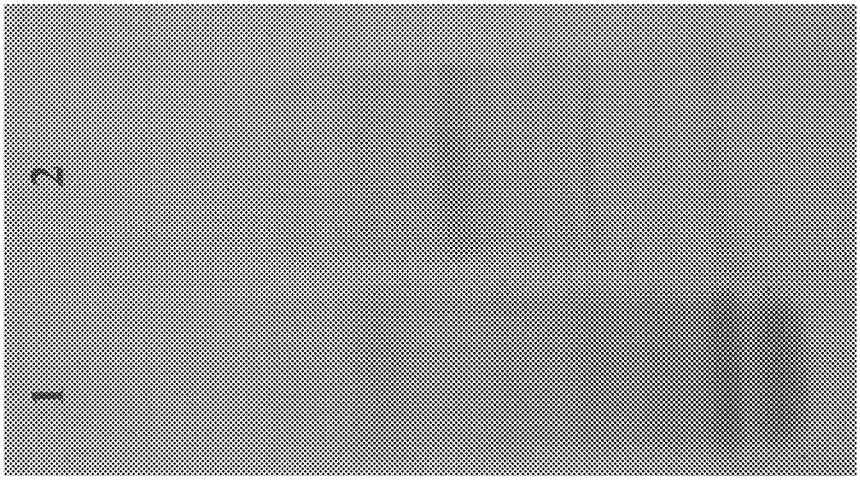
FIG. 4 is a photograph of an SDS-PAGE gel showing a protein marker standard (lane 1) and proteins from exosporium fragments generated using a recombinant *Bacillus cereus* family member having a knock-out mutation of its CotE gene (lane 2).

The purification of the exosporium fragments was performed as follows: CotE::kan spores were grown in brain heart infusion broth overnight at 30° C. and swabbed onto nutrient agar plates and grown at 30° C. for 3 days. After 3 days, the spores were collected by swabbing the plates with cotton swabs wetted with PBS and resuspended into 1 ml of PBS in a microcentrifuge tube. The spores were separated from the culture by centrifugation, and the supernatant containing the exosporium fragments was filtered through a 0.22 μM filter to remove any residual spores. The filtrate was then filtered through a 100 kDa filter to collect exosporium fragments but allow free proteins to pass through the filter. The 100 kDa filter was washed, and the collected exosporium fragments boiled in SDS buffer for 5 minutes and separated by SDS-PAGE electrophoresis. FIG. 4 provides a photograph of an SDS-PAGE gel showing the purified exosporium fragments (lane 2) and a protein marker standard (lane 1). The exosporium fragments shown in lane 2 represent the individual proteins that constitute the exosporium fragments. Only a subset of bands that would normally be seen in a whole spore SDS-PAGE preparation is apparent.

Figure 5:
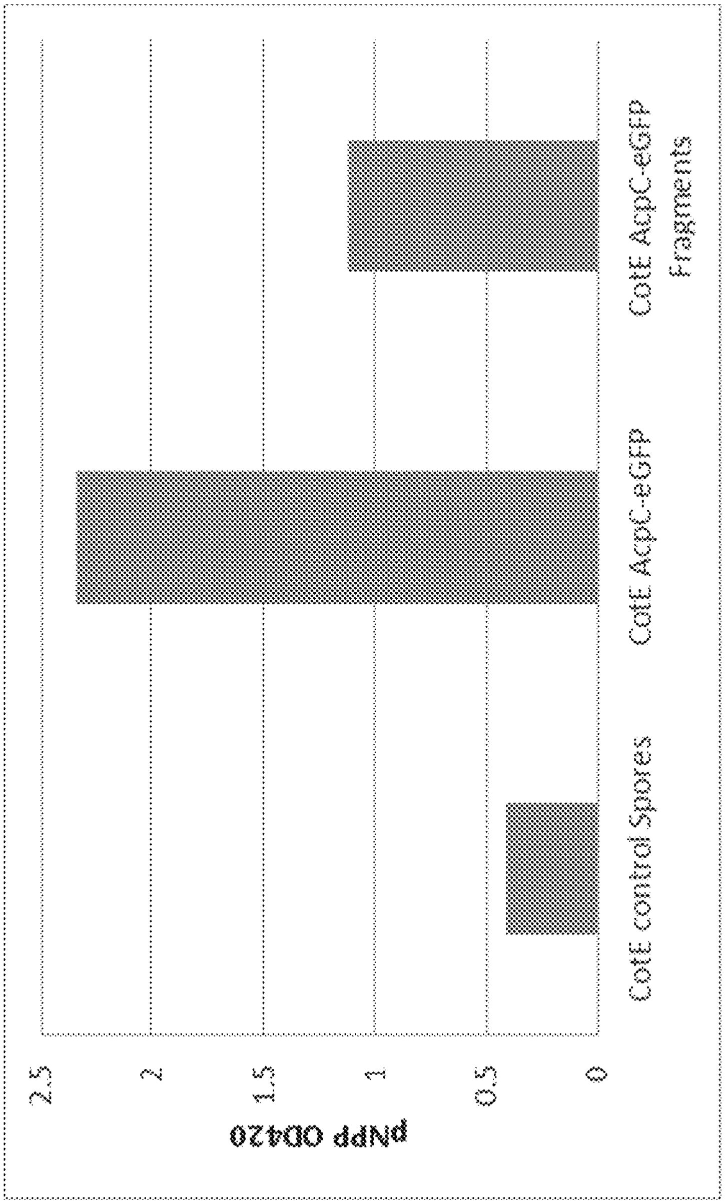
FIG. 5 provides data illustrating enzyme activity of an acid phosphatase in exosporium fragments derived from a *Bacillus cereus* family member having a knock-out mutation of its CotE gene.

Ten microliters of the exosporium fragment preparation containing the AcpC-eGFP fusion protein was tested for activity in a phosphatase assay against pNPP (p-nitrophenyl polyphosphate). Acid phosphatase activity was detected by spectrophotometry based on release of p-nitrophenol from phosphate through phosphatase activity. Briefly, 1 ml of 10 mM pNPP in phosphate buffer at pH 6.0 was incubated with exosporium fragments in a 1 ml microcentrifuge tube and allowed to incubate at 37° C. for 10 minutes. After 10 minutes, the tube was centrifuged for 1 minute to remove excess spores, and the supernatant read on a spectrophotometer at 420 nm for free p-nitrophenol. It was found that the purified exosporium fragments were able to effectively release the phosphate groups from pNPP, demonstrating that the AcpC was present in the exosporium fragments. The results of this assay are shown in FIG. 5. In FIG. 5, "CotE control spores" refers to CotE knock-out spores alone (not expressing the AcpC-eGFP fusion protein), "CotE Acp-eGFP" refers to the CotE knock-out spores expressing the AcpC-eGFP fusion protein, and "CotE AcpC-eGFP fragments" refers to the exosporium fragments obtained as described above from the CotE knock-out spores expressing the AcpC-eGFP fusion protein.

These results demonstrate that mutations that disrupt the exosporium, such as a knock-out mutation in the CotE gene, can be used to generate exosporium fragments that are substantially free of spores, and demonstrates that these exosporium fragments contain fusion proteins that are targeted to the exosporium.

Example 8: Generation of Recombinant *Bacillus cereus* Family Members Displaying Ovalbumin or the *Bacillus anthracis* Protective Antigen The *Gallus gallus* ovalbumin gene from GenScript ORF clone OGa28271C and the *Bacillus anthracis* protective antigen (pagA) gene were amplified via polymerase chain reaction (PCR) using the primers shown below in Table 11. The amino acid sequence encoded by the ovalbumin gene is provided in SEQ ID NO: 217 and the amino acid sequence encoded by the pagA gene is provided in SEQ ID NO: 218.

TABLE 11

| | OvaL | PagA |
|---|---|---|
| forward | GCAGCTGCGGCAGCTGGC TCCATCGGCGCAGCAAGC (SEQ ID NO: 200) | GCAGCTGCGGCAGCTATGA AAAAACGAAAAGTGTTAAT (SEQ ID NO: 202) |
| reverse | CTGCAGTTACTCGAGCTG CAGTTAAGGGGAAACACA (SEQ ID NO: 201) | CTGCAGTTACTCGAGTTAT CCTATCTCATAGCCTTT (SEQ ID NO: 203) |

The resulting PCR fragments were cloned into one of three expression plasmids (pSUPER-BclA-FL, pSUPER-BclA 20-35, or pSUPER-AcpC) using the splicing by overlapping extension (SOE) technique. The pSUPER-BclA-FL plasmid was generated through fusion of a PCR fragment which contained the BclA promoter (SEQ ID NO: 149), start codon, and coding sequence for full-length (FL) BclA fused in frame into the pSUPER plasmid. The pSUPER-BclA-20-35 plasmid was generated through fusion of a PCR fragment which contained the BclA promoter (SEQ ID NO: 149), start codon, and a coding sequence for amino acids 20-35 of BclA (amino acids 20-35 of SEQ ID NO: 1) fused in frame into the pSUPER plasmid. The pSUPER-AcpC plasmid was generated through fusion of a PCR fragment with included the native AcpC promoter (SEQ ID NO: 141), ribosomal binding site, and coding sequence for AcpC (from *B. thuringiensis* BT013A; SEQ ID NO: 120), fused in frame into the pSUPER plasmid. The pSUPER plasmid was generated through fusion of the pUC57 plasmid (containing an ampicillin resistance cassette) with the pBC16-1 plasmid from *Bacillus* (containing a tetracycline resistance). This 5.5 kbp plasmid can replicate in both *E. coli* and *Bacillus* spp.

The pSUPER-BclA-FL-OVAL construct generated using these methods encodes a fusion protein comprising full-length BclA and ovalbumin, and the pSUPER-BclA-FL-PAG encodes a fusion protein comprising full-length BclA and the *B. anthracis* protective antigen. These constructs were transformed into and propagated in *E. coli* strains. The sequences of the plasmids were verified by DNA sequencing.

In order to remove the *E. coli*-derived portions of the pSUPER plasmids and create smaller plasmids for expression in *Bacillus*, sequence-verified pSUPER constructs were amplified with primers that amplify the *Bacillus*-derived segment of the plasmid backbone. The resulting PCR products were self-ligated to generate the pBC plasmids (pBC-BclA-FL-OVAL plasmid and pBC-BclA-FL-PAG) that were used to transform various *Bacillus* strains in the examples below.

Example 9: Preparation and Purification of Exosporium Fragments

Knock Out (KO) Mutants:

To make exsY and cotE knockout (KO) mutant strains of *Bacillus thuringiensis* BT013A, the plasmid pKOKI shuttle and integration vector was constructed that contained the pUC57 backbone, which is able to replicate in *E. coli*, as well as the origin of replication erythromycin resistance cassette from pE194. This construct is able to replicate in both *E. coli* and *Bacillus* spp. A 1 kb DNA region that corresponded to the upstream region of the cotE gene and a 1 kb region that corresponded to the downstream region of the gene cotE were PCR amplified from *Bacillus thuringiensis* BT013A. A second construct was made that contained the 1 kb DNA region that corresponded to the upstream region of the exsY gene and a 1 kb region that corresponded to the downstream region of the gene exsY, both of which were PCR amplified from *Bacillus thuringiensis* BT013A. For each construct, the two 1 kb regions were then spliced together using homologous recombination with overlapping regions with the pKOKI plasmid. The plasmid constructs were verified by digestion and DNA sequencing. Clones were screened by looking for erythromycin resistance.

Clones were passaged under high temperature (40° C.) in brain heart infusion (BHI) broth. Individual colonies were toothpicked onto LB agar plates containing erythromycin 5 μg/ml, grown at 30° C., and screened for the presence of the pKOKI plasmid as a free plasmid by colony PCR. Colonies that had an integration event were continued through passaging to screen for single colonies that lost erythromycin resistance (signifying loss of the plasmid but recombination and removal of the exsY or cotE gene). Verified deletions were confirmed by PCR amplification and sequencing of the target region of the chromosome. The pBC-BclA-FL-OVAL plasmid was transformed into the exsY knockout mutant and the pBC-BclA-FL-PAG plasmid was transformed into the cotE KO mutant. The pBC-BclA-FL-OVAL and pBC-BclA-FL-PAG plasmids are described above in Example 8.

Exosporium Fragment Creation:

For each of the two KO mutants, overnight cultures were grown in BHI media at 30° C., 300 rpm, in baffled flasks with antibiotic selection. One milliliter of this overnight culture was inoculated into a yeast extract-based media (50 ml) in a baffled flask and grown at 30° C. for 3 days. An aliquot of spores was removed, 1% Tween was added, and the spores were agitated by vortexing for one minute. The spores were collected via centrifugation at 10,000×g for 5 minutes, and supernatant containing the exosporium fragments was filtered through a 0.22 μM filter to remove any residual spores. The supernatant (containing the exosporium fragments) was filtered through a 100,000 Da membrane filter to obtain purified exosporium fragments containing the fusion proteins. Smaller molecular weight proteins were removed by passaging through the 100 kDa filter. No spores were found in the filtrate or retentate of the supernatant.

Figure 6:
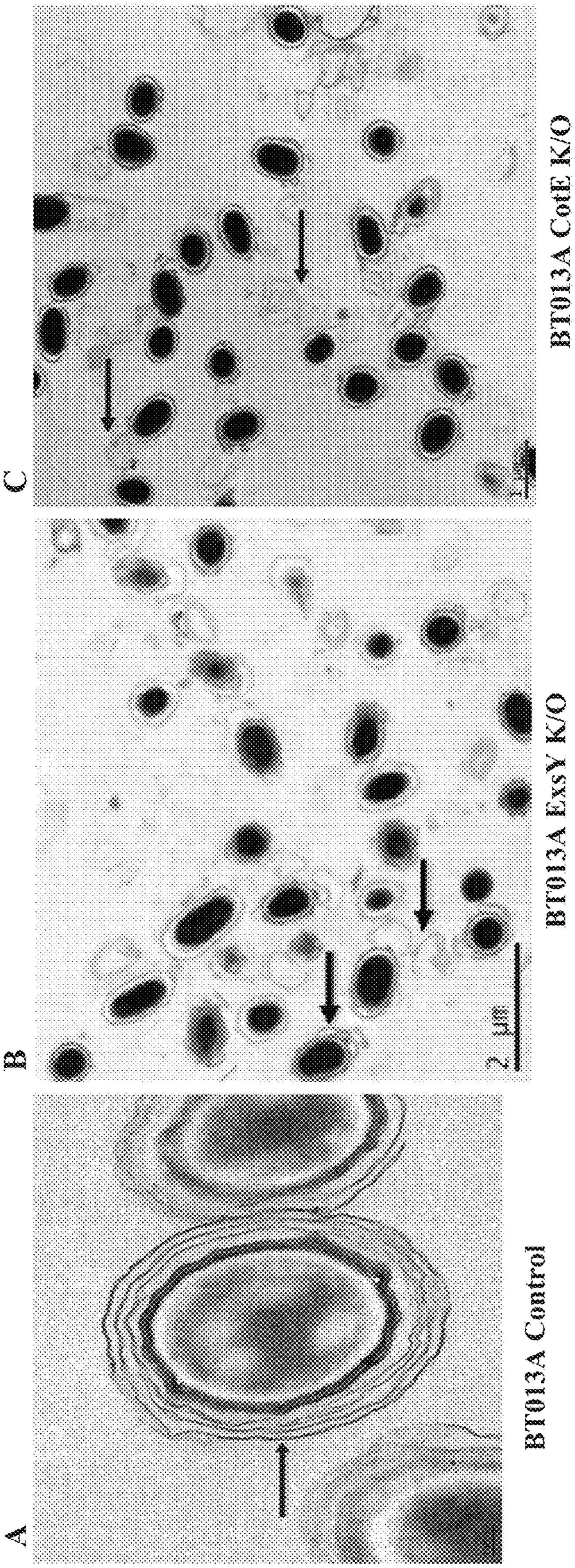
FIG. 6 provides a transmission electron micrographs showing: (A) intact spores of *Bacillus thuringiensis* BT013A surrounded by attached exosporium; (B) spores of an ExsY knockout strain of *Bacillus thuringiensis* BT013A, with detached exosporium; and (C) spores of a CotE knockout strain of *Bacillus thuringiensis* BT013A, with detached exosporium.

Transmission electron micrographs are provided in FIG. 6 showing intact spores of *Bacillus thuringiensis* BT013A (panel A) surrounded by attached exosporium, spores of the *Bacillus thuringiensis* BT013A ExsY knock-out mutant (panel B), and spores of the *Bacillus thuringiensis* BT013A CotE knock-out mutant (panel C) from which the exosporium has detached. The arrow in panel A of FIG. 6 indicates the layers of exosporium of intact BT013A spores, while arrows in panels B and C of FIG. 6 indicate exosporium that has detached from the spores in both the CotE and ExsY mutants. Images were taken on a JEOL JEM 1400 transmission electron microscope. No visible exosporium fragments were observed when control spores expressing a fusion protein (*Bacillus thuringiensis* BT013A without the CotE knockout, expressing the BclA-FL-OVAL fusion protein, data not shown) were subjected to same centrifugation and filtration procedures described above.

Presence of BclA-FL-OVAL or BclA-FL-PAG Protective Antigen in Exosporium Fragments Collected from the CotE and ExsY Knockout Mutants:

Exosporium fragments were created and purified as described above from spores that contained the pBC-BclA-FL-OVAL or pBC-BclA-FL-PAG plasmid. These spores create an exosporium that contains fusion proteins comprising full-length BclA and ovalbumin or protective antigen A. Exosporium fragments containing these constructs were created from the cotE knockout mutant spores and the exsY knockout mutant spores. The ovalbumin or protective antigen A protein concentration was determined by dot blot. Table 12 below summarizes the dot blot results as compared to purified protein. Briefly, an enriched exosporium fragment fraction generated as described above, whole cell broth, or purified ovalbumin or protective antigen was blotted onto nitrocellulose and then probed with commercially available rabbit polyclonal antibodies against full-length ovalbumin or *Bacillus anthracis* protective antigen. Whole cell broth was taken from the overnight cultures as described above in Example 9, and not subjected to any vortexing, filtration, or centrifugation steps. The blots were then developed with horseradish peroxidase (HRP)-conjugated secondary antibodies. The ovalbumin and protective antigen antibodies were verified by Western blot for size and specificity. Western blots were performed using purified ovalbumin and protective antigen proteins. The ovalbumin and protective antigen antibodies recognized bands of the correct size and did not cross-react with untransformed whole cell broth from *Bacillus thuringiensis* BT013A.

Dot blot results are shown below in Table 12. The results show that the protein of interest (OVAL or PAG) was present in both the whole cell broth and exosporium fragment-enriched fractions. Most of the protein of interest was retained in the exosporium fragment-enriched fractions, demonstrating that the proteins of interest were present on the exosporium fragments.

TABLE 12

PAG and OVAL expression detected by polyclonoal antibodies

| Host | Construct | Fraction Collected | Protein detected relative to the standard curve of the purified protein over background |
|---|---|---|---|
| exsY KO | BclA-FL-OVAL | Exosporium Fragment-Enriched | 1.66-fold increase |
| exsY KO | BclA-FL-OVAL | Whole Cell Broth | 1.85-fold increase |
| cotE KO | BclA-FL-PAG | Exosporium Fragment-Enriched | 1.12-fold increase |
| cotE KO | BclA-FL-PAG | Whole Cell Broth | 1.03-fold increase |

Example 10: Presence of BclA 20-35-Endoglucanase in Exosporium Fragments Collected from the CotE and ExsY Knockout and CotO Dominant Negative Mutants To provide a further demonstration that exosporium fragments containing fusion proteins can be generated using the CotE knockout and ExsY knockout strains, and to demonstrate that exosporium fragments can be generated using CotO dominant negative strains, PCR fragments were generated that contained the BclA promoter (SEQ ID NO: 149), start codon, and amino acids 20-35 of BclA fused in frame to *Bacillus subtilis* 168 endoglucanase. These PCR fragments were digested with XhoI and ligated into the SalI site of the pSUPER plasmid to generate the plasmid pSUPER-BclA 20-35-Endoglucanase.

The CotE and ExsY knockout mutants were generated as described above in Example 9.

Dominant Negative Mutants:

To create dominant negative mutants, PCR amplification was performed on the N-terminal half and the C-terminal half of CotO (SEQ ID NO: 199), containing amino acids 1-81 and 81-199 respectively. These fragments were cloned into the pHP13 *E coli/Bacillus* shuttle vector using homologous recombination. Correct clones were verified by Sanger sequencing. Each of the two CotO dominant negative mutants was introduced into *Bacillus thuringiensis* BT013A.

Exosporium fragments were created and purified as described in Example 9 from spores that contained the pSUPER BclA 20-35-Endo plasmid. These spores create an exosporium that displays fusion proteins comprising full-length BclA linked to endoglucanase. Exosporium fragments containing this construct were created from the cotE knockout mutant spores, exsY knockout mutant spores, CotO N-terminal dominant negative mutant spores, or CotO C-terminal dominant negative mutant spores. In each of these experiments, the amount of activity for the endoglucanase on the exosporium fragments was quantified as a percentage of the total enzyme levels. These results were compared against results generating using wild-type *Bacillus thuringiensis* BT013A that did not contain any mutations, but did contain the pSUPER BclA 20-35-Endo plasmid. The results are shown in Table 13 below.

TABLE 13

Exosporium Fragment Enzyme Activity

| Mutation | Construct | Endoglucanase Activity, Exosporium Fragments (mU/ml) |
|---|---|---|
| Wild-type BT013A | BclA 20-35 Endo | 10.3 |
| cotE KO | BclA 20-35 Endo | 269.0 |
| exsY KO | BclA 20-35 Endo | 238.0 |
| CotO NTD dominant | BclA 20-35 Endo | 22.4 |
| CotO CTD dominant | BclA 20-35 Endo | 27.5 |

These results demonstrate that mutations that disrupt the exosporium, such as a knock-out mutation in the cotE or exsY gene, or a dominant negative mutation in the CotO protein, can be used to generate exosporium fragments that are substantially free of spores, and demonstrates that these exosporium fragments contain fusion proteins that are targeted to the exosporium. There was a small amount of background endoglucanase activity in the exosporium fragment preparation from the BT013 strain having no mutations and expressing the BclA 20-25 Endo construct (BT013A BclA 20-35 Endo). This was unexpected and may represent a low level of unstable exosporium that is being released from spores and captured during the exosporium fragment collection process. CotE and ExsY KO strains contain the highest amount of enzyme in the exosporium fragment fraction. The CotO dominant negative mutants that express a fusion protein also have an elevated level of enzyme in the exosporium fragment fraction.

Example 11: Use of Exosporium Fragments for Vaccination of Fish and to Generate Simultaneous Protection Against Two Antigens Vaccination of Fish Using Exosporium Fragments Containing Full-Length BclA Linked to Antigenic Proteins, and Use to Simultaneously Generate Immunity Against Two Different Antigens:

Full-length BclA linked to ovalbumin (pBC-BclA-FL-OVAL) was expressed in the exsY KO mutant and full-length BclA linked to protective antigen (pBC-BclA-FL-PAG) was expressed in the cotE KO mutant as described above in Example 9. Purified exosporium fragments were prepared as described above in Example 9.

Purified exosporium fragments were diluted into in endotoxin-free Dulbecco's phosphate buffered saline (DPBS) for a final concentration of 1 mg/ml protein. Both types of purified exosporium fragments (the fragments from the exsY KO mutant containing the BclA-FL-OVAL fusion protein and the fragments from the cotE KO mutant containing the BclA-FL-PAG fusion protein) were coinjected or fed to adult zebrafish with and without Freund's Complete Adjuvant (FCA). Kidney tissue was collected and examined for detection of an antibody response (by dot blot) and for specific antibodies (ELISA).

Two different immunization methods were used: intramuscular injection and feed immunization. For immunization by intramuscular injection, fish were anaesthetized with 0.168 mg/ml tricaine (3-amino benzoic acid ethylester). Adult zebrafish were injected intramuscularly between the dorsal fin and the lateral line with 5 μl of the exosporium fragment solution (containing both types of exosporium fragments) with a fine Hamilton syringe with a 36 G needle to prevent negative effects of delivery.

Feed immunization was also performed. Zebrafish were given an immunization food mixture containing a 1:10 ratio of purified exosporium fragments carrying BclA-antigen fusion proteins in liver paste that was hand fed by oral droplet into holding tanks to each animal to ensure the total amount was ingested.

No booster immunizations were performed for either immunization method.

Detection of Antibodies by Dot Blot Analysis and ELISA in Fish Injected or Fed with Exosporium Fragments Containing BclA-Antigen Fusion Proteins:

Generation of OVAL-specific antibodies, PAG-specific antibodies, and memory antibodies in the fish immunized by intramuscular injection was measured in the kidney 14 days after immunization in 8 animals per group. Zebrafish were euthanized by immersion in ice. Kidneys were removed from each fish and pooled into a single group on ice, homogenized, and centrifuged to pellet cellular debris. The supernatants containing soluble proteins were assayed for activity.

In the feeding assay, animals were sacrificed at 3, 5 and 7 days post immunization with 3 animals per group and assayed for the generation of an immune response. Serum and kidneys were collected in the same manner as described above for the animals immunized by injection. Table 14 below shows the immune response as determined by dot blot analysis for zebrafish immune cells in this feeding assay. For detection of zebrafish IgM (zIgM), the kidney lysates were serially diluted and 2 μL placed on nitrocellulose membranes and allowed to dry. The membrane was washed three times with PBST (phosphate-buffered saline with TWEEN detergent) and then blocked with 5% (w/v) skim milk in PBST for 2 hours. After washing with PBST, monoclonal mouse anti-zIgM was incubated with the membrane for 2 hours. Lysates from unimmunized zebrafish served as a negative control. After further washing steps, the membranes were incubated with anti-mouse HRP-linked antibody at a dilution of 1:3000 as a secondary antibody for 1 hour. Finally, the membrane was observed by developing with PIERCE Fast Western Blot Kit Enhanced Chemiluminescense (ECL) Substrate (a peroxidase substrate). Results are shown in Table 14 below. The images were quantified using GENESYS image acquisition software.

TABLE 14

Zebrafish Immune Response to Feeding of Exosporium Fragments as Assessed by Kidney Immune Cell Generation

| Days after Treatment | Treatment | Immune response as compared to saline fed at matched day | Scoring of immune response generated |
|---|---|---|---|
| 0 | exsY KO/BclA-FL-OVAL | 1.96 | + |
| | cotE KO/BclA-FL-PAG | 9.97 | +++ |
| 5 | exsY KO/BclA-FL-OVAL | 0.34 | − |
| | cotE KO/BclA-FL-PAG | 4.92 | ++ |
| 7 | exsY KO/BclA-FL-OVAL | 0.95 | − |
| | cotE KO/BclA-FL-PAG | 1.36 | + |

For zebrafish immunized by intramuscular injection, screening for generation of target-specific antibodies was also determined by enzyme-linked immunosorbent assay (ELISA) with NUNCIMMUNO plates (96-wellplates for ELISA assays). Briefly, samples were collected from zebrafish after immunization to detect whether zIgM immune cells would cross react with poyclonal OVAL antibody generated from rabbit. The plates were coated by incubation with zIgM overnight. The kidney lysate was serially diluted and allowed to bind to the zIgM coated plate to retrieve all the immunoglobulin from the sample. The rabbit polyclonal antibody to OVAL was then allowed to bind to the specific fish immunoglobulin. Horseradish peroxidase (HRP)-conjugated goat anti-rabbit was then used as a conjugate to develop the ELISA. Results were quantified with a BIO-TEK microplate reader and GENS software.

For detection of zIgM by dot blot, the kidney cell lysates were serially diluted and placed on solid-phased PVDF membranes and allowed to dry. The membrane was washed three times with PB ST (phosphate-buffered saline with TWEEN detergent) and then blocked with 5% (w/v) skim milk in PBST for 2 hours. After washing with PBST, monoclonal mouse anti-zIgM was incubated with the membrane for 2 hours. Lysates from unimmunized zebrafish served as a negative control. After further washing steps, the membranes were incubated with anti-mouse HRP-linked antibody at a dilution of 1:3000 as a secondary antibody for 1 hour. Finally, the membrane was observed by developing with PIERCE Fast Western Blot Kit Enhanced Chemiluminescense (ECL) Substrate (a peroxidase substrate). Results are shown in Table 15 below. * indicates statistically significant results by paired student t-test as compared to the negative control (saline injected). "Peptide OVA/PAG" refers to a mixture of purified ovalbumin and protective antigen A. "exsY K/O, cotE K/O" refers to a mixture of exosporium fragments derived from exsY KO and cotE KO mutants that were not transformed with the BclA-FL-OVAL or BclA-FL-PAG constructs. † indicates that the results for the exosporium fragments derived from the non-transformed mutants represent total antibody.

TABLE 15

Zebrafish Immune Response to Two Antigens Codelivered at 14 Days After Injection of Exosporium Fragments, as Assessed by Kidney Immune Cell Generation and Specific Reaction

| | | Compared to saline injected | |
|---|---|---|---|
| Adjuvant (FCA) | Treatment | IgM generation by Dot Blot | ELISA against OVAL antibody, % over control |
| − | Peptide OVAL/PAG | + | 98.2 |
| | exsY KO/BclA-FL-OVAL, cotE KO/BclA-FL-PAG | +++ | **141.9*** |
| | exsY KO, cotE KO | +++† | 99.1 |
| + | Peptide OVAL/PAG | − | 114.1 |
| | exsY KO/BclA-FL-OVAL, cotE KO/BclA-FL-PAG | ++ | **120.0*** |
| | exsY K/O, cotE K/O | +† | 104.7† |

Example 12: Use of Exosporium Fragments for Vaccination of Fish Using Antigenic Proteins Derived from Fish Pathogens Expression of Fusion Proteins Containing Full-Length BclA and Antigenic Proteins in *Bacillus cereus* Family Member Mutants that Allow for Collection of Free Exosporium.

Proteins of fish pathogens are useful as antigens in developing fish vaccines. Table 16 below describes constructs encoding fusion proteins comprising BclA linked to various antigenic proteins from fish pathogens. Each of these constructs will be cloned into *Bacillus cereus* family members having one of the mutations described above in Example 9 and 10 that allow for the collection of exosporium fragments (the exsY and CotE knockout and CotO dominant negative mutant strains of *Bacillus thuringiensis* BT013A). Exosporium fragments will be purified from these strains as described above in Example 9 and fish immunized as described above.

Vaccination against two known infecting microbes, *Flavobacterium columnare* and *Edwardsiella ictaluri*, will be used as examples. The antigens to be used are summarized in Table 16. Genetic sequences coding for Lipopolysaccharide (LPS), an essential component of Gram-negative bacteria, will be cloned into the pBC-BclA-FL vector (using the method described above in Example 8). Nucleotide sequences encoding DNAk, a protein in the cellular chaperone system for protein folding of infectious flavobacteria, will be cloned into same vector. FlgD is a soluble scaffolding flagellar basal body rod modification protein of *Edwardsiella tarda* that is necessary for flagellum hook assembly. EseD, a gene important in the type III secretion system (T3SS) of *Edwardsiella ictaluri*, a key virulence factor that contributes to pathogenesis in fish, will also be cloned into the same expression vector. The EseD protein is one of several possible translocon proteins, which form pores in the host membrane, which could be expressed as an antigen from a vaccine.

TABLE 16

Antigenic proteins for protection from specific pathogens

| Plasmid | Exosporium Protein | Antigen | Pathogen |
|---|---|---|---|
| pBC | Full-length BclA | O-PS (LPS O-polysaccharide) | *Flavobacterium columnare* |
| pBC | Full-length BclA | DNAk (chaperonin) | *Flavobacterium columnare* |
| pBC | Full-length BclA | FlgD | *Edwardsiella ictaluri* |
| pBC | Full-length BclA | EseD | *Edwardsiella ictaluri* |

Detection of Antibodies by Dot Blot Analysis in Fish Injected, Fed or Bathed with Exosporium Fragments Containing BclA-Antigen Fusion Proteins.

As described above in Example 8, the pSUPER-BclA-OVAL plasmid encodes ovalbumin fused to the BclA sequence. The pSUPER-BclA-O-PS, pSUPER-BclA-DNAk, pSUPER-BclA-LPS/FlgD, and pSUPER-BclA-EseD plasmids encode the LPS β-polysaccharide, DNAk, LPS/FlgD, and EseD antigens, respectively, fused to the BclA sequence. Purified exosporium fragments derived from the *Bacillus thuringiensis* BT013A exsY knockout, CotE knockout or CotO dominant negative mutant strains expressing the BclA-O-PS, BclA-DNAk, BclA-LPS/FlgD, or BclA-EseD fusion proteins will be dissolved in endotoxin-free Dulbecco's phosphate buffered saline (DPBS) without calcium chloride or magnesium chloride, or in 0.15 M NaCl dissolved in deionized distilled water for a final concentration of 0.001 mg/ml to 5 mg/ml protein.

Three different immunization methods will be used: intramuscular injection, feed immunization, and immersion immunization. For immunization by intramuscular injection, fish will first be anaesthetized with 0.168 mg/ml tricaine (3-amino benzoic acid ethylester) in water or by placing the fish on ice for 30-60 seconds before injection. Zebrafish will injected intramuscularly between the dorsal fin and the lateral line with 10 μl of the exosporium fragment solution.

Feed immunization will also be performed. Zebrafish will be given an immunization food mixture containing a 1:4 ratio of purified exosporium fragments carrying BclA-antigen fusion proteins:TetraMin fish food, supplemented with ampicillin (final concentration 40 mg/g). A booster immunization will be given 10 days after the first immunization.

For immunization by immersion, adult zebrafish will immersed in a tank containing the exosporium fragments (500 μg/mL) for 30 min, and then returned to a tank of clean water. A booster immunization will be given 10 days after the first immunization.

Generation of antibodies to the fish pathogen antigens will be measured in the antiserum, muscle, and gills 2.5 days after final immunization. Zebrafish will be killed by immersion in ice. The serum will be collected first and then the muscle and gills of the fish will be removed on ice, homogenized, and centrifuged to pellet cellular debris. The supernatants containing soluble proteins will be assayed for activity.

Screening for polyclonal antibodies will be done by dot blot analysis. Briefly, sample will be collected from zebrafish after immunization to detect whether zebrafish IgM (zIgM) immune cross reacts with the fish pathogen antigens using dot blotting. First, the recombinant protein (e.g., recombinant EseD) (50 to 500 ng) will be solid-phased on PVDF membranes and dry-up overnight. The membrane will be washed three times with PBST (phosphate-buffered saline with TWEEN detergent) and then blocked with 5% (w/v) skim milk in PBST for 2 hours. After washing with PBST, 10-μl zebrafish antiserum at a dilution of 1:100 will incubated with the membrane for 2 h. Unimmunized zebrafish serum will serve as a negative control. After further washing steps, the membranes will be incubated with anti-zebrafish IgM HRP-linked antibody at a dilution of 1:3000 as a secondary antibody for 1 h. Finally the membrane will be observed by developing with Pierce Fast Western Blot Kit ECL Substrate.

It is expected that antibodies to the fish pathogen antigens will be generated following immunization with exosporium fragments by intramuscular injection, feeding, or immersion.

Immunity of Fish Immunized with the Exosporium Fragments Against Infecting Pathogens.

Bacterial isolates *F. columnare* (ATCC 23463) and *E. ictaluri* (ATCC 33202) will be used throughout the study. All isolates will be retrieved from frozen glycerol stocks stored at −80° C. and streaked onto *F. columnare* Growth Medium (FCGM); or tryptic soy agar with 5% sheep's blood (ThermoFisher, Waltham, MA). After 48 h of growth at 28° C., isolates will be dislodged from the agar using a sterile loop and inoculated into 50 mL of FCGM or brain-heart infusion medium (Becton Dickinson, Sparks, MD) and incubated in broth at 28° C. for 24 hours. Bacterial cells will be harvested and counted before bacterial challenge is performed.

Bacterial Challenge:

Zebrafish will be prophylactically treated with 4 mg/L potassium permanganate for 30 min. After acclimatization and before bacterial challenge, two zebrafish will be randomly selected and routine diagnostic procedures will be performed. External skin scrapings from multiple sites and gill clips will be viewed microscopically to determine whether external bacteria or parasites are present. Three days after the last immunization the fish will be inoculated with bacteria. Groups of zebrafish (20 per group) will be immersed in *F. columnare* or *E. ictaluria* at concentrations of $2.4\times10^4$ colony-forming units (CFU)/mL, $2.4\times10^5$ CFU/mL, and $2.4\times10^6$ CFU/mL, *E. coli* at a concentration of $2.4\times10^6$ CFU/mL, or PBS, respectively for 5 h. The eight groups will then be kept in five separate 3-L aquaria and observed for 21 days.

Relative Percent Survival Experiments:

Fish will be monitored daily and humane end-point criteria suggested by the national ethical board will be followed. Fish will be euthanized with an anesthetic overdose if they show any of the following signs: abnormal swimming, gasping, observable swelling or wasting, tissue damage, or lack of response to touch.

Bacterial Counts in Infected Fish:

Zebrafish from each group will be sampled for recovery of *F. columnare* or *E. ictaluria* at their deaths. Ascitic fluid will be aspirated and the wounds, livers, and pancreas will be separately homogenized in 10 mL of tryptic soy broth (TSB). The ascitic fluid and homogenized tissues will be plated on cefoperazone MacConkey agar and incubated at 37° C. for 24 h. Suspected bacterial isolates will be identified phenotypically by standard conventional biochemical methods. Isolates suspected to be *F. columnare* or *E. ictaluria* will be subject to partial 16S rRNA identification.

Example 13: Use of Exosporium Fragments for Vaccination of Mice to Generate Protection to Two Antigens Concurrently Administration of Exosporium Fragments Containing Fusion Proteins of Full-Length BclA and Antigenic Proteins to Generate an Immune Response.

BclA linked to ovalbumin (pBC-BclA-FL-OVAL) expressed in the exsY KO mutant and protective antigen (pBC-BclA-FL-PAG) expressed in the cotE KO mutant as described above in Example 9 were coinjected subcutaneously or coadministered intranasally to adult mice with and without an adjuvant (FCA). For immunization by subcutaneous injection, groups of six BALB/c mice were immunized two times at an interval of two weeks. Each dose of antigen solution was a mixture of 25 μl of the two types of antigenic exosporium fragments (12.5 μl of each type of exosporium fragment, prepared as described above in Example 9; equivalent to $10^8$ CFU/ml of whole cell broth), with or without the adjuvant. For intranasal immunization, groups of six BALB/c mice were immunized two times at an interval of two weeks. Each dose of antigen solution was a mixture of 25 μl of two antigenic exosporium fragments (12.5 μl of each type of exosporium fragment, prepared as described above in Example 9; equivalent to $10^8$ CFU/ml of whole cell broth). Intranasal immunizations were carried out with the mouse held in a supine position with the head down while the antigen solution was delivered slowly with a micropipette onto the nares so that the mouse could sniff it in.

Serum was collected and examined for detection of longer-term immunity as assessed by specific antibodies (ELISA) four weeks after the first injection (two weeks after the booster injection). Blood was obtained from the lateral femoral vein in heparinized capillary tubes and was separated and stored at −20° C. until it was analyzed.

Detection of Antibodies by ELISA from Mice Injected with Exosporium Fragments Containing BclA-Antigen Fusion Proteins.

Immunoglobulin IgG and IgA antibodies to OVAL and PAG were measured by enzyme-linked immunosorbent assay (ELISA) with COSTAR High-Binding Assay plates (96-wellplates for ELISA assays). Briefly, the plates were coated with 100 nM of protein by incubation with OVAL or PAG protein. Plasma samples were neutralized and diluted to 50 mg/mL, determined by bicinchoninic acid (BCA) protein assay. Horseradish peroxidase (HRP)-conjugated goat anti-mouse IgG (γ chain specific) was used as a conjugate. Results are shown in Table 17 below. "Peptide OVAL/PAG" refers to a mixture of purified ovalbumin and protective antigen A injected as described above at (0.05 μg). "exsY K/O, cotE K/O" refers to a mixture of exosporium fragments derived from exsY KO and cotE KO mutants that were not transformed with the BclA-FL-OVAL or BclA-FL-PAG constructs. A standard curve for each protein was generated from known purified antibody and used to quantify the ng/mL of specific antibody produced in each animal. The values in the Table 17 represent the average of seven individual mice including the standard deviation. As can be seen from Table 17, antibodies to both PAG and OVA were generated simultaneously in response to both subcutaneous injection and intranasal administration. The exosporium-carried protein performed equally as well or better than the protein alone. Using the adjuvant (FCA) did not significantly increase the generation of protective antibody expressed on the exosporium, showing that it was unnecessary to add in order reach similar levels of specific antibody protection to the protein with the adjuvant.

TABLE 17

Generation of multiple antibodies to exosporium fragments administered to adult mice intranasally or subcutaneously

| Adjuvant (FCA) | Treatment | ELISA Compared to saline injected: Serum IgG to OVA generation from Subcutaneous administration (STD) | Serum IgG to PAG generation from Subcutaneous administration (STD) | Serum IgG to OVA generation from Intranasal administration (STD) | Serum IgG to PAG generation from Intranasal administration (STD) |
|---|---|---|---|---|---|
| − | Saline | 1.3 ± 2.1 | 13.0 ± 10.8 | 3.5 ± 0.2 | 6.7 ± 4.3 |
| | Peptide OVAL/PAG | 17.2 ± 14.6 | 48.9 ± 19.6 | 19.8 ± 11.9 | 33.0 ± 13.1 |
| | exsY KO/BclA-FL-OVAL, cotE KO/BclA-FL-PAG | 16.4 ± 6.9 | 119.6 ± 69.6 | 39.7 ± 26.5 | 26.8 ± 12.2 |
| | exsY K/O, cotE K/O | 26.5 ± 4.1 | 68.4 ± 50.5 | 24.3 ± 21.1 | 43.7 ± 11.7 |
| + | Adjuvant | 2.0 ± 0.7 | 8.3 ± 4.3 | 3.5 ± 0.5 | 4.4 ± 4.1 |
| | Peptide OVAL/PAG | 50.1 ± 34.3 | 84.0 ± 34.0 | 25.9 ± 23.6 | 69.6 ± 49.7 |
| | exsY KO/BclA-FL-OVAL, cotE KO/BclA-FL-PAG | 25.8 ± 20.3 | 63.1 ± 39.7 | 16.1 ± 10.6 | 29.7 ± 17.3 |
| | exsY K/O, cotE K/O | 9.0 ± 4.8 | 13.2 ± 10.7 | 3.9 ± 0.7 | 18.8 ± 11.1 |

Example 14: Use of Exosporium Fragments Displaying Proteases or Lactonases for Protecting Animals from Pathogens Exosporium fragments that contain fusion proteins containing a targeting sequence or exosporium protein (e.g., BclA) and a protein or peptide that protects an animal from a pathogen can be generated using the methods described above in Examples 8 and 9. For example, these exosporium fragments can be used to display proteases or lactonases that protect animals from one or more pathogens. Certain bacterial pathogens can communicate between individual members via secretion of bacterial lactone homoserines or related signaling molecules. This signaling between bacteria results in secretion of toxins by the bacteria and upregulation of virulence factors. Thus, proteases or lactonases specific for bacterial lactone homoserine signaling molecules can protect animals from such bacterial pathogens by disrupting communication between bacteria. Suitable proteases specific for bacterial lactone homoserine signaling molecules include endopeptidases and exopeptidases. Fusion proteins containing proteases specific for bacterial lactone homoserine signaling molecules can be expressed in the exsY and CotE knockout and CotO dominant negative mutant strains of *Bacillus thuringiensis* BT013A described above. Exosporium fragments containing the fusion proteins can then be prepared as described above.

Example 15: Use of Exosporium Fragments Containing a Lactonase or Protease Fusion Protein for Prevention of Bacterial Growth and Disruption of Biofilm Formation N-Acylated homoserine lactone (AHL) lactonases are capable of degrading signaling molecules involved in bacterial quorum sensing. Lactonases can therefore be used to control bacterial infection. The precise regulation of protein levels is required for proper growth and function of all bacterial cells; a balance of the rate of protein synthesis and degradation maintains this. Addition of external proteases disrupts this balance. *Bacillus subtilis* serine proteases are especially effective against biofilm and bacterial growth because of their ability to influence the proteome during an adaptive response to changes in the bacteria's extracellular environment.

Genes responsible for the AHL lactonase activity in the *Bacillus* family (AiiA) or for protease activity were cloned into the pBC plasmid to generate a plasmid encoding a fusion protein containing an AiiA or a protease linked to a targeting sequence or exosporium protein (amino acids 20-25 of BclA or full-length BclA). The fusion proteins were then expressed in the exsY knockout strain of *Bacillus thuringiensis* BT013A using the methods described above in Example 9. Exosporium fragments were purified as described in Example 9. The fusion proteins used in the experiments described in this Example are summarized in Table 18 below.

TABLE 18

Fusion Proteins Containing a Lactonase or a Protease

| Protease or Lactonase (SEQ ID NO.) | Targeting Sequence or Exosporium Protein Fragment |
|---|---|
| *Bacillus thuringiensis* B184 AiiA (SEQ ID NO: 207) | Full-length BclA |
| *Bacillus pseudomycoides* B30 AiiA (SEQ ID NO: 208) | Full-length BclA |
| *Bacillus subtilis* Serine Protease (SEQ ID NO: 209) | Amino acids 20-35 of BclA (amino acids 20-35 of SEQ ID NO: 1) |
| *Bacillus subtilis* Serine Protease (SEQ ID NO: 210) | Amino acids 20-35 of BclA (amino acids 20-35 of SEQ ID NO: 1) |

Confirmation of Quorum Quenching Activity.

AHL inactivation assays were conducted using bioassay plates. Briefly, aliquots of N-hexanoyl-L-Homoserine lactone (C6-HSL) were incubated at 37° C. for 2 hours with 0, 40 or 80 μL of whole cell broth or exosporium fragments purified from the exsY KO mutant expressing a fusion protein comprising a lactonase (*Bacillus thuringiensis* B184 AiiA). The reaction mixture was inoculated onto LB agar seeded with the bio-reporter *Chromobacterium violaceum* CV026 and incubated at 30° C. overnight. Disappearance of C6-HSL from the mixture was assessed by the loss of purple pigment that *C. violaceum* CV026 produces in response to C6-HSL. Results are summarized in Table 19 below. * indicates a statistically significant decrease as measured by students paired T-test as compared to the control (exosporium fragments from exsY KO spores that do not express a fusion protein).

The reduction in the total area of purple pigment produced by the reporting strain indicates that the lactone was degraded by both the whole cell broth and the purified exosporium fragments expressing the lactonase gene. Importantly, the exosporium fragments were more effective at degrading the lactone than the whole cell broth.

TABLE 19

Summary of Lactone Degradation by Exosporium Fragments Displaying a Lactonase

| Plasmid | Exosporium Mutant | Fraction Collected | % Area of purple pigment ($cm^2$) relative to control 0 μL | 40 μL | 80 μL |
|---|---|---|---|---|---|
| Control | exsY KO | None | 100 | 100 | 100 |
| pBC-BclA AiiA | exsY KO | Purified exosporium fragments | 160 | 125 | **11*** |
| pBC-BclA AiiA | exsY KO | Whole Cell Broth | 138 | 134 | **57*** |

Prevention of Bacterial Growth.

Bacterial cultures of *Chromobacterium violaceum, Acinetobacter baumanii, Pseudomonas aeroginosa*, and *Staphylococcus epidermidis* were grown for 24 hours to an O.D. 600 of 2.0. These cultures were inoculated into a plate assay at 1 μL into 500 μL LB media, were allowed to grow in the plate for 4 hours before the addition of exosporium fragments. Exosporium fragments displaying a protease or a lactonase (16% v/v) were then added and the cultures were then incubated without shaking at 30° C. for an additional 4 hours. XTT salt solution was then added to each well. XTT salt cleavage by bacterial dehydrogenases is an indicator of active cells and was measured as the absorbance at 490 nm after 3 hours of incubation at 30° C. Results are shown in Table 20 below.

Prevention and Dispersion of Biofilm.

Bacterial cultures of *Chromobacterium violaceum, Acinetobacter baumanii, Pseudomonas aeroginosa*, and *Staphylococcus epidermidis* were grown for 24 hours to an O.D. 600 of 2.0. These cultures were inoculated into a plate assay at 1 μL into 500 μL LB media, were allowed to grow in the plate for 8 hours before the addition exosporium fragments. Exosporium fragments displaying a protease or a lactonase (16% v/v) were then added and the cultures were then incubated without shaking at 30° C. for an additional 8 hours.

Additionally, the *Acinetobacter baumanii* strain was assessed for the ability to break up a formed biofilm. The assay was performed in the same manner as described above for assaying the prevention of biofilm formation, except that the exosporium fragments were added at 24 hours post inoculation. Following the incubation period, the bacterial cultures were poured out and the wells stained with XTT salt solution. XTT salt cleavage by bacterial dehydrogenases is a reading of active cells and was measured as the absorbance at 490 nm after 3 hours incubation at 30° C. Results are shown in Table 20 below. * indicates a statistically significant decrease as measured by students paired T-test as compared to the control (exosporium fragments from exsY KO spores that do not express a fusion protein).

TABLE 20

Summary of Activity of Exosporium Fragments Displaying Lactonase or *Bacillus subtilis* Serine Protease (16% v/v) on Bacterial Species

| Species | Exosporium Mutant | Fusion protein [1]BclA or [2]$BclA_{20-35}$ | % Bacterial growth relative to no fusion protein (Average +/− SD) | % Biofilm formation relative to no fusion protein (Average +/− SD) | % Biofilm survival relative to no fusion protein (Average +/− SD) |
|---|---|---|---|---|---|
| *C. violaceum* | exsY KO | None | 100 +/− 10 | 100 +/− 15 | — |
| | | [1]AiiA, *B. thuringiensis* | **80 +/− 3*** | 108 +/− 16 | — |
| | | [1]AiiA, *B. pseudomycoides* | 92 +/− 5 | 100 +/− 6 | — |
| | | [2]Serine Protease (SEQ ID NO: 209) | 122 +/− 27 | 124 +/− 22 | — |
| | | [2]Serine Protease (SEQ ID NO: 210) | **47 +/− 14*** | **33 +/− 5*** | — |
| *A. baumanii* | | None | 100 +/− 39 | 100 +/− 5 | 100 +/− 18 |
| | | [1]AiiA, *B. thuringiensis* | 117 +/− 13 | 140 +/− 87 | 172 +/− 47 |
| | | AiiA, *B. pseudomycoides* | 149 +/− 11 | 191 +/− 93 | 122 +/− 21 |
| | | [2]Serine Protease (SEQ ID NO: 209) | 118 +/− 5 | 123 +/− 6 | 282 +/− 80 |
| | | [2]Serine Protease (SEQ ID NO: 210) | **74 +/− 6*** | 98 +/− 5 | **63 +/− 61*** |
| *P. aeroginosa* | | None | 100 +/− 13 | 100 +/− 9 | — |
| | | [1]AiiA, *B. thuringiensis* | 150 +/− 2 | 127 +/− 74 | — |
| | | [1]AiiA, *B. pseudomycoides* | 149 +/− 24 | 158 +/− 71 | — |
| | | [2]Serine Protease (SEQ ID NO: 209) | 92 +/− 24 | 103 +/− 14 | — |
| | | [2]Serine Protease (SEQ ID NO: 210) | **45 +/− 16*** | **76 +/− 7*** | — |

TABLE 20-continued

Summary of Activity of Exosporium Fragments Displaying Lactonase or *Bacillus subtilis* Serine Protease (16% v/v) on Bacterial Species

| Species | Exosporium Mutant | Fusion protein [1]BclA or [2]$BclA_{20-35}$ | % Bacterial growth relative to no fusion protein (Average +/− SD) | % Biofilm formation relative to no fusion protein (Average +/− SD) | % Biofilm survival relative to no fusion protein (Average +/− SD) |
|---|---|---|---|---|---|
| *S. epidermidis* | | None | 100 +/− 6 | 100 +/− 4 | — |
| | | [1]AiiA, *B. thuringiensis* | **70 +/− 12*** | **76 +/− 1*** | — |
| | | [1]AiiA, *B. pseudomycoides* | 95 +/− 23 | 100 +/− 4 | — |
| | | [2]Serine Protease (SEQ ID NO: 209) | 91 +/− 13 | 83 +/− 18 | — |
| | | [2]Serine Protease (SEQ ID NO: 210) | **13 +/− 2*** | **32 +/− 7*** | — |

Example 16: Use of Exosporium Fragments Containing a Lactonase or Protease Fusion Protein in a Fish Farm for Prevention of Bacterial Infection It is expected that oral administration of the exosporium fragments containing the AiiA or protease fusion described above in Example 15 by supplementation of fish feed or administration by immersion bathing will significantly attenuate *Aeromonas hydrophila* infection in zebrafish.

Wild-type zebrafish (4 months of age, with an average weight of ~200 mg and an average length of ~2.5 cm) will be randomly divided into test and control groups and fed a diet supplemented with exosporium fragments over a range of ($2\text{-}2\times10^{-3}$ U) per gram of feed and immersed in *A. hydrophila* NJ-1-containing water. Alternatively, the fish will be submerged in a bath containing lower concentrations of the exosporium fragments and placed in *A. hydrophila* NJ-1-containing water. Mortality during the 25-day experimental period will be recorded each day. Dead fish will be removed daily and examined for bacteriological contamination. The water containing *A. hydrophila* NJ-1 will also be examined daily for bacteriological contamination. To test bacterial contamination, the fish body will be sterilized with 75% ethanol and the body fluid will be extracted with a syringe under sterile conditions and streaked onto an ampicillin blood agar plate. Water samples will be streaked onto the same plate directly.

Example 17: Use of Exosporium Fragments Containing Antimicrobial Peptide Fusion Proteins for Prevention of Bacterial Growth and Disruption of Biofilm Formation Construction of Fusion Proteins Containing Antimicrobial Peptides and Generation of Exosporium Fragments.

Genes were synthesized that code for either of two antimicrobial peptides, LfcinB (derived from bovine lactoferrin, SEQ ID NO: 212) and LysM (derived from chicken lysozyme, SEQ ID NO: 213), linked to amino acids 20-35 of BclA (amino acids 20-35 of SEQ ID NO: 1), under the control of the BclA promoter (SEQ ID NO: 149). These genes were cloned into the pBC plasmid to create the constructs pBC-BclA 20-35-LfcinB and pBC-BclA 20-35-LysM. These constructs are summarized in Table 21 below. The constructs were then introduced into the exsY knockout mutant of *Bacillus thuringiensis* BT013A and exosporium fragments were prepared using the method described above in Example 9.

TABLE 21

Antimicrobial Fusion Proteins Containing LfcinB or LysM

| Antimicrobial peptide | Targeting Sequence |
|---|---|
| *Bos Taurus* Lactoferrin peptide (LfcinB) (SEQ ID NO: 212) | Amino acids 20-35 of BclA (amino acids 20-35 of SEQ ID NO: 1) |
| *Gallus gallus* Lysozyme (LysM) (SEQ ID NO: 213) | Amino acids 20-35 of BclA (amino acids 20-35 of SEQ ID NO: 1) |

Antimicrobial and Antibiofilm Activity of Exosporium Fragments Containing LysM or LfcinB Fusion Proteins.

Using the methods described above in Example 15, a diverse set of microbes was assayed for the ability of exosporium fragments carrying LysM or LfcinB to prevent bacterial growth or biofilm formation. Results are shown in Table 22 below. * indicates a statistically significant decrease as measured by students paired T-test as compared to the control (exosporium fragments from exsY KO spores that do not express a fusion protein). Data are from two independent experiments.

TABLE 22

Summary of Activity Exosporium Fragments Displaying LysM or LfcinB antimicrobial peptide (16% v/v) on Bacterial Species

| Species | Exosporium Mutant | Fusion protein | % Bacterial growth relative to no fusion protein (Average +/− SD) | % Biofilm formation relative to no fusion protein (Average +/− SD) |
|---|---|---|---|---|
| *C. violaceum* | exsY KO | None | 100 +/− 10 | 100 +/− 15 |
| | | AA20-35 of BclA-LfcinB | **82 +/− 5*** | **83 +/− 13*** |
| | | AA20-35 of BclA-LysM | 102 +/− 5 | 113 +/− 15 |
| *A. baumanii* | | None | 100 +/− 39 | 100 +/− 5 |
| | | AA20-35 of BclA-LfcinB | 112 +/− 31 | **74 +/− 4*** |
| | | AA20-35 of BclA-LysM | 124 +/− 16 | 165 +/− 3 |

TABLE 22-continued

Summary of Activity Exosporium Fragments Displaying LysM or LfcinB antimicrobial peptide (16% v/v) on Bacterial Species

| Species | Exosporium Mutant | Fusion protein | % Bacterial growth relative to no fusion protein (Average +/− SD) | % Biofilm formation relative to no fusion protein (Average +/− SD) |
|---|---|---|---|---|
| *P. aeroginosa* | | None | 100 +/− 13 | 100 +/− 9 |
| | | AA20-35 of BclA-LfcinB | 128 +/− 17 | **83 +/− 4*** |
| | | AA20-35 of BclA-LysM | 154 +/− 9 | 109 +/− 2 |
| *S. epidermidis* | | None | 100 +/− 6 | 100 +/− 4 |
| | | AA20-35 of BclA-LfcinB | **72 +/− 20*** | **83 +/− 24*** |
| | | AA20-35 of BclA-LysM | 92 +/− 28 | 104 +/− 3 |

Example 18: Use of Exosporium Fragments Containing LfcinB or LysM Fusion Proteins to Treat Feedlot Bloat It is expected that the exosporium fragments containing the fusion proteins containing the LysM or LfcinB peptides described above in Example 17 will kill a significant number of *Streptococcus* sp. cells. This would be expected to directly translate into killing of bacteria in the alimentary tracts of ruminants (e.g., cows, sheep, or horses) suffering from feedlot bloat. Feedlot bloat (ruminal acidosis) occurs when large amounts of starch are added to the diet. Under these conditions, the growth of *Streptococcus bovis* is no longer restricted by a lack of this energy source and the bacterial population of *S. bovis* grows faster than other species of rumen bacteria. *S. bovis* produces lactic acid, an acid ten times stronger than acetic, propionic or butyric acid, the accumulation of which eventually exceeds the buffering capacity of rumen fluid resulting in disease.

Example 19: Use of Exosporium Fragments Containing LfcinB or LysM Fusion Proteins to Treat Foot Rot in Cattle Sheep and cattle are prone to bacterial hoof infections that can be quite debilitating. Interdigital phlegmon is an infection of the soft tissue between the claws of the feet and is caused by two anaerobic bacteria, *Fusobacterium necrophorum* and *Prevotella melaninogenicus*. Using the exosporium fragments described above in Example 17, growth of *F. necrophorum* and *P. melaningogenicus* cultures will be inhibited using the LfcinB or LysM exosporium fragments derived from the *Bacillus thuringiensis* BT013A mutants. Using these verified exosporium fragments, yearling steers with clinical signs of acute interdigital phlegmon (lameness with interdigital swelling, interdigital lesions, or both) will be randomly assigned to treatment groups: with different concentrations of the LfcinB or LysM exosporium fragments, with and without an antiseptic and astringent solution (e.g., copper or zinc sulfate [7%-10% in water]). The groups will be treated by footbath method. All animals will be treated for 3 days. Treatment will be considered successful if animals are no longer lame on day 4. Biopsy specimens will be collected prior to treatment in each group and submitted for bacterial culture and histologic examination.

Example 20: Inhibiting or Preventing Biofilm Formation or Promoting Biofilm Dissolution from Surfaces in an Aquaculture System Using Exosporium Fragments Containing an Apyrase Fusion Protein Biofilms can form on surfaces within aquaculture systems such as pipes, pumps, filters, and collecting tanks, or even the gills of fish being cultivated in the aquaculture system. Apyrase hydrolyzes ATP to AMP and inorganic phosphate and has been shown to reduce biofilm biomass. Exosporium fragments containing an apyrase fusion protein (containing an apyrase encoded by the Rrop1 gene of *Solanum tuberosum* or the ytkD gene of *Bacillus subtilis*) were generated using the methods described in Examples 8 and 9. These constructs are summarized in Table 23 below. Bacterial strains were grown and then passaged in new medium containing isolated exosporium fragments containing the BclA-apyrase fusion proteins. The ability of apyrase exosporium fragments to inhibit biofilm formation or promote its dissolution was then measured. Using the methods described above in Example 15, a diverse set of microbes was assayed for the ability of the exosporium fragments to affect biofilms or microbial growth. Results are shown in Table 24 below. * indicates a statistically significant decrease as measured by students paired T-test as compared to the negative control (exosporium fragments from exsY KO or cotE KO spores that do not express a fusion protein).

TABLE 23

Antibiofilm Fusion Proteins Containing an Apyrase

| Apyrase | Targeting Sequence |
|---|---|
| *Solanum tuberosum* Rrop1 (SEQ ID NO: 204) | Amino acids 20-35 of Bcl A (amino acids 20-35 of SEQ ID NO: 1) |
| *Bacillus subtilis* YtkD (SEQ ID NO: 205) | Amino acids 20-35 of Bcl A (amino acids 20-35 of SEQ ID NO: 1) |

TABLE 24

Summary of Activity of Exosporium Fragments Displaying an Apyrase (16% v/v) on Bacterial Species

| Species | Exosporium Mutant | Fusion protein $BclA_{20-35}$ | % Biofilm formation relative to no fusion protein (Average +/− SD) | % Biofilm survival relative to no fusion protein (Average +/− SD) |
|---|---|---|---|---|
| *C. violaceum* | BT013A | Rrop1 | 146 +/− 27 | — |
| | exsY | ytkD | 99 +/− 0 | — |
| *A. baumanii* | BT013A | Rrop1 | 133 +/− 20 | — |
| | exsY | ytkD | 120 +/− 5 | — |
| | BT013A | Rrop1 | — | 181 +/− 96 |
| | cotE | ytkD | — | **32 +/− 6*** |
| *P. aeroginosa* | BT013A | Rrop1 | 101 +/− 6 | — |
| | exsY | ytkD | 96 +/− 11 | — |
| *S. epidermidis* | BT013A | Rrop1 | 101 +/− 0 | — |
| | exsY | ytkD | 105 +/− 2 | — |

Example 21: Effect of Exosporium Fragments Containing an Apyrase Fusion Protein on *Acinetobacter Baumannii* Initial Biofilm Adherence in an In Vitro Cell Culture Model of Bovine Epithelial Cells Biofilms can also form within wounds. To show that exosporium fragments containing an apyrase fusion protein can be used to prevent or inhibit formation of such biofilms, several experiments will be performed. First, an in vitro bacterial adherence assay will be performed on bovine fibroblasts treated with or without exosporium fragments containing a BclA-apyrase fusion protein (made as described in Examples 8 and 9). Bovine epithelial cell line NBL-4 (ATCC CCL-44; American Tissue Culture Collection, Rockville, Md., USA) will be cultured in a Petri dish at 37° C. in DMEM media (Gibco BRL, Grand Island, N.Y., USA) supplemented with penicillin G 100,000 U/L, streptomycin 50 mg/L and 5% (v/v) of fetal bovine serum (Gibco BRL) in a humidified atmosphere containing 5% (v/v) of $CO_2$. When the fibroblasts have reached about 80% confluence on the bottom of the Petri dish, the medium will be replaced with 0.25% trypsin-EDTA (1689649, MP Biomedicals, Solon Ohio) and the Petri dish will be incubated at 37° C. for 10 min. Cells will be collected using a cell scraper and washed with fresh medium three times by centrifuging at 300×g for 3 minutes. Washed cells will be adjusted to a concentration of $1\times10^5$ cells per mL with fresh media and 2 mL of cell solution will be transferred to each well of a 12-well plate containing a 13-mm-diameter plastic coverslip (Thermanox, Nunc, Rochester, N.Y., USA) in each well. The cells will be incubated at 37° C. for about 3 days until cells cover about 90% of each coverslip and will then be washed with phosphate buffered saline (PBS) three times. *Acinetobacter baumannii* ATCC 17978 grown overnight in Luria Bertani (LB) medium will be collected and washed three times with fresh medium by centrifuging at 6,000 rpm for 3 minutes. Bacterial cells will be adjusted to a concentration of $1\times10^8$ CFU/mL and mixed with the exosporium fragments containing BclA-apyrase fusion proteins. Each cell monolayer will be infected with 1 mL of bacterial suspension and incubated for 60 min at 37° C. in a 5% (v/v) $CO_2$ atmosphere. For damaged cell assays, fibroblast cells in the central area of plastic coverslips will be damaged using the tip of a knife before the infection is performed. After infection with *Acinetobacter baumannii*, plastic coverslips will be washed with PBS buffer three times to remove non-adherent bacteria and then fixed in 100% of methanol for 20 min before being stained in a Giemsa staining solution for 30 minutes at room temperature. The coverslips will be air-dried, mounted and observed under a light microscope with a 60× objective lens. The number of bacteria adhering to 100 cells will be determined. Three independent experiments will be performed for each treatment.

Example 22: Effect of Exosporium Fragments Containing a BclA-Apyrase Fusion Protein on *Acinetobacter Baumannii* Initial Biofilm Adherence in an In Vivo Mouse Wound Infection Model Female pathogen-free C57BL/6 mice (Harlan, Indianapolis, Ind.), 12 weeks old, weighing approximately 20-23 grams will be used in all experiments. The animals will be kept on a 12 hour light cycle and will be provided with rodent chow (LabDiet 5001, PMI Richmond, Ind.) and water ad libitum throughout the study. Pentobarbital (Nembutal, Ovation Pharmaceuticals, Inc., Deerfield, Ill., manufactured by Hospira, Lake Forest, Ill.) will be administered intraperitoneally (50 mg/kg IP) for anesthesia. During the study, all mice will be singly housed and will all receive 0.1 mg/kg buprenorphine (Buprenex; Reckitt Benckiser Pharmaceuticals Inc., Richmond, Va.) subcutaneously (SQ) twice daily for post-burn pain control. The skin over the lumbosacral and back region will be clipped using a 35-W model 5-55E electrical clipper (Oyster-Golden A-S, Head no. 80, blade size 40). Depilatory cream (Nair® lotion) will be applied for about 1.5 minutes, and then wiped off with a damp paper towel. Skin will be rinsed in lukewarm water and then blotted dry. The first buprenorphine dose (67 µl/20 g, 83 µl/25 g mouse or 0.1 µg/g) will be administered SQ under the skin of the upper back.

To create burns, anesthetized mice will be placed in an insulated, custom-made mold which exposes only a lumbosacral and back region that is approximately 30% of the total body area. Partial thickness burns will be achieved by exposure of the skin to 60° C. water for 18 seconds.

Overnight-grown *Acinetobacter baumannii* cultures will be harvested and washed with 0.9% saline three times. The final cell concentration will be adjusted to $1\times10^6$ CFU/ml with 0.9% saline and used for inoculation. Either control (bacteria only) or treatment (bacteria with BclA-apyrase exosporium fragments) will be applied to each burn. TEGADERM wound dressing will be applied over the burn with MASTISOL liquid adhesive glue, taking care to not get MASTISOL on the wound.

At the time points for tissue harvest (24 and 48 hours), the mice will be given lethal IP injections of pentobarbital (150 mg/kg) and skin samples will be collected for bacteria counts, and for slides/staining. The skin will be removed with a scalpel and scissors. A small piece of skin will be placed in 5 mL of PBS buffer and homogenized for 1 min. The mixture will be diluted serially 10-fold and 50 µl of each dilution will be put on LB agar plates for bacteria counts.

Example 23: Use of Exosporium Fragments Containing Antifungal Enzyme Fusion Proteins for Preventing Fungal Growth Fusion proteins containing anti-fungal enzymes were prepared using the methods described in Example 9 above. These constructs are summarized in Table 25 below. The constructs contained either full-length BclA or amino acids 20-35 of BclA (amino acids 20-35 of SEQ ID NO: 1) under the control of the BclA promoter (SEQ ID NO: 149). These constructs were introduced into the ExsY and CotE knockout mutants of *Bacillus thuringiensis* BT013A. Exosporium fragments were prepared according to the method described above in Example 9.

A fungicidal assay using clear 96 well flat bottom polystyrene tissue culture plates (BD-Falcon, USA) was performed. Fungal spores from *Aspergillus niger, Aspergillus fumigatus* and *Penicillium chrysogenum* were grown on potato dextrose agar with chloramphenicol and chlortetracycline (PDCC) slant and allowed to sporulate at 30° C. The spores were collected off the slants by vortexing in PBS. The suspended spores were counted by hemocytometer and diluted to $10^6$ CFU/mL. Suspended spores were then serially diluted in nutrient broth in a 96-well plate, exosporium fragments containing fusion proteins were added in varying concentrations, and the plate was incubated at 30° C. to allow inhibition of the fungal spore growth. Fungal growth was quantified by addition XTT to each well of the plate for 3 hours and read at $A_{490nm}$ as described in Example 15 above. Results are shown in Table 26 below. * indicates a statistically significant decrease as measured by students paired T-test as compared to the negative control (exosporium fragments from exsY KO or cotE KO spores that do not express a fusion protein).

TABLE 25

Fusion proteins containing antifungal enzymes

| Enzyme | Targeting Sequence or Exosporium Protein |
|---|---|
| *Bacillus circulans* β-1,3 glucanase (BglH) (SEQ ID NO: 216) | Full-length BclA |
| *Hordeum vulgare* β-1,3-glucanase (HvGII) (SEQ ID NO: 214) | Full-length BclA |
| *Bacillus thuringiensis* Endochitinase (SEQ ID NO: 206) | Full-length BclA |
| *Gallus gallus* Lysozyme (LysM) (SEQ ID NO: 213) | Amino acids 20-35 of BclA (amino acids 20-35 of SEQ ID NO: 1) |
| *Bacillus subtilis* Serine Protease (SEQ ID NO: 209) | Amino acids 20-35 of BclA (amino acids 20-35 of SEQ ID NO: 1) |
| *Bacillus subtilis*/ Serine Protease (SEQ ID NO: 210) | Amino acids 20-35 of BclA (amino acids 20-35 of SEQ ID NO: 1) |

TABLE 26

Effect of Exosporium Fragments on Fungi Growth

| Exosporium | Fusion protein | % growth relative to blank (Average +/− SD) | | |
|---|---|---|---|---|
| Fragments | [1]BclA or [2]$BclA_{20-35}$ | *A. niger* | *A. fumigatus* | *P. chrysogenum* |
| exsY KO | None | 100 +/− 3 | 100 +/− 58 | 100 +/− 20 |
| | [1]β-1,3 Glucanase (HvGII) | ND | 115 +/− 11 | ND |
| | [1]β-1,3 Endoglucanase (BglH) | ND | 92 +/− 23 | **15 +/− 13*** |
| | [1]Endochitinase | ND | 159 +/− 14 | **48 +/− 33*** |
| | [2]LysM | 98 +/− 24 | **64 +/− 38*** | ND |
| | [2]Serine Protease (SEQ ID NO: 209) | **64 +/− 19*** | ND | ND |
| | [2]Serine Protease (SEQ ID NO: 210) | 96 +/− 0 | 92 +/− 81 | ND |
| cotE KO | None | 100 +/− 7 | 100 +/− 61 | ND |
| | [2]Serine Protease (SEQ ID NO: 209) | 94 +/− 4 | **54 +/− 28*** | ND |
| | [2]Serine Protease (SEQ ID NO: 210) | 102 +/− 2 | 108 +/− 1 | ND |

ND = not determined

Example 24: Use of Exosporium Fragments Displaying Antifungal Enzyme Fusion Proteins for Protection from Pathogens in Aquaculture World shrimp aquaculture now produces well over 4 million metric tons of shrimp. This reflects the dramatic increase in white leg shrimp culture in Southeast Asia. Shrimp production in many regions suffers from a wide variety of diseases. Fungal infection among shrimp is one of the most common disease infections in shrimp larvae and normally occurs during the dry season. Some species of fungus attack the larvae while others attack the grown shrimp.

Among the different species of fungal pathogens of shrimp, the most dangerous are *Lagenidium* sp. and *Sirolpidium* sp. Infection starts when zoospores settle on the body of the shrimp larvae. The spores then grow to become hyphae. The hyphae penetrate the bodies of the larvae and develop into mycelium and start to feed on the tissues. The mycelium develops and eventually invades the entire bodies of the shrimp larvae.

The exosporium fragments containing antifungal fusion proteins as described above in Example 23 will be incubated in PBS with the *Lagenidium* for 1 hour at 37° C., with shaking. *Lagenidium myophilum* (ATCC 200325) cultures will be grown overnight in By+ broth at 37° C. Typical media for cultivating marine microorganisms are based on sea water (e.g., 790 By+ medium [yeast extract 1.0 g, peptone 1.0 g, D+ glucose 5.0 g, sea water 1 L]).

The overnight cultures will then be pelleted, washed in PBS, and resuspended in PBS. The exosporium fragments containing the fusion proteins will be incubated in the PBS with the *Lagenidium* for 1 hour at 37° C., with shaking. A control sample of *Lagenidium* will be left untreated (no exosporium fragments). After the 3 hour incubation, dilution plates of the *Lagenidium* will be made and incubated at 37° C. overnight. *Lagenidium* cultures will be counted the next day, and the percent killed quantified. This can translate into a method for dip treating infected shrimp or for treating entire shrimp ponds for the fungus.

Example 25: Use of Exosporium Fragments Containing Antifungal Enzyme Fusion Proteins for the Prevention of Yeast Growth Mastitis in dairy animals is an inflammatory reaction of the udder. Infection of the mammary gland is the most common and most costly disease in the dairy industry. *Cryptococcus neoformans* and *Candida albicans* are the most common species of yeast to cause caprine mastitis, and the trend of fungal mastitis instead of bacterial has been increasing. Currently, when mastitis is diagnosed the immediate course of action is through antibiotic therapy. However, antibiotic therapy is refractory if the organism is in fact fungal.

Antifungal exosporium fragments prepared as described in Example 23 were used to inhibit the growth of *Saccharomyces cerevisiae* as a model for yeast. Results are shown in Table 27 below. * indicates a statistically significant decrease as measured by students paired T-test as compared to the negative control (exosporium fragments from exsY KO spores that do not express a fusion protein). These data demonstrate a strong ability for multiple fusion proteins prepared from exosporium mutants to inhibit yeast growth.

TABLE 27

Effect of Exosporium Fragments on *Saccharomyces* growth

| Exosporium fragments | Fusion protein [1]BclA or $BclA_{20-35}$ | % growth relative to blank (Average +/− SD) *S. cerevisiae* |
|---|---|---|
| BT013A exsY mutant | None | 100 +/− 7 |
| | [1]β-1,3 Glucanase (HvGII) | **86 +/− 0*** |
| | [1]β-1,3 Endoglucanase (BglH) | 100 +/− 2 |
| | [1]Endochitinase | **82 +/− 13*** |
| | LysM | 93 +/− 4 |
| | Serine Protease (SEQ ID NO: 209) | **81 +/− 3*** |
| | Serine Protease (SEQ ID NO: 210) | 100 +/− 6 |

Example 26: Use of Exosporium Fragments Containing Antifungal Enzyme Fusion Proteins for Treatment of Mastitis is Dairy Animals Lactating female goats aged 2-4 years will be kept under observation for a fortnight in a thoroughly cleaned premise before the start of the experiment and will be adjudged to be healthy. All of the animals selected for the study will be free from sub-clinical mastitis and no bacteria or fungi will be isolated from the pre-inoculation milk samples. A strain of *C. albicans* isolated from a natural case of mastitis will be used and the isolate will be grown on Sabouraud's dextrose agar (SDA) containing 0.03% chloramphenicol. After incubation for 5-6 days at 37° C., the growth will be harvested and the suspension homogenized and made ready for inoculation of half of the udder of each goat.

Treatment of the infected udders with exosporium fragments containing antifungal enzymes as described above in Example 23 will be performed for 3 days. The exosporium fragments will be prepared as described above in Example 9.

Re-isolation of the fungus will be attempted from milk and udder lesions. Isolates will be cultured on Sabouraud dextrose agar (SDA) slants at 37° C. for 2-7 days. Detection of the fungus in impression smears of milk and from udder tissues and paraffin tissue sections will be performed using Grocott's methanamine silver (GMS), Periodic acid schiff (PAS) and combined GMS-H&E.

Example 27: Use of Exosporium Fragments Containing Fusion Proteins for Protecting Animals from Insect or Worm Pathogens Delivery of Exosporium Fragments Containing Fusion Protein to Mosquito Larva by Ingestion.

Mosquito larvae [2-4 mm size range] were purchased from Sachs Systems Aquaculture and maintained at 27° C. in a room with 80% relative humidity and fed with plankton. To demonstrate that exosporium fragments can be used to deliver proteins or peptides to mosquito larva, fusion proteins were constructed that contained proteins having insecticidal and antihelminthic properties linked to amino acids 20-35 of BclA (amino acids 20-35 of SEQ ID NO: 1)), under the control of the BclA promoter (SEQ ID NO: 149). These constructs are summarized below in Table 28. The constructs were introduced into the ExsY and CotE knockout strain of *Bacillus thuringiensis* BT013A and exosporium fragments were prepared according to the methods described above in Example 9. Groups of ten mosquito larvae were transferred to 15 mL Falcon tubes in water and treated with an aqueous suspension mix of plankton and exosporium fragments containing fusion protein. Live larvae were recorded after 24 hours. Results are shown in Table 29 below. * indicates a statistically significant decrease as measured by students paired T-test as compared to the negative control (exosporium fragments from exsY KO spores that do not express a fusion protein).

TABLE 28

Fusion proteins containing antihelminthic and insecticidal peptides or proteins

| Anithelminthic or Insecticidal Protein or Peptide | Targeting Sequence |
|---|---|
| *Bacillus sphaericus* Mtx1 (SEQ ID NO: 211) | Amino acids 20-35 of BclA (amino acids 20-35 of SEQ ID NO: 1) |
| *Bacillus thuringiensis* Cry21a (SEQ ID NO: 215) | Amino acids 20-35 of BclA (amino acids 20-35 of SEQ ID NO: 1) |
| *Bacillus thuringiensis* Endochitinase (SEQ ID NO: 206) | Amino acids 20-35 of BclA (amino acids 20-35 of SEQ ID NO: 1) |

TABLE 29

Mosquito Larva survival 24 and 48 hr after exposure to exosporium fragments

| Exosporium fragments | $BclA_{20-35}$ Fusion protein | Exosporium/ water (%, v/v) | % Mosquito Larva Survival at 24 hours (Average +/− SD) | % Mosquito Larva Survival at 48 hours (Average +/− SD) |
|---|---|---|---|---|
| None (blank) | None | | 100 +/− 0 | 100 +/− 0 |
| ExsY KO | None | 10 | 100 +/− 0 | 95 +/− 7 |
| | | 20 | 100 +/− 0 | N.D. |
| | Cry21A | 10 | 95 +/− 7 | 100 +/− 11 |
| | Mtx1 | 10 | 100 +/− 0 | **47 +/− 7*** |
| | Endochitinase | 10 | **45 +/− 35*** | **37 +/− 5*** |
| | | 20 | **5 +/− 7*** | N.D. |

N.D. = not determined

Example 28: Delivery of Exosporium Fragments Containing Insecticidal Mtx-Like Toxin Fusion Proteins to Equine Animals by Topical Application to Prevent Fly Infestation Five horses will be used in this study with one horse per group. The control group will be untreated. Four groups will be treated with an aqueous suspension of exosporium fragments containing the BclA20-35-Mtx1 fusion protein described above in Example 27. The exosporium fragments will be diluted in water just prior to use and applied as a spray to each horse. Each horse will be treated with a pressurized spray apparatus by spraying each diluted spray over the dorsum and each side (barrel) of the body from the shoulders to the hips.

After the applied spray has dried, 6 Petri dish cages (3 per side) of unfed stable fly and 6 Petri dish cages (3 per side) of housefly, each containing 10 adult flies per dish, will be placed under a screened belt that will be tied around the animal. The bottom of the Petri dishes will have a mesh that allows the stable flies to probe through and obtain a blood meal and the house flies to probe through with their mouth parts with both being exposed to the treated hair and skin. The flies in the Petri dishes will be exposed to the treated surface of each horse for 20 minutes, after which the plates will be removed and taken to the laboratory to evaluate percent kill at 4, 8 and 24 hours post-exposure. Petri dishes will be positioned on and exposed to each treated horse immediately after treatment and again on days 1, 3, 5, 7 and 14 post-treatment to evaluate residual activity.

Example 29: Delivery of Antihelminthic Peptides to *Caenorhabditis elegans* Nematodes by Ingestion of Exosporium Fragments Wild type *C. elegans* nematodes were purchased from Carolina Biological (North Carolina) and maintained at 23° C. on nematode growth media (NGM)-Lite agar plates coated with OP50 *E. coli* for food. The constructs described above in Table 28 were transformed into the ExsY and CotE knockout strains of *Bacillus thuringiensis* BT013A.

To prepare concentrated spores for feeding to nematodes, 1 mL of protein-free culture media containing the transformed ExsY KO and CotE KO strains was concentrated by high speed centrifugation and 900 μL of the media was removed. To feed spores to the worms, 10 μL of the concentrated suspension was added to a 60 mm NGM-lite agar plate with 10 μL of PBS (phosphate buffered saline) to aid in spreading. No other food source was made available. In one experiment, twenty wild-type nematodes of various ages were transferred to the plates immediately. The plates were monitored for survival over time and percent survival was calculated. Survival was determined by monitoring under a microscope and recording the death rates of nematodes. Nematodes that did not move when prodded with a needle were considered dead at 24 hours. Survivability data are summarized in Table 30 below (column 3).

In a second experiment, an agar plug from a wildtype plate containing approximately 300 worms was placed in the center of a treated plate. The number of nematodes that migrated from the transferred plug was assessed by counting the number of live worms in one field of view a certain distance from the center of the plate at 72 hours post transfer. These data are summarized in Table 30 below (column 4). * indicates a statistically significant decrease as measured by students paired T-test as compared to the negative control (exosporium fragments from exsY KO or cotE KO spores that do not express a fusion protein). The exosporium mutants of ExsY and CotE equivalently killed nematodes when carrying the Cry21a protein.

TABLE 30

Antihelminthic Activity of Exosporium Fragments on *C. elegans*

| Exosporium fragments | Fusion protein $BclA_{20-35}$ | % Survival (Average +/− SD) (experiment 1 at 24 hours) | Number visible in FOV (Average +/− SD) (experiment 2 at 72 hours) |
|---|---|---|---|
| None (blank) | None | 100 +/− 0 | 70 +/− 7 |
| ExsY KO | None | 96 +/− 5 | 64 +/− 9 |
| | Endochitinase | N.D. | 43 +/− 7 |
| | Mtx1 | 92 +/− 12 | 83 +/− 11 |
| | Cry21A | **8 +/− 12*** | **2 +/− 0.5*** |
| CotE KO | None | 100 +/− 0 | 67 +/− 5 |
| | Mtx1 | 76 +/− 13 | 50 +/− 5 |
| | Cry21A | **4 +/− 5*** | **6 +/− 2*** |

Intestinal animal infections of flat worms, e.g., flukes (trematodes) and tapeworms (cestodes) as well as round worms (nematodes) could be treated using exosporium fragments containing antihelminthic chitinase fusion proteins. Parasitic worms that infect livestock and companion animals are an important animal welfare issue and place a major economic burden on food production.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. A method for protecting an animal from a bacterial pathogen comprising administering exosporium fragments to the animal, to the environment of the animal, or to the bacterial pathogen, wherein the exosporium fragments are from spores of a recombinant *Bacillus cereus* family member and are substantially free of said spores, and wherein the exosporium fragments comprise a fusion protein having serine protease activity, the fusion protein comprising an amino acid sequence having at least 98% sequence identity to SEQ ID NO: 210 and a targeting sequence, wherein the targeting sequence targets the fusion protein to the exosporium of the recombinant *Bacillus cereus* family member; wherein the targeting sequence comprises:

(a) a targeting sequence comprising an amino acid sequence having at least 81% identity with amino acids 20-35 of SEQ ID NO: 1, wherein the identity with amino acids 25-35 is at least 90%;

(b) a targeting sequence comprising amino acids 1-35 of SEQ ID NO: 1;

(c) a targeting sequence comprising amino acids 20-35 of SEQ ID NO: 1; or (d) a targeting sequence comprising SEQ ID NO: 1 and wherein the exosporium fragments are from spores of a recombinant *Bacillus cereus* family member comprising a mutation in an ExsY gene of the recombinant *Bacillus cereus* family member.

2. The method of claim 1, wherein the fusion protein further comprises an amino acid linker between (a) the amino acid sequence having at least 98% sequence identity to SEQ ID NO: 210, and (b) the targeting sequence.

3. The method of claim 1, wherein the method comprises administering the exosporium fragments to the animal.

4. The method of claim 1, wherein the method comprises administering the exosporium fragments to the animal by:

(a) topical, oral, intraperitoneal, intra-arterial, intravenous, intramuscular, subcutaneous, intrapleural, intranasal, rectal, intradermal, inhalation, transdermal, or transepithelial administration, or (b) by immersing the animal into a solution comprising the exosporium fragments.

5. The method of claim 1, wherein the animal is selected from mammals, birds, fish, amphibians, reptiles, crustaceans, mollusks, worms, insects, corals, and sponges.

6. The method of claim 1, wherein the method is a method for protecting an aquatic animal from a pathogen and the method comprises cultivating the aquatic animal in an aquaculture system and administering the exosporium fragments to the aquatic animal by introducing the exosporium fragments into the aquaculture system.

7. The method of claim 1, wherein administering the exosporium fragments to the animal comprises applying the exosporium fragments to a wound of the animal.

8. The method of claim 1, wherein the animal is a hooved animal and administering the exosporium fragments to the animal comprises applying the exosporium fragments to one or more hooves of the animal.

9. The method of claim 1, wherein the animal is a ruminant and the method comprises orally administering the exosporium fragments to the ruminant.

10. The method of claim 1, wherein the method comprises administering the exosporium fragments to an animal for prevention or treatment of mastitis.

11. The method of claim 1, wherein the method comprises prevention or treatment of an infection or infestation by an insect, arachnid, or nematode.

12. The method of claim 1, wherein the fusion protein is expressed:

under the control of a sporulation promoter native to a gene that encodes the targeting sequence or exosporium protein of the fusion protein; and/or under the control of a high-expression sporulation promoter.

13. The method of claim 1, wherein the exosporium fragments are from spores of *Bacillus cereus, Bacillus thuringiensis, Bacillus mycoides, Bacillus pseudomycoides, Bacillus samanii, Bacillus gaemokensis, Bacillus weihenstephensis, Bacillus toyonensis*, or any combination thereof.

* * * * *

SEQUENCE LISTING

```
<160> NUMBER OF SEQ ID NOS: 218

<210> SEQ ID NO 1
<211> LENGTH: 41
<212> TYPE: PRT
<213> ORGANISM: Bacillus anthracis

<400> SEQUENCE: 1

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40
```

<210> SEQ ID NO 2
<211> LENGTH: 332
<212> TYPE: PRT
<213> ORGANISM: Bacillus anthracis

<400> SEQUENCE: 2

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
        195                 200                 205

Ile Ser Leu Asp Leu Gly Ile Asn Asp Pro Val Pro Phe Asn Thr Val
    210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
        275                 280                 285

Pro Phe Thr Ile Val Ile Gln Ala Ile Thr Gln Ile Thr Thr Thr Pro
    290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
                325                 330
```

<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1 5 10 15

Leu Ile Gly Pro Thr Leu Pro Pro Ile Pro Pro Phe Thr Phe Pro Asn
20 25 30

Gly

<210> SEQ ID NO 4
<211> LENGTH: 209
<212> TYPE: PRT
<213> ORGANISM: Bacillus anthracis

<400> SEQUENCE: 4

Met Ser Glu Lys Tyr Ile Ile Leu His Gly Thr Ala Leu Glu Pro Asn
1 5 10 15

Leu Ile Gly Pro Thr Leu Pro Pro Ile Pro Pro Phe Thr Phe Pro Asn
20 25 30

Gly Pro Thr Gly Ile Thr Gly Pro Thr Gly Ala Thr Gly Phe Thr Gly
35 40 45

Ile Gly Ile Thr Gly Pro Thr Gly Val Thr Gly Pro Thr Gly Ile Gly
50 55 60

Ile Thr Gly Pro Thr Gly Ala Thr Gly Leu Gly Ile Leu Pro Val Phe
65 70 75 80

Gly Thr Ile Thr Thr Asp Val Gly Ile Gly Phe Ser Val Ile Val Asn
85 90 95

Thr Asn Ile Asn Phe Thr Leu Pro Gly Pro Val Ser Gly Thr Thr Leu
100 105 110

Asn Pro Val Asp Asn Ser Ile Ile Ile Asn Thr Thr Gly Val Tyr Ser
115 120 125

Val Ser Phe Ser Ile Val Phe Val Ile Gln Ala Ile Ser Ser Ser Ile
130 135 140

Leu Asn Leu Thr Ile Asn Asp Ser Ile Gln Phe Ala Ile Glu Ser Arg
145 150 155 160

Ile Gly Gly Gly Pro Gly Val Arg Ala Thr Ser Ala Arg Thr Asp Leu
165 170 175

Leu Ser Leu Asn Gln Gly Asp Val Leu Arg Val Arg Ile Arg Glu Ala
180 185 190

Thr Gly Asp Ile Ile Tyr Ser Asn Ala Ser Leu Val Val Ser Lys Val
195 200 205

Asp

<210> SEQ ID NO 5
<211> LENGTH: 44
<212> TYPE: PRT
<213> ORGANISM: Bacillus anthracis

<400> SEQUENCE: 5

Met Val Lys Val Val Glu Gly Asn Gly Gly Lys Ser Lys Ile Lys Ser
1 5 10 15

Pro Leu Asn Ser Asn Phe Lys Ile Leu Ser Asp Leu Val Gly Pro Thr
20 25 30

Phe Pro Pro Val Pro Thr Gly Met Thr Gly Ile Thr
35 40

<210> SEQ ID NO 6
<211> LENGTH: 647
<212> TYPE: PRT

<213> ORGANISM: Bacillus anthracis

<400> SEQUENCE: 6

Val Val Lys Val Val Glu Gly Asn Gly Gly Lys Ser Lys Ile Lys Ser
1 5 10 15

Pro Leu Asn Ser Asn Phe Lys Ile Leu Ser Asp Leu Val Gly Pro Thr
20 25 30

Phe Pro Pro Val Pro Thr Gly Met Thr Gly Ile Thr Gly Ser Thr Gly
35 40 45

Ala Thr Gly Asn Thr Gly Pro Thr Gly Glu Thr Gly Ala Thr Gly Ser
50 55 60

Ala Gly Ile Thr Gly Ser Thr Gly Pro Thr Gly Asn Thr Gly Gly Thr
65 70 75 80

Gly Ser Thr Gly Pro Thr Gly Asn Thr Gly Ala Thr Gly Ser Thr Gly
85 90 95

Val Thr Gly Ser Thr Gly Val Thr Gly Ser Thr Gly Val Thr Gly Ser
100 105 110

Thr Gly Val Thr Gly Ser Thr Gly Pro Thr Gly Glu Thr Gly Gly Thr
115 120 125

Gly Ser Thr Gly Val Thr Gly Ser Thr Gly Ala Thr Gly Ser Thr Gly
130 135 140

Val Thr Gly Asn Thr Gly Pro Thr Gly Ser Thr Gly Ala Thr Gly Asn
145 150 155 160

Thr Gly Ser Ile Gly Glu Thr Gly Gly Thr Gly Ser Met Gly Pro Thr
165 170 175

Gly Glu Thr Gly Val Thr Gly Ser Thr Gly Gly Thr Gly Ser Thr Gly
180 185 190

Val Thr Gly Asn Thr Gly Pro Thr Gly Ser Thr Gly Val Thr Gly Ser
195 200 205

Thr Gly Val Thr Gly Ser Thr Gly Pro Thr Gly Ser Thr Gly Val Thr
210 215 220

Gly Ser Thr Gly Pro Thr Gly Ser Thr Gly Val Thr Gly Ser Thr Gly
225 230 235 240

Val Thr Gly Asn Met Gly Pro Thr Gly Ser Thr Gly Val Thr Gly Asn
245 250 255

Thr Gly Ser Thr Gly Thr Thr Gly Ala Thr Gly Glu Thr Gly Pro Met
260 265 270

Gly Ser Thr Gly Ala Thr Gly Thr Thr Gly Pro Thr Gly Glu Thr Gly
275 280 285

Glu Thr Gly Glu Thr Gly Gly Thr Gly Ser Thr Gly Pro Thr Gly Asn
290 295 300

Thr Gly Ala Thr Gly Ser Thr Gly Val Thr Gly Ser Thr Gly Val Thr
305 310 315 320

Gly Ser Thr Gly Val Thr Gly Glu Thr Gly Pro Thr Gly Ser Thr Gly
325 330 335

Ala Thr Gly Asn Thr Gly Pro Thr Gly Glu Thr Gly Gly Thr Gly Ser
340 345 350

Thr Gly Ala Thr Gly Ser Thr Gly Val Thr Gly Asn Thr Gly Pro Thr
355 360 365

Gly Ser Thr Gly Val Thr Gly Asn Thr Gly Ala Thr Gly Glu Thr Gly
370 375 380

Pro Thr Gly Asn Thr Gly Ala Thr Gly Asn Thr Gly Pro Thr Gly Glu
385 390 395 400

```
Thr Gly Val Thr Gly Ser Thr Gly Pro Thr Gly Glu Thr Gly Val Thr
                405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
        435                 440                 445

Thr Gly Pro Thr Gly Ser Thr Gly Pro Thr Gly Ser Thr Gly Ala Thr
    450                 455                 460

Gly Val Thr Gly Asn Thr Gly Pro Thr Gly Ser Thr Gly Ala Thr Gly
465                 470                 475                 480

Ala Thr Gly Ser Thr Gly Pro Thr Gly Ser Thr Gly Thr Thr Gly Asn
                485                 490                 495

Thr Gly Val Thr Gly Asp Thr Gly Pro Thr Gly Ala Thr Gly Val Ser
            500                 505                 510

Thr Thr Ala Thr Tyr Ala Phe Ala Asn Asn Thr Ser Gly Ser Val Ile
        515                 520                 525

Ser Val Leu Leu Gly Gly Thr Asn Ile Pro Leu Pro Asn Asn Gln Asn
    530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
                565                 570                 575

Gly Leu Leu Val Ser Ser Arg Ile Thr Val Asn Gly Ser Pro Leu Ala
            580                 585                 590

Gly Thr Ile Asn Ser Pro Thr Val Ala Thr Gly Ser Phe Ser Ala Thr
        595                 600                 605

Ile Ile Ala Ser Leu Pro Ala Gly Ala Ala Val Ser Leu Gln Leu Phe
    610                 615                 620

Gly Val Val Ala Leu Ala Thr Leu Ser Thr Ala Thr Pro Gly Ala Thr
625                 630                 635                 640

Leu Thr Ile Ile Arg Leu Ser
                645


<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly


<210> SEQ ID NO 8
<211> LENGTH: 366
<212> TYPE: PRT
<213> ORGANISM: Bacillus anthracis

<400> SEQUENCE: 8

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
```

```
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110

Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140

Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365


<210> SEQ ID NO 9
<211> LENGTH: 30
<212> TYPE: PRT
<213> ORGANISM: Bacillus anthracis

<400> SEQUENCE: 9

Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly
            20                  25                  30


<210> SEQ ID NO 10
<211> LENGTH: 77
```

<212> TYPE: PRT
<213> ORGANISM: Bacillus anthracis

<400> SEQUENCE: 10

Met Asp Glu Phe Leu Ser Ser Ala Ala Leu Asn Pro Gly Ser Val Gly
1 5 10 15

Pro Thr Leu Pro Pro Met Gln Pro Phe Gln Phe Arg Thr Gly Pro Thr
20 25 30

Gly Ser Thr Gly Ala Lys Gly Ala Ile Gly Asn Thr Glu Pro Tyr Trp
35 40 45

His Thr Gly Pro Pro Gly Ile Val Leu Leu Thr Tyr Asp Phe Lys Ser
50 55 60

Leu Ile Ile Ser Phe Ala Phe Arg Ile Leu Pro Ile Ser
65 70 75

<210> SEQ ID NO 11
<211> LENGTH: 39
<212> TYPE: PRT
<213> ORGANISM: Bacillus weihenstephensis

<400> SEQUENCE: 11

Met Phe Asp Lys Asn Glu Ile Gln Lys Ile Asn Gly Ile Leu Gln Ala
1 5 10 15

Asn Ala Leu Asn Pro Asn Leu Ile Gly Pro Thr Leu Pro Pro Ile Pro
20 25 30

Pro Phe Thr Leu Pro Thr Gly
35

<210> SEQ ID NO 12
<211> LENGTH: 299
<212> TYPE: PRT
<213> ORGANISM: Bacillus weihenstephensis

<400> SEQUENCE: 12

Met Phe Asp Lys Asn Glu Ile Gln Lys Ile Asn Gly Ile Leu Gln Ala
1 5 10 15

Asn Ala Leu Asn Pro Asn Leu Ile Gly Pro Thr Leu Pro Pro Ile Pro
20 25 30

Pro Phe Thr Leu Pro Thr Gly Pro Thr Gly Val Thr Gly Pro Thr Gly
35 40 45

Val Thr Gly Pro Thr Gly Val Thr Gly Pro Thr Gly Val Thr Gly Pro
50 55 60

Thr Gly Val Thr Gly Pro Thr Gly Val Thr Gly Pro Thr Gly Val Thr
65 70 75 80

Gly Pro Thr Gly Val Thr Gly Pro Thr Gly Val Thr Gly Pro Thr Gly
85 90 95

Val Thr Gly Pro Thr Gly Val Thr Gly Pro Thr Gly Val Thr Gly Pro
100 105 110

Thr Gly Val Thr Gly Pro Thr Gly Val Thr Gly Pro Thr Gly Glu Thr
115 120 125

Gly Pro Thr Gly Gly Thr Glu Gly Cys Leu Cys Asp Cys Cys Val Leu
130 135 140

Pro Met Gln Ser Val Leu Gln Gln Leu Ile Gly Glu Thr Val Ile Leu
145 150 155 160

Gly Thr Ile Ala Asp Thr Pro Asn Thr Pro Pro Leu Phe Phe Leu Phe
165 170 175

Thr Ile Thr Ser Val Asn Asp Phe Leu Val Thr Val Thr Asp Gly Thr

```
            180                 185                 190

Thr Thr Phe Val Val Asn Ile Ser Asp Val Thr Gly Val Gly Phe Leu
        195                 200                 205

Pro Pro Gly Pro Pro Ile Thr Leu Leu Pro Pro Thr Asp Val Gly Cys
    210                 215                 220

Glu Cys Glu Cys Arg Glu Arg Pro Ile Arg Gln Leu Leu Asp Ala Phe
225                 230                 235                 240

Ile Gly Ser Thr Val Ser Leu Leu Ala Ser Asn Gly Ser Ile Ala Ala
                245                 250                 255

Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285

Ile Thr Ala Val Asn Ile Thr Pro Ile Thr Met
    290                 295


<210> SEQ ID NO 13
<211> LENGTH: 39
<212> TYPE: PRT
<213> ORGANISM: Bacillus weihenstephensis

<400> SEQUENCE: 13

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly
        35


<210> SEQ ID NO 14
<211> LENGTH: 289
<212> TYPE: PRT
<213> ORGANISM: Bacillus weihenstephensis

<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
65                  70                  75                  80

Gly Pro Thr Gly Pro Thr Gly Leu Thr Gly Pro Thr Gly Leu Thr Gly
                85                  90                  95

Pro Thr Gly Pro Thr Gly Leu Thr Gly Gln Thr Gly Ser Thr Gly Pro
            100                 105                 110

Thr Gly Ala Thr Glu Gly Cys Leu Cys Asp Cys Cys Val Phe Pro Met
        115                 120                 125

Gln Glu Val Leu Arg Gln Leu Val Gly Gln Thr Val Ile Leu Ala Thr
    130                 135                 140

Ile Ala Asp Ala Pro Asn Val Ala Pro Arg Phe Phe Leu Phe Asn Ile
145                 150                 155                 160

Thr Ser Val Asn Asp Phe Leu Val Thr Val Thr Asp Pro Val Ser Asn
```

```
                165                 170                 175

Thr Thr Phe Val Val Asn Ile Ser Asp Val Ile Gly Val Gly Phe Ser
            180                 185                 190

Leu Thr Val Pro Pro Leu Thr Leu Leu Pro Pro Ala Asp Leu Gly Cys
        195                 200                 205

Glu Cys Asp Cys Arg Glu Arg Pro Ile Arg Glu Leu Leu Asp Thr Leu
    210                 215                 220

Ile Gly Ser Thr Val Asn Leu Leu Val Ser Asn Gly Ser Ile Ala Thr
225                 230                 235                 240

Gly Phe Asn Val Glu Gln Thr Ala Leu Gly Ile Val Ile Gly Thr Leu
                245                 250                 255

Pro Ile Pro Ile Asn Pro Pro Pro Pro Thr Leu Phe Arg Phe Ala Ile
            260                 265                 270

Ser Thr Cys Lys Ile Thr Ala Val Asp Ile Thr Pro Thr Pro Thr Ala
        275                 280                 285

Thr


<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly


<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140
```

Gly Thr Pro Gln Leu Glu Ile Thr Thr Ile Ile Asp Leu Leu Ala Ser
145 150 155 160

Gln Thr Ile Asp Ile Gln Phe Ser Ala Ala Glu Ser Gly Thr Leu Thr
165 170 175

Val Gly Ser Ser Asn Phe Phe Ser Gly Ala Leu Leu Pro
180 185

<210> SEQ ID NO 17
<211> LENGTH: 33
<212> TYPE: PRT
<213> ORGANISM: Bacillus cereus

<400> SEQUENCE: 17

Met Asn Glu Glu Tyr Ser Ile Leu His Gly Pro Ala Leu Glu Pro Asn
1 5 10 15

Leu Ile Gly Pro Thr Leu Pro Ser Ile Pro Pro Phe Thr Phe Pro Thr
20 25 30

Gly

<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1 5 10 15

Leu Ile Gly Pro Thr Leu Pro Ser Ile Pro Pro Phe Thr Phe Pro Thr
20 25 30

Gly Pro Thr Gly Ile Thr Gly Pro Thr Gly Ala Thr Gly Phe Thr Gly
35 40 45

Ile Gly Ile Thr Gly Pro Thr Gly Val Thr Gly Pro Thr Gly Ile Gly
50 55 60

Ile Thr Gly Pro Thr Gly Ala Thr Gly Pro Thr Gly Ile Gly Ile Thr
65 70 75 80

Gly Pro Thr Gly

<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1 5 10 15

Phe Arg Ile Pro Pro Glu Leu Ile Gly Pro Thr Phe Pro Pro Val Pro
20 25 30

Thr Gly Phe Thr Gly Ile Gly
35

<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1 5 10 15

Phe Arg Ile Pro Pro Glu Leu Ile Gly Pro Thr Phe Pro Pro Val Pro

```
        20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445
```

```
Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Leu Thr Gly Ser Gln Gly Pro Thr Gly
    690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Glu Thr Gly Ala Thr Gly Ala Thr Gly Glu
    850                 855                 860
```

Gly Thr Thr Gly Pro Thr Gly Val Thr Gly Pro Thr Gly Val Thr Gly
865 870 875 880

Pro Ser Gly Gly Pro Ala Gly Pro Thr Gly Pro Thr Gly Pro Ser Gly
885 890 895

Pro Ala Gly Val Thr Gly Pro Ser Gly Gly Pro Pro Gly Pro Thr Gly
900 905 910

Ala Thr Gly Ala Thr Gly Val Thr Gly Asp Thr Gly Ala Thr Gly Ser
915 920 925

Thr Gly Val Thr Gly Ala Thr Gly Ala Thr Gly Ala Thr Gly Val Thr
930 935 940

Gly Leu Gln Gly Pro Gln Gly Ile Gln Gly Val Gln Gly Glu Ile Gly
945 950 955 960

Pro Thr Gly Pro Gln Gly Ile Gln Gly Pro Gln Gly Ile Gln Gly Val
965 970 975

Thr Gly Ala Thr Gly Ala Gln Gly Pro Gln Gly Ile Gln Gly Pro Gln
980 985 990

Gly Asp Ile Gly Pro Thr Gly Ser Gln Gly Ile Gln Gly Pro Gln Gly
995 1000 1005

Pro Gln Gly Ile Gln Gly Ala Thr Gly Ala Thr Gly Ala Gln Gly
1010 1015 1020

Pro Gln Gly Ile Gln Gly Pro Gln Gly Glu Ile Gly Pro Thr Gly
1025 1030 1035

Pro Gln Gly Pro Gln Gly Ile Gln Gly Pro Gln Gly Ile Gln Gly
1040 1045 1050

Pro Thr Gly
1055

<210> SEQ ID NO 21
<211> LENGTH: 39
<212> TYPE: PRT
<213> ORGANISM: Bacillus weihenstephensis

<400> SEQUENCE: 21

Met Ser Asp Lys His Gln Met Lys Lys Ile Ser Glu Val Leu Gln Ala
1 5 10 15

His Ala Leu Asp Pro Asn Leu Ile Gly Pro Pro Leu Pro Pro Ile Thr
20 25 30

Pro Phe Thr Phe Pro Thr Gly
35

<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1 5 10 15

His Ala Leu Asp Pro Asn Leu Ile Gly Pro Pro Leu Pro Pro Ile Thr
20 25 30

Pro Phe Thr Phe Pro Thr Gly Ser Thr Gly Pro Thr Gly Ser Thr Gly
35 40 45

Ser Thr Gly Pro Thr Gly Ser Thr Gly Asn Thr Gly Pro Thr Gly Pro
50 55 60

Thr Gly Pro Pro Val Gly Thr Asn Leu Asp Thr Ile Tyr Val Thr Asn
65 70 75 80

Asp Ile Ser Asn Asn Val Ser Ala Ile Asp Gly Asn Thr Asn Thr Val
85 90 95

Leu Thr Thr Ile Pro Val Gly Thr Asn Pro Val Gly Val Gly Val Asn
100 105 110

Ser Ser Thr Asn Leu Ile Tyr Val Val Asn Asn Gly Ser Asp Asn Ile
115 120 125

Ser Val Ile Asn Gly Ser Thr Asn Thr Val Val Ala Thr Ile Pro Val
130 135 140

Gly Thr Gln Pro Phe Gly Val Gly Val Asn Pro Ser Thr Asn Leu Ile
145 150 155 160

Tyr Val Ala Asn Arg Thr Ser Asn Asn Val Ser Val Ile Lys Gly Gly
165 170 175

Thr Asn Thr Val Leu Thr Thr Ile Pro Val Gly Thr Asn Pro Val Gly
180 185 190

Val Gly Val Asn Ser Ser Thr Asn Leu Ile Tyr Val Thr Asn Glu Ile
195 200 205

Pro Asn Ser Val Ser Val Ile Lys Gly Gly Thr Asn Thr Val Val Ala
210 215 220

Thr Ile Pro Val Gly Leu Phe Pro Phe Gly Val Gly Val Asn Ser Leu
225 230 235 240

Thr Asn Leu Ile Tyr Val Val Asn Asn Ser Pro His Asn Val Ser Val
245 250 255

Ile Asp Gly Asn Thr Asn Thr Val Leu Thr Thr Ile Ser Val Gly Thr
260 265 270

Ser Pro Val Gly Val Gly Val Asn Leu Ser Thr Asn Leu Ile Tyr Val
275 280 285

Ala Asn Glu Val Pro Asn Asn Ile Ser Val Ile Asn Gly Asn Thr Asn
290 295 300

Thr Val Leu Thr Thr Ile Pro Val Gly Thr Thr Pro Phe Glu Val Gly
305 310 315 320

Val Asn Ser Ser Thr Asn Leu Ile Tyr Val Ser Asn Leu Asn Ser Asn
325 330 335

Asn Val Ser Val Ile Asn Gly Ser Ala Asn Thr Val Ile Ala Thr Val
340 345 350

Pro Val Gly Ser Val Pro Arg Gly Ile Gly Val Lys Pro
355 360 365

<210> SEQ ID NO 23
<211> LENGTH: 30
<212> TYPE: PRT
<213> ORGANISM: Bacillus weihenstephensis

<400> SEQUENCE: 23

Met Asp Glu Phe Leu Ser Phe Ala Ala Leu Asn Pro Gly Ser Ile Gly
1 5 10 15

Pro Thr Leu Pro Pro Val Pro Pro Phe Gln Phe Pro Thr Gly
20 25 30

<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1 5 10 15

```
Pro Thr Leu Pro Pro Val Pro Pro Phe Gln Phe Pro Thr Gly Pro Thr
            20                  25                  30

Gly Ser Thr Gly Ser Thr Gly Pro Thr Gly Ser Thr Gly Ser Thr Gly
        35                  40                  45

Pro Thr Gly Phe Asn Leu Pro Ala Gly Pro Ala Ser Ile Thr Leu Thr
    50                  55                  60

Ser Asn Glu Thr Thr Ala Cys Val Ser Thr Gln Gly Asn Asn Thr Leu
65                  70                  75                  80

Phe Phe Ser Gly Gln Val Leu Val Asn Gly Ser Pro Thr Pro Gly Val
                85                  90                  95

Val Val Ser Phe Ser Phe Ser Asn Pro Ser Leu Ala Phe Met Val Pro
            100                 105                 110

Leu Ala Val Ile Thr Asn Ala Ser Gly Asn Phe Thr Ala Val Phe Leu
        115                 120                 125

Ala Ala Asn Gly Pro Gly Thr Val Thr Val Thr Ala Ser Leu Leu Asp
    130                 135                 140

Ser Pro Gly Thr Met Ala Ser Val Thr Ile Thr Ile Val Asn Cys Pro
145                 150                 155                 160


<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly
            20                  25                  30


<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35                  40                  45

Asn Thr Gly Leu Thr Gly Asn Thr Gly Pro Thr Gly Ile Thr Gly Pro
    50                  55                  60

Thr Gly Asp Thr Gly
65


<210> SEQ ID NO 27
<211> LENGTH: 36
<212> TYPE: PRT
<213> ORGANISM: Bacillus weihenstephensis

<400> SEQUENCE: 27

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
```

35

<210> SEQ ID NO 28
<211> LENGTH: 934
<212> TYPE: PRT
<213> ORGANISM: Bacillus weihenstephensis

<400> SEQUENCE: 28

Met Lys Glu Arg Asp Arg Gln Asn Ser Leu Asn Ser Asn Phe Arg Ile
1 5 10 15

Ser Pro Asn Leu Ile Gly Pro Thr Phe Pro Pro Val Pro Thr Gly Phe
20 25 30

Thr Gly Ile Gly Ile Thr Gly Pro Thr Gly Pro Gln Gly Pro Thr Gly
35 40 45

Pro Gln Gly Pro Arg Gly Phe Gln Gly Pro Met Gly Glu Met Gly Pro
50 55 60

Thr Gly Pro Gln Gly Val Gln Gly Ile Gln Gly Pro Ala Gly Gln Met
65 70 75 80

Gly Ala Thr Gly Pro Glu Gly Gln Gln Gly Pro Gln Gly Leu Arg Gly
85 90 95

Pro Gln Gly Glu Thr Gly Ala Thr Gly Pro Gln Gly Val Gln Gly Leu
100 105 110

Gln Gly Pro Ile Gly Pro Thr Gly Ala Thr Gly Ala Gln Gly Ile Gln
115 120 125

Gly Ile Gln Gly Leu Gln Gly Pro Ile Gly Ala Thr Gly Pro Glu Gly
130 135 140

Pro Gln Gly Ile Gln Gly Val Gln Gly Val Pro Gly Ala Thr Gly Ser
145 150 155 160

Gln Gly Ile Gln Gly Ala Gln Gly Ile Gln Gly Pro Gln Gly Pro Ser
165 170 175

Gly Asn Thr Gly Ala Thr Gly Val Thr Gly Gln Gly Ile Ser Gly Pro
180 185 190

Thr Gly Ile Thr Gly Pro Thr Gly Ile Thr Gly Pro Ser Gly Gly Pro
195 200 205

Pro Gly Pro Thr Gly Ala Thr Gly Ala Thr Gly Pro Gly Gly Gly Pro
210 215 220

Ser Gly Ser Thr Gly Ala Thr Gly Ala Thr Gly Asn Thr Gly Val Thr
225 230 235 240

Gly Ser Ala Gly Val Thr Gly Asn Thr Gly Ser Thr Gly Ser Thr Gly
245 250 255

Glu Thr Gly Ala Gln Gly Leu Gln Gly Ile Gln Gly Val Gln Gly Pro
260 265 270

Ile Gly Pro Thr Gly Pro Glu Gly Pro Gln Gly Ile Gln Gly Ile Pro
275 280 285

Gly Pro Thr Gly Val Thr Gly Glu Gln Gly Ile Gln Gly Val Gln Gly
290 295 300

Ile Gln Gly Ile Thr Gly Ala Thr Gly Asp Gln Gly Pro Gln Gly Ile
305 310 315 320

Gln Gly Ala Ile Gly Pro Gln Gly Ile Thr Gly Ala Thr Gly Asp Gln
325 330 335

Gly Pro Gln Gly Ile Gln Gly Val Pro Gly Pro Thr Gly Asp Thr Gly
340 345 350

Ser Gln Gly Val Gln Gly Ile Gln Gly Pro Met Gly Asp Ile Gly Pro
355 360 365

-continued

```
Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly
        435                 440                 445

Ala Thr Gly Pro Glu Gly Pro Gln Gly Val Gln Gly Thr Gln Gly Asp
    450                 455                 460

Ile Gly Pro Thr Gly Pro Met Gly Pro Gln Gly Val Gln Gly Ile Gln
465                 470                 475                 480

Gly Ile Gln Gly Pro Thr Gly Ala Gln Gly Val Gln Gly Pro Gln Gly
                485                 490                 495

Ile Gln Gly Ile Gln Gly Pro Thr Gly Val Thr Gly Asp Thr Gly Thr
            500                 505                 510

Thr Gly Ala Thr Gly Glu Gly Thr Thr Gly Ala Thr Gly Val Thr Gly
        515                 520                 525

Pro Ser Gly Val Thr Gly Pro Ser Gly Gly Pro Ala Gly Pro Thr Gly
    530                 535                 540

Pro Thr Gly Pro Ser Gly Pro Thr Gly Leu Thr Gly Pro Ser Gly Gly
545                 550                 555                 560

Pro Pro Gly Pro Thr Gly Ala Thr Gly Val Thr Gly Gly Val Gly Asp
                565                 570                 575

Thr Gly Ala Thr Gly Ser Thr Gly Val Thr Gly Ala Thr Gly Val Thr
            580                 585                 590

Gly Ala Thr Gly Ala Thr Gly Leu Gln Gly Pro Gln Gly Ile Gln Gly
        595                 600                 605

Val Gln Gly Asp Ile Gly Pro Thr Gly Pro Gln Gly Val Gln Gly Pro
    610                 615                 620

Gln Gly Ile Gln Gly Ile Thr Gly Ala Thr Gly Asp Gln Gly Pro Gln
625                 630                 635                 640

Gly Ile Gln Gly Pro Gln Gly Ile Gln Gly Pro Thr Gly Pro Gln Gly
                645                 650                 655

Ile Gln Gly Gly Gln Gly Pro Gln Gly Ile Gln Gly Ala Thr Gly Ala
            660                 665                 670

Thr Gly Ala Gln Gly Pro Gln Gly Ile Gln Gly Ile Gln Gly Val Gln
        675                 680                 685

Gly Pro Thr Gly Pro Gln Gly Pro Thr Gly Ile Gln Gly Val Gln Gly
    690                 695                 700

Glu Ile Gly Pro Thr Gly Pro Gln Gly Val Gln Gly Leu Gln Gly Pro
705                 710                 715                 720

Gln Gly Pro Thr Gly Asp Thr Gly Pro Thr Gly Pro Gln Gly Pro Gln
                725                 730                 735

Gly Ile Gln Gly Pro Thr Gly Ala Thr Gly Ala Thr Gly Ser Gln Gly
            740                 745                 750

Ile Gln Gly Pro Thr Gly Ala Thr Gly Ala Thr Gly Ser Gln Gly Ile
        755                 760                 765

Gln Gly Pro Thr Gly Ala Thr Gly Ala Thr Gly Ala Thr Gly Ala Thr
    770                 775                 780

Gly Ala Thr Gly Ala Thr Gly Ala Thr Gly Val Thr Gly Val Ser Thr
```

```
785                 790                 795                 800

Thr Ala Thr Tyr Ser Phe Ala Asn Asn Thr Ser Gly Ser Ala Ile Ser
                805                 810                 815

Val Leu Leu Gly Gly Thr Asn Ile Pro Leu Pro Asn Asn Gln Asn Ile
            820                 825                 830

Gly Pro Gly Ile Thr Val Ser Gly Gly Asn Thr Val Phe Thr Val Thr
        835                 840                 845

Asn Ala Gly Asn Tyr Tyr Ile Ala Tyr Thr Ile Asn Ile Thr Ala Ala
    850                 855                 860

Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
                885                 890                 895

Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
    930


<210> SEQ ID NO 29
<211> LENGTH: 39
<212> TYPE: PRT
<213> ORGANISM: Bacillus mycoides

<400> SEQUENCE: 29

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35


<210> SEQ ID NO 30
<211> LENGTH: 287
<212> TYPE: PRT
<213> ORGANISM: Bacillus mycoides

<400> SEQUENCE: 30

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Gly Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Gly Thr Glu Gly Cys Leu Cys Asp
        115                 120                 125

Cys Cys Val Leu Pro Met Gln Ser Val Leu Gln Gln Leu Ile Gly Glu
```

```
    130                 135                 140

Thr Val Ile Leu Gly Thr Ile Ala Asp Thr Pro Asn Thr Pro Pro Leu
145                 150                 155                 160

Phe Phe Leu Phe Thr Ile Thr Ser Val Asn Asp Phe Leu Val Thr Val
                165                 170                 175

Thr Asp Gly Thr Thr Thr Phe Val Val Asn Ile Ser Asp Val Thr Gly
            180                 185                 190

Val Gly Phe Leu Pro Pro Gly Pro Pro Ile Thr Leu Leu Pro Pro Thr
        195                 200                 205

Asp Val Gly Cys Glu Cys Glu Cys Arg Glu Arg Pro Ile Arg Gln Leu
    210                 215                 220

Leu Asp Ala Phe Ile Gly Ser Thr Val Ser Leu Leu Ala Ser Asn Gly
225                 230                 235                 240

Ser Ile Ala Ala Asp Phe Ser Val Glu Gln Thr Gly Leu Gly Ile Val
                245                 250                 255

Leu Gly Thr Leu Pro Ile Asn Pro Thr Thr Thr Val Arg Phe Ala Ile
            260                 265                 270

Ser Thr Cys Lys Ile Thr Ala Val Asn Ile Thr Pro Ile Thr Met
        275                 280                 285


<210> SEQ ID NO 31
<211> LENGTH: 30
<212> TYPE: PRT
<213> ORGANISM: Bacillus mycoides

<400> SEQUENCE: 31

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly
            20                  25                  30


<210> SEQ ID NO 32
<211> LENGTH: 190
<212> TYPE: PRT
<213> ORGANISM: Bacillus mycoides

<400> SEQUENCE: 32

Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly Pro Thr
            20                  25                  30

Gly Ser Thr Gly Ala Thr Gly Ser Thr Gly Ser Thr Gly Ser Thr Gly
        35                  40                  45

Pro Thr Gly Ser Thr Gly Ser Thr Gly Ser Thr Gly Ser Thr Gly Pro
    50                  55                  60

Thr Gly Pro Thr Gly Pro Thr Gly Ser Thr Gly Pro Thr Gly Pro Thr
65                  70                  75                  80

Gly Phe Asn Leu Pro Ala Gly Pro Ala Ser Ile Thr Leu Thr Ser Asn
                85                  90                  95

Glu Thr Thr Ala Cys Val Ser Thr Gln Gly Asn Asn Thr Leu Phe Phe
            100                 105                 110

Ser Gly Gln Val Leu Val Asn Gly Ser Pro Thr Pro Gly Val Val Val
        115                 120                 125

Ser Phe Ser Phe Ser Asn Pro Ser Leu Ala Phe Met Val Pro Leu Ala
    130                 135                 140

Val Ile Thr Asn Ala Ser Gly Asn Phe Thr Ala Val Phe Leu Ala Ala
```

145 150 155 160

Asn Gly Pro Gly Thr Val Thr Val Thr Ala Ser Leu Leu Asp Ser Pro
165 170 175

Gly Thr Met Ala Ser Val Thr Ile Thr Ile Val Asn Cys Pro
180 185 190

<210> SEQ ID NO 33
<211> LENGTH: 21
<212> TYPE: PRT
<213> ORGANISM: Bacillus mycoides

<400> SEQUENCE: 33

Met Asp Ser Lys Asn Ile Gly Pro Thr Phe Pro Pro Leu Pro Ser Ile
1 5 10 15

Asn Phe Pro Thr Gly
20

<210> SEQ ID NO 34
<211> LENGTH: 335
<212> TYPE: PRT
<213> ORGANISM: Bacillus mycoides

<400> SEQUENCE: 34

Met Asp Ser Lys Asn Ile Gly Pro Thr Phe Pro Pro Leu Pro Ser Ile
1 5 10 15

Asn Phe Pro Thr Gly Val Thr Gly Glu Thr Gly Ala Thr Gly Glu Thr
20 25 30

Gly Ala Thr Gly Ala Thr Gly Glu Thr Gly Ala Thr Gly Glu Thr Gly
35 40 45

Glu Thr Gly Ala Thr Gly Ala Thr Gly Ala Thr Gly Ala Thr Gly Glu
50 55 60

Thr Gly Ala Thr Gly Ala Thr Gly Ala Thr Gly Ala Ala Gly Ala Thr
65 70 75 80

Gly Glu Thr Gly Ala Thr Gly Glu Thr Gly Ala Thr Gly Glu Thr Gly
85 90 95

Ala Thr Gly Glu Thr Gly Ala Thr Gly Val Thr Gly Glu Thr Gly Ala
100 105 110

Thr Gly Glu Thr Gly Ala Ala Gly Glu Thr Gly Ile Thr Gly Val Thr
115 120 125

Gly Pro Thr Gly Glu Thr Gly Ala Thr Gly Glu Thr Gly Ala Thr Gly
130 135 140

Ala Thr Gly Ile Thr Gly Ala Thr Gly Ile Thr Gly Val Ala Gly Ala
145 150 155 160

Thr Gly Glu Thr Gly Ala Ala Gly Glu Thr Gly Pro Thr Gly Ala Thr
165 170 175

Gly Ala Ile Gly Ala Ile Gly Ala Thr Gly Ala Thr Gly Ile Thr Gly
180 185 190

Val Thr Gly Ala Thr Gly Glu Thr Gly Ala Ala Gly Ala Thr Gly Ile
195 200 205

Thr Gly Val Thr Gly Ala Thr Gly Glu Thr Gly Ala Ala Gly Ala Thr
210 215 220

Gly Ile Thr Gly Ala Thr Gly Ile Thr Gly Val Ala Gly Ala Thr Gly
225 230 235 240

Ile Thr Gly Pro Thr Gly Ile Pro Gly Thr Ile Pro Thr Thr Asn Leu
245 250 255

Leu Tyr Phe Thr Phe Ser Asp Gly Glu Lys Leu Ile Tyr Thr Asn Ala

```
            260                 265                 270

Asp Gly Ile Ala Gln Tyr Gly Thr Thr Gln Ile Leu Ser Pro Ser Glu
        275                 280                 285

Val Ser Tyr Ile Asn Leu Phe Ile Asn Gly Ile Leu Gln Pro Gln Pro
    290                 295                 300

Phe Tyr Glu Val Thr Ala Gly Gln Leu Thr Leu Leu Asp Asp Glu Pro
305                 310                 315                 320

Pro Ser Gln Gly Ser Ser Ile Ile Leu Gln Phe Ile Ile Ile Asn
                325                 330                 335
```

<210> SEQ ID NO 35
<211> LENGTH: 22
<212> TYPE: PRT
<213> ORGANISM: Bacillus thuringiensis

<400> SEQUENCE: 35

```
Met Ile Gly Pro Glu Asn Ile Gly Pro Thr Phe Pro Ile Leu Pro Pro
1               5                   10                  15

Ile Tyr Ile Pro Thr Gly
            20
```

<210> SEQ ID NO 36
<211> LENGTH: 234
<212> TYPE: PRT
<213> ORGANISM: Bacillus thuringiensis

<400> SEQUENCE: 36

```
Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
    130                 135                 140

Gly Gly Ile Gly Pro Ile Thr Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
```

225 230

<210> SEQ ID NO 37
<211> LENGTH: 299
<212> TYPE: DNA
<213> ORGANISM: Bacillus cereus

<400> SEQUENCE: 37
tttcttaatc ctttaccctt tacttttgta aaagttgata cacttccatc cggctctgta 60
atttctaatt catcaataaa tggtcttcgc aaaaagcctg taattttatc ataaacaatt 120
aaacgagtga gcctaaaagc agctaacgcg aaaataaaaa ataaaagcca gcttgtaaac 180
agcataattc caccttccct tatcctcttt cgcctattta aaaaaaggtc ttgagattgt 240
gaccaaatct cctcaactcc aatatcttat taatgtaaat acaaacaaga agataagga 299

<210> SEQ ID NO 38
<211> LENGTH: 58
<212> TYPE: DNA
<213> ORGANISM: Bacillus cereus

<400> SEQUENCE: 38
accaaatctc ctcaactcca atatcttatt aatgtaaata caaacaagaa gataagga 58

<210> SEQ ID NO 39
<211> LENGTH: 300
<212> TYPE: DNA
<213> ORGANISM: Bacillus anthracis

<400> SEQUENCE: 39
accacctacc gacgatccaa tctgtacatt cctagctgta ccaaatgcaa gattaatatc 60
gactaacact tgtcttactg ttgatttaag ttgcttctgt gcgattcaat gcttgcgtga 120
tgttacgatt taaaactaaa taatgagcta agcatggatt gggtggcaga attatctgcc 180
acccaatcca tgcttaacga gtattattat gtaaatttct taaaattggg aacttgtcta 240
gaacatagaa cctgtccttt tcattaactg aaagtagaaa cagataaagg agtgaaaaac 300

<210> SEQ ID NO 40
<211> LENGTH: 58
<212> TYPE: DNA
<213> ORGANISM: Bacillus anthracis

<400> SEQUENCE: 40
acatagaacc tgtccttttc attaactgaa agtagaaaca gataaaggag tgaaaaac 58

<210> SEQ ID NO 41
<211> LENGTH: 300
<212> TYPE: DNA
<213> ORGANISM: Bacillus anthracis

<400> SEQUENCE: 41
tagaagaaga acgccgacta ctttatgtcg caattacacg ggcgaaagaa gaactttaca 60
tttcctctcc gcaatttttt agaggaaaaa aattagatat atctcgtttt ttatacactg 120
tgcgaaaaga tttacctgaa aagacatcca ctaaataagg atgtcttttt ttatattgta 180
ttatgtacat ccctactata taaattccct gcttttatcg taagaattaa cgtaatatca 240
accatatccc gttcatattg tagtagtgta tgtcagaact cacgagaagg agtgaacata 300

<210> SEQ ID NO 42
<211> LENGTH: 63

<212> TYPE: DNA
<213> ORGANISM: Bacillus anthracis

<400> SEQUENCE: 42
tcaaccatat cccgttcata ttgtagtagt gtatgtcaga actcacgaga aggagtgaac 60
ata 63

<210> SEQ ID NO 43
<211> LENGTH: 35
<212> TYPE: PRT
<213> ORGANISM: Bacillus cereus

<400> SEQUENCE: 43

Met Ser Asn Asn Asn Ile Pro Ser Pro Phe Phe Phe Asn Asn Phe Asn
1 5 10 15

Pro Glu Leu Ile Gly Pro Thr Phe Pro Pro Ile Pro Pro Leu Thr Leu
20 25 30

Pro Thr Gly
35

<210> SEQ ID NO 44
<211> LENGTH: 222
<212> TYPE: PRT
<213> ORGANISM: Bacillus cereus

<400> SEQUENCE: 44

Met Ser Asn Asn Asn Ile Pro Ser Pro Phe Phe Phe Asn Asn Phe Asn
1 5 10 15

Pro Glu Leu Ile Gly Pro Thr Phe Pro Pro Ile Pro Pro Leu Thr Leu
20 25 30

Pro Thr Gly Pro Thr Gly Ser Thr Gly Ala Thr Gly Ala Thr Gly Pro
35 40 45

Thr Gly Ala Thr Gly Pro Thr Gly Ala Thr Gly Pro Thr Gly Ala Thr
50 55 60

Gly Ala Thr Gly Ser Thr Gly Ala Thr Gly Pro Thr Gly Ala Thr Gly
65 70 75 80

Thr Phe Ser Ser Ala Asn Ala Ser Ile Val Thr Pro Ala Pro Gln Thr
85 90 95

Val Asn Asn Leu Ala Pro Ile Gln Phe Thr Ala Pro Val Leu Ile Ser
100 105 110

Lys Asn Val Thr Phe Asn Gly Ile Asp Thr Phe Thr Ile Gln Ile Pro
115 120 125

Gly Asn Tyr Phe Phe Ile Gly Ala Val Met Thr Ser Asn Asn Gln Ala
130 135 140

Gly Pro Val Ala Val Gly Val Gly Phe Asn Gly Ile Pro Val Pro Ser
145 150 155 160

Leu Asp Gly Ala Asn Tyr Gly Thr Pro Thr Gly Gln Glu Val Val Cys
165 170 175

Phe Gly Phe Ser Gly Gln Ile Pro Ala Gly Thr Thr Ile Asn Leu Tyr
180 185 190

Asn Ile Ser Asp Lys Thr Ile Ser Ile Gly Gly Ala Thr Ala Ala Gly
195 200 205

Ser Ser Ile Val Ala Ala Arg Leu Ser Phe Phe Arg Ile Ser
210 215 220

<210> SEQ ID NO 45
<211> LENGTH: 41

<212> TYPE: PRT
<213> ORGANISM: Bacillus cereus

<400> SEQUENCE: 45

Met Phe Ser Glu Lys Lys Arg Lys Asp Leu Ile Pro Asp Asn Phe Leu
1 5 10 15

Ser Ala Pro Ala Leu Asp Pro Asn Leu Ile Gly Pro Thr Phe Pro Pro
20 25 30

Ile Pro Ser Phe Thr Leu Pro Thr Gly
35 40

<210> SEQ ID NO 46
<211> LENGTH: 293
<212> TYPE: PRT
<213> ORGANISM: Bacillus cereus

<400> SEQUENCE: 46

Met Phe Ser Glu Lys Lys Arg Lys Asp Leu Ile Pro Asp Asn Phe Leu
1 5 10 15

Ser Ala Pro Ala Leu Asp Pro Asn Leu Ile Gly Pro Thr Phe Pro Pro
20 25 30

Ile Pro Ser Phe Thr Leu Pro Thr Gly Ser Thr Gly Pro Thr Gly Pro
35 40 45

Thr Gly Asp Thr Gly Pro Thr Gly Pro Thr Ala Thr Ile Cys Ile Arg
50 55 60

Thr Asp Pro Asp Asn Gly Cys Ser Val Ala Glu Gly Ser Gly Thr Val
65 70 75 80

Ala Ser Gly Phe Ala Ser His Ala Glu Ala Cys Asn Thr Gln Ala Ile
85 90 95

Gly Asp Cys Ser His Ala Glu Gly Gln Phe Ala Thr Ala Ser Gly Thr
100 105 110

Ala Ser His Ala Glu Gly Phe Gln Thr Thr Ala Ser Gly Phe Ala Ser
115 120 125

His Thr Glu Gly Ser Gly Thr Thr Ala Asp Ala Asn Phe Ser His Thr
130 135 140

Glu Gly Ile Asn Thr Ile Val Asp Val Leu His Pro Gly Ser His Ile
145 150 155 160

Met Gly Lys Asn Gly Thr Thr Arg Ser Ser Phe Ser Trp His Leu Ala
165 170 175

Asn Gly Leu Ala Val Gly Pro Ser Leu Asn Ser Ala Val Ile Glu Gly
180 185 190

Val Thr Gly Asn Leu Tyr Leu Asp Gly Val Val Ile Ser Pro Asn Ala
195 200 205

Ala Asp Tyr Ala Glu Met Phe Glu Thr Ile Asp Gly Asn Leu Ile Asp
210 215 220

Val Gly Tyr Phe Val Thr Leu Tyr Gly Glu Lys Ile Arg Lys Ala Asn
225 230 235 240

Ala Asn Asp Asp Tyr Ile Leu Gly Val Val Ser Ala Thr Pro Ala Met
245 250 255

Ile Ala Asp Ala Ser Asp Leu Arg Trp His Asn Leu Phe Val Arg Asp
260 265 270

Glu Trp Gly Arg Thr Gln Tyr His Glu Val Val Val Pro Glu Lys Lys
275 280 285

Met Ala Met Glu Glu
290

<210> SEQ ID NO 47
<211> LENGTH: 49
<212> TYPE: PRT
<213> ORGANISM: Bacillus cereus

<400> SEQUENCE: 47

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
        35                  40                  45

Gly

<210> SEQ ID NO 48
<211> LENGTH: 83
<212> TYPE: PRT
<213> ORGANISM: Bacillus cereus

<400> SEQUENCE: 48

Met Thr Arg Lys Asp Lys Phe Asn Arg Ser Arg Ile Ser Arg Arg Asp
1               5                   10                  15

Arg Phe Asn Ser Pro Lys Ile Lys Ser Glu Ile Leu Ile Ser Pro Asp
            20                  25                  30

Leu Val Gly Pro Thr Phe Pro Pro Ile Pro Ser Phe Thr Leu Pro Thr
        35                  40                  45

Gly Val Thr Gly Pro Thr Gly Asn Thr Gly Pro Thr Gly Ile Thr Gly
    50                  55                  60

Pro Thr Gly Asp Thr Gly Pro Thr Gly Asp Thr Gly Pro Thr Gly Ile
65                  70                  75                  80

Thr Gly Pro

<210> SEQ ID NO 49
<211> LENGTH: 38
<212> TYPE: PRT
<213> ORGANISM: Bacillus cereus

<400> SEQUENCE: 49

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly
        35

<210> SEQ ID NO 50
<211> LENGTH: 163
<212> TYPE: PRT
<213> ORGANISM: Bacillus cereus

<400> SEQUENCE: 50

Met Ser Arg Lys Asp Arg Phe Asn Ser Pro Lys Ile Lys Ser Glu Ile
1               5                   10                  15

Ser Ile Ser Pro Asp Leu Val Gly Pro Thr Phe Pro Pro Ile Pro Ser
            20                  25                  30

Phe Thr Leu Pro Thr Gly Ile Thr Gly Pro Thr Gly Asn Thr Gly Pro
        35                  40                  45

Thr Gly Asp Thr Gly Pro Thr Gly Pro Thr Phe Asn Ile Asn Phe Arg

```
    50                  55                  60

Ala Glu Lys Asn Gly Ala Gln Ser Phe Thr Pro Pro Ala Asp Ile Gln
65                  70                  75                  80

Val Ser Tyr Gly Asn Ile Ile Phe Asn Asn Gly Gly Gly Tyr Ser Ser
                85                  90                  95

Val Thr Asn Thr Phe Thr Ala Pro Ile Asn Gly Ile Tyr Leu Phe Ser
            100                 105                 110

Ala Asn Ile Gly Phe Asn Pro Thr Leu Gly Thr Thr Ser Thr Leu Arg
        115                 120                 125

Ile Thr Ile Arg Lys Asn Leu Val Ser Val Ala Ser Gln Thr Ile Asp
    130                 135                 140

Ile Gln Phe Ser Ala Ala Glu Ser Gly Thr Leu Thr Val Gly Ser Ser
145                 150                 155                 160

Asn Phe Phe


<210> SEQ ID NO 51
<211> LENGTH: 39
<212> TYPE: PRT
<213> ORGANISM: Bacillus cereus

<400> SEQUENCE: 51

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 52
<211> LENGTH: 323
<212> TYPE: PRT
<213> ORGANISM: Bacillus cereus

<400> SEQUENCE: 52

Met Lys Glu Arg Asp Asn Lys Gly Lys Gln His Ser Leu Asn Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Phe Gln Gly Pro Met Gly Glu
    50                  55                  60

Met Gly Pro Thr Gly Pro Gln Gly Val Gln Gly Ile Gln Gly Pro Ala
65                  70                  75                  80

Gly Gln Met Gly Ala Thr Gly Pro Glu Gly Gln Gln Gly Pro Glu Gly
                85                  90                  95

Leu Arg Gly Pro Val Gly Ala Thr Gly Ala Thr Gly Leu Gln Gly Val
            100                 105                 110

Gln Gly Ile Gln Gly Pro Ile Gly Ser Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Pro Gln Gly Ile Gln Gly Val Gln Gly Leu Pro Gly Ala
145                 150                 155                 160

Thr Gly Pro Gln Gly Val Gln Gly Val Gln Gly Val Ile Gly Pro Gln
                165                 170                 175
```

Gly Pro Ser Gly Ser Thr Gly Gly Thr Gly Ala Thr Gly Gln Gly Val
180 185 190

Thr Gly Pro Thr Gly Ile Thr Gly Ser Thr Gly Val Thr Gly Pro Ser
195 200 205

Gly Gly Pro Pro Gly Pro Thr Gly Pro Thr Gly Ala Thr Gly Pro Gly
210 215 220

Gly Gly Pro Ser Gly Ser Thr Gly Val Thr Gly Ser Thr Gly Asn Thr
225 230 235 240

Gly Ala Thr Gly Ser Pro Gly Val Thr Gly Ala Thr Gly Pro Thr Gly
245 250 255

Ser Thr Gly Ala Thr Gly Ile Gln Gly Ser Gln Gly Ile Gln Gly Ile
260 265 270

Gln Gly Ile Gln Gly Pro Leu Gly Pro Thr Gly Pro Glu Gly Pro Gln
275 280 285

Gly Ile Gln Gly Ile Pro Gly Pro Thr Gly Ile Thr Gly Glu Gln Gly
290 295 300

Ile Gln Gly Val Gln Gly Ile Gln Gly Ile Thr Gly Ala Thr Gly Asp
305 310 315 320

Gln Gly Thr

<210> SEQ ID NO 53
<211> LENGTH: 39
<212> TYPE: PRT
<213> ORGANISM: Bacillus cereus

<400> SEQUENCE: 53

Met Arg Glu Arg Asp Asn Lys Arg Gln Gln His Ser Leu Asn Pro Asn
1 5 10 15

Phe Arg Ile Ser Pro Glu Leu Ile Gly Pro Thr Phe Pro Pro Val Pro
20 25 30

Thr Gly Phe Thr Gly Ile Gly
35

<210> SEQ ID NO 54
<211> LENGTH: 436
<212> TYPE: PRT
<213> ORGANISM: Bacillus cereus

<400> SEQUENCE: 54

Met Arg Glu Arg Asp Asn Lys Arg Gln Gln His Ser Leu Asn Pro Asn
1 5 10 15

Phe Arg Ile Ser Pro Glu Leu Ile Gly Pro Thr Phe Pro Pro Val Pro
20 25 30

Thr Gly Phe Thr Gly Ile Gly Ile Thr Gly Pro Thr Gly Pro Gln Gly
35 40 45

Pro Thr Gly Pro Gln Gly Pro Arg Gly Phe Gln Gly Pro Met Gly Glu
50 55 60

Met Gly Pro Thr Gly Pro Gln Gly Val Gln Gly Ile Gln Gly Pro Val
65 70 75 80

Gly Pro Ile Gly Ala Thr Gly Pro Glu Gly Gln Gln Gly Pro Gln Gly
85 90 95

Leu Arg Gly Pro Gln Gly Glu Thr Gly Ala Thr Gly Pro Gly Gly Val
100 105 110

Gln Gly Leu Gln Gly Pro Ile Gly Pro Thr Gly Ala Thr Gly Ala Gln
115 120 125

```
Gly Val Gln Gly Ile Gln Gly Leu Gln Gly Pro Ile Gly Ala Thr Gly
    130                 135                 140

Pro Glu Gly Pro Gln Gly Ile Gln Gly Val Gln Gly Leu Pro Gly Ala
145                 150                 155                 160

Thr Gly Ser Gln Gly Ile Gln Gly Val Gln Gly Ile Gln Gly Pro Gln
                165                 170                 175

Gly Pro Ser Gly Asn Thr Gly Ala Thr Gly Ala Thr Gly Gln Gly Ile
            180                 185                 190

Thr Gly Pro Thr Gly Ile Thr Gly Pro Thr Gly Ile Thr Gly Pro Ser
        195                 200                 205

Gly Gly Pro Pro Gly Pro Thr Gly Pro Thr Gly Ala Thr Gly Pro Gly
    210                 215                 220

Gly Gly Pro Ser Gly Ser Thr Gly Ala Thr Gly Ala Thr Gly Asn Thr
225                 230                 235                 240

Gly Ala Thr Gly Asn Thr Gly Ile Thr Gly Ala Thr Gly Ser Thr Gly
                245                 250                 255

Pro Thr Gly Ser Thr Gly Ala Gln Gly Leu Gln Gly Ile Gln Gly Ile
            260                 265                 270

Gln Gly Pro Ile Gly Pro Thr Gly Pro Glu Gly Pro Gln Gly Ile Gln
        275                 280                 285

Gly Ile Pro Gly Pro Thr Gly Val Thr Gly Glu Gln Gly Ile Gln Gly
    290                 295                 300

Val Gln Gly Ile Gln Gly Ile Thr Gly Ala Thr Gly Asp Gln Gly Pro
305                 310                 315                 320

Gln Gly Ile Gln Gly Val Ile Gly Ala Gln Gly Val Thr Gly Ala Thr
                325                 330                 335

Gly Asp Gln Gly Pro Gln Gly Ile Gln Gly Val Pro Gly Pro Ser Gly
            340                 345                 350

Ala Thr Gly Pro Gln Gly Val Gln Gly Ile Gln Gly Pro Met Gly Asp
        355                 360                 365

Ile Gly Pro Thr Gly Pro Glu Gly Pro Glu Gly Leu Gln Gly Pro Gln
    370                 375                 380

Gly Ile Gln Gly Val Pro Gly Pro Val Gly Ala Thr Gly Pro Glu Gly
385                 390                 395                 400

Pro Gln Gly Ile Gln Gly Ile Gln Gly Val Gln Gly Ala Thr Gly Pro
                405                 410                 415

Gln Gly Pro Gln Gly Ile Gln Gly Ile Gln Gly Val Gln Gly Ile Thr
            420                 425                 430

Gly Ala Thr Gly
        435


<210> SEQ ID NO 55
<211> LENGTH: 36
<212> TYPE: PRT
<213> ORGANISM: Bacillus thuringiensis

<400> SEQUENCE: 55

Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly
        35


<210> SEQ ID NO 56
```

<211> LENGTH: 470
<212> TYPE: PRT
<213> ORGANISM: Bacillus thuringiensis

<400> SEQUENCE: 56

```
Met Lys Asn Arg Asp Asn Lys Gly Lys Gln Gln Ser Asn Phe Arg Ile
1               5                   10                  15

Pro Pro Glu Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
    50                  55                  60

Thr Gly Pro Gln Gly Val Gln Gly Ile Gln Gly Pro Val Gly Pro Ile
65                  70                  75                  80

Gly Ala Thr Gly Pro Glu Gly Gln Gln Gly Ala Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Ile Gln Gly Thr Gln Gly Pro Ser
                165                 170                 175

Gly Asn Thr Gly Ala Thr Gly Ala Thr Gly Gln Gly Leu Thr Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Pro Thr Gly Ala Thr Gly Pro Gly Gly Gly Pro
    210                 215                 220

Ser Gly Ser Thr Gly Ala Thr Gly Ala Thr Gly Asp Thr Gly Ala Thr
225                 230                 235                 240

Gly Ser Thr Gly Val Thr Gly Ala Thr Gly Ala Gln Gly Pro Gln Gly
                245                 250                 255

Val Gln Gly Ile Gln Gly Pro Thr Gly Ala Thr Gly Ala Thr Gly Ala
            260                 265                 270

Thr Gly Pro Gln Gly Ile Gln Gly Pro Gln Gly Ile Gln Gly Pro Thr
        275                 280                 285

Gly Ala Thr Gly Ala Thr Gly Ser Gln Gly Pro Thr Gly Asn Thr Gly
    290                 295                 300

Pro Thr Gly Ser Gln Gly Ile Gln Gly Pro Thr Gly Pro Thr Gly Ala
305                 310                 315                 320

Gly Ala Thr Gly Ala Thr Gly Ala Thr Gly Ala Thr Gly Val Ser Thr
                325                 330                 335

Thr Ala Thr Tyr Ala Phe Ala Asn Asn Thr Ser Gly Ser Ile Ile Ser
            340                 345                 350

Val Leu Leu Gly Gly Thr Asn Ile Pro Leu Pro Asn Asn Gln Asn Ile
        355                 360                 365

Gly Pro Gly Ile Thr Val Ser Gly Gly Asn Thr Val Phe Thr Val Ala
    370                 375                 380

Asn Ala Gly Asn Tyr Tyr Ile Ala Tyr Thr Ile Asn Leu Thr Ala Gly
```

385 390 395 400

Leu Leu Val Ser Ser Arg Ile Thr Val Asn Gly Ser Pro Leu Ala Gly
405 410 415

Thr Ile Asn Ser Pro Ala Val Ala Ala Gly Ser Phe Ser Ala Thr Ile
420 425 430

Ile Ala Asn Leu Pro Ala Gly Ala Ala Val Ser Leu Gln Leu Phe Gly
435 440 445

Val Ile Ala Leu Ala Thr Leu Ser Thr Ala Thr Pro Gly Ala Thr Leu
450 455 460

Thr Ile Ile Arg Leu Ser
465 470

<210> SEQ ID NO 57
<211> LENGTH: 136
<212> TYPE: PRT
<213> ORGANISM: Bacillus mycoides

<400> SEQUENCE: 57

Met Lys Phe Ser Lys Lys Ser Thr Val Asp Ser Ser Ile Val Gly Lys
1 5 10 15

Arg Val Val Ser Lys Val Asn Ile Leu Arg Phe Tyr Asp Ala Arg Ser
20 25 30

Cys Gln Asp Lys Asp Val Asp Gly Phe Val Asp Val Gly Glu Leu Phe
35 40 45

Thr Ile Phe Arg Lys Leu Asn Met Glu Gly Ser Val Gln Phe Lys Ala
50 55 60

His Asn Ser Ile Gly Lys Thr Tyr Tyr Ile Thr Ile Asn Glu Val Tyr
65 70 75 80

Val Phe Val Thr Val Leu Leu Gln Tyr Ser Thr Leu Ile Gly Gly Ser
85 90 95

Tyr Val Phe Asp Lys Asn Glu Ile Gln Lys Ile Asn Gly Ile Leu Gln
100 105 110

Ala Asn Ala Leu Asn Pro Asn Leu Ile Gly Pro Thr Leu Pro Pro Ile
115 120 125

Pro Pro Phe Thr Leu Pro Thr Gly
130 135

<210> SEQ ID NO 58
<211> LENGTH: 384
<212> TYPE: PRT
<213> ORGANISM: Bacillus mycoides

<400> SEQUENCE: 58

Met Lys Phe Ser Lys Lys Ser Thr Val Asp Ser Ser Ile Val Gly Lys
1 5 10 15

Arg Val Val Ser Lys Val Asn Ile Leu Arg Phe Tyr Asp Ala Arg Ser
20 25 30

Cys Gln Asp Lys Asp Val Asp Gly Phe Val Asp Val Gly Glu Leu Phe
35 40 45

Thr Ile Phe Arg Lys Leu Asn Met Glu Gly Ser Val Gln Phe Lys Ala
50 55 60

His Asn Ser Ile Gly Lys Thr Tyr Tyr Ile Thr Ile Asn Glu Val Tyr
65 70 75 80

Val Phe Val Thr Val Leu Leu Gln Tyr Ser Thr Leu Ile Gly Gly Ser
85 90 95

Tyr Val Phe Asp Lys Asn Glu Ile Gln Lys Ile Asn Gly Ile Leu Gln

```
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly Pro Thr
    130                 135                 140

Gly Val Thr Gly Pro Thr Gly Val Thr Gly Pro Thr Gly Val Thr Gly
145                 150                 155                 160

Pro Thr Gly Val Thr Gly Pro Thr Gly Val Thr Gly Pro Thr Gly Val
                165                 170                 175

Thr Gly Pro Thr Gly Val Thr Gly Pro Thr Gly Val Thr Gly Pro Thr
            180                 185                 190

Gly Val Thr Gly Pro Thr Gly Val Thr Gly Pro Thr Gly Val Thr Gly
        195                 200                 205

Pro Thr Gly Val Thr Gly Pro Thr Gly Gly Thr Glu Gly Cys Leu Cys
    210                 215                 220

Asp Cys Cys Val Leu Pro Met Gln Ser Val Leu Gln Gln Leu Ile Gly
225                 230                 235                 240

Glu Thr Val Ile Leu Gly Thr Ile Ala Asp Thr Pro Asn Thr Pro Pro
                245                 250                 255

Leu Phe Phe Leu Phe Thr Ile Thr Ser Val Asn Asp Phe Leu Val Thr
            260                 265                 270

Val Thr Asp Gly Thr Thr Thr Phe Val Val Asn Ile Ser Asp Val Thr
        275                 280                 285

Gly Val Gly Phe Leu Pro Pro Gly Pro Pro Ile Thr Leu Leu Pro Pro
    290                 295                 300

Thr Asp Val Gly Cys Glu Cys Glu Cys Arg Glu Arg Pro Ile Arg Gln
305                 310                 315                 320

Leu Leu Asp Ala Phe Ile Gly Ser Thr Val Ser Leu Leu Ala Ser Asn
                325                 330                 335

Gly Ser Ile Ala Ala Asp Phe Ser Val Glu Gln Thr Gly Leu Gly Ile
            340                 345                 350

Val Leu Gly Thr Leu Pro Ile Asn Pro Thr Thr Thr Val Arg Phe Ala
        355                 360                 365

Ile Ser Thr Cys Lys Ile Thr Ala Val Asn Ile Thr Pro Ile Thr Met
    370                 375                 380
```

<210> SEQ ID NO 59
<211> LENGTH: 36
<212> TYPE: PRT
<213> ORGANISM: Bacillus cereus

<400> SEQUENCE: 59

```
Met Lys Glu Arg Asp Lys Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35
```

<210> SEQ ID NO 60
<211> LENGTH: 1321
<212> TYPE: PRT
<213> ORGANISM: Bacillus cereus

<400> SEQUENCE: 60

```
Met Lys Glu Arg Asp Lys Gln Asn Ser Leu Asn Ser Asn Phe Arg Ile
```

-continued

```
1               5                   10                  15

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Leu Gln Gly Pro Met Gly Glu Met Gly Pro
    50                  55                  60

Thr Gly Pro Gln Gly Val Gln Gly Ile Gln Gly Pro Val Gly Ser Ile
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ala Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Leu Pro Gly Ala Thr Gly Pro
145                 150                 155                 160

Gln Gly Ile Gln Gly Ala Gln Gly Met Gln Gly Leu Gln Gly Pro Ser
                165                 170                 175

Gly Asn Thr Gly Ala Thr Gly Ala Thr Gly Gln Gly Ile Thr Gly Pro
            180                 185                 190

Thr Gly Val Thr Gly Pro Thr Gly Ile Thr Gly Pro Ser Gly Gly Pro
        195                 200                 205

Pro Gly Pro Thr Gly Pro Thr Gly Ala Thr Gly Pro Gly Gly Gly Pro
    210                 215                 220

Ser Gly Ser Thr Gly Ala Thr Gly Ala Thr Gly Asn Thr Gly Ala Thr
225                 230                 235                 240

Gly Ser Thr Gly Val Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Pro Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Ala Ile Gly Pro Gln Gly Ala Thr
                325                 330                 335

Gly Ala Thr Gly Asp Gln Gly Pro Gln Gly Ile Gln Gly Val Pro Gly
            340                 345                 350

Pro Ser Gly Ala Thr Gly Pro Gln Gly Val Gln Gly Leu Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430
```

```
Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Gly Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Ile Gln Gly Ile
            500                 505                 510

Gln Gly Pro Thr Gly Ala Thr Gly Asp Thr Gly Ala Thr Gly Ala Thr
        515                 520                 525

Gly Glu Gly Thr Thr Gly Pro Thr Gly Val Thr Gly Pro Thr Gly Pro
    530                 535                 540

Ser Gly Gly Pro Ala Gly Pro Thr Gly Pro Thr Gly Pro Ser Gly Pro
545                 550                 555                 560

Ala Gly Val Thr Gly Pro Ser Gly Gly Pro Pro Gly Pro Thr Gly Ala
                565                 570                 575

Thr Gly Ala Thr Gly Val Thr Gly Asp Thr Gly Ala Thr Gly Ser Thr
            580                 585                 590

Gly Val Thr Gly Ala Thr Gly Glu Thr Gly Ala Thr Gly Val Thr Gly
        595                 600                 605

Leu Gln Gly Pro Gln Gly Ile Gln Gly Val Gln Gly Glu Ile Gly Pro
    610                 615                 620

Thr Gly Pro Gln Gly Val Gln Gly Pro Gln Gly Ile Gln Gly Val Thr
625                 630                 635                 640

Gly Ala Thr Gly Asp Gln Gly Pro Gln Gly Val Gln Gly Pro Gln Gly
                645                 650                 655

Asp Ile Gly Pro Thr Gly Pro Gln Gly Ile Gln Gly Pro Gln Gly Ser
            660                 665                 670

Gln Gly Ile Gln Gly Ala Thr Gly Gly Thr Gly Ala Gln Gly Pro Gln
        675                 680                 685

Gly Ile Gln Gly Pro Gln Gly Asp Val Gly Pro Thr Gly Pro Gln Gly
    690                 695                 700

Pro Thr Gly Ile Gln Gly Ile Gln Gly Glu Ile Gly Pro Thr Gly Pro
705                 710                 715                 720

Glu Gly Pro Glu Gly Leu Gln Gly Pro Gln Gly Ile Gln Gly Val Gln
                725                 730                 735

Gly Pro Val Gly Ala Thr Gly Pro Glu Gly Pro Gln Gly Ile Gln Gly
            740                 745                 750

Ile Gln Gly Val Gln Gly Ala Thr Gly Ser Gln Gly Pro Gln Gly Ile
        755                 760                 765

Gln Gly Ile Gln Gly Val Gln Gly Ile Thr Gly Ala Thr Gly Ala Gln
    770                 775                 780

Gly Ala Thr Gly Ile Gln Gly Ile Gln Gly Glu Ile Gly Ala Thr Gly
785                 790                 795                 800

Pro Glu Gly Pro Gln Gly Val Gln Gly Val Gln Gly Glu Ile Gly Pro
                805                 810                 815

Thr Gly Pro Met Gly Pro Gln Gly Val Gln Gly Val Gln Gly Ile Gln
            820                 825                 830

Gly Ala Thr Gly Ala Gln Gly Val Gln Gly Pro Gln Gly Ile Gln Gly
        835                 840                 845
```

Ile Gln Gly Pro Thr Gly Ala Thr Gly Glu Thr Gly Ala Thr Gly Ala
850 855 860

Thr Gly Glu Gly Thr Thr Gly Pro Thr Gly Val Thr Gly Pro Thr Gly
865 870 875 880

Val Thr Gly Pro Ser Gly Gly Pro Ala Gly Pro Thr Gly Pro Thr Gly
885 890 895

Pro Ser Gly Pro Ala Gly Val Thr Gly Pro Ser Gly Gly Pro Pro Gly
900 905 910

Pro Thr Gly Ala Thr Gly Ala Thr Gly Ala Thr Gly Val Thr Gly Asp
915 920 925

Thr Gly Ala Thr Gly Ser Thr Gly Val Thr Gly Ala Thr Gly Glu Thr
930 935 940

Gly Ala Thr Gly Val Thr Gly Leu Gln Gly Pro Gln Gly Ile Gln Gly
945 950 955 960

Val Gln Gly Glu Ile Gly Pro Thr Gly Pro Gln Gly Ile Gln Gly Pro
965 970 975

Gln Gly Ile Gln Gly Val Thr Gly Ala Thr Gly Ala Gln Gly Pro Gln
980 985 990

Gly Ile Gln Gly Pro Gln Gly Asp Ile Gly Pro Thr Gly Pro Gln Gly
995 1000 1005

Ile Gln Gly Pro Gln Gly Pro Gln Gly Ile Gln Gly Ala Thr Gly
1010 1015 1020

Ala Thr Gly Ala Gln Gly Pro Gln Gly Ile Gln Gly Pro Gln Gly
1025 1030 1035

Glu Ile Gly Pro Thr Gly Pro Gln Gly Pro Gln Gly Ile Gln Gly
1040 1045 1050

Pro Gln Gly Ile Gln Gly Pro Thr Gly Ala Thr Gly Ala Thr Gly
1055 1060 1065

Ala Thr Gly Leu Gln Gly Ile Gln Gly Pro Gln Gly Ile Gln Gly
1070 1075 1080

Pro Gln Gly Ile Gln Gly Pro Thr Gly Ala Thr Gly Ala Thr Gly
1085 1090 1095

Ala Thr Gly Leu Gln Gly Ile Gln Gly Pro Gln Gly Ile Gln Gly
1100 1105 1110

Pro Gln Gly Ile Gln Gly Pro Thr Gly Ala Thr Gly Ala Thr Gly
1115 1120 1125

Ala Thr Gly Leu Gln Gly Ile Gln Gly Pro Gln Gly Ile Gln Gly
1130 1135 1140

Pro Gln Gly Ile Gln Gly Pro Thr Gly Ala Thr Gly Ala Thr Gly
1145 1150 1155

Ala Thr Gly Ser Gln Gly Pro Thr Gly Asp Thr Gly Pro Thr Gly
1160 1165 1170

Ala Gly Ala Thr Gly Ala Thr Gly Ala Thr Gly Val Ser Thr Thr
1175 1180 1185

Ala Thr Tyr Ala Phe Ala Asn Asn Thr Ser Gly Thr Ala Ile Ser
1190 1195 1200

Val Leu Leu Gly Gly Thr Asn Ile Pro Leu Pro Asn Asn Gln Asn
1205 1210 1215

Ile Gly Pro Gly Ile Thr Val Ser Gly Gly Asn Thr Val Phe Thr
1220 1225 1230

Val Ala Ser Ala Gly Asn Tyr Tyr Ile Ala Tyr Thr Ile Asn Leu
1235 1240 1245

Thr Ala Gly Leu Leu Val Ser Ser Arg Ile Thr Val Asn Gly Ser

```
    1250                1255                1260

Pro Leu  Ala Gly Thr Ile Asn  Ala Pro Thr Val Ala  Thr Gly Ser
    1265                1270                1275

Phe Ser  Ala Thr Ile Ile Ala  Asn Leu Pro Ala Gly  Ala Ala Ile
    1280                1285                1290

Ser Leu  Gln Leu Phe Gly Leu  Val Ala Ile Ala Thr  Leu Ser Thr
    1295                1300                1305

Thr Thr  Pro Gly Ala Thr Leu  Thr Ile Ile Arg Leu  Ser
    1310                1315                1320


<210> SEQ ID NO 61
<211> LENGTH: 39
<212> TYPE: PRT
<213> ORGANISM: Bacillus cereus

<400> SEQUENCE: 61

Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

Ser Phe Thr Leu Pro Thr Gly
        35


<210> SEQ ID NO 62
<211> LENGTH: 309
<212> TYPE: PRT
<213> ORGANISM: Bacillus cereus

<400> SEQUENCE: 62

Met Met Glu Asn Lys Lys Gly Ser Lys His Asn Glu Phe Leu Ser Ala
1               5                   10                  15

Lys Ala Phe Asn Pro Asn Leu Val Gly Pro Thr Leu Pro Pro Val Pro
            20                  25                  30

Ser Phe Thr Leu Pro Thr Gly Pro Thr Gly Ala Thr Gly Ala Thr Gly
        35                  40                  45

Val Thr Gly Ala Thr Gly Ala Thr Gly Ala Thr Gly Ala Thr Gly Val
    50                  55                  60

Thr Gly Ala Thr Gly Ala Thr Gly Val Thr Gly Ala Thr Gly Ala Thr
65                  70                  75                  80

Gly Val Thr Gly Ala Thr Gly Ala Thr Gly Ala Thr Gly Ala Thr Gly
                85                  90                  95

Val Thr Gly Ala Thr Gly Ala Thr Gly Val Thr Gly Ala Thr Gly Ala
            100                 105                 110

Thr Gly Val Thr Gly Ala Thr Gly Ala Thr Gly Val Thr Gly Val Thr
        115                 120                 125

Gly Ala Thr Gly Ala Thr Gly Ala Thr Gly Val Thr Gly Pro Thr Gly
    130                 135                 140

Ala Thr Gly Ala Thr Gly Ala Thr Gly Val Thr Gly Pro Thr Gly Ala
145                 150                 155                 160

Thr Gly Ala Thr Gly Ala Thr Gly Gly Leu Ala Val Ala Ser Ala Ser
                165                 170                 175

Ala Met Thr Ser Thr Ala Gln Thr Val Asp Asn Leu Val Ala Val Gln
            180                 185                 190

Phe Thr Ala Pro Val Leu Glu Leu Asp Ser Val Ile Phe Asn Gly Thr
        195                 200                 205

Asp Thr Phe Thr Val Leu Val Pro Gly Asn Tyr Tyr Cys Ile Gly Ser
```

```
    210                 215                 220

Leu Met Pro Ala Glu Thr Gln Thr Gly Pro Phe Ala Val Gly Ile Gly
225                 230                 235                 240

Leu Asn Gly Ile Pro Val Pro Ala Leu Asp Gly Ala Asn Tyr Ala Gln
                245                 250                 255

Ser Ala Gly Gln Glu Val Val Gly Phe Gly Leu Thr Gly Gln Ile Pro
            260                 265                 270

Ala Gly Thr Thr Ile Ser Leu Phe Asn Leu Ser Gly His Thr Ile Ser
        275                 280                 285

Ile Gly Gly Thr Ile Ser Gly Ala Thr Ser Val Ala Ala Arg Leu Leu
    290                 295                 300

Leu Phe Arg Ile Ser
305


<210> SEQ ID NO 63
<211> LENGTH: 41
<212> TYPE: PRT
<213> ORGANISM: Bacillus weihenstephanensis

<400> SEQUENCE: 63

Met Ser Asn Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40


<210> SEQ ID NO 64
<211> LENGTH: 292
<212> TYPE: PRT
<213> ORGANISM: Bacillus weihenstephanensis

<400> SEQUENCE: 64

Met Ser Asn Asn Asn Tyr Ser Asp Gly Leu Asn Pro Asp Glu Phe Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Thr Gly Pro
        35                  40                  45

Thr Gly Pro Thr Gly Pro Thr Val Pro Thr Gly Pro Thr Gly Pro Thr
    50                  55                  60

Gly Pro Thr Gly Pro Thr Gly Pro Thr Gly Asp Thr Gly Thr Thr Gly
65                  70                  75                  80

Ala Thr Gly Asp Thr Gly Ala Thr Gly Asp Thr Gly Ala Thr Gly Pro
                85                  90                  95

Thr Gly Pro Thr Gly Asp Thr Gly Ala Thr Gly Pro Thr Gly Pro Thr
            100                 105                 110

Gly Asp Thr Gly Ala Thr Gly Pro Thr Gly Pro Thr Gly Asp Thr Gly
        115                 120                 125

Ala Thr Gly Pro Thr Gly Pro Thr Gly Asp Thr Gly Ala Thr Gly Ala
    130                 135                 140

Thr Gly Pro Thr Gly Pro Thr Gly Pro Thr Gly Pro Ser Gly Leu Gly
145                 150                 155                 160

Leu Pro Ala Gly Leu Tyr Ala Phe Asn Ser Ala Thr Ile Ser Leu Ala
                165                 170                 175

Leu Gly Ile Asn Asp Pro Val Pro Phe Asn Thr Val Gly Ser Gln Phe
```

```
            180                 185                 190

Gly Thr Ala Ile Ser Gln Leu Asp Ala Asp Thr Phe Ile Ile Ser Glu
        195                 200                 205

Thr Gly Phe Tyr Lys Ile Thr Val Ile Ala Tyr Thr Ala Ala Val Ser
    210                 215                 220

Ile Leu Gly Ser Leu Ala Ile Gln Val Asn Gly Val Asn Ile Pro Gly
225                 230                 235                 240

Ala Gly Thr Ser Leu Ile Ser Leu Gly Ala Pro Leu Val Ile Gln Ala
                245                 250                 255

Ile Thr Gln Ile Thr Ile Thr Pro Ser Met Val Glu Ala Val Val Thr
            260                 265                 270

Gly Leu Gly Leu Ser Leu Ala Leu Gly Thr Ser Ala Ser Ile Ile Ile
        275                 280                 285

Glu Lys Ile Ala
    290


<210> SEQ ID NO 65
<211> LENGTH: 30
<212> TYPE: PRT
<213> ORGANISM: Bacillus thuringiensis

<400> SEQUENCE: 65

Met Asp Glu Phe Leu Ser Ser Ala Ala Ile Asn Pro Asn Leu Val Gly
1               5                   10                  15

Pro Thr Leu Pro Pro Val Pro Pro Phe Thr Leu Pro Thr Gly
            20                  25                  30


<210> SEQ ID NO 66
<211> LENGTH: 233
<212> TYPE: PRT
<213> ORGANISM: Bacillus thuringiensis

<400> SEQUENCE: 66

Met Asp Glu Phe Leu Ser Ser Ala Ala Ile Asn Pro Asn Leu Val Gly
1               5                   10                  15

Pro Thr Leu Pro Pro Val Pro Pro Phe Thr Leu Pro Thr Gly Pro Thr
            20                  25                  30

Gly Ser Thr Gly Pro Thr Gly Thr Thr Gly Pro Thr Gly Pro Thr Gly
        35                  40                  45

Thr Thr Gly Thr Thr Gly Thr Thr Gly Pro Thr Gly Pro Thr Gly Thr
    50                  55                  60

Thr Gly Pro Thr Gly Pro Thr Gly Thr Thr Gly Thr Thr Gly Pro Thr
65                  70                  75                  80

Gly Thr Thr Gly Thr Leu Ser Val Ala Tyr Gly His Phe Trp Gln Thr
                85                  90                  95

Asp Ile Ile Thr Val Pro Phe Glu Ser Pro Phe Ser Phe Asp Gln Ala
            100                 105                 110

Gly Pro Met Val Gly Gly Ile Ser Leu Leu Asn Pro Thr Thr Ile Ser
        115                 120                 125

Ile Thr Gln Pro Gly Asp Tyr Arg Val Ser Phe Ile Ser Ser Ile Asn
    130                 135                 140

Leu Thr Val Ala Leu Val Phe Pro Tyr Ser Pro Thr Ile Ser Ile Leu
145                 150                 155                 160

Leu Asn Asn Ser Leu Ile Pro Asn Phe Lys Ala Thr Phe Gly Leu Leu
                165                 170                 175

Ile Gln Asp Leu Glu Asp Val Asp Cys Asp Gln Leu Thr Gly Glu Thr
```

```
            180                 185                 190

Ile Leu Ser Ile Pro Ala Asn Ser Thr Leu Gln Leu Ile Asn Asn Ser
        195                 200                 205

Phe Val Gly Asn Arg Asp Ile Arg Thr Cys Asp Asn Gly Ile Asn Ala
    210                 215                 220

Leu Glu Leu Thr Ile Ile Lys Leu Asn
225                 230


<210> SEQ ID NO 67
<211> LENGTH: 33
<212> TYPE: PRT
<213> ORGANISM: Bacillus cereus

<400> SEQUENCE: 67

Met Phe Asp Lys Asn Lys Ile Leu Gln Ala Asn Ala Phe Asn Ser Asn
1               5                   10                  15

Leu Ile Gly Pro Thr Leu Pro Pro Ile Pro Pro Phe Thr Leu Pro Thr
            20                  25                  30

Gly


<210> SEQ ID NO 68
<211> LENGTH: 295
<212> TYPE: PRT
<213> ORGANISM: Bacillus cereus

<400> SEQUENCE: 68

Met Phe Asp Lys Asn Lys Ile Leu Gln Ala Asn Ala Phe Asn Ser Asn
1               5                   10                  15

Leu Ile Gly Pro Thr Leu Pro Pro Ile Pro Pro Phe Thr Leu Pro Thr
            20                  25                  30

Gly Pro Thr Gly Gly Thr Gly Pro Thr Gly Val Thr Gly Pro Thr Gly
        35                  40                  45

Val Thr Gly Pro Ile Gly Val Thr Gly Pro Thr Gly Val Thr Gly Pro
    50                  55                  60

Thr Gly Val Thr Gly Pro Thr Gly Ile Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Val Thr Gly Pro Thr Gly Val Thr
        115                 120                 125

Gly Pro Thr Gly Ser Thr Glu Ser Cys Leu Cys Asp Cys Cys Val Leu
    130                 135                 140

Pro Met Gln Asn Val Leu Gln Gln Leu Ile Gly Glu Thr Val Leu Leu
145                 150                 155                 160

Gly Thr Ile Ala Asp Ala Pro Asn Thr Pro Pro Leu Phe Phe Leu Phe
                165                 170                 175

Thr Ile Thr Ser Val Asn Asp Phe Leu Val Thr Val Thr Asp Gly Ser
            180                 185                 190

Thr Ser Tyr Val Val Asn Ile Ser Asp Val Thr Gly Val Gly Phe Leu
        195                 200                 205

Pro Pro Gly Pro Ser Ile Thr Leu Leu Pro Pro Val Asp Ile Gly Cys
    210                 215                 220

Glu Cys Asp Cys Arg Glu Arg Pro Ile Arg Glu Leu Leu Asp Thr Leu
225                 230                 235                 240
```

Ile Gly Ser Thr Val Asn Leu Leu Ala Ser Thr Gly Ser Ile Ala Ala
245 250 255

Asp Phe Asn Val Glu Gln Thr Gly Leu Gly Ile Val Leu Gly Thr Leu
260 265 270

Pro Ile Asn Pro Thr Thr Ile Val Arg Phe Ala Ile Ser Thr Cys Lys
275 280 285

Ile Thr Ala Val Asn Ile Leu
290 295

<210> SEQ ID NO 69
<211> LENGTH: 44
<212> TYPE: PRT
<213> ORGANISM: Bacillus cereus

<400> SEQUENCE: 69

Met Ser Asp Glu Asn Glu Lys Lys Tyr Ser Asn Glu Leu Ala Gln Ala
1 5 10 15

Asp Phe Ile Ser Ala Ala Ala Phe Asp Pro Ser Leu Val Gly Pro Thr
20 25 30

Leu Pro Pro Thr Pro Pro Phe Thr Leu Pro Thr Gly
35 40

<210> SEQ ID NO 70
<211> LENGTH: 639
<212> TYPE: PRT
<213> ORGANISM: Bacillus cereus

<400> SEQUENCE: 70

Met Ser Asp Glu Asn Glu Lys Lys Tyr Ser Asn Glu Leu Ala Gln Ala
1 5 10 15

Asp Phe Ile Ser Ala Ala Ala Phe Asp Pro Ser Leu Val Gly Pro Thr
20 25 30

Leu Pro Pro Thr Pro Pro Phe Thr Leu Pro Thr Gly Pro Thr Gly Ala
35 40 45

Thr Gly Pro Thr Gly Ala Thr Gly Pro Thr Gly Ala Thr Gly Ser Thr
50 55 60

Gly Val Thr Gly Pro Thr Gly Val Thr Gly Pro Thr Gly Ala Thr Gly
65 70 75 80

Pro Thr Gly Ala Thr Gly Ser Thr Gly Val Thr Gly Pro Thr Gly Ala
85 90 95

Thr Gly Pro Ser Gly Ala Thr Gly Ser Thr Gly Thr Thr Gly Pro Thr
100 105 110

Gly Asp Thr Gly Pro Thr Gly Ile Thr Gly Pro Thr Gly Val Thr Gly
115 120 125

Pro Thr Gly Ala Thr Gly Pro Thr Gly Ala Thr Gly Pro Thr Gly Ala
130 135 140

Thr Gly Ser Thr Gly Val Thr Gly Pro Thr Gly Val Thr Gly Pro Thr
145 150 155 160

Gly Ala Thr Gly Pro Thr Gly Ala Thr Gly Ser Thr Gly Val Thr Gly
165 170 175

Pro Thr Gly Ile Thr Gly Pro Thr Gly Ala Thr Gly Thr Thr Gly Ser
180 185 190

Thr Gly Pro Thr Gly Val Thr Gly Pro Thr Gly Ala Thr Gly Pro Thr
195 200 205

Gly Ala Thr Gly Pro Thr Gly Ala Thr Gly Ser Thr Gly Val Thr Gly
210 215 220

```
Pro Thr Gly Ile Thr Gly Pro Thr Gly Ala Thr Gly Thr Thr Gly Ser
225                 230                 235                 240

Thr Gly Pro Thr Gly Val Thr Gly Pro Thr Gly Ala Thr Gly Pro Thr
                245                 250                 255

Gly Ala Thr Gly Pro Thr Gly Ala Thr Gly Ser Thr Gly Val Thr Gly
            260                 265                 270

Pro Thr Gly Val Thr Gly Pro Thr Gly Ala Thr Gly Pro Thr Gly Ala
        275                 280                 285

Thr Gly Ser Thr Gly Val Thr Gly Pro Thr Gly Ala Thr Gly Pro Thr
    290                 295                 300

Gly Ala Thr Gly Ser Thr Gly Val Thr Gly Pro Thr Gly Val Thr Gly
305                 310                 315                 320

Pro Thr Gly Ala Thr Gly Ser Thr Gly Ala Thr Gly Pro Thr Gly Ala
                325                 330                 335

Thr Gly Ser Thr Gly Val Thr Gly Pro Thr Gly Ala Thr Gly Pro Thr
            340                 345                 350

Gly Ala Thr Gly Pro Thr Gly Ala Thr Gly Ser Thr Gly Val Thr Gly
        355                 360                 365

Pro Thr Gly Ile Thr Gly Pro Thr Gly Ala Thr Gly Thr Thr Gly Ser
    370                 375                 380

Thr Gly Pro Thr Gly Val Thr Gly Pro Thr Gly Val Thr Gly Pro Thr
385                 390                 395                 400

Gly Val Thr Gly Pro Thr Gly Ala Thr Gly Pro Thr Gly Ala Thr Gly
                405                 410                 415

Ser Thr Gly Val Thr Gly Pro Thr Gly Ile Thr Gly Pro Thr Gly Ala
            420                 425                 430

Thr Gly Thr Thr Gly Ser Thr Gly Pro Thr Gly Val Thr Gly Pro Thr
        435                 440                 445

Gly Val Thr Gly Pro Thr Gly Ala Thr Gly Pro Thr Gly Val Thr Gly
    450                 455                 460

Pro Thr Gly Ala Thr Gly Pro Thr Gly Ala Thr Gly Ala Thr Ala Thr
465                 470                 475                 480

Thr Ser Thr Lys Ala Ile Leu Phe Gly Gly Thr Asn Ala Gly Phe Gln
                485                 490                 495

Arg Ile Ala Gly Ser Pro Gly Ala Asp Ser Gln Thr Leu Pro Tyr Val
            500                 505                 510

Thr Ala Gly Ala Gly Ser Val Val Ala Phe Ser Ala Ser Ile Asn Val
        515                 520                 525

Asn Asn Leu Gly Thr Gly Val Tyr Leu Leu Arg Val Cys Asp Asn Val
    530                 535                 540

Pro Thr Asn Leu Ala Ser Pro Gly Ala Gly Gln Ile Val Ser Thr Ile
545                 550                 555                 560

Thr Leu Thr Leu Thr Ala Asn Ile Thr Gly Thr Ile Val Phe Ser Ile
                565                 570                 575

Lys Pro Thr Asp Ile Gly Ala Gln Pro Val Lys Val Phe Asn Pro Asn
            580                 585                 590

Pro Val Val Ala Pro Ala Thr Val Thr Trp Thr Ser Thr Ile Pro Gly
        595                 600                 605

Asn Pro Val Ala Arg Thr Asp Ala Ile Ser Leu Phe Ile Thr Pro Gly
    610                 615                 620

Ile Thr Gln Ser Ala Val Tyr Ser Val Phe Ile Ser Thr Ala Val
625                 630                 635
```

<210> SEQ ID NO 71
<211> LENGTH: 38
<212> TYPE: PRT
<213> ORGANISM: Bacillus cereus

<400> SEQUENCE: 71

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly
35

<210> SEQ ID NO 72
<211> LENGTH: 163
<212> TYPE: PRT
<213> ORGANISM: Bacillus cereus

<400> SEQUENCE: 72

Met Ser Arg Lys Asp Arg Phe Asn Ser Pro Lys Ile Lys Ser Glu Ile
1 5 10 15

Ser Ile Ser Pro Asp Leu Val Gly Pro Thr Phe Pro Pro Ile Pro Ser
20 25 30

Phe Thr Leu Pro Thr Gly Ile Thr Gly Pro Thr Gly Asn Thr Gly Ala
35 40 45

Thr Gly Asp Thr Gly Pro Thr Gly Pro Thr Phe Asn Ile Asn Phe Arg
50 55 60

Ala Glu Lys Asn Gly Ala Gln Ser Phe Thr Pro Pro Ala Asp Ile Gln
65 70 75 80

Val Ser Tyr Gly Asn Ile Ile Phe Asn Asn Gly Gly Gly Tyr Ser Ser
85 90 95

Val Thr Asn Thr Phe Thr Ala Pro Ile Asn Gly Ile Tyr Leu Phe Ser
100 105 110

Ala Asn Ile Gly Phe Asn Pro Thr Leu Gly Thr Thr Ser Thr Leu Arg
115 120 125

Ile Thr Ile Arg Lys Asn Leu Val Ser Val Ala Ser Gln Thr Ile Asp
130 135 140

Ile Gln Phe Ser Ala Ala Glu Ser Gly Thr Leu Thr Val Gly Ser Ser
145 150 155 160

Asn Phe Phe

<210> SEQ ID NO 73
<211> LENGTH: 30
<212> TYPE: PRT
<213> ORGANISM: Bacillus cereus

<400> SEQUENCE: 73

Met Asp Glu Phe Leu Ser Ser Ala Ala Leu Asn Pro Gly Ser Val Gly
1 5 10 15

Pro Thr Leu Pro Pro Met Gln Pro Phe Gln Phe Ser Thr Gly
20 25 30

<210> SEQ ID NO 74
<211> LENGTH: 77
<212> TYPE: PRT
<213> ORGANISM: Bacillus cereus

<400> SEQUENCE: 74

-continued

```
Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Ser Thr Gly Pro Thr
            20                  25                  30

Gly Ser Thr Gly Ala Thr Gly Ala Thr Gly Asn Thr Glu Pro Tyr Trp
        35                  40                  45

His Thr Gly Pro Pro Gly Ile Val Leu Leu Thr Tyr Asp Phe Lys Ser
    50                  55                  60

Leu Ile Ile Ser Phe Ala Phe Gln Ile Leu Pro Ile Ser
65                  70                  75


<210> SEQ ID NO 75
<211> LENGTH: 48
<212> TYPE: PRT
<213> ORGANISM: Bacillus weihenstephanensis

<400> SEQUENCE: 75

Met Phe Leu Gly Gly Gly Tyr Met Glu Arg Lys Asn Lys Trp Tyr Gly
1               5                   10                  15

Leu Asn Ser Asn Val Asn Leu Ser Ala Ser Ser Phe Asp Pro Asn Leu
            20                  25                  30

Val Gly Pro Thr Leu Pro Pro Ile Ser Pro Ile Ser Val Pro Thr Gly
        35                  40                  45


<210> SEQ ID NO 76
<211> LENGTH: 247
<212> TYPE: PRT
<213> ORGANISM: Bacillus weihenstephanensis

<400> SEQUENCE: 76

Met Phe Leu Gly Gly Gly Tyr Met Glu Arg Lys Asn Lys Trp Tyr Gly
1               5                   10                  15

Leu Asn Ser Asn Val Asn Leu Ser Ala Ser Ser Phe Asp Pro Asn Leu
            20                  25                  30

Val Gly Pro Thr Leu Pro Pro Ile Ser Pro Ile Ser Val Pro Thr Gly
        35                  40                  45

Pro Thr Gly Glu Thr Gly Ile Thr Gly Pro Thr Gly Pro Thr Gly Pro
    50                  55                  60

Thr Gly Pro Thr Gly Val Thr Gly Ile Thr Gly Pro Thr Gly Pro Thr
65                  70                  75                  80

Gly Ala Thr Gly Ile Thr Gly Pro Thr Gly Pro Thr Gly Glu Thr Gly
                85                  90                  95

Ile Thr Gly Pro Thr Gly Pro Gly Pro Thr Val Ser Leu Lys Phe Leu
            100                 105                 110

Tyr Val Ala Asn Phe Asn Glu Asn Thr Val Glu Ile Tyr Asp Ile Phe
        115                 120                 125

Asn Pro Ile Phe Pro Val Arg Ile Gly Glu Phe Asn Gly Gly Asn Leu
    130                 135                 140

Ala Asn Pro Ala Gly Leu Ala Ile Thr Gly Thr Thr Leu Tyr Val Thr
145                 150                 155                 160

Asn Asn Gly Asp Asn Thr Val Glu Ile Tyr Asp Ile Leu Asn Pro Ile
                165                 170                 175

Ala Pro Val His Val Gly Glu Phe Asn Gly Gly Asn Leu Ser Glu Pro
            180                 185                 190

Asp Gly Leu Ala Ile Thr Gly Thr Thr Leu Tyr Val Ala Asn Phe Asn
        195                 200                 205
```

```
Asp Asn Thr Val Glu Ile Tyr Asp Ile Leu Asn Pro Ile Ala Pro Val
    210                 215                 220

Arg Val Gly Glu Phe Asn Ala Gly Asn Leu Ser Ser Pro Ala Gly Leu
225                 230                 235                 240

Ile Ile Phe Ser Leu Phe Gly
                245


<210> SEQ ID NO 77
<211> LENGTH: 30
<212> TYPE: PRT
<213> ORGANISM: Bacillus cereus

<400> SEQUENCE: 77

Met Asp Glu Leu Leu Ser Ser Thr Leu Ile Asn Pro Asp Leu Leu Gly
1               5                   10                  15

Pro Thr Leu Pro Ala Ile Pro Pro Phe Thr Leu Pro Thr Gly
            20                  25                  30


<210> SEQ ID NO 78
<211> LENGTH: 536
<212> TYPE: PRT
<213> ORGANISM: Bacillus cereus

<400> SEQUENCE: 78

Met Asp Glu Leu Leu Ser Ser Thr Leu Ile Asn Pro Asp Leu Leu Gly
1               5                   10                  15

Pro Thr Leu Pro Ala Ile Pro Pro Phe Thr Leu Pro Thr Gly Pro Thr
            20                  25                  30

Gly Ser Thr Gly Pro Thr Gly Pro Thr Gly Ser Thr Gly Pro Thr Gly
        35                  40                  45

Pro Thr Gly Ser Thr Gly Pro Thr Gly Pro Thr Gly Ser Thr Gly Leu
    50                  55                  60

Thr Gly Leu Thr Gly Pro Thr Gly Pro Thr Gly Pro Thr Gly Pro Thr
65                  70                  75                  80

Gly Pro Thr Gly Pro Thr Gly Ser Thr Gly Leu Thr Gly Pro Thr Gly
                85                  90                  95

Pro Asn Ser Asp Thr Gly Pro Thr Gly Pro Thr Gly Pro Thr Gly Pro
            100                 105                 110

Ser Asp Gly Pro Thr Gly Pro Thr Gly Ala Thr Gly Pro Thr Gly Pro
        115                 120                 125

Pro Asp Gly Pro Thr Gly Asp Thr Gly Pro Thr Gly Ser Thr Gly Pro
    130                 135                 140

Thr Gly Asp Thr Gly Pro Thr Gly Ser Thr Gly Pro Thr Gly Asp Thr
145                 150                 155                 160

Gly Pro Thr Gly Ser Thr Gly Pro Thr Gly Asp Thr Gly Pro Thr Gly
                165                 170                 175

Ser Thr Gly Pro Thr Gly Asp Thr Gly Pro Thr Gly Ser Thr Gly Pro
            180                 185                 190

Thr Gly Asp Thr Gly Pro Thr Gly Ser Thr Gly Pro Thr Gly Pro Gly
        195                 200                 205

Cys Ile Glu Pro Leu Pro Thr Phe Thr Gln Ile Val Tyr Val Asn Lys
    210                 215                 220

Ala Gly Asn Asp Ala Thr Ala Asp Gly Ser Glu Cys Ala Pro Phe Leu
225                 230                 235                 240

Thr Val Thr Ala Ala Met Ala Ser Ile Thr Asp Ala Ile Ala Pro Phe
                245                 250                 255
```

```
Pro Asp Pro Leu Asn Ile Thr Lys Arg Tyr Ala Ile Ser Ile Gly Pro
            260                 265                 270

Gly Asn Tyr Ile Glu Pro Leu Ile His Leu Lys Ala Asn Val Gln Leu
        275                 280                 285

Val Gly Thr Ser Thr Leu Leu Thr Arg Leu Gln Ile Pro Phe Asp Ile
    290                 295                 300

Asn Asp Pro Ser Trp Phe Asp Leu Asn Phe Ser Gln Asp Pro Arg Ser
305                 310                 315                 320

Gly Phe Val Asn Leu Thr Leu Leu Ser Gly Pro Leu Asp Phe Asn Phe
                325                 330                 335

Gln Thr Ala Gln Ser Val Ser Gly Lys Leu Phe Phe Val Ser Val Asn
            340                 345                 350

Ile Thr Pro Thr Pro Ile Phe Thr Ala Leu Ser Thr Ser Val Asn Gln
        355                 360                 365

Val Asn Ile Arg Asp Ser Met Leu Ser Gly Gly Tyr Thr Gln Asn Gly
    370                 375                 380

Ile Asn Met Ala Met Phe Ala Ser Phe Val Ser Ser Gly Asn Ile Thr
385                 390                 395                 400

Ile Asn Ser Gln Ala Thr Thr Asp Thr Gln Val Asn Leu Val Gly Gly
                405                 410                 415

Gly Ile Asn Gly Asn Val Ile Ile Asn Val Leu Pro Gly His Ile Pro
            420                 425                 430

Ile Asp Pro Leu Asn Leu Thr Ser Phe Ala Ile Thr Glu Asn Ile Phe
        435                 440                 445

Asn Pro Ser Pro Asn Ser Gly Asn Leu Phe Val Asn Gly Ala Asn Asn
    450                 455                 460

Val Ile Thr Arg Val Arg Ala Thr Val Asp Ser Leu Pro Ile Arg Ser
465                 470                 475                 480

Arg Ile Asn Leu Ile Gly Thr Ser Thr Ser Leu Ile Arg Val Asp Asp
                485                 490                 495

Ala Phe Asp Leu Ala Tyr Thr Pro Ile Asn Pro Ala Asn Trp Ala Pro
            500                 505                 510

Leu Pro Pro Thr Thr Val Gln Glu Ala Leu Asp Arg Ile Ala Ala Leu
        515                 520                 525

Met Ala Ile Thr Ile Gly Thr Pro
    530                 535


<210> SEQ ID NO 79
<211> LENGTH: 39
<212> TYPE: PRT
<213> ORGANISM: Bacillus cereus

<400> SEQUENCE: 79

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 80
<211> LENGTH: 1309
<212> TYPE: PRT
<213> ORGANISM: Bacillus cereus

<400> SEQUENCE: 80
```

```
Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125

Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
```

```
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Pro Thr Gly Ser Gln Gly Pro Thr Gly
    690                 695                 700

Ile Gln Gly Ile Gln Gly Glu Ile Gly Pro Thr Gly Pro Arg Arg Pro
705                 710                 715                 720

Glu Gly Cys Arg Gly Arg Lys Arg Ile Gln Gly Val Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845
```

```
Pro Thr Gly Ala Thr Gly Asp Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Val Thr Gly Leu Gln
    930                 935                 940

Gly Pro Gln Gly Ile Gln Gly Val Gln Gly Glu Ile Gly Pro Thr Gly
945                 950                 955                 960

Pro Gln Gly Ile Gln Gly Pro Gln Gly Ile Gln Gly Val Thr Gly Ala
                965                 970                 975

Thr Gly Ala Gln Gly Pro Gln Gly Ile Gln Gly Pro Gln Gly Asp Ile
            980                 985                 990

Gly Pro Thr Gly Ser Gln Gly Ile  Gln Gly Pro Gln Gly  Pro Gln Gly
        995                 1000                1005

Ile Gln  Gly Ala Thr Gly Ala  Thr Gly Ala Gln Gly  Pro Gln Gly
    1010                1015                1020

Ile Gln  Gly Pro Gln Gly Glu  Ile Gly Pro Thr Gly  Pro Gln Gly
    1025                1030                1035

Pro Gln  Gly Ile Gln Gly Pro  Gln Gly Ile Gln Gly  Pro Thr Gly
    1040                1045                1050

Ala Thr  Gly Ala Thr Gly Ala  Thr Gly Pro Gln Gly  Ile Gln Gly
    1055                1060                1065

Pro Gln  Gly Ile Gln Gly Pro  Gln Gly Ile Gln Gly  Pro Thr Gly
    1070                1075                1080

Val Thr  Gly Ala Thr Gly Ala  Thr Gly Pro Gln Gly  Ile Gln Gly
    1085                1090                1095

Pro Gln  Gly Ile Gln Gly Pro  Gln Gly Ile Gln Gly  Pro Thr Gly
    1100                1105                1110

Ala Thr  Gly Ala Thr Gly Ala  Thr Gly Pro Gln Gly  Ile Gln Gly
    1115                1120                1125

Pro Gln  Gly Ile Gln Gly Pro  Gln Gly Ile Gln Gly  Pro Thr Gly
    1130                1135                1140

Ala Thr  Gly Ala Thr Gly Ser  Gln Gly Pro Thr Gly  Asp Thr Gly
    1145                1150                1155

Pro Thr  Gly Ala Gly Ala Thr  Gly Ala Thr Gly Ala  Thr Gly Val
    1160                1165                1170

Ser Thr  Thr Ala Thr Tyr Ala  Phe Ala Asn Asn Thr  Ser Gly Thr
    1175                1180                1185

Ala Ile  Ser Val Leu Leu Gly  Gly Thr Asn Val Pro  Leu Pro Asn
    1190                1195                1200

Asn Gln  Asn Ile Gly Pro Gly  Ile Thr Val Ser Gly  Gly Asn Thr
    1205                1210                1215

Val Phe  Thr Val Ala Asn Ala  Gly Asn Tyr Tyr Ile  Ala Tyr Thr
    1220                1225                1230

Ile Asn  Leu Thr Ala Gly Leu  Leu Val Ser Ser Arg  Ile Thr Val
    1235                1240                1245
```

Asn Gly Ser Pro Leu Ala Gly Thr Ile Asn Ala Pro Thr Val Ala
1250 1255 1260

Thr Gly Ser Phe Ser Ala Thr Ile Ile Ala Asn Leu Pro Ala Gly
1265 1270 1275

Ala Ala Val Ser Leu Gln Leu Phe Gly Val Val Ala Val Ala Thr
1280 1285 1290

Leu Ser Thr Ala Thr Pro Gly Ala Thr Leu Thr Ile Ile Arg Leu
1295 1300 1305

Ser

<210> SEQ ID NO 81
<211> LENGTH: 44
<212> TYPE: PRT
<213> ORGANISM: Bacillus cereus

<400> SEQUENCE: 81

Met Val Lys Val Val Glu Gly Asn Ser Gly Lys Ser Lys Ile Lys Ser
1 5 10 15

Ser Leu Asn Ser Asn Phe Lys Leu Ser Ser Gly Leu Val Gly Pro Thr
20 25 30

Phe Pro Pro Val Pro Thr Gly Met Thr Gly Ile Thr
35 40

<210> SEQ ID NO 82
<211> LENGTH: 815
<212> TYPE: PRT
<213> ORGANISM: Bacillus cereus

<400> SEQUENCE: 82

Met Val Lys Val Val Glu Gly Asn Ser Gly Lys Ser Lys Ile Lys Ser
1 5 10 15

Ser Leu Asn Ser Asn Phe Lys Leu Ser Ser Gly Leu Val Gly Pro Thr
20 25 30

Phe Pro Pro Val Pro Thr Gly Met Thr Gly Ile Thr Gly Ser Thr Gly
35 40 45

Ala Thr Gly Asn Thr Gly Pro Thr Gly Glu Thr Gly Ala Thr Gly Ser
50 55 60

Thr Gly Val Thr Gly Asn Thr Gly Pro Thr Gly Glu Thr Gly Val Thr
65 70 75 80

Gly Ser Thr Gly Pro Thr Gly Glu Thr Gly Ser Thr Gly Asn Thr Gly
85 90 95

Ala Thr Gly Glu Thr Gly Pro Thr Gly Ser Thr Gly Ala Thr Gly Ser
100 105 110

Thr Gly Val Thr Gly Ser Thr Gly Pro Thr Gly Asn Thr Gly Pro Thr
115 120 125

Gly Glu Thr Gly Val Thr Gly Ser Thr Gly Pro Thr Gly Asn Thr Gly
130 135 140

Ala Thr Gly Glu Thr Gly Pro Thr Gly Ser Thr Gly Pro Thr Gly Glu
145 150 155 160

Thr Gly Val Thr Gly Ser Thr Gly Val Thr Gly Pro Thr Gly Ala Thr
165 170 175

Gly Asn Thr Gly Ala Thr Gly Ser Thr Gly Val Thr Gly Asn Thr Gly
180 185 190

Pro Thr Gly Glu Thr Gly Val Thr Gly Ser Thr Gly Pro Thr Gly Asn
195 200 205

Thr Gly Ala Thr Gly Asn Thr Gly Pro Thr Gly Glu Thr Gly Ser Thr

```
    210                 215                 220

Gly Val Thr Gly Ser Thr Gly Ala Thr Gly Ser Thr Gly Val Thr Gly
225                 230                 235                 240

Pro Thr Gly Val Thr Gly Pro Thr Gly Glu Thr Gly Val Thr Gly Ser
                245                 250                 255

Thr Gly Pro Thr Gly Asn Thr Gly Ala Thr Gly Asn Thr Gly Pro Thr
            260                 265                 270

Gly Glu Thr Gly Val Thr Gly Ser Thr Gly Pro Thr Gly Asn Thr Gly
        275                 280                 285

Ala Thr Gly Asn Thr Gly Ala Thr Gly Glu Thr Gly Ser Thr Gly Val
    290                 295                 300

Thr Gly Ser Thr Gly Val Thr Gly Ser Thr Gly Ala Thr Gly Ser Thr
305                 310                 315                 320

Gly Val Thr Gly Asn Thr Gly Ala Thr Gly Ser Thr Gly Ala Thr Gly
                325                 330                 335

Asn Thr Gly Pro Thr Gly Ala Thr Gly Ser Thr Gly Val Thr Gly Asn
            340                 345                 350

Thr Gly Pro Thr Gly Glu Thr Gly Pro Thr Gly Ser Thr Gly Pro Thr
        355                 360                 365

Gly Asn Thr Gly Ala Thr Gly Asn Thr Gly Ala Thr Gly Ala Thr Gly
    370                 375                 380

Ala Thr Gly Ala Thr Gly Ser Thr Gly Pro Thr Gly Asn Thr Gly Ala
385                 390                 395                 400

Thr Gly Asn Thr Gly Pro Thr Gly Val Thr Gly Ser Thr Gly Pro Thr
                405                 410                 415

Gly Ser Thr Gly Glu Thr Gly Glu Thr Gly Pro Thr Gly Glu Thr Gly
            420                 425                 430

Val Thr Gly Ser Thr Gly Pro Thr Gly Pro Thr Gly Ala Thr Gly Asn
        435                 440                 445

Thr Gly Pro Thr Gly Glu Thr Gly Ala Thr Gly Ser Thr Gly Glu Thr
    450                 455                 460

Gly Glu Thr Gly Pro Thr Gly Glu Thr Gly Val Thr Gly Ser Thr Gly
465                 470                 475                 480

Pro Thr Gly Asn Thr Gly Ala Thr Gly Asn Thr Gly Pro Thr Gly Glu
                485                 490                 495

Thr Gly Val Thr Gly Ser Thr Gly Pro Thr Gly Asn Thr Gly Ala Thr
            500                 505                 510

Gly Asn Thr Gly Pro Thr Gly Glu Thr Gly Glu Thr Gly Val Thr Gly
        515                 520                 525

Ser Thr Gly Val Thr Gly Asn Thr Gly Ala Thr Gly Ser Thr Gly Ala
    530                 535                 540

Thr Gly Asn Thr Gly Pro Thr Gly Glu Thr Gly Ala Thr Gly Pro Thr
545                 550                 555                 560

Gly Ala Thr Gly Val Thr Gly Ser Thr Gly Pro Thr Gly Asn Thr Gly
                565                 570                 575

Pro Thr Gly Glu Thr Gly Ser Thr Gly Ser Thr Gly Ala Thr Gly Ser
            580                 585                 590

Thr Gly Val Thr Gly Asn Thr Gly Ala Thr Gly Glu Thr Gly Pro Thr
        595                 600                 605

Gly Ser Thr Gly Ala Thr Gly Asn Thr Gly Ala Thr Gly Glu Thr Gly
    610                 615                 620

Pro Thr Gly Ala Thr Gly Val Thr Gly Pro Thr Gly Ser Thr Gly Val
625                 630                 635                 640
```

Thr Gly Ser Thr Gly Pro Thr Gly Ser Thr Gly Ala Thr Gly Ala Thr
645 650 655

Gly Ser Thr Gly Pro Thr Gly Ser Thr Gly Thr Thr Gly Asp Thr Gly
660 665 670

Pro Thr Gly Ala Thr Gly Val Ser Thr Thr Ala Thr Tyr Ala Phe Ala
675 680 685

Asn Asn Thr Ser Gly Ser Val Ile Ser Val Leu Leu Gly Gly Thr Asn
690 695 700

Ile Pro Leu Pro Asn Asn Gln Asn Ile Gly Pro Gly Ile Thr Val Ser
705 710 715 720

Gly Gly Asn Thr Val Phe Thr Val Ala Asn Ala Gly Asn Tyr Tyr Ile
725 730 735

Ala Tyr Thr Ile Asn Leu Thr Ala Gly Leu Leu Val Ser Ser Arg Ile
740 745 750

Thr Val Asn Gly Ser Pro Leu Ala Gly Thr Ile Asn Ser Pro Thr Val
755 760 765

Ala Thr Gly Ser Phe Asn Ala Thr Ile Ile Ala Ser Leu Pro Ala Gly
770 775 780

Ala Ala Val Ser Leu Gln Leu Phe Gly Val Val Ala Leu Ala Thr Leu
785 790 795 800

Ser Thr Ala Thr Pro Gly Ala Thr Leu Thr Ile Ile Arg Leu Ser
805 810 815

<210> SEQ ID NO 83
<211> LENGTH: 40
<212> TYPE: PRT
<213> ORGANISM: Bacillus anthracis

<400> SEQUENCE: 83

Met Glu Gly Asn Gly Gly Lys Ser Lys Ile Lys Ser Pro Leu Asn Ser
1 5 10 15

Asn Phe Lys Ile Leu Ser Asp Leu Val Gly Pro Thr Phe Pro Pro Val
20 25 30

Pro Thr Gly Met Thr Gly Ile Thr
35 40

<210> SEQ ID NO 84
<211> LENGTH: 469
<212> TYPE: PRT
<213> ORGANISM: Bacillus anthracis

<400> SEQUENCE: 84

Met Glu Gly Asn Gly Gly Lys Ser Lys Ile Lys Ser Pro Leu Asn Ser
1 5 10 15

Asn Phe Lys Ile Leu Ser Asp Leu Val Gly Pro Thr Phe Pro Pro Val
20 25 30

Pro Thr Gly Met Thr Gly Ile Thr Gly Ser Thr Gly Ala Thr Gly Asn
35 40 45

Thr Gly Pro Thr Gly Glu Thr Gly Ala Thr Gly Ser Ala Gly Ile Thr
50 55 60

Gly Ser Thr Gly Pro Thr Gly Asn Thr Gly Gly Thr Gly Ser Thr Gly
65 70 75 80

Ser Thr Gly Asn Thr Gly Ala Thr Gly Ser Thr Gly Val Thr Gly Ser
85 90 95

Thr Gly Val Thr Gly Ser Thr Gly Val Thr Gly Ser Thr Gly Val Thr
100 105 110

Gly Ser Thr Gly Pro Thr Gly Glu Thr Gly Gly Thr Gly Ser Thr Gly
115 120 125

Val Thr Gly Ser Thr Gly Ala Thr Gly Ser Thr Gly Val Thr Gly Ser
130 135 140

Thr Gly Val Thr Gly Glu Thr Gly Pro Thr Gly Ser Thr Gly Ala Thr
145 150 155 160

Gly Asn Thr Gly Pro Thr Gly Glu Thr Gly Gly Thr Gly Ser Thr Gly
165 170 175

Ala Thr Gly Ser Thr Gly Val Thr Gly Asn Thr Gly Pro Thr Gly Ser
180 185 190

Thr Gly Val Thr Gly Asn Thr Gly Ala Thr Gly Glu Thr Gly Pro Thr
195 200 205

Gly Asn Thr Gly Ala Thr Gly Asn Thr Gly Pro Thr Gly Glu Thr Gly
210 215 220

Val Thr Gly Ser Thr Gly Pro Thr Gly Glu Thr Gly Val Thr Gly Ser
225 230 235 240

Thr Gly Pro Thr Gly Asn Thr Gly Ala Thr Gly Glu Thr Gly Ala Thr
245 250 255

Gly Ser Thr Gly Val Thr Gly Asn Thr Gly Ser Thr Gly Glu Thr Gly
260 265 270

Pro Thr Gly Ser Thr Gly Pro Thr Gly Ser Thr Gly Ala Thr Gly Val
275 280 285

Thr Gly Asn Thr Gly Pro Thr Gly Ser Thr Gly Ala Thr Gly Ala Thr
290 295 300

Gly Ser Thr Gly Pro Thr Gly Ser Thr Gly Thr Thr Gly Asn Thr Gly
305 310 315 320

Val Thr Gly Asp Thr Gly Pro Thr Gly Ala Thr Gly Val Ser Thr Thr
325 330 335

Ala Thr Tyr Ala Phe Ala Asn Asn Thr Ser Gly Ser Val Ile Ser Val
340 345 350

Leu Leu Gly Gly Thr Asn Ile Pro Leu Pro Asn Asn Gln Asn Ile Gly
355 360 365

Pro Gly Ile Thr Val Ser Gly Gly Asn Thr Val Phe Thr Val Ala Asn
370 375 380

Ala Gly Asn Tyr Tyr Ile Ala Tyr Thr Ile Asn Leu Thr Ala Gly Leu
385 390 395 400

Leu Val Ser Ser Arg Ile Thr Val Asn Gly Ser Pro Leu Ala Gly Thr
405 410 415

Ile Asn Ser Pro Thr Val Ala Thr Gly Ser Phe Ser Ala Thr Ile Ile
420 425 430

Ala Ser Leu Pro Ala Gly Ala Ala Val Ser Leu Gln Leu Phe Gly Val
435 440 445

Val Ala Leu Ala Thr Leu Ser Thr Ala Thr Pro Gly Ala Thr Leu Thr
450 455 460

Ile Ile Arg Leu Ser
465

<210> SEQ ID NO 85
<211> LENGTH: 34
<212> TYPE: PRT
<213> ORGANISM: Bacillus thuringiensis

<400> SEQUENCE: 85

Met Lys Gln Asn Asp Lys Leu Trp Leu Asp Lys Gly Ile Ile Gly Pro

-continued

```
1               5                   10                  15

Glu Asn Ile Gly Pro Thr Phe Pro Val Leu Pro Pro Ile His Ile Pro
            20                  25                  30

Thr Gly


<210> SEQ ID NO 86
<211> LENGTH: 285
<212> TYPE: PRT
<213> ORGANISM: Bacillus thuringiensis

<400> SEQUENCE: 86

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Ala Thr Gly Pro Thr Gly Ile Thr Gly Ala Thr Gly Pro Ala
                85                  90                  95

Gly Ile Thr Gly Ala Thr Gly Pro Ala Gly Ile Thr Gly Ala Thr Gly
            100                 105                 110

Pro Ala Gly Ile Thr Gly Ala Thr Gly Pro Thr Gly Ile Thr Gly Ala
        115                 120                 125

Thr Gly Pro Thr Gly Ile Thr Gly Ala Thr Gly Pro Thr Gly Ile Thr
    130                 135                 140

Gly Ala Thr Gly Pro Ala Gly Ile Thr Gly Ala Thr Gly Pro Thr Gly
145                 150                 155                 160

Thr Thr Gly Val Thr Gly Ala Thr Gly Ile Thr Gly Val Thr Gly Ala
                165                 170                 175

Thr Gly Ile Thr Gly Ala Thr Gly Pro Thr Gly Thr Thr Gly Val Thr
            180                 185                 190

Gly Pro Thr Gly Val Ile Gly Pro Ile Thr Thr Thr Asn Leu Leu Phe
        195                 200                 205

Tyr Thr Phe Ala Asp Gly Glu Lys Leu Ile Tyr Thr Asp Ser Asp Gly
    210                 215                 220

Leu Ala Gln Tyr Gly Thr Thr His Ile Leu Ser Pro Asp Glu Val Ser
225                 230                 235                 240

Tyr Ile Asn Leu Phe Ile Asn Gly Ile Leu Gln Pro Gln Pro Leu Tyr
                245                 250                 255

Gln Val Ser Thr Gly Gln Leu Thr Leu Leu Asp Asn Gln Pro Pro Ser
            260                 265                 270

Gln Gly Ser Ser Ile Ile Leu Gln Phe Ile Ile Ile Asn
        275                 280                 285


<210> SEQ ID NO 87
<211> LENGTH: 34
<212> TYPE: PRT
<213> ORGANISM: Bacillus cereus

<400> SEQUENCE: 87

Met Asn Ser Asn Glu Lys Leu Ser Leu Asn Lys Gly Met Val Arg Pro
1               5                   10                  15
```

Glu Asn Ile Gly Pro Thr Phe Pro Val Leu Pro Pro Ile Tyr Ile Pro
20 25 30

Thr Gly

<210> SEQ ID NO 88
<211> LENGTH: 258
<212> TYPE: PRT
<213> ORGANISM: Bacillus cereus

<400> SEQUENCE: 88

Met Asn Ser Asn Glu Lys Leu Ser Leu Asn Lys Gly Met Val Arg Pro
1 5 10 15

Glu Asn Ile Gly Pro Thr Phe Pro Val Leu Pro Pro Ile Tyr Ile Pro
20 25 30

Thr Gly Ala Thr Gly Ala Thr Gly Ala Thr Gly Ala Thr Gly Ala Thr
35 40 45

Gly Ala Thr Gly Ala Thr Gly Ala Thr Gly Ala Thr Gly Ala Thr Gly
50 55 60

Ala Thr Gly Ala Thr Gly Ala Thr Gly Ala Thr Gly Val Thr Gly Ala
65 70 75 80

Thr Gly Ala Thr Gly Ala Thr Gly Val Thr Gly Ala Thr Gly Ala Thr
85 90 95

Gly Val Thr Gly Ala Thr Gly Val Thr Gly Ala Thr Gly Ala Thr Gly
100 105 110

Val Thr Gly Ala Thr Gly Val Thr Gly Ala Thr Gly Ala Thr Gly Ala
115 120 125

Thr Gly Val Thr Gly Ala Thr Gly Ala Thr Gly Ala Thr Gly Ala Thr
130 135 140

Gly Val Thr Gly Ala Thr Gly Val Thr Gly Val Thr Gly Val Thr Gly
145 150 155 160

Ala Thr Gly Ala Thr Gly Pro Thr Gly Val Ile Gly Pro Ile Thr Thr
165 170 175

Thr Asn Leu Leu Phe Tyr Thr Phe Ser Asp Gly Glu Lys Leu Ile Tyr
180 185 190

Thr Asp Ser Asp Gly Leu Ala Gln Tyr Gly Thr Thr His Ile Leu Ser
195 200 205

Pro Asp Glu Val Ser Tyr Ile Asn Leu Phe Ile Asn Gly Ile Leu Gln
210 215 220

Pro Gln Pro Leu Tyr Gln Val Ser Thr Gly Gln Leu Thr Leu Leu Asp
225 230 235 240

Asn Gln Pro Pro Ser Gln Gly Ser Ser Ile Ile Leu Gln Phe Ile Ile
245 250 255

Ile Asn

<210> SEQ ID NO 89
<211> LENGTH: 34
<212> TYPE: PRT
<213> ORGANISM: Bacillus cereus

<400> SEQUENCE: 89

Met Lys Arg Asn Asp Asn Leu Ser Leu Asn Lys Gly Met Ile Gly Pro
1 5 10 15

Glu Asn Ile Gly Pro Thr Phe Pro Ile Leu Pro Pro Ile Tyr Ile Pro
20 25 30

Thr Gly

<210> SEQ ID NO 90
<211> LENGTH: 279
<212> TYPE: PRT
<213> ORGANISM: Bacillus cereus

<400> SEQUENCE: 90

Met Lys Arg Asn Asp Asn Leu Ser Leu Asn Lys Gly Met Ile Gly Pro
1 5 10 15

Glu Asn Ile Gly Pro Thr Phe Pro Ile Leu Pro Pro Ile Tyr Ile Pro
20 25 30

Thr Gly Ala Thr Gly Pro Thr Gly Ile Thr Gly Pro Thr Gly Glu Thr
35 40 45

Gly Pro Thr Gly Ile Thr Gly Pro Thr Gly Val Thr Gly Pro Thr Gly
50 55 60

Ile Thr Gly Pro Thr Gly Ala Thr Gly Pro Thr Gly Ile Thr Gly Pro
65 70 75 80

Thr Gly Ala Thr Gly Pro Thr Gly Ile Thr Gly Pro Thr Gly Ala Thr
85 90 95

Gly Pro Thr Gly Glu Thr Gly Pro Thr Gly Ile Thr Gly Pro Thr Gly
100 105 110

Ala Thr Gly Pro Thr Gly Ile Thr Gly Pro Thr Gly Ala Thr Gly Pro
115 120 125

Thr Gly Glu Thr Gly Pro Thr Gly Glu Thr Gly Pro Thr Gly Val Thr
130 135 140

Gly Pro Thr Gly Ile Thr Gly Pro Thr Gly Ala Thr Gly Pro Thr Gly
145 150 155 160

Ile Thr Gly Pro Thr Gly Ala Thr Gly Pro Thr Gly Glu Thr Gly Pro
165 170 175

Thr Gly Ile Thr Gly Pro Thr Gly Ala Thr Gly Pro Thr Gly Gly Ile
180 185 190

Gly Pro Ile Thr Thr Thr Asn Leu Leu Tyr Tyr Thr Phe Ala Asp Gly
195 200 205

Glu Lys Leu Ile Tyr Thr Asp Ala Asp Gly Ile Pro Gln Tyr Gly Thr
210 215 220

Thr Asn Ile Leu Ser Pro Ser Glu Val Ser Tyr Ile Asn Leu Phe Val
225 230 235 240

Asn Gly Ile Leu Gln Pro Gln Pro Leu Tyr Glu Val Ser Thr Gly Lys
245 250 255

Leu Thr Leu Leu Asp Thr Gln Pro Pro Ser Gln Gly Ser Ser Ile Ile
260 265 270

Leu Gln Phe Ile Ile Ile Asn
275

<210> SEQ ID NO 91
<211> LENGTH: 99
<212> TYPE: PRT
<213> ORGANISM: Bacillus cereus

<400> SEQUENCE: 91

Met Asp Ser Phe Val Asp Val Gly Glu Ile Phe Thr Ile Phe Arg Lys
1 5 10 15

Leu Asn Met Glu Gly Ser Leu Gln Phe Lys Val His Asn Ser Met Gly
20 25 30

Lys Thr Tyr Tyr Ile Thr Ile Asn Glu Val Tyr Val Tyr Val Thr Val
35 40 45

```
Leu Leu Gln Tyr Ser Thr Leu Ile Gly Gly Ser Tyr Val Phe Asp Lys
    50                  55                  60

Asn Glu Ile Gln Lys Ile Asn Gly Ile Leu Gln Ala Asn Ala Leu Asn
65                  70                  75                  80

Pro Asn Leu Ile Gly Pro Thr Leu Pro Pro Ile Pro Pro Phe Thr Leu
                85                  90                  95

Pro Thr Gly


<210> SEQ ID NO 92
<211> LENGTH: 145
<212> TYPE: PRT
<213> ORGANISM: Bacillus cereus

<400> SEQUENCE: 92

Met Asp Ser Phe Val Asp Val Gly Glu Ile Phe Thr Ile Phe Arg Lys
1               5                   10                  15

Leu Asn Met Glu Gly Ser Leu Gln Phe Lys Val His Asn Ser Met Gly
            20                  25                  30

Lys Thr Tyr Tyr Ile Thr Ile Asn Glu Val Tyr Val Tyr Val Thr Val
        35                  40                  45

Leu Leu Gln Tyr Ser Thr Leu Ile Gly Gly Ser Tyr Val Phe Asp Lys
    50                  55                  60

Asn Glu Ile Gln Lys Ile Asn Gly Ile Leu Gln Ala Asn Ala Leu Asn
65                  70                  75                  80

Pro Asn Leu Ile Gly Pro Thr Leu Pro Pro Ile Pro Pro Phe Thr Leu
                85                  90                  95

Pro Thr Gly Pro Thr Gly Val Thr Gly Pro Thr Gly Gly Thr Gly Pro
            100                 105                 110

Thr Gly Val Thr Gly Pro Thr Gly Val Thr Gly Pro Thr Gly Val Thr
        115                 120                 125

Gly Val Thr Gly Pro Thr Gly Val Thr Gly Pro Thr Gly Val Thr Gly
    130                 135                 140

Pro
145


<210> SEQ ID NO 93
<211> LENGTH: 136
<212> TYPE: PRT
<213> ORGANISM: Bacillus weihenstephanensis

<400> SEQUENCE: 93

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Trp Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110
```

```
Ala Asn Ala Leu Asn Pro Asn Leu Ile Gly Pro Thr Leu Pro Pro Ile
        115                 120                 125

Pro Pro Phe Thr Leu Pro Thr Gly
    130                 135


<210> SEQ ID NO 94
<211> LENGTH: 142
<212> TYPE: PRT
<213> ORGANISM: Bacillus weihenstephanensis

<400> SEQUENCE: 94

Met Lys Phe Ser Lys Lys Ser Thr Val Asp Ser Ser Ile Val Gly Lys
1               5                   10                  15

Arg Val Val Ser Lys Val Asn Ile Leu Arg Phe Tyr Asp Ala Arg Ser
            20                  25                  30

Trp Gln Asp Lys Asp Val Asp Gly Phe Val Asp Val Gly Glu Leu Phe
        35                  40                  45

Thr Ile Phe Arg Lys Leu Asn Met Glu Gly Ser Val Gln Phe Lys Ala
    50                  55                  60

His Asn Ser Ile Gly Lys Thr Tyr Tyr Ile Thr Ile Asn Glu Val Tyr
65                  70                  75                  80

Val Phe Val Thr Val Leu Leu Gln Tyr Ser Thr Leu Ile Gly Gly Ser
                85                  90                  95

Tyr Val Phe Asp Lys Asn Glu Ile Gln Lys Ile Asn Gly Ile Leu Gln
            100                 105                 110

Ala Asn Ala Leu Asn Pro Asn Leu Ile Gly Pro Thr Leu Pro Pro Ile
        115                 120                 125

Pro Pro Phe Thr Leu Pro Thr Gly Pro Thr Gly Gly Thr Gly
    130                 135                 140


<210> SEQ ID NO 95
<211> LENGTH: 196
<212> TYPE: PRT
<213> ORGANISM: Bacillus anthracis

<400> SEQUENCE: 95

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60

Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160
```

```
Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly
        195


<210> SEQ ID NO 96
<211> LENGTH: 17
<212> TYPE: PRT
<213> ORGANISM: Bacillus anthracis

<400> SEQUENCE: 96

Met Ala Phe Asp Pro Asn Leu Val Gly Pro Thr Leu Pro Pro Ile Pro
1               5                   10                  15

Pro


<210> SEQ ID NO 97
<211> LENGTH: 17
<212> TYPE: PRT
<213> ORGANISM: Bacillus anthracis

<400> SEQUENCE: 97

Met Ala Leu Glu Pro Asn Leu Ile Gly Pro Thr Leu Pro Pro Ile Pro
1               5                   10                  15

Pro


<210> SEQ ID NO 98
<211> LENGTH: 17
<212> TYPE: PRT
<213> ORGANISM: Bacillus weihenstephanensis

<400> SEQUENCE: 98

Met Ala Leu Asn Pro Asn Leu Ile Gly Pro Thr Leu Pro Pro Ile Pro
1               5                   10                  15

Pro


<210> SEQ ID NO 99
<211> LENGTH: 17
<212> TYPE: PRT
<213> ORGANISM: Bacillus weihenstephanensis

<400> SEQUENCE: 99

Met Ala Leu Asp Pro Asn Ile Ile Gly Pro Thr Leu Pro Pro Ile Pro
1               5                   10                  15

Pro


<210> SEQ ID NO 100
<211> LENGTH: 17
<212> TYPE: PRT
<213> ORGANISM: Bacillus cereus

<400> SEQUENCE: 100

Met Ala Leu Glu Pro Asn Leu Ile Gly Pro Thr Leu Pro Ser Ile Pro
1               5                   10                  15

Pro


<210> SEQ ID NO 101
<211> LENGTH: 17
<212> TYPE: PRT
<213> ORGANISM: Bacillus weihenstephanensis
```

<400> SEQUENCE: 101

```
Met Ala Leu Asp Pro Asn Leu Ile Gly Pro Pro Leu Pro Pro Ile Thr
1               5                   10                  15

Pro
```

<210> SEQ ID NO 102
<211> LENGTH: 17
<212> TYPE: PRT
<213> ORGANISM: Bacillus weihenstephanensis

<400> SEQUENCE: 102

```
Met Ala Leu Asn Pro Gly Ser Ile Gly Pro Thr Leu Pro Pro Val Pro
1               5                   10                  15

Pro
```

<210> SEQ ID NO 103
<211> LENGTH: 17
<212> TYPE: PRT
<213> ORGANISM: Bacillus weihenstephanensis

<400> SEQUENCE: 103

```
Met Ala Leu Asn Pro Cys Ser Ile Gly Pro Thr Leu Pro Pro Met Gln
1               5                   10                  15

Pro
```

<210> SEQ ID NO 104
<211> LENGTH: 17
<212> TYPE: PRT
<213> ORGANISM: Bacillus mycoides

<400> SEQUENCE: 104

```
Met Ala Leu Asn Pro Gly Ser Ile Gly Pro Thr Leu Pro Pro Val Gln
1               5                   10                  15

Pro
```

<210> SEQ ID NO 105
<211> LENGTH: 17
<212> TYPE: PRT
<213> ORGANISM: Bacillus anthracis

<400> SEQUENCE: 105

```
Met Ala Leu Asn Pro Gly Ser Val Gly Pro Thr Leu Pro Pro Met Gln
1               5                   10                  15

Pro
```

<210> SEQ ID NO 106
<211> LENGTH: 17
<212> TYPE: PRT
<213> ORGANISM: Bacillus cereus

<400> SEQUENCE: 106

```
Met Ala Leu Asp Pro Asn Leu Ile Gly Pro Thr Phe Pro Pro Ile Pro
1               5                   10                  15

Ser
```

<210> SEQ ID NO 107
<211> LENGTH: 18
<212> TYPE: PRT
<213> ORGANISM: Bacillus thuringiensis

<400> SEQUENCE: 107

```
Met Ala Ala Ile Asn Pro Asn Leu Val Gly Pro Thr Leu Pro Pro Val
1               5                   10                  15

Pro Pro
```

<210> SEQ ID NO 108
<211> LENGTH: 799
<212> TYPE: PRT
<213> ORGANISM: Bacillus mycoides

<400> SEQUENCE: 108

```
Met Lys Arg Lys Thr Pro Phe Lys Val Phe Ser Ser Leu Ala Ile Thr
1               5                   10                  15

Thr Met Leu Gly Cys Thr Phe Ala Leu Gly Thr Ser Val Ala Tyr Ala
            20                  25                  30

Glu Thr Thr Ser Gln Ser Lys Gly Ser Ile Ser Thr Thr Pro Ile Asp
        35                  40                  45

Asn Asn Leu Ile Gln Glu Glu Arg Leu Ala Glu Ala Leu Lys Glu Arg
    50                  55                  60

Gly Thr Ile Asp Gln Ser Ala Ser Lys Glu Glu Thr Gln Lys Ala Val
65                  70                  75                  80

Glu Gln Tyr Ile Glu Lys Lys Lys Gly Asp Gln Pro Asn Lys Glu Ile
                85                  90                  95

Leu Pro Asp Asp Pro Ala Lys Glu Ala Ser Asp Phe Val Lys Lys Val
            100                 105                 110

Lys Glu Lys Lys Met Glu Glu Lys Glu Lys Val Lys Lys Ser Val Glu
        115                 120                 125

Asn Ala Ser Ser Glu Gln Thr Pro Ser Gln Asn Lys Lys Gln Leu Asn
    130                 135                 140

Gly Lys Val Pro Thr Ser Pro Ala Lys Gln Ala Pro Tyr Asn Gly Ala
145                 150                 155                 160

Val Arg Thr Asp Lys Val Leu Val Leu Leu Val Glu Phe Ser Asp Tyr
                165                 170                 175

Lys His Asn Asn Ile Glu Gln Ser Pro Gly Tyr Met Tyr Ala Asn Asp
            180                 185                 190

Phe Ser Arg Glu His Tyr Gln Lys Met Leu Phe Gly Asn Glu Pro Phe
        195                 200                 205

Thr Leu Phe Asp Gly Ser Lys Val Lys Thr Phe Lys Gln Tyr Tyr Glu
    210                 215                 220

Glu Gln Ser Gly Gly Ser Tyr Thr Thr Asp Gly Tyr Val Thr Glu Trp
225                 230                 235                 240

Leu Thr Val Pro Gly Lys Ala Ala Asp Tyr Gly Ala Asp Gly Lys Thr
                245                 250                 255

Gly His Asp Asn Lys Gly Pro Lys Gly Ala Arg Asp Leu Val Lys Glu
            260                 265                 270

Ala Leu Lys Ala Ala Ala Glu Lys Gly Leu Asp Leu Ser Gln Phe Asp
        275                 280                 285

Gln Phe Asp Arg Tyr Asp Thr Asn Gly Asp Gly Asn Gln Asn Glu Pro
    290                 295                 300

Asp Gly Val Ile Asp His Leu Met Val Ile His Ala Gly Val Gly Gln
305                 310                 315                 320

Glu Ala Gly Gly Gly Lys Leu Gly Asp Asp Ala Ile Trp Ser His Arg
                325                 330                 335

Ser Lys Leu Ala Gln Asp Pro Val Ala Ile Glu Gly Thr Lys Ser Lys
```

```
            340                 345                 350

Val Ser Tyr Trp Asp Gly Lys Val Ala Ala His Asp Tyr Thr Ile Glu
        355                 360                 365

Pro Glu Asp Gly Ala Val Gly Val Phe Ala His Glu Phe Gly His Asp
    370                 375                 380

Leu Gly Leu Pro Asp Glu Tyr Asp Thr Asn Tyr Thr Gly Ala Gly Ser
385                 390                 395                 400

Pro Val Glu Ala Trp Ser Leu Met Ser Gly Gly Ser Trp Thr Gly Arg
                405                 410                 415

Ile Ala Gly Thr Glu Pro Thr Ser Phe Ser Pro Gln Asn Lys Asp Phe
            420                 425                 430

Leu Gln Lys Asn Met Asp Gly Asn Trp Ala Lys Ile Val Glu Val Asp
        435                 440                 445

Tyr Asp Lys Ile Lys Arg Gly Val Gly Phe Pro Thr Tyr Ile Asp Gln
    450                 455                 460

Ser Val Thr Lys Ser Asn Arg Pro Gly Leu Val Arg Val Asn Leu Pro
465                 470                 475                 480

Glu Lys Ser Val Glu Thr Ile Lys Thr Gly Phe Gly Lys His Ala Tyr
                485                 490                 495

Tyr Ser Thr Arg Gly Asp Asp Met His Thr Thr Leu Glu Thr Pro Leu
            500                 505                 510

Phe Asp Leu Thr Lys Ala Ala Asn Ala Lys Phe Asp Tyr Lys Ala Asn
        515                 520                 525

Tyr Glu Leu Glu Ala Glu Cys Asp Phe Ile Glu Val His Ala Val Thr
    530                 535                 540

Glu Asp Gly Thr Lys Thr Leu Ile Asp Lys Leu Gly Asp Lys Val Val
545                 550                 555                 560

Lys Gly Asp Gln Asp Thr Thr Glu Gly Lys Trp Ile Asp Lys Ser Tyr
                565                 570                 575

Asp Leu Ser Gln Phe Lys Gly Lys Lys Val Lys Leu Gln Phe Asp Tyr
            580                 585                 590

Ile Thr Asp Pro Ala Leu Thr Tyr Lys Gly Phe Ala Met Asp Asn Val
        595                 600                 605

Asn Val Thr Val Asp Gly Lys Val Val Phe Ser Asp Asp Ala Glu Gly
    610                 615                 620

Gln Ala Lys Met Lys Leu Asn Gly Phe Val Val Ser Asp Gly Thr Glu
625                 630                 635                 640

Lys Lys Pro His Tyr Tyr Tyr Leu Glu Trp Arg Asn Tyr Ala Gly Ser
                645                 650                 655

Asp Glu Gly Leu Lys Val Gly Arg Gly Pro Val Tyr Asn Thr Gly Leu
            660                 665                 670

Val Val Trp Tyr Ala Asp Asp Ser Phe Lys Asp Asn Trp Val Gly Arg
        675                 680                 685

His Pro Gly Glu Gly Phe Leu Gly Val Val Asp Ser His Pro Glu Ala
    690                 695                 700

Val Val Gly Asn Leu Asn Gly Lys Pro Val Tyr Gly Asn Thr Gly Leu
705                 710                 715                 720

Gln Ile Ala Asp Ala Ala Phe Ser Leu Asp Gln Thr Pro Ala Trp Asn
                725                 730                 735

Val Asn Ser Phe Thr Arg Gly Gln Phe Asn Tyr Pro Gly Leu Pro Gly
            740                 745                 750

Val Ala Thr Phe Asp Asp Ser Lys Val Tyr Ser Asn Thr Gln Ile Pro
        755                 760                 765
```

```
Asp Ala Gly Arg Lys Val Pro Gln Leu Gly Leu Lys Phe Gln Val Val
    770                 775                 780

Gly Gln Ala Asp Asp Lys Ser Ala Gly Ala Ile Trp Ile Arg Arg
785                 790                 795


<210> SEQ ID NO 109
<211> LENGTH: 152
<212> TYPE: PRT
<213> ORGANISM: Bacillus anthracis

<400> SEQUENCE: 109

Met Ser Cys Asn Glu Asn Lys His His Gly Ser Ser His Cys Val Val
1               5                   10                  15

Asp Val Val Lys Phe Ile Asn Glu Leu Gln Asp Cys Ser Thr Thr Thr
            20                  25                  30

Cys Gly Ser Gly Cys Glu Ile Pro Phe Leu Gly Ala His Asn Thr Ala
        35                  40                  45

Ser Val Ala Asn Thr Arg Pro Phe Ile Leu Tyr Thr Lys Ala Gly Ala
    50                  55                  60

Pro Phe Glu Ala Phe Ala Pro Ser Ala Asn Leu Thr Ser Cys Arg Ser
65                  70                  75                  80

Pro Ile Phe Arg Val Glu Ser Val Asp Asp Asp Ser Cys Ala Val Leu
                85                  90                  95

Arg Val Leu Ser Val Val Leu Gly Asp Ser Ser Pro Val Pro Pro Thr
            100                 105                 110

Asp Asp Pro Ile Cys Thr Phe Leu Ala Val Pro Asn Ala Arg Leu Val
        115                 120                 125

Ser Thr Ser Thr Cys Ile Thr Val Asp Leu Ser Cys Phe Cys Ala Ile
    130                 135                 140

Gln Cys Leu Arg Asp Val Thr Ile
145                 150


<210> SEQ ID NO 110
<211> LENGTH: 167
<212> TYPE: PRT
<213> ORGANISM: Bacillus anthracis

<400> SEQUENCE: 110

Met Phe Ser Ser Asp Cys Glu Phe Thr Lys Ile Asp Cys Glu Ala Lys
1               5                   10                  15

Pro Ala Ser Thr Leu Pro Ala Phe Gly Phe Ala Phe Asn Ala Ser Ala
            20                  25                  30

Pro Gln Phe Ala Ser Leu Phe Thr Pro Leu Leu Leu Pro Ser Val Ser
        35                  40                  45

Pro Asn Pro Asn Ile Thr Val Pro Val Ile Asn Asp Thr Val Ser Val
    50                  55                  60

Gly Asp Gly Ile Arg Ile Leu Arg Ala Gly Ile Tyr Gln Ile Ser Tyr
65                  70                  75                  80

Thr Leu Thr Ile Ser Leu Asp Asn Ser Pro Val Ala Pro Glu Ala Gly
                85                  90                  95

Arg Phe Phe Leu Ser Leu Gly Thr Pro Ala Asn Ile Ile Pro Gly Ser
            100                 105                 110

Gly Thr Ala Val Arg Ser Asn Val Ile Gly Thr Gly Glu Val Asp Val
        115                 120                 125

Ser Ser Gly Val Ile Leu Ile Asn Leu Asn Pro Gly Asp Leu Ile Arg
    130                 135                 140
```

Ile Val Pro Val Glu Leu Ile Gly Thr Val Asp Ile Arg Ala Ala Ala
145                 150                 155                 160

Leu Thr Val Ala Gln Ile Ser
                165

<210> SEQ ID NO 111
<211> LENGTH: 156
<212> TYPE: PRT
<213> ORGANISM: Bacillus anthracis

<400> SEQUENCE: 111

Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155

<210> SEQ ID NO 112
<211> LENGTH: 182
<212> TYPE: PRT
<213> ORGANISM: Bacillus anthracis

<400> SEQUENCE: 112

Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145 150 155 160

Pro Asn Ser Met Arg Asp Ile Arg Leu Ser Ile Glu Glu Ile Lys Ser
165 170 175

Ile Asp Met Ala Gly Phe
180

<210> SEQ ID NO 113
<211> LENGTH: 174
<212> TYPE: PRT
<213> ORGANISM: Bacillus anthracis

<400> SEQUENCE: 113

Met Lys Glu Arg Ser Glu Asn Met Arg Ser Ser Ser Arg Lys Leu Thr
1 5 10 15

Asn Phe Asn Cys Arg Ala Gln Ala Pro Ser Thr Leu Pro Ala Leu Gly
20 25 30

Phe Ala Phe Asn Ala Thr Ser Pro Gln Phe Ala Thr Leu Phe Thr Pro
35 40 45

Leu Leu Leu Pro Ser Thr Gly Pro Asn Pro Asn Ile Thr Val Pro Val
50 55 60

Ile Asn Asp Thr Ile Ser Thr Gly Thr Gly Ile Arg Ile Gln Val Ala
65 70 75 80

Gly Ile Tyr Gln Ile Ser Tyr Thr Leu Thr Ile Ser Leu Asp Asn Val
85 90 95

Pro Val Thr Pro Glu Ala Ala Arg Phe Phe Leu Thr Leu Asn Ser Ser
100 105 110

Thr Asn Ile Ile Ala Gly Ser Gly Thr Ala Val Arg Ser Asn Ile Ile
115 120 125

Gly Thr Gly Glu Val Asp Val Ser Ser Gly Val Ile Leu Ile Asn Leu
130 135 140

Asn Pro Gly Asp Leu Ile Gln Ile Val Pro Val Glu Val Ile Gly Thr
145 150 155 160

Val Asp Ile Arg Ser Ala Ala Leu Thr Val Ala Gln Ile Arg
165 170

<210> SEQ ID NO 114
<211> LENGTH: 796
<212> TYPE: PRT
<213> ORGANISM: Bacillus thuringiensis

<400> SEQUENCE: 114

Met Ser Lys Lys Pro Phe Lys Val Leu Ser Ser Ile Ala Leu Thr Ala
1 5 10 15

Val Leu Gly Leu Ser Phe Gly Ala Gly Thr Gln Ser Ala Tyr Ala Glu
20 25 30

Thr Pro Val Asn Lys Thr Ala Thr Ser Pro Val Asp Asp His Leu Ile
35 40 45

Pro Glu Glu Arg Leu Ala Asp Ala Leu Lys Lys Arg Gly Val Ile Asp
50 55 60

Ser Lys Ala Ser Glu Thr Glu Thr Lys Lys Ala Val Glu Lys Tyr Val
65 70 75 80

Glu Asn Lys Lys Gly Glu Asn Pro Gly Lys Glu Ala Ala Asn Gly Asp
85 90 95

Gln Leu Thr Lys Asp Ala Ser Asp Phe Leu Lys Lys Val Lys Asp Ala
100 105 110

```
Lys Ala Asp Thr Lys Glu Lys Leu Asn Gln Pro Ala Thr Gly Thr Pro
        115                 120                 125

Ala Ala Thr Gly Pro Val Lys Gly Gly Leu Asn Gly Lys Val Pro Thr
    130                 135                 140

Ser Pro Ala Lys Gln Lys Asp Tyr Asn Gly Glu Val Arg Lys Asp Lys
145                 150                 155                 160

Val Leu Val Leu Leu Val Glu Tyr Ala Asp Phe Lys His Asn Asn Ile
                165                 170                 175

Asp Lys Glu Pro Gly Tyr Met Tyr Ser Asn Asp Phe Asn Lys Glu His
            180                 185                 190

Tyr Glu Lys Met Leu Phe Gly Asn Glu Pro Phe Thr Leu Asp Asp Gly
        195                 200                 205

Ser Lys Ile Glu Thr Phe Lys Gln Tyr Tyr Glu Glu Gln Ser Gly Gly
    210                 215                 220

Ser Tyr Thr Val Asp Gly Thr Val Thr Lys Trp Leu Thr Val Pro Gly
225                 230                 235                 240

Lys Ala Ala Asp Tyr Gly Ala Asp Ala Pro Gly Gly Gly His Asp Asn
                245                 250                 255

Lys Gly Pro Lys Gly Pro Arg Asp Leu Val Lys Asp Ala Leu Lys Ala
            260                 265                 270

Ala Val Asp Ser Gly Ile Asp Leu Ser Glu Phe Asp Gln Phe Asp Gln
        275                 280                 285

Tyr Asp Val Asn Gly Asp Gly Asn Lys Asn Gln Pro Asp Gly Leu Ile
    290                 295                 300

Asp His Leu Met Ile Ile His Ala Gly Val Gly Gln Glu Ala Gly Gly
305                 310                 315                 320

Gly Lys Leu Gly Asp Asp Ala Ile Trp Ser His Arg Trp Thr Val Gly
                325                 330                 335

Pro Lys Pro Phe Pro Ile Glu Gly Thr Gln Ala Lys Val Pro Tyr Trp
            340                 345                 350

Gly Gly Lys Met Ala Ala Phe Asp Tyr Thr Ile Glu Pro Glu Asp Gly
        355                 360                 365

Ala Val Gly Val Phe Ala His Glu Tyr Gly His Asp Leu Gly Leu Pro
    370                 375                 380

Asp Glu Tyr Asp Thr Gln Tyr Ser Gly Gln Gly Glu Pro Ile Glu Ala
385                 390                 395                 400

Trp Ser Ile Met Ser Gly Gly Ser Trp Ala Gly Lys Ile Ala Gly Thr
                405                 410                 415

Thr Pro Thr Ser Phe Ser Pro Gln Asn Lys Glu Phe Phe Gln Lys Thr
            420                 425                 430

Ile Gly Gly Asn Trp Ala Asn Ile Val Glu Val Asp Tyr Glu Lys Leu
        435                 440                 445

Asn Lys Gly Ile Gly Leu Ala Thr Tyr Leu Asp Gln Ser Val Thr Lys
    450                 455                 460

Ser Ala Arg Pro Gly Met Ile Arg Val Asn Leu Pro Asp Lys Asp Val
465                 470                 475                 480

Lys Thr Ile Glu Pro Ala Phe Gly Lys Gln Tyr Tyr Tyr Ser Thr Lys
                485                 490                 495

Gly Asp Asp Leu His Thr Lys Met Glu Thr Pro Leu Phe Asp Leu Thr
            500                 505                 510

Asn Ala Thr Ser Ala Lys Phe Asp Phe Lys Ser Leu Tyr Glu Ile Glu
        515                 520                 525
```

```
Ala Gly Tyr Asp Phe Leu Glu Val His Ala Val Thr Glu Asp Gly Lys
    530                 535                 540

Gln Thr Leu Ile Glu Arg Leu Gly Glu Lys Ala Asn Ser Gly Asn Ala
545                 550                 555                 560

Asp Ser Thr Asn Gly Lys Trp Ile Asp Lys Ser Tyr Asp Leu Ser Gln
                565                 570                 575

Phe Lys Gly Lys Lys Val Lys Leu Thr Phe Asp Tyr Ile Thr Asp Gly
            580                 585                 590

Gly Leu Ala Leu Asn Gly Phe Ala Leu Asp Asn Ala Ser Leu Thr Val
        595                 600                 605

Asp Gly Lys Val Val Phe Ser Asp Asp Ala Glu Gly Thr Pro Gln Leu
    610                 615                 620

Lys Leu Asp Gly Phe Val Val Ser Asn Gly Thr Glu Lys Lys Lys His
625                 630                 635                 640

Asn Tyr Tyr Val Glu Trp Arg Asn Tyr Ala Gly Ala Asp Asn Ala Leu
                645                 650                 655

Lys Phe Ala Arg Gly Pro Val Phe Asn Thr Gly Met Val Val Trp Tyr
            660                 665                 670

Ala Asp Ser Ala Tyr Thr Asp Asn Trp Val Gly Val His Pro Gly His
        675                 680                 685

Gly Phe Leu Gly Val Val Asp Ser His Pro Glu Ala Ile Val Gly Thr
    690                 695                 700

Leu Asn Gly Lys Pro Thr Val Lys Ser Ser Thr Arg Phe Gln Ile Ala
705                 710                 715                 720

Asp Ala Ala Phe Ser Phe Asp Lys Thr Pro Ala Trp Lys Val Val Ser
                725                 730                 735

Pro Thr Arg Gly Thr Phe Thr Tyr Asp Gly Leu Ala Gly Val Pro Lys
            740                 745                 750

Phe Asp Asp Ser Lys Thr Tyr Ile Asn Gln Gln Ile Pro Asp Ala Gly
        755                 760                 765

Arg Ile Leu Pro Lys Leu Gly Leu Lys Phe Glu Val Val Gly Gln Ala
    770                 775                 780

Asp Asp Asn Ser Ala Gly Ala Val Arg Leu Tyr Arg
785                 790                 795


<210> SEQ ID NO 115
<211> LENGTH: 430
<212> TYPE: PRT
<213> ORGANISM: Bacillus cereus

<400> SEQUENCE: 115

Met Lys His Asn Asp Cys Phe Asp His Asn Asn Cys Asn Pro Ile Val
1               5                   10                  15

Phe Ser Ala Asp Cys Cys Lys Asn Pro Gln Ser Val Pro Ile Thr Arg
            20                  25                  30

Glu Gln Leu Ser Gln Leu Ile Thr Leu Leu Asn Ser Leu Val Ser Ala
        35                  40                  45

Ile Ser Ala Phe Phe Ala Asn Pro Ser Asn Ala Asn Arg Leu Val Leu
    50                  55                  60

Leu Asp Leu Phe Asn Gln Phe Leu Ile Phe Leu Asn Ser Leu Leu Pro
65                  70                  75                  80

Ser Pro Glu Val Asn Phe Leu Lys Gln Leu Thr Gln Ser Ile Ile Val
                85                  90                  95

Leu Leu Gln Ser Pro Ala Pro Asn Leu Gly Gln Leu Ser Thr Leu Leu
            100                 105                 110
```

```
Gln Gln Phe Tyr Ser Ala Leu Ala Gln Phe Phe Phe Ala Leu Asp Leu
        115                 120                 125

Ile Pro Ile Ser Cys Asn Ser Asn Val Asp Ser Ala Thr Leu Gln Leu
    130                 135                 140

Leu Phe Asn Leu Leu Ile Gln Leu Ile Asn Ala Thr Pro Gly Ala Thr
145                 150                 155                 160

Gly Pro Thr Gly Pro Thr Gly Pro Thr Gly Pro Thr Gly Pro Ala Gly
                165                 170                 175

Thr Gly Ala Gly Pro Thr Gly Ala Thr Gly Ala Thr Gly Ala Thr Gly
            180                 185                 190

Pro Thr Gly Ala Thr Gly Pro Ala Gly Thr Gly Gly Ala Thr Gly Ala
        195                 200                 205

Thr Gly Ala Thr Gly Val Thr Gly Ala Thr Gly Ala Thr Gly Ala Thr
    210                 215                 220

Gly Pro Thr Gly Pro Thr Gly Ala Thr Gly Pro Thr Gly Ala Thr Gly
225                 230                 235                 240

Ala Thr Gly Ala Thr Gly Pro Thr Gly Ala Thr Gly Pro Thr Gly Ala
                245                 250                 255

Thr Gly Leu Thr Gly Ala Thr Gly Ala Ala Gly Gly Gly Ala Ile Ile
            260                 265                 270

Pro Phe Ala Ser Gly Thr Thr Pro Ser Ala Leu Val Asn Ala Leu Val
        275                 280                 285

Ala Asn Thr Gly Thr Leu Leu Gly Phe Gly Phe Ser Gln Pro Gly Val
    290                 295                 300

Ala Leu Thr Gly Gly Thr Ser Ile Thr Leu Ala Leu Gly Val Gly Asp
305                 310                 315                 320

Tyr Ala Phe Val Ala Pro Arg Ala Gly Thr Ile Thr Ser Leu Ala Gly
                325                 330                 335

Phe Phe Ser Ala Thr Ala Ala Leu Ala Pro Ile Ser Pro Val Gln Val
            340                 345                 350

Gln Ile Gln Ile Leu Thr Ala Pro Ala Ala Ser Asn Thr Phe Thr Val
        355                 360                 365

Gln Gly Ala Pro Leu Leu Leu Thr Pro Ala Phe Ala Ala Ile Ala Ile
    370                 375                 380

Gly Ser Thr Ala Ser Gly Ile Ile Ala Glu Ala Ile Pro Val Ala Ala
385                 390                 395                 400

Gly Asp Lys Ile Leu Leu Tyr Val Ser Leu Thr Ala Ala Ser Pro Ile
                405                 410                 415

Ala Ala Val Ala Gly Phe Val Ser Ala Gly Ile Asn Ile Val
            420                 425                 430
```

<210> SEQ ID NO 116
<211> LENGTH: 437
<212> TYPE: PRT
<213> ORGANISM: Bacillus cereus

<400> SEQUENCE: 116

```
Met Lys His Asn Asp Cys Phe Gly His Asn Asn Cys Asn Asn Pro Ile
1               5                   10                  15

Val Phe Thr Pro Asp Cys Cys Asn Asn Pro Gln Thr Val Pro Ile Thr
            20                  25                  30

Ser Glu Gln Leu Gly Arg Leu Ile Thr Leu Leu Asn Ser Leu Ile Ala
        35                  40                  45

Ala Ile Ala Ala Phe Phe Ala Asn Pro Ser Asp Ala Asn Arg Leu Ala
```

```
    50                  55                  60

Leu Leu Asn Leu Phe Thr Gln Leu Leu Asn Leu Leu Asn Glu Leu Ala
65                  70                  75                  80

Pro Ser Pro Glu Gly Asn Phe Leu Lys Gln Leu Ile Gln Ser Ile Ile
                85                  90                  95

Asn Leu Leu Gln Ser Pro Asn Pro Asn Leu Gly Gln Leu Leu Ser Leu
            100                 105                 110

Leu Gln Gln Phe Tyr Ser Ala Leu Ala Pro Phe Phe Phe Ser Leu Ile
        115                 120                 125

Leu Asp Pro Ala Ser Leu Gln Leu Leu Leu Asn Leu Leu Ala Gln Leu
    130                 135                 140

Ile Gly Val Thr Pro Gly Gly Gly Ala Thr Gly Pro Thr Gly Pro Thr
145                 150                 155                 160

Gly Pro Gly Gly Gly Ala Thr Gly Pro Thr Gly Pro Thr Gly Pro Gly
                165                 170                 175

Gly Gly Ala Thr Gly Pro Thr Gly Ala Thr Gly Pro Thr Gly Asp Thr
            180                 185                 190

Gly Leu Ala Gly Ala Thr Gly Ala Thr Gly Pro Thr Gly Asp Thr Gly
        195                 200                 205

Val Ala Gly Pro Ala Gly Pro Thr Gly Pro Thr Gly Asp Thr Gly Leu
    210                 215                 220

Ala Gly Ala Thr Gly Pro Thr Gly Pro Thr Gly Asp Thr Gly Leu Ala
225                 230                 235                 240

Gly Ala Thr Gly Pro Thr Gly Ala Thr Gly Leu Ala Gly Ala Thr Gly
                245                 250                 255

Pro Thr Gly Ala Thr Gly Leu Thr Gly Ala Thr Gly Ala Thr Gly Ala
            260                 265                 270

Ala Gly Gly Gly Ala Ile Ile Pro Phe Ala Ser Gly Thr Thr Pro Ala
        275                 280                 285

Ala Leu Val Asn Ala Leu Ile Ala Asn Thr Gly Thr Leu Leu Gly Phe
    290                 295                 300

Gly Phe Ser Gln Pro Gly Ile Gly Leu Ala Gly Gly Thr Ser Ile Thr
305                 310                 315                 320

Leu Ala Leu Gly Val Gly Asp Tyr Ala Phe Val Ala Pro Arg Asp Gly
                325                 330                 335

Val Ile Thr Ser Leu Ala Gly Phe Phe Ser Ala Thr Ala Ala Leu Ser
            340                 345                 350

Pro Leu Ser Pro Val Gln Val Gln Ile Gln Ile Leu Thr Ala Pro Ala
        355                 360                 365

Ala Ser Asn Thr Phe Thr Val Gln Gly Ala Pro Leu Leu Leu Thr Pro
    370                 375                 380

Ala Phe Ala Ala Ile Ala Ile Gly Ser Thr Ala Ser Gly Ile Ile Pro
385                 390                 395                 400

Glu Ala Ile Pro Val Val Ala Gly Asp Lys Ile Leu Leu Tyr Val Ser
                405                 410                 415

Leu Thr Ala Ala Ser Pro Ile Ala Ala Val Ala Gly Phe Val Ser Ala
            420                 425                 430

Gly Ile Asn Ile Val
        435
```

<210> SEQ ID NO 117
<211> LENGTH: 119
<212> TYPE: PRT
<213> ORGANISM: Bacillus anthracis

<400> SEQUENCE: 117

Met Leu Phe Thr Ser Trp Leu Leu Phe Phe Ile Phe Ala Leu Ala Ala
1 5 10 15

Phe Arg Leu Thr Arg Leu Ile Val Tyr Asp Lys Ile Thr Gly Phe Leu
20 25 30

Arg Arg Pro Phe Ile Asp Glu Leu Glu Ile Thr Glu Pro Asp Gly Ser
35 40 45

Val Ser Thr Phe Thr Lys Val Lys Gly Lys Gly Leu Arg Lys Trp Ile
50 55 60

Gly Glu Leu Leu Ser Cys Tyr Trp Cys Thr Gly Val Trp Val Ser Ala
65 70 75 80

Phe Leu Leu Val Leu Tyr Asn Trp Ile Pro Ile Val Ala Glu Pro Leu
85 90 95

Leu Ala Leu Leu Ala Ile Ala Gly Ala Ala Ala Ile Ile Glu Thr Ile
100 105 110

Thr Gly Tyr Phe Met Gly Glu
115

<210> SEQ ID NO 118
<211> LENGTH: 61
<212> TYPE: PRT
<213> ORGANISM: Bacillus anthracis

<400> SEQUENCE: 118

Met Phe Ala Val Ser Asn Asn Pro Arg Gln Asn Ser Tyr Asp Leu Gln
1 5 10 15

Gln Trp Tyr His Met Gln Gln Gln His Gln Ala Gln Gln Gln Ala Tyr
20 25 30

Gln Glu Gln Leu Gln Gln Gln Gly Phe Val Lys Lys Lys Gly Cys Asn
35 40 45

Cys Gly Lys Lys Lys Ser Thr Ile Lys His Tyr Glu Glu
50 55 60

<210> SEQ ID NO 119
<211> LENGTH: 481
<212> TYPE: PRT
<213> ORGANISM: Bacillus anthracis

<400> SEQUENCE: 119

Met Ser Arg Tyr Asp Asp Ser Gln Asn Lys Phe Ser Lys Pro Cys Phe
1 5 10 15

Pro Ser Ser Ala Gly Arg Ile Pro Asn Thr Pro Ser Ile Pro Val Thr
20 25 30

Lys Ala Gln Leu Arg Thr Phe Arg Ala Ile Ile Ile Asp Leu Thr Lys
35 40 45

Ile Ile Pro Lys Leu Phe Ala Asn Pro Ser Pro Gln Asn Ile Glu Asp
50 55 60

Leu Ile Asp Thr Leu Asn Leu Leu Ser Lys Phe Ile Cys Ser Leu Asp
65 70 75 80

Ala Ala Ser Ser Leu Lys Ala Gln Gly Leu Ala Ile Ile Lys Asn Leu
85 90 95

Ile Thr Ile Leu Lys Asn Pro Thr Phe Val Ala Ser Ala Val Phe Ile
100 105 110

Glu Leu Gln Asn Leu Ile Asn Tyr Leu Leu Ser Ile Thr Lys Leu Phe
115 120 125

Arg Ile Asp Pro Cys Thr Leu Gln Glu Leu Leu Lys Leu Ile Ala Ala
    130                 135                 140

Leu Gln Thr Ala Leu Val Asn Ser Ala Ser Phe Ile Gln Gly Pro Thr
145                 150                 155                 160

Gly Pro Thr Gly Pro Thr Gly Pro Thr Gly Pro Ala Gly Ala Thr Gly
                165                 170                 175

Ala Thr Gly Pro Gln Gly Val Gln Gly Pro Ala Gly Ala Thr Gly Ala
            180                 185                 190

Thr Gly Pro Gln Gly Val Gln Gly Pro Ala Gly Ala Thr Gly Ala Thr
        195                 200                 205

Gly Pro Gln Gly Ala Gln Gly Pro Ala Gly Ala Thr Gly Ala Thr Gly
    210                 215                 220

Pro Gln Gly Ala Gln Gly Pro Ala Gly Ala Thr Gly Ala Thr Gly Pro
225                 230                 235                 240

Gln Gly Ile Gln Gly Pro Ala Gly Ala Thr Gly Ala Thr Gly Pro Gln
                245                 250                 255

Gly Val Gln Gly Pro Thr Gly Ala Thr Gly Ile Gly Val Thr Gly Pro
            260                 265                 270

Thr Gly Pro Ser Gly Gly Pro Ala Gly Ala Thr Gly Pro Gln Gly Pro
        275                 280                 285

Gln Gly Asn Thr Gly Ala Thr Gly Pro Gln Gly Ile Gln Gly Pro Ala
    290                 295                 300

Gly Ala Thr Gly Ala Thr Gly Pro Gln Gly Ala Gln Gly Pro Ala Gly
305                 310                 315                 320

Ala Thr Gly Ala Thr Gly Pro Gln Gly Val Gln Gly Pro Thr Gly Ala
                325                 330                 335

Thr Gly Ile Gly Val Thr Gly Pro Thr Gly Pro Ser Gly Pro Ser Phe
            340                 345                 350

Pro Val Ala Thr Ile Val Val Thr Asn Asn Ile Gln Gln Thr Val Leu
        355                 360                 365

Gln Phe Asn Asn Phe Ile Phe Asn Thr Ala Ile Asn Val Asn Asn Ile
    370                 375                 380

Ile Phe Asn Gly Thr Asp Thr Val Thr Val Ile Asn Ala Gly Ile Tyr
385                 390                 395                 400

Val Ile Ser Val Ser Ile Ser Thr Thr Ala Pro Gly Cys Ala Pro Leu
                405                 410                 415

Gly Val Gly Ile Ser Ile Asn Gly Ala Val Ala Thr Asp Asn Phe Ser
            420                 425                 430

Ser Asn Leu Ile Gly Asp Ser Leu Ser Phe Thr Thr Ile Glu Thr Leu
        435                 440                 445

Thr Ala Gly Ala Asn Ile Ser Val Gln Ser Thr Leu Asn Glu Ile Thr
    450                 455                 460

Ile Pro Ala Thr Gly Asn Thr Asn Ile Arg Leu Thr Val Phe Arg Ile
465                 470                 475                 480

Ala

<210> SEQ ID NO 120
<211> LENGTH: 275
<212> TYPE: PRT
<213> ORGANISM: Bacillus thuringiensis

<400> SEQUENCE: 120

Met Lys Met Lys Arg Gly Ile Thr Thr Leu Leu Ser Val Ala Val Leu
1               5                   10                  15

```
Ser Thr Ser Leu Val Ala Cys Ser Gly Ile Thr Glu Lys Thr Val Ala
            20                  25                  30

Lys Glu Glu Lys Val Lys Leu Thr Asp Gln Gln Leu Met Ala Asp Leu
        35                  40                  45

Trp Tyr Gln Thr Ala Gly Glu Met Lys Ala Leu Tyr Tyr Gln Gly Tyr
    50                  55                  60

Asn Ile Gly Gln Leu Lys Leu Asp Ala Val Leu Ala Lys Gly Thr Glu
65                  70                  75                  80

Lys Lys Pro Ala Ile Val Leu Asp Leu Asp Glu Thr Val Leu Asp Asn
                85                  90                  95

Ser Pro His Gln Ala Met Ser Val Lys Thr Gly Lys Gly Tyr Pro Tyr
            100                 105                 110

Lys Trp Asp Asp Trp Ile Asn Lys Ala Glu Ala Glu Ala Leu Pro Gly
        115                 120                 125

Ala Ile Asp Phe Leu Lys Tyr Thr Glu Ser Lys Gly Val Asp Ile Tyr
    130                 135                 140

Tyr Ile Ser Asn Arg Lys Thr Asn Gln Leu Asp Ala Thr Ile Lys Asn
145                 150                 155                 160

Leu Glu Arg Val Gly Ala Pro Gln Ala Thr Lys Glu His Ile Leu Leu
                165                 170                 175

Gln Asp Pro Lys Glu Lys Gly Lys Glu Lys Arg Arg Glu Leu Val Ser
            180                 185                 190

Gln Thr His Asp Ile Val Leu Phe Phe Gly Asp Asn Leu Ser Asp Phe
        195                 200                 205

Thr Gly Phe Asp Gly Lys Ser Val Lys Asp Arg Asn Gln Ala Val Ala
    210                 215                 220

Asp Ser Lys Ala Gln Phe Gly Glu Lys Phe Ile Ile Phe Pro Asn Pro
225                 230                 235                 240

Met Tyr Gly Asp Trp Glu Gly Ala Leu Tyr Asp Tyr Asp Phe Lys Lys
                245                 250                 255

Ser Asp Ala Glu Lys Asp Lys Ile Arg Arg Asp Asn Leu Lys Ser Phe
            260                 265                 270

Asp Thr Lys
        275


<210> SEQ ID NO 121
<211> LENGTH: 795
<212> TYPE: PRT
<213> ORGANISM: Bacillus thuringiensis

<400> SEQUENCE: 121

Met Lys Lys Lys Lys Lys Leu Lys Pro Leu Ala Val Leu Thr Thr Ala
1               5                   10                  15

Ala Val Leu Ser Ser Thr Phe Ala Phe Gly Gly His Ala Ala Tyr Ala
            20                  25                  30

Glu Thr Pro Thr Ser Ser Leu Pro Ile Asp Glu His Leu Ile Pro Glu
        35                  40                  45

Glu Arg Leu Ala Glu Ala Leu Lys Gln Arg Gly Val Ile Asp Gln Ser
    50                  55                  60

Ala Ser Gln Ala Glu Thr Ser Lys Ala Val Glu Lys Tyr Val Glu Lys
65                  70                  75                  80

Lys Lys Gly Glu Asn Pro Gly Lys Glu Ile Leu Thr Gly Asp Ser Leu
                85                  90                  95

Thr Gln Glu Ala Ser Asp Phe Met Lys Lys Val Lys Asp Ala Lys Met
            100                 105                 110
```

```
Arg Glu Asn Glu Gln Ala Gln Gln Pro Glu Val Gly Pro Val Ala Gly
        115                 120                 125

Gln Gly Ala Ala Leu Asn Pro Gly Lys Leu Asn Gly Lys Val Pro Thr
    130                 135                 140

Thr Ser Ala Lys Gln Glu Glu Tyr Asn Gly Ala Val Arg Lys Asp Lys
145                 150                 155                 160

Val Leu Val Leu Leu Val Glu Phe Ser Asp Phe Lys His Asn Asn Ile
                165                 170                 175

Asp Gln Glu Pro Gly Tyr Met Tyr Ser Lys Asp Phe Asn Arg Glu His
            180                 185                 190

Tyr Gln Lys Met Leu Phe Gly Asp Glu Pro Phe Thr Leu Phe Asp Gly
        195                 200                 205

Ser Lys Ile Asn Thr Phe Lys Gln Tyr Tyr Glu Glu Gln Ser Gly Gly
    210                 215                 220

Ser Tyr Thr Val Asp Gly Thr Val Thr Glu Trp Leu Thr Val Pro Gly
225                 230                 235                 240

Lys Ala Ser Asp Tyr Gly Ala Asp Ala Gly Thr Gly His Asp Asn Lys
                245                 250                 255

Gly Pro Leu Gly Pro Lys Asp Leu Val Lys Glu Ala Leu Lys Ala Ala
            260                 265                 270

Val Ala Lys Gly Ile Asn Leu Ala Asp Phe Asp Gln Tyr Asp Gln Tyr
        275                 280                 285

Asp Gln Asn Gly Asn Gly Asn Lys Asn Glu Pro Asp Gly Ile Ile Asp
    290                 295                 300

His Leu Met Val Val His Ala Gly Val Gly Gln Glu Ala Gly Gly Gly
305                 310                 315                 320

Lys Leu Lys Asp Asp Ala Ile Trp Ser His Arg Ser Lys Leu Gly Ser
                325                 330                 335

Lys Pro Tyr Ala Ile Asp Gly Thr Lys Ser Ser Val Ser Asn Trp Gly
            340                 345                 350

Gly Lys Met Ala Ala Tyr Asp Tyr Thr Ile Glu Pro Glu Asp Gly Ala
        355                 360                 365

Val Gly Val Phe Ala His Glu Tyr Gly His Asp Leu Gly Leu Pro Asp
    370                 375                 380

Glu Tyr Asp Thr Lys Tyr Ser Gly Gln Gly Glu Pro Val Glu Ser Trp
385                 390                 395                 400

Ser Ile Met Ser Gly Gly Ser Trp Ala Gly Lys Ile Ala Gly Thr Glu
                405                 410                 415

Pro Thr Ser Phe Ser Pro Gln Asn Lys Glu Phe Phe Gln Lys Asn Met
            420                 425                 430

Lys Gly Asn Trp Ala Asn Ile Leu Glu Val Asp Tyr Asp Lys Leu Ser
        435                 440                 445

Lys Gly Ile Gly Val Ala Thr Tyr Val Asp Gln Ser Thr Thr Lys Ser
    450                 455                 460

Lys Arg Pro Gly Ile Val Arg Val Asn Leu Pro Asp Lys Asp Ile Lys
465                 470                 475                 480

Asn Ile Glu Ser Ala Phe Gly Lys Lys Phe Tyr Tyr Ser Thr Lys Gly
                485                 490                 495

Asn Asp Ile His Thr Thr Leu Glu Thr Pro Val Phe Asp Leu Thr Asn
            500                 505                 510

Ala Lys Asp Ala Lys Phe Asp Tyr Lys Ala Phe Tyr Glu Leu Glu Ala
        515                 520                 525
```

```
Lys Tyr Asp Phe Leu Asp Val Tyr Ala Ile Ala Glu Asp Gly Thr Lys
    530                 535                 540

Thr Arg Ile Asp Arg Met Gly Glu Lys Asp Ile Lys Gly Gly Ala Asp
545                 550                 555                 560

Thr Thr Asp Gly Lys Trp Val Asp Lys Ser Tyr Asp Leu Ser Gln Phe
                565                 570                 575

Lys Gly Lys Lys Val Lys Leu Gln Phe Glu Tyr Leu Thr Asp Ile Ala
            580                 585                 590

Val Ala Tyr Lys Gly Phe Ala Leu Asp Asn Ala Ala Leu Thr Val Asp
        595                 600                 605

Gly Lys Val Val Phe Ser Asp Asp Ala Glu Gly Gln Pro Ala Met Thr
    610                 615                 620

Leu Lys Gly Phe Thr Val Ser Asn Gly Phe Glu Gln Lys Lys His Asn
625                 630                 635                 640

Tyr Tyr Val Glu Trp Arg Asn Tyr Ala Gly Ser Asp Thr Ala Leu Gln
                645                 650                 655

Tyr Ala Arg Gly Pro Val Phe Asn Thr Gly Met Val Val Trp Tyr Ala
            660                 665                 670

Asp Gln Ser Phe Thr Asp Asn Trp Val Gly Val His Pro Gly Glu Gly
        675                 680                 685

Phe Leu Gly Val Val Asp Ser His Pro Glu Ala Ile Val Gly Thr Leu
    690                 695                 700

Asn Gly Gln Pro Thr Val Lys Ser Ser Thr Arg Tyr Gln Ile Ala Asp
705                 710                 715                 720

Ala Ala Phe Ser Phe Asp Gln Thr Pro Ala Trp Lys Val Asn Ser Pro
                725                 730                 735

Thr Arg Gly Ile Phe Asp Tyr Lys Gly Leu Pro Gly Val Ala Lys Phe
            740                 745                 750

Asp Asp Ser Lys Gln Tyr Ile Asn Ser Val Ile Pro Asp Ala Gly Arg
        755                 760                 765

Lys Leu Pro Lys Leu Gly Leu Lys Phe Glu Val Val Gly Gln Ala Glu
    770                 775                 780

Asp Lys Ser Ala Gly Ala Val Trp Leu His Arg
785                 790                 795
```

<210> SEQ ID NO 122
<211> LENGTH: 798
<212> TYPE: PRT
<213> ORGANISM: Bacillus mycoides

<400> SEQUENCE: 122

```
Lys Arg Lys Thr Pro Phe Lys Val Phe Ser Ser Leu Ala Ile Thr Thr
1               5                   10                  15

Met Leu Gly Cys Thr Phe Ala Leu Gly Thr Ser Val Ala Tyr Ala Glu
            20                  25                  30

Thr Thr Ser Gln Ser Lys Gly Ser Ile Ser Thr Thr Pro Ile Asp Asn
        35                  40                  45

Asn Leu Ile Gln Glu Glu Arg Leu Ala Glu Ala Leu Lys Glu Arg Gly
    50                  55                  60

Thr Ile Asp Gln Ser Ala Ser Lys Glu Glu Thr Gln Lys Ala Val Glu
65                  70                  75                  80

Gln Tyr Ile Glu Lys Lys Lys Gly Asp Gln Pro Asn Lys Glu Ile Leu
                85                  90                  95

Pro Asp Asp Pro Ala Lys Glu Ala Ser Asp Phe Val Lys Lys Val Lys
            100                 105                 110
```

```
Glu Lys Lys Met Glu Glu Lys Glu Lys Val Lys Lys Ser Val Glu Asn
        115                 120                 125

Ala Ser Ser Glu Gln Thr Pro Ser Gln Asn Lys Lys Gln Leu Asn Gly
    130                 135                 140

Lys Val Pro Thr Ser Pro Ala Lys Gln Ala Pro Tyr Asn Gly Ala Val
145                 150                 155                 160

Arg Thr Asp Lys Val Leu Val Leu Leu Val Glu Phe Ser Asp Tyr Lys
                165                 170                 175

His Asn Asn Ile Glu Gln Ser Pro Gly Tyr Met Tyr Ala Asn Asp Phe
            180                 185                 190

Ser Arg Glu His Tyr Gln Lys Met Leu Phe Gly Asn Glu Pro Phe Thr
        195                 200                 205

Leu Phe Asp Gly Ser Lys Val Lys Thr Phe Lys Gln Tyr Tyr Glu Glu
    210                 215                 220

Gln Ser Gly Gly Ser Tyr Thr Thr Asp Gly Tyr Val Thr Glu Trp Leu
225                 230                 235                 240

Thr Val Pro Gly Lys Ala Ala Asp Tyr Gly Ala Asp Gly Lys Thr Gly
                245                 250                 255

His Asp Asn Lys Gly Pro Lys Gly Ala Arg Asp Leu Val Lys Glu Ala
            260                 265                 270

Leu Lys Ala Ala Ala Glu Lys Gly Leu Asp Leu Ser Gln Phe Asp Gln
        275                 280                 285

Phe Asp Arg Tyr Asp Thr Asn Gly Asp Gly Asn Gln Asn Glu Pro Asp
    290                 295                 300

Gly Val Ile Asp His Leu Met Val Ile His Ala Gly Val Gly Gln Glu
305                 310                 315                 320

Ala Gly Gly Gly Lys Leu Gly Asp Asp Ala Ile Trp Ser His Arg Ser
                325                 330                 335

Lys Leu Ala Gln Asp Pro Val Ala Ile Glu Gly Thr Lys Ser Lys Val
            340                 345                 350

Ser Tyr Trp Asp Gly Lys Val Ala Ala His Asp Tyr Thr Ile Glu Pro
        355                 360                 365

Glu Asp Gly Ala Val Gly Val Phe Ala His Glu Phe Gly His Asp Leu
    370                 375                 380

Gly Leu Pro Asp Glu Tyr Asp Thr Asn Tyr Thr Gly Ala Gly Ser Pro
385                 390                 395                 400

Val Glu Ala Trp Ser Leu Met Ser Gly Gly Ser Trp Thr Gly Arg Ile
                405                 410                 415

Ala Gly Thr Glu Pro Thr Ser Phe Ser Pro Gln Asn Lys Asp Phe Leu
            420                 425                 430

Gln Lys Asn Met Asp Gly Asn Trp Ala Lys Ile Val Glu Val Asp Tyr
        435                 440                 445

Asp Lys Ile Lys Arg Gly Val Gly Phe Pro Thr Tyr Ile Asp Gln Ser
    450                 455                 460

Val Thr Lys Ser Asn Arg Pro Gly Leu Val Arg Val Asn Leu Pro Glu
465                 470                 475                 480

Lys Ser Val Glu Thr Ile Lys Thr Gly Phe Gly Lys His Ala Tyr Tyr
                485                 490                 495

Ser Thr Arg Gly Asp Asp Met His Thr Thr Leu Glu Thr Pro Leu Phe
            500                 505                 510

Asp Leu Thr Lys Ala Ala Asn Ala Lys Phe Asp Tyr Lys Ala Asn Tyr
        515                 520                 525
```

Glu Leu Glu Ala Glu Cys Asp Phe Ile Glu Val His Ala Val Thr Glu
    530                 535                 540

Asp Gly Thr Lys Thr Leu Ile Asp Lys Leu Gly Asp Lys Val Val Lys
545                 550                 555                 560

Gly Asp Gln Asp Thr Thr Glu Gly Lys Trp Ile Asp Lys Ser Tyr Asp
                565                 570                 575

Leu Ser Gln Phe Lys Gly Lys Lys Val Lys Leu Gln Phe Asp Tyr Ile
            580                 585                 590

Thr Asp Pro Ala Leu Thr Tyr Lys Gly Phe Ala Met Asp Asn Val Asn
        595                 600                 605

Val Thr Val Asp Gly Lys Val Val Phe Ser Asp Asp Ala Glu Gly Gln
    610                 615                 620

Ala Lys Met Lys Leu Asn Gly Phe Val Val Ser Asp Gly Thr Glu Lys
625                 630                 635                 640

Lys Pro His Tyr Tyr Tyr Leu Glu Trp Arg Asn Tyr Ala Gly Ser Asp
                645                 650                 655

Glu Gly Leu Lys Val Gly Arg Gly Pro Val Tyr Asn Thr Gly Leu Val
            660                 665                 670

Val Trp Tyr Ala Asp Asp Ser Phe Lys Asp Asn Trp Val Gly Arg His
        675                 680                 685

Pro Gly Glu Gly Phe Leu Gly Val Val Asp Ser His Pro Glu Ala Val
    690                 695                 700

Val Gly Asn Leu Asn Gly Lys Pro Val Tyr Gly Asn Thr Gly Leu Gln
705                 710                 715                 720

Ile Ala Asp Ala Ala Phe Ser Leu Asp Gln Thr Pro Ala Trp Asn Val
                725                 730                 735

Asn Ser Phe Thr Arg Gly Gln Phe Asn Tyr Pro Gly Leu Pro Gly Val
            740                 745                 750

Ala Thr Phe Asp Asp Ser Lys Val Tyr Ser Asn Thr Gln Ile Pro Asp
        755                 760                 765

Ala Gly Arg Lys Val Pro Gln Leu Gly Leu Lys Phe Gln Val Val Gly
    770                 775                 780

Gln Ala Asp Asp Lys Ser Ala Gly Ala Ile Trp Ile Arg Arg
785                 790                 795

<210> SEQ ID NO 123
<211> LENGTH: 300
<212> TYPE: DNA
<213> ORGANISM: Bacillus cereus

<400> SEQUENCE: 123
taactcaatc ttaagagaaa ttgaggagcg cgcaccactt cgtcgtacaa caacgcaaga 60
agaagttggg gatacagcag tattcttatt cagtgattta gcacgcggcg taacaggaga 120
aaacattcac gttgattcag ggtatcatat cttaggataa atataatatt aattttaaag 180
gacaatctct acatgttgag attgtccttt ttatttgttc ttagaaagaa cgatttttaa 240
cgaaagttct taccacgtta tgaatataag tataatagta cacgatttat tcagctacgt 300

<210> SEQ ID NO 124
<211> LENGTH: 172
<212> TYPE: DNA
<213> ORGANISM: Bacillus cereus

<400> SEQUENCE: 124
acgttgattc agggtatcat atcttaggat aaatataata ttaattttaa aggacaatct 60
ctacatgttg agattgtcct ttttatttgt tcttagaaag aacgattttt aacgaaagtt 120
cttaccacgt tatgaatata agtataatag tacacgattt attcagctac gt 172

<210> SEQ ID NO 125
<211> LENGTH: 291
<212> TYPE: DNA
<213> ORGANISM: Bacillus cereus

<400> SEQUENCE: 125
cataaaaatc tacttttctt gtcaaagagt atgcttatat gcgtgctctt tttatttggt 60
tttctttcat ttctaaataa cattttcaac tctattcata ctattctttc aactttaggt 120
tacaaactat ttctgtaagc gtagtgtttc ttttgtacta taggcagtta gttttatcca 180
taacagtaca cctctgcact attcactata aattttcata tattatattg tgcttgtcca 240
aaacatgtgg ttattactca cgcgatctaa atgaaagaaa ggagtgaaaa t 291

<210> SEQ ID NO 126
<211> LENGTH: 94
<212> TYPE: DNA
<213> ORGANISM: Bacillus cereus

<400> SEQUENCE: 126
actattcact ataaattttc atatattata ttgtgcttgt ccaaaacatg tggttattac 60
tcacgcgatc taaatgaaag aaaggagtga aaat 94

<210> SEQ ID NO 127
<211> LENGTH: 300
<212> TYPE: DNA
<213> ORGANISM: Bacillus thuringiensis

<400> SEQUENCE: 127
aatacatgat aatgaaatcc gattttgtgt tttatatagt gaattatcaa atattgtgta 60
gatgaaacaa agataaaatc cccattaaac tccctctatg gaaattataa attgttcgat 120
aaaaactttc aatattttca gaaaacattg ttgaattgtg atatattcgt atgctaacta 180
tgaaattttt acaaatatat taaaaacatt acataatatg actaaatatt gaaaaaatat 240
tgaattttta ataaaattta atttgtaata catattattt attaggggag gaaataaggg 300

<210> SEQ ID NO 128
<211> LENGTH: 48
<212> TYPE: DNA
<213> ORGANISM: Bacillus thuringiensis

<400> SEQUENCE: 128
aaaatttaat ttgtaataca tattatttat taggggagga aataaggg 48

<210> SEQ ID NO 129
<211> LENGTH: 300
<212> TYPE: DNA
<213> ORGANISM: Bacillus mycoides

<400> SEQUENCE: 129
aattgtgcat attgtctttt aaattttcta tctaagttat ttaatatata ataaataact 60 ctttttgtg agttttttg atacgaggta aataatcagt acagggtctg accagaggac 120
tggagggcat gattctataa gggaatattt actattccat gattatagaa ctatgtcttt 180
tttattgtat atagaagggg ggataggtct atattataga acttatatat attgtgcatt 240
ccatattatc aattatctaa attttaagtc ttgttacaat taataaggga ggaaatagta 300

<210> SEQ ID NO 130
<211> LENGTH: 80
<212> TYPE: DNA
<213> ORGANISM: Bacillus mycoides

<400> SEQUENCE: 130
acttatatat attgtgcatt ccatattatc aattatctaa attttaagtc ttgttacaat 60
taataaggga ggaaatagta 80

<210> SEQ ID NO 131
<211> LENGTH: 141
<212> TYPE: DNA
<213> ORGANISM: Bacillus thuringiensis

<400> SEQUENCE: 131
aatgacgttt tcaagtttga ttatcattca tgtttcctat tttaagagaa acatataact 60
caactacttt tttcaatggc atcttttata gtacttagaa taggaaaaca ctcaactata 120
agaaaagtaa ggaggaaata a 141

<210> SEQ ID NO 132
<211> LENGTH: 79
<212> TYPE: DNA
<213> ORGANISM: Bacillus thuringiensis

<400> SEQUENCE: 132
actacttttt tcaatggcat cttttatagt acttagaata ggaaaacact caactataag 60
aaaagtaagg aggaaataa 79

<210> SEQ ID NO 133
<211> LENGTH: 300
<212> TYPE: DNA
<213> ORGANISM: Bacillus cereus

<400> SEQUENCE: 133
atatgctaat gcttagtttt tatactcaag ttaaaatgtg cttttggacc taagagataa 60
acgtggaaaa ataaaataaa ctcttaagtt taggtgttta atctaagcag tcaattatta 120
aaaacatata attaatatgt gagtcatgaa cataattaaa taatgttttc aagtttaatt 180
atcgttcatg tttcctattt taagcagaac aaataactca attacttttt tcgattggat 240 ctttttaac tcttataata ggaaaacact caactataaa aataagtaag gaggaaataa 300

<210> SEQ ID NO 134
<211> LENGTH: 167
<212> TYPE: DNA
<213> ORGANISM: Bacillus cereus

<400> SEQUENCE: 134
aatatgtgag tcatgaacat aattaaataa tgttttcaag tttaattatc gttcatgttt 60
cctattttaa gcagaacaaa taactcaatt actttttcg attggatctt ttttaactct 120
tataatagga aaacactcaa ctataaaaat aagtaaggag gaaataa 167

<210> SEQ ID NO 135
<211> LENGTH: 300
<212> TYPE: DNA
<213> ORGANISM: Bacillus thuringiensis

<400> SEQUENCE: 135

```
tataaaataa aagggcgtgt atttgctact gatgcagtat tgtgtgcgcc taaaaatgga     60

atttcacaac cagatccaca tgttgttgta gaacaatctt gtaattcatt gatgaatttt    120

acaacgtcaa ctacacaatg agaagagcca tggtgtttat tttcgttaca actcattaat    180

gtcactcctt atcttcttgt ttgtatttac attaataaga tattggagtt gaggagattt    240

ggtcacaatc tcaagacctt ttttttaaat aggcgaaaga ggataaggga aggtggaatt    300


<210> SEQ ID NO 136
<211> LENGTH: 106
<212> TYPE: DNA
<213> ORGANISM: Bacillus thuringiensis

<400> SEQUENCE: 136

tcttgtttgt atttacatta ataagatatt ggagttgagg agatttggtc acaatctcaa     60

gacctttttt ttaaataggc gaaagaggat aagggaaggt ggaatt                   106


<210> SEQ ID NO 137
<211> LENGTH: 300
<212> TYPE: DNA
<213> ORGANISM: Bacillus thuringiensis

<400> SEQUENCE: 137

atcaactttt acaaaagtaa agggtaaagg attaagaaag tggattggcg aattattaag     60

ctgttattgg tgtacaggtg tatgggttag tgctttttta ttagttttat ataattggat    120

tccgatcgtt gcagagccgt tacttgcatt attagctatt gcaggagcag cagcaatcat    180

tgaaacgatt acaggatatt ttatgggaga ataatatatt ttcataatac gagaaaaagc    240

ggagtttaaa agaatgaggg aacggaaata aagagttgtt catatagtaa atagacagaa    300


<210> SEQ ID NO 138
<211> LENGTH: 39
<212> TYPE: DNA
<213> ORGANISM: Bacillus thuringiensis

<400> SEQUENCE: 138

acggaaataa agagttgttc atatagtaaa tagacagaa                            39


<210> SEQ ID NO 139
<211> LENGTH: 300
<212> TYPE: DNA
<213> ORGANISM: Bacillus anthracis

<400> SEQUENCE: 139

tgaagtatct agagctaatt tacgcaaagg aatctcagga caacactttc gcaacaccta     60

tattttaaat ttaataaaaa aagagactcc ggagtcagaa attataaagc tagctgggtt    120

caaatcaaaa atttcactaa aacgatatta tcaatacgca gaaaatggaa aaaacgcctt    180

atcataaggc gtttttttcca ttttttcttc aaacaaacga ttttactatg accatttaac    240

taatttttgc atctactatg atgagtttca ttcacattct cattagaaag gagagattta    300


<210> SEQ ID NO 140
<211> LENGTH: 70
<212> TYPE: DNA
<213> ORGANISM: Bacillus anthracis

<400> SEQUENCE: 140

accatttaac taatttttgc atctactatg atgagtttca ttcacattct cattagaaag     60

gagagattta                                                            70
```

<210> SEQ ID NO 141
<211> LENGTH: 300
<212> TYPE: DNA
<213> ORGANISM: Bacillus cereus

<400> SEQUENCE: 141
gactatgttt attcaggata aaatatagca ctacactctc tcctcttatt atgtagcatc 60
tctctaatcc atcatttgtt tcatttagtt aaaattgtaa ataaaatcac atgatttgtc 120
aattataatt gtcatttcga caattaaact tgtcaaaata attctcatca tttttctca 180 tctttctaat ataggacata ctactatata tacaaaagac aatatgcaaa tgttcataca 240
aaaaatatta tttttcgata tataatatta actgattttc taacatcaag gagggtacat 300

<210> SEQ ID NO 142
<211> LENGTH: 84
<212> TYPE: DNA
<213> ORGANISM: Bacillus cereus

<400> SEQUENCE: 142
agacaatatg caaatgttca tacaaaaaat attatttttc gatatataat attaactgat 60
tttctaacat caaggagggt acat 84

<210> SEQ ID NO 143
<211> LENGTH: 300
<212> TYPE: DNA
<213> ORGANISM: Bacillus thuringiensis

<400> SEQUENCE: 143
atagtgagta atatggtaat ccatagatta aatagtatag aaaatattta attcttattt 60
ttattaaaaa agcatgaatc ccagatttac tgggttttga ttgtaactaa gaacatataa 120
aagttcactg ttatttatag gagagtctgt ttgtttttat atcttatgta tttcaccctg 180
cataaaaaaa tatttctcaa cattttattt gttgaaaaat attgaatatt cgtattataa 240
cgaatattat gttgttatcg gcaaaaaacg ataatttgca gacactgggg aggaaataca 300

<210> SEQ ID NO 144
<211> LENGTH: 139
<212> TYPE: DNA
<213> ORGANISM: Bacillus thuringiensis

<400> SEQUENCE: 144
tcttatgtat ttcaccctgc ataaaaaaat atttctcaac attttatttg ttgaaaaata 60
ttgaatattc gtattataac gaatattatg ttgttatcgg caaaaaacga taatttgcag 120
acactgggga ggaaataca 139

<210> SEQ ID NO 145
<211> LENGTH: 300
<212> TYPE: DNA
<213> ORGANISM: Bacillus cereus

<400> SEQUENCE: 145
cttcgtcagc aataagtgtg agcggagaat tggttgatct tggctttaca attggagcat 60
tgacgaaaga ctctttaacg tggtcgcata acggagtaga atatatgctc gtgtctaaag 120
gtttagagcc gaaggagcta ttaatggttg ctcgttcagt tacagagaag caagtgaagt 180
aaacttctta gacgtggtga tatatgtgca ccacgtcttt tcttagtttg aagggtggat 240
ttcataaaag aagcatataa aagaataagc ttcgcatatc gtgtataagg aagtgtattt 300

<210> SEQ ID NO 146
<211> LENGTH: 44
<212> TYPE: DNA
<213> ORGANISM: Bacillus cereus

<400> SEQUENCE: 146
ataaaagaat aagcttcgca tatcgtgtat aaggaagtgt attt 44

<210> SEQ ID NO 147
<211> LENGTH: 300
<212> TYPE: DNA
<213> ORGANISM: Bacillus thuringiensis

<400> SEQUENCE: 147
catttcaaat aatgaacgct tcgattgaat cggagctatt ttcaaatcaa tttcagtata 60
ttgatccagc atttgaatag aagtatcaac agcaacttta agttgatgca atgcagattg 120
tacaaacatt gtaattctcc tcttctccgt atataatagt ttcttgaggg tattatatca 180
tgctcaaaat tccgaaaatt ctagtagttt gactagcata ttgaaaagta ttatattgta 240
aaaggtcata tgaaacgtga aatagaatgg aatgcaatta ttgagttagg agttagacca 300

<210> SEQ ID NO 148
<211> LENGTH: 70
<212> TYPE: DNA
<213> ORGANISM: Bacillus thuringiensis

<400> SEQUENCE: 148
ttatattgta aaaggtcata tgaaacgtga aatagaatgg aatgcaatta ttgagttagg 60
agttagacca 70

<210> SEQ ID NO 149
<211> LENGTH: 300
<212> TYPE: DNA
<213> ORGANISM: Bacillus cereus

<400> SEQUENCE: 149
atcgatggaa cctgtatcaa ccactataat ttcatccaca attttttcaa ctgagtctaa 60
acaacgggct attgtcttct cctcatctcg aacaatcata cataaactaa ttgtaattcc 120
ttgcttgttc aacataatca ccctcttcca aatcaatcat atgttataca tatactaaac 180
tttccatttt tttaaattgt tcaagtagtt taagatttct tttcaataat tcaaatgtcc 240
gtgtcatttt ctttcggttt tgcatctact atataatgaa cgctttatgg aggtgaattt 300

<210> SEQ ID NO 150
<211> LENGTH: 150
<212> TYPE: DNA
<213> ORGANISM: Bacillus cereus

<400> SEQUENCE: 150
aatcaatcat atgttataca tatactaaac tttccatttt tttaaattgt tcaagtagtt 60
taagatttct tttcaataat tcaaatgtcc gtgtcatttt ctttcggttt tgcatctact 120
atataatgaa cgctttatgg aggtgaattt 150

<210> SEQ ID NO 151
<211> LENGTH: 300
<212> TYPE: DNA
<213> ORGANISM: Bacillus thuringiensis

<400> SEQUENCE: 151
gacctgtaag tctgtaggga agaataattt caagagccag tgataataga ttttttttgtt 60 ttttcattct tatcttgaat ataaatcacc tcatctttta attagaacgt aaccaattta 120
gtattttgaa atagagctat cattttataa tatgaatact actagttata gaaacggcaa 180
aaagtttaat atatgtaaaa atcatttgga tatgaaaaaa gtagccatag attttttcga 240
aatgataaat gttttatttt gttaattagg aaacaaaaat gtggaatgag ggggatttaa 300

<210> SEQ ID NO 152
<211> LENGTH: 91
<212> TYPE: DNA
<213> ORGANISM: Bacillus thuringiensis

<400> SEQUENCE: 152
atatgaaaaa agtagccata gatttttttcg aaatgataaa tgttttattt tgttaattag 60
gaaacaaaaa tgtggaatga gggggattta a 91

<210> SEQ ID NO 153
<211> LENGTH: 300
<212> TYPE: DNA
<213> ORGANISM: Bacillus anthracis

<400> SEQUENCE: 153
ttttcatctg ctacatcgtg aagtaatgct gccatttcaa ttataaaacg atttcctcct 60
tcttgctcgg ataaagaaat cgccagttta tgtacacgct caatatgata ccaatcatgc 120
ccactggcat ctttttctaa aatatgtttt acaaaagtaa ttgtttttttc tatcttttct 180 tgttttgtca ttttatcttc acccagttac ttattgtaac acgcccgcat tttttcatca 240
catattttct tgtccgccca tacactaggt ggtaggcatc atcatgaagg aggaatagat 300

<210> SEQ ID NO 154
<211> LENGTH: 61
<212> TYPE: DNA
<213> ORGANISM: Bacillus anthracis

<400> SEQUENCE: 154
acatattttc ttgtccgccc atacactagg tggtaggcat catcatgaag gaggaataga 60
t 61

<210> SEQ ID NO 155
<211> LENGTH: 300
<212> TYPE: DNA
<213> ORGANISM: Bacillus anthracis

<400> SEQUENCE: 155
ggtgacgaca acatatacaa gaggcactcc tgctggtact gtaacaggaa caaatatggg 60
gcaaagtgta aatacatcgg gtatagcaca agctgtcccg aatacagata atatggattc 120
aacggcggga ctcccttaag aaattagggg agtctttatt tggaaaaaga gcttatgtta 180
cataaaaaca ggagtaattg ttttaaaagt agtattggtg acgttgttag aaaatacaat 240
ttaagtagaa ggtgcgtttt tatatgaaat atattttata gctgtacttt acctttcaag 300

<210> SEQ ID NO 156
<211> LENGTH: 213
<212> TYPE: DNA
<213> ORGANISM: Bacillus anthracis

<400> SEQUENCE: 156
acaagctgtc ccgaatacag ataatatgga ttcaacggcg ggactccctt aagaaattag 60
gggagtcttt atttggaaaa agagcttatg ttacataaaa acaggagtaa ttgttttaaa 120
agtagtattg gtgacgttgt tagaaaatac aatttaagta gaaggtgcgt ttttatatga 180
aatatatttt atagctgtac tttacctttc aag 213

<210> SEQ ID NO 157
<211> LENGTH: 300
<212> TYPE: DNA
<213> ORGANISM: Bacillus anthracis

<400> SEQUENCE: 157
atttatttca ttcaattttt cctatttagt acctaccgca ctcacaaaaa gcacctctca 60
ttaatttata ttatagtcat tgaaatctaa tttaatgaaa tcatcatact atatgtttta 120
taagaagtaa aggtaccata cttaattaat acatatctat acacttcaat atcacagcat 180
gcagttgaat tatatccaac tttcatttca aattaaataa gtgcctccgc tattgtgaat 240
gtcatttact ctccctacta catttaataa ttatgacaag caatcatagg aggttactac 300

<210> SEQ ID NO 158
<211> LENGTH: 180
<212> TYPE: DNA
<213> ORGANISM: Bacillus anthracis

<400> SEQUENCE: 158
taagaagtaa aggtaccata cttaattaat acatatctat acacttcaat atcacagcat 60
gcagttgaat tatatccaac tttcatttca aattaaataa gtgcctccgc tattgtgaat 120
gtcatttact ctccctacta catttaataa ttatgacaag caatcatagg aggttactac 180

<210> SEQ ID NO 159
<211> LENGTH: 300
<212> TYPE: DNA
<213> ORGANISM: Bacillus cereus

<400> SEQUENCE: 159
agttgtacaa gaatttaaat cttcacaaac atatgtaaat gacttactac agctagttgc 60
aagtacgatt tctaacaacg taacagatga aatattaatt tcaactaatg gcgatgtatt 120
gaagggtgaa acgggcgcag cggtagaaag taaaaaagga aattgtggtt gttaaagaga 180
tgtcgaaatg acatctcttt ttttagtgga ttaaacgtaa gttcttctca aaaaaagaat 240
gacacattcc gctattgtca cgcatatgat taagtgaata gtgattgagg agggttacga 300

<210> SEQ ID NO 160
<211> LENGTH: 57
<212> TYPE: DNA
<213> ORGANISM: Bacillus cereus

<400> SEQUENCE: 160
acattccgct attgtcacgc atatgattaa gtgaatagtg attgaggagg gttacga 57

<210> SEQ ID NO 161
<211> LENGTH: 300
<212> TYPE: DNA
<213> ORGANISM: Bacillus cereus

<400> SEQUENCE: 161
aacgttatta gcgtagacaa acaagtaacg gcagaagcag ttcttgcatt aaatcgtatg 60
ttagagcgtg tgtaaagcaa cggtattccc gttgcttttt ttcatacata taatcataac 120
gagaacgaaa tgggcataca ttgttttgaa gaaatcattg tggttcttta tgcttattcc 180
acttcgaatg atattgaaaa tcgaagaagt gataaaagta aaaagaagtt aatgttattt 240
agaaagagtt acttcatgag atttgttact tatagataag ttatacagga gggggaaaat 300

<210> SEQ ID NO 162
<211> LENGTH: 47
<212> TYPE: DNA
<213> ORGANISM: Bacillus cereus

<400> SEQUENCE: 162
tcatgagatt tgttacttat agataagtta tacaggaggg ggaaaat 47

<210> SEQ ID NO 163
<211> LENGTH: 300
<212> TYPE: DNA
<213> ORGANISM: Bacillus thuringiensis

<400> SEQUENCE: 163
aagccgcggt caatgctgta tatgcaaata agattgcagc tttacctgaa gaagagcgtg 60
atagcttcat tgctgaaaaa cgagaagagt ataagaaaga tattgatatt taccatttag 120
catcagagat ggtcattgat ggtattgttc atccaaacaa tttaagagaa gagttaaaag 180
gacgattcga aatgtatatg agtaaatatc aagtatttac ggatcgtaaa catcctgttt 240
atccagttta aaagccctat ttagggcttt cttgctcaaa aagttaagga ggggaaaaca 300

<210> SEQ ID NO 164
<211> LENGTH: 92
<212> TYPE: DNA
<213> ORGANISM: Bacillus thuringiensis

<400> SEQUENCE: 164
tcaagtattt acggatcgta aacatcctgt ttatccagtt taaaagccct atttagggct 60
ttcttgctca aaaagttaag gaggggaaaa ca 92

<210> SEQ ID NO 165
<211> LENGTH: 300
<212> TYPE: DNA
<213> ORGANISM: Bacillus cereus

<400> SEQUENCE: 165
aggatttcag tgggacgcct cctctcttct tacattaaat taatcatact ataaaatgaa 60
agaaatgaaa tgaaaaatag cggaaaaatc agaaattttt tctggtagta tacaatatgt 120
tacaataagc tttgtcaatg aaagaaggaa ttccgtgcaa tgcacgggag aggttcgcga 180
actccctcta taaaaaacta tggaaacaac aatatcttta ggtattgttt tgttttttta 240
ttgtgacagt tcaagaacgt tctttcttct tattcgtagt agagaaggag aatgagtgaa 300

<210> SEQ ID NO 166
<211> LENGTH: 104
<212> TYPE: DNA
<213> ORGANISM: Bacillus cereus

<400> SEQUENCE: 166
actatggaaa caacaatatc tttaggtatt gttttgtttt tttattgtga cagttcaaga 60
acgttctttc ttcttattcg tagtagagaa ggagaatgag tgaa 104

<210> SEQ ID NO 167
<211> LENGTH: 300
<212> TYPE: DNA
<213> ORGANISM: Bacillus cereus

<400> SEQUENCE: 167
ttttgcacaa cgccgtaaaa ctttaatgaa taatttatca aataatttaa atggtttccc 60
gaaagataaa gagctgttgg atcgaatttt aacagaagta ggaattgatc caaaacgaag 120
aggcgaaacg ctatctatcg aagagtttgc gacattaagt aatgcattag ttcttcataa 180
gttatcataa gaatacaaaa gggacagttc aatttgaact gtcccttttg tcacctttct 240
cctcctaaat tcatacttta aaaacaggta agatggccta acgagtttgg aggtaggaga 300

<210> SEQ ID NO 168
<211> LENGTH: 63
<212> TYPE: DNA
<213> ORGANISM: Bacillus cereus

<400> SEQUENCE: 168
tctcctccta aattcatact ttaaaaacag gtaagatggc ctaacgagtt tggaggtagg 60
aga 63

<210> SEQ ID NO 169
<211> LENGTH: 300
<212> TYPE: DNA
<213> ORGANISM: Bacillus thuringiensis

<400> SEQUENCE: 169
ggaaacagaa gtcatcccat ttgaaaatgc agcaggtcgt attatagctg atttcgttat 60
ggtttatccg ccagggattc caatctttac tccgggggaa attattacac aagacaactt 120
agagtatatt cgtaaaaact tagaagcagg tttacctgta caaggtcctg aagatatgac 180
attacaaaca ttacgcgtga tcaaagagta caagcctatc agttgatagg ctttttttca 240 cccttttcc cttttctcat acgatattat gtaatgtaac gtataggtgg ggatactact 300

<210> SEQ ID NO 170
<211> LENGTH: 61
<212> TYPE: DNA
<213> ORGANISM: Bacillus thuringiensis

<400> SEQUENCE: 170 acccttttc ccttttctca tacgatatta tgtaatgtaa cgtataggtg gggatactac 60
t 61

<210> SEQ ID NO 171
<211> LENGTH: 300
<212> TYPE: DNA
<213> ORGANISM: Bacillus cereus

<400> SEQUENCE: 171
attgtggacc cttagctcag ctggttagag cagacggctc ataaccgtcc ggtcgtaggt 60
tcgagtccta cagggtccat atccatttca catgtttatt atgtcggcag gaagcttcct 120
tgtagaaggg agcttttttt atgaaatata tgagcatttt aattgaaatg aagtgggaat 180
tttgctactt taatgatagc aagacaatgt gatttatttg tttgcaccct atggcaatta 240
gggtagaatg aagttgtatg tcacttaagt ggcaatacat aaactgggag gaatataaca 300

<210> SEQ ID NO 172
<211> LENGTH: 38
<212> TYPE: DNA
<213> ORGANISM: Bacillus cereus

<400> SEQUENCE: 172
acttaagtgg caatacataa actgggagga atataaca 38

<210> SEQ ID NO 173
<211> LENGTH: 300
<212> TYPE: DNA
<213> ORGANISM: Bacillus cereus

<400> SEQUENCE: 173
aatataacag aaaattctga tgttttttca aatcctataa taaggagtgt tccgtatgat 60
gcctttatat tttccggaag ataaaacaga atatattatt ccagggattg tttgtgttct 120
atttatcatc ggtgcgattg ctacgtggcg tatgttcatt cgtgtatcaa aacgagaagc 180
agagcgatta cagaaagttg aagaaaagct gttagctgaa aagaaacagt aactcatttt 240
tgtatgtttc cctctatgct cggacaatct aagggcagaa tgtattttgg agggaatgaa 300

<210> SEQ ID NO 174
<211> LENGTH: 228
<212> TYPE: DNA
<213> ORGANISM: Bacillus cereus

<400> SEQUENCE: 174
tccggaagat aaaacagaat atattattcc agggattgtt tgtgttctat ttatcatcgg 60
tgcgattgct acgtggcgta tgttcattcg tgtatcaaaa cgagaagcag agcgattaca 120
gaaagttgaa gaaaagctgt tagctgaaaa gaaacagtaa ctcatttttg tatgtttccc 180
tctatgctcg gacaatctaa gggcagaatg tattttggag ggaatgaa 228

<210> SEQ ID NO 175
<211> LENGTH: 166
<212> TYPE: DNA
<213> ORGANISM: Bacillus anthracis

<400> SEQUENCE: 175
taatcaccct cttccaaatc aatcatatgt tatacatata ctaaactttc catttttttta 60 aattgttcaa gtagtttaag atttcttttc aataattcaa atgtccgtgt cattttcttt 120
cggttttgca tctactatat aatgaacgct ttatggaggt gaattt 166

<210> SEQ ID NO 176
<211> LENGTH: 173
<212> TYPE: DNA
<213> ORGANISM: Bacillus anthracis

<400> SEQUENCE: 176
aattacataa caagaactac attagggagc aagcagtcta gcgaaagcta actgcttttt 60
tattaaataa ctattttatt aaatttcata tatacaatcg cttgtccatt tcatttggct 120
ctacccacgc atttactatt agtaatatga atttttcaga ggtggatttt att 173

<210> SEQ ID NO 177
<211> LENGTH: 121
<212> TYPE: DNA
<213> ORGANISM: Bacillus weihenstephanensis

<400> SEQUENCE: 177

```
ctatgattta agatacacaa tagcaaaaga gaaacatatt atataacgat aaatgaaact     60

tatgtatatg tatggtaact gtatatatta ctacaataca gtatactcat aggaggtagg    120

t                                                                    121


<210> SEQ ID NO 178
<211> LENGTH: 373
<212> TYPE: DNA
<213> ORGANISM: Bacillus weihenstephanensis

<400> SEQUENCE: 178

ggtaggtaga tttgaaatat gatgaagaaa aggaataact aaaaggagtc gatatccgac     60

tccttttagt tataaataat gtggaattag agtataattt tatataggta tattgtatta    120

gatgaacgct ttatccttta attgtgatta atgatggatt gtaagagaag gggcttacag    180

tccttttttt atggtgttct ataagccttt ttaaaagggg taccacccca cacccaaaaa    240

caggggggt tataactaca tattggatgt tttgtaacgt acaagaatcg gtattaatta    300

ccctgtaaat aagttatgtg tatataaggt aactttatat attctcctac aataaaataa    360

aggaggtaat aaa                                                       373


<210> SEQ ID NO 179
<211> LENGTH: 225
<212> TYPE: DNA
<213> ORGANISM: Bacillus thuringiensis

<400> SEQUENCE: 179

aacccttaat gcattggtta aacattgtaa agtctaaagc atggataatg ggcgagaagt     60

aagtagattg ttaacaccct gggtcaaaaa ttgatattta gtaaaattag ttgcactttg    120

tgcatttttt cataagatga gtcatatgtt ttaaattgta gtaatgaaaa acagtattat    180

atcataatga attggtatct taataaaaga gatggaggta actta                    225


<210> SEQ ID NO 180
<211> LENGTH: 115
<212> TYPE: DNA
<213> ORGANISM: Bacillus thuringiensis

<400> SEQUENCE: 180

taattccacc ttcccttatc ctctttcgcc tatttaaaaa aaggtcttga gattgtgacc     60

aaatctcctc aactccaata tcttattaat gtaaatacaa acaagaagat aagga         115


<210> SEQ ID NO 181
<211> LENGTH: 144
<212> TYPE: DNA
<213> ORGANISM: Bacillus thuringiensis

<400> SEQUENCE: 181

aggatgtctt tttttatatt gtattatgta catccctact atataaattc cctgctttta     60

tcgtaagaat taacgtaata tcaaccatat cccgttcata ttgtagtagt gtatgtcaga    120

actcacgaga aggagtgaac ataa                                           144


<210> SEQ ID NO 182
<211> LENGTH: 125
<212> TYPE: DNA
<213> ORGANISM: Bacillus thuringiensis

<400> SEQUENCE: 182

ttaatgtcac tccttatctt cttgtttgta tttacattaa taagatattg gagttgagga     60
```

gatttggtca caatctcaag accttttttt taaataggcg aaagaggata agggaaggtg 120
gaatt 125

<210> SEQ ID NO 183
<211> LENGTH: 87
<212> TYPE: DNA
<213> ORGANISM: Bacillus thuringiensis

<400> SEQUENCE: 183
atatattttc ataatacgag aaaaagcgga gtttaaaaga atgagggaac ggaaataaag 60
agttgttcat atagtaaata gacagaa 87

<210> SEQ ID NO 184
<211> LENGTH: 168
<212> TYPE: DNA
<213> ORGANISM: Bacillus thuringiensis

<400> SEQUENCE: 184
aaactaaata atgagctaag catggattgg gtggcagaat tatctgccac ccaatccatg 60
cttaacgagt attattatgt aaatttctta aaattgggaa cttgtctaga acatagaacc 120
tgtccttttc attaactgaa agtagaaaca gataaaggag tgaaaaac 168

<210> SEQ ID NO 185
<211> LENGTH: 111
<212> TYPE: DNA
<213> ORGANISM: Bacillus thuringiensis

<400> SEQUENCE: 185
attcactaca acggggatga gtttgatgcg gatacatatg agaagtaccg gaaagtgttt 60
gtagaacatt acaaagatat attatctcca tcataaagga gagatgcaaa g 111

<210> SEQ ID NO 186
<211> LENGTH: 273
<212> TYPE: DNA
<213> ORGANISM: Bacillus anthracis

<400> SEQUENCE: 186
cgcgcaccac ttcgtcgtac aacaacgcaa gaagaagttg gggatacagc agtattctta 60
ttcagtgatt tagcacgcgg cgtaacagga gaaaacattc acgttgattc agggtatcat 120
atcttaggat aaatataata ttaattttaa aggacaatct ctacatgttg agattgtcct 180
ttttatttgt tcttagaaag aacgattttt aacgaaagtt cttaccacgt tatgaatata 240
agtataatag tacacgattt attcagctac gta 273

<210> SEQ ID NO 187
<211> LENGTH: 240
<212> TYPE: DNA
<213> ORGANISM: Bacillus anthracis

<400> SEQUENCE: 187
tatatcatat gtaaaattag ttcttattcc cacatatcat atagaatcgc catattatac 60
atgcagaaaa ctaagtatgg tattattctt aaattgttta gcaccttcta atattacaga 120
tagaatccgt cattttcaac agtgaacatg gatttcttct gaacacaact ctttttcttt 180
ccttatttcc aaaaagaaaa gcagcccatt ttaaaatacg gctgcttgta atgtacatta 240

<210> SEQ ID NO 188

<211> LENGTH: 267
<212> TYPE: DNA
<213> ORGANISM: Bacillus thuringiensis

<400> SEQUENCE: 188
tatcacataa ctctttattt ttaatatttc gacataaagt gaaactttaa tcagtggggg 60
ctttgttcat ccccccactg attattaatt gaaccaaggg ataaaaagat agagggtctg 120
accagaaaac tggagggcat gattctataa caaaaagctt aatgtttata gaattatgtc 180
tttttatata gggagggtag taaacagaga tttggacaaa aatgcaccga tttatctgaa 240
ttttaagttt tataaagggg agaaatg 267

<210> SEQ ID NO 189
<211> LENGTH: 124
<212> TYPE: DNA
<213> ORGANISM: Bacillus thuringiensis

<400> SEQUENCE: 189
attttttact tagcagtaaa actgatatca gttttactgc tttttcattt ttaaattcaa 60
tcattaaatc ttccttttct acatagtcat aatgttgtat gacattccgt aggaggcact 120
tata 124

<210> SEQ ID NO 190
<211> LENGTH: 170
<212> TYPE: DNA
<213> ORGANISM: Bacillus thuringiensis

<400> SEQUENCE: 190
acataaattc acctccataa agcgttcatt atatagtaga tgcaaaaccg aaagaaaatg 60
acacggacat ttgaattatt gaaaagaaat cttaaactac ttgaacaatt taaaaaaatg 120
gaaagtttag tatatgtata acatatgatt gatttggaag agggtgatta 170

<210> SEQ ID NO 191
<211> LENGTH: 212
<212> TYPE: DNA
<213> ORGANISM: Bacillus thuringiensis

<400> SEQUENCE: 191
ttctattttc caacataaca tgctacgatt aaatggtttt ttgcaaatgc cttcttggga 60
agaaggatta gagcgttttt ttatagaaac caaaagtcat taacaatttt aagttaatga 120 ctttttttgtt tgcctttaag aggttttatg ttactataat tatagtatca ggtactaata 180
acaagtataa gtatttctgg gaggatatat ca 212

<210> SEQ ID NO 192
<211> LENGTH: 180
<212> TYPE: PRT
<213> ORGANISM: Bacillus cereus

<400> SEQUENCE: 192

Met Ser Glu Phe Arg Glu Ile Ile Thr Lys Ala Val Val Gly Lys Gly
1 5 10 15

Arg Lys Tyr Thr Lys Ser Thr His Thr Cys Glu Ser Asn Asn Glu Pro
20 25 30

Thr Ser Ile Leu Gly Cys Trp Val Ile Asn His Ser Tyr Glu Ala Arg
35 40 45

Lys Asn Gly Lys His Val Glu Ile Glu Gly Phe Tyr Asp Val Asn Thr
50 55 60

```
Trp Tyr Ser Phe Asp Gly Asn Thr Lys Thr Glu Val Val Thr Glu Arg
65                  70                  75                  80

Val Asn Tyr Thr Asp Glu Val Ser Ile Gly Tyr Arg Asp Lys Asn Phe
                85                  90                  95

Ser Gly Asp Asp Leu Glu Ile Ile Ala Arg Val Ile Gln Pro Pro Asn
            100                 105                 110

Cys Leu Glu Ala Leu Val Ser Pro Asn Gly Asn Lys Ile Val Val Thr
        115                 120                 125

Val Glu Arg Glu Phe Val Thr Glu Val Val Gly Glu Thr Lys Ile Cys
    130                 135                 140

Val Ser Val Asn Pro Glu Gly Cys Val Glu Ser Asp Glu Asp Phe Gln
145                 150                 155                 160

Ile Asp Asp Asp Glu Phe Glu Glu Leu Asp Pro Asn Phe Ile Val Asp
                165                 170                 175

Ala Glu Glu Glu
            180


<210> SEQ ID NO 193
<211> LENGTH: 155
<212> TYPE: PRT
<213> ORGANISM: Bacillus thuringiensis

<400> SEQUENCE: 193

Met Thr Leu Met Ser Cys Asn Glu Asn Lys His His Gly Ser Ser His
1               5                   10                  15

Cys Val Val Asp Val Val Lys Phe Ile Asn Glu Leu Gln Asp Cys Ser
            20                  25                  30

Thr Thr Thr Cys Gly Ser Gly Cys Glu Ile Pro Phe Leu Gly Ala His
        35                  40                  45

Asn Thr Ala Ser Val Ala Asn Thr Arg Pro Phe Ile Leu Tyr Thr Lys
    50                  55                  60

Ala Gly Ala Pro Phe Glu Ala Phe Ala Pro Ser Ala Asn Leu Thr Ser
65                  70                  75                  80

Cys Arg Ser Pro Ile Phe Arg Val Glu Ser Val Asp Asp Asp Ser Cys
                85                  90                  95

Ala Val Leu Arg Val Leu Ser Val Val Leu Gly Asp Ser Ser Pro Val
            100                 105                 110

Pro Pro Thr Asp Asp Pro Ile Cys Thr Phe Leu Ala Val Pro Asn Ala
        115                 120                 125

Arg Leu Val Ser Thr Ser Thr Cys Ile Thr Val Asp Leu Ser Cys Phe
    130                 135                 140

Cys Ala Ile Gln Cys Leu Arg Asp Val Thr Ile
145                 150                 155


<210> SEQ ID NO 194
<211> LENGTH: 366
<212> TYPE: PRT
<213> ORGANISM: Bacillus anthracis

<400> SEQUENCE: 194

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45
```

Gly Pro Thr Gly Thr Thr Gly Ala Thr Gly Ala Thr Gly Ile Thr Gly
50 55 60

Val Thr Gly Ala Thr Gly Ile Thr Gly Val Thr Gly Ala Thr Gly Ile
65 70 75 80

Thr Gly Val Thr Gly Ala Thr Gly Ile Thr Gly Val Thr Gly Pro Thr
85 90 95

Gly Ile Thr Gly Ala Thr Gly Pro Thr Gly Ile Thr Gly Ala Thr Gly
100 105 110

Pro Ala Gly Ile Thr Gly Val Thr Gly Pro Thr Gly Ile Thr Gly Ala
115 120 125

Thr Gly Pro Thr Gly Thr Thr Gly Val Thr Gly Pro Thr Gly Asp Thr
130 135 140

Gly Leu Ala Gly Ala Thr Gly Pro Thr Gly Ala Thr Gly Leu Ala Gly
145 150 155 160

Ala Thr Gly Pro Thr Gly Asp Thr Gly Ala Thr Gly Pro Thr Gly Ala
165 170 175

Thr Gly Leu Ala Gly Ala Thr Gly Pro Thr Gly Ala Thr Gly Leu Thr
180 185 190

Gly Ala Thr Gly Ala Thr Gly Ala Thr Gly Gly Gly Ala Ile Ile Pro
195 200 205

Phe Ala Ser Gly Thr Thr Pro Ala Leu Leu Val Asn Ala Val Leu Ala
210 215 220

Asn Thr Gly Thr Leu Leu Gly Phe Gly Phe Ser Gln Pro Gly Ile Ala
225 230 235 240

Pro Gly Val Gly Gly Thr Leu Thr Ile Leu Pro Gly Val Val Gly Asp
245 250 255

Tyr Ala Phe Val Ala Pro Arg Asp Gly Ile Ile Thr Ser Leu Ala Gly
260 265 270

Phe Phe Ser Ala Thr Ala Ala Leu Ala Pro Leu Thr Pro Val Gln Ile
275 280 285

Gln Met Gln Ile Phe Ile Ala Pro Ala Ala Ser Asn Thr Phe Thr Pro
290 295 300

Val Ala Pro Pro Leu Leu Leu Thr Pro Ala Leu Pro Ala Ile Ala Ile
305 310 315 320

Gly Thr Thr Ala Thr Gly Ile Gln Ala Tyr Asn Val Pro Val Val Ala
325 330 335

Gly Asp Lys Ile Leu Val Tyr Val Ser Leu Thr Gly Ala Ser Pro Ile
340 345 350

Ala Ala Val Ala Gly Phe Val Ser Ala Gly Leu Asn Ile Val
355 360 365

<210> SEQ ID NO 195
<211> LENGTH: 347
<212> TYPE: PRT
<213> ORGANISM: Bacillus anthracis

<400> SEQUENCE: 195

Met Gln Asn Asp Lys Leu Trp Leu Asp Lys Gly Ile Ile Gly Pro Glu
1 5 10 15

Asn Ile Gly Pro Thr Phe Pro Val Leu Pro Pro Ile His Ile Pro Thr
20 25 30

Gly Ile Thr Gly Ala Thr Gly Ala Thr Gly Ile Thr Gly Ala Thr Gly
35 40 45

Pro Thr Gly Thr Thr Gly Ala Thr Gly Ala Thr Gly Ile Thr Gly Val

```
    50                  55                  60

Thr Gly Ala Thr Gly Ile Thr Gly Val Thr Gly Ala Thr Gly Ile Thr
65                  70                  75                  80

Gly Val Thr Gly Ala Thr Gly Ile Thr Gly Val Thr Gly Ala Thr Gly
                85                  90                  95

Ile Thr Gly Val Thr Gly Pro Thr Gly Ile Thr Gly Ala Thr Gly Pro
            100                 105                 110

Thr Gly Thr Thr Gly Val Thr Gly Pro Thr Gly Asp Thr Gly Leu Ala
        115                 120                 125

Gly Ala Thr Gly Pro Thr Gly Ala Thr Gly Leu Ala Gly Ala Thr Gly
    130                 135                 140

Pro Thr Gly Asp Thr Gly Ala Thr Gly Pro Thr Gly Ala Thr Gly Leu
145                 150                 155                 160

Ala Gly Ala Thr Gly Pro Thr Gly Ala Thr Gly Leu Thr Gly Ala Thr
                165                 170                 175

Gly Ala Thr Gly Ala Thr Gly Gly Gly Ala Ile Ile Pro Phe Ala Ser
            180                 185                 190

Gly Thr Thr Pro Ala Leu Leu Val Asn Ala Val Leu Ala Asn Thr Gly
        195                 200                 205

Thr Leu Leu Gly Phe Gly Phe Ser Gln Pro Gly Ile Ala Pro Gly Val
    210                 215                 220

Gly Gly Thr Leu Thr Ile Leu Pro Gly Val Val Gly Asp Tyr Ala Phe
225                 230                 235                 240

Val Ala Pro Arg Asp Gly Ile Ile Thr Ser Leu Ala Gly Phe Phe Ser
                245                 250                 255

Ala Thr Ala Ala Leu Ala Pro Leu Thr Pro Val Gln Ile Gln Met Gln
            260                 265                 270

Ile Phe Ile Ala Pro Ala Ala Ser Asn Thr Phe Thr Pro Val Ala Pro
        275                 280                 285

Pro Leu Leu Leu Thr Pro Ala Leu Pro Ala Ile Ala Ile Gly Thr Thr
    290                 295                 300

Ala Thr Gly Ile Gln Ala Tyr Asn Val Pro Val Val Ala Gly Asp Lys
305                 310                 315                 320

Ile Leu Val Tyr Val Ser Leu Thr Gly Ala Ser Pro Ile Ala Ala Val
                325                 330                 335

Ala Gly Phe Val Ser Ala Gly Leu Asn Ile Val
            340                 345


<210> SEQ ID NO 196
<211> LENGTH: 61
<212> TYPE: PRT
<213> ORGANISM: Bacillus cereus

<400> SEQUENCE: 196

Met Phe Ala Val Ser Asn Asn Pro Arg Gln Asn Ser Tyr Asp Leu Gln
1               5                   10                  15

Gln Trp Tyr His Met Gln Gln Gln His Gln Ala Gln Gln Gln Ala Tyr
            20                  25                  30

Gln Glu Gln Leu Gln Gln Gln Gly Phe Val Lys Lys Lys Gly Cys Asn
        35                  40                  45

Cys Gly Lys Lys Lys Ser Thr Ile Lys His Tyr Glu Glu
    50                  55                  60


<210> SEQ ID NO 197
<211> LENGTH: 66
```

<212> TYPE: PRT
<213> ORGANISM: Bacillus cereus

<400> SEQUENCE: 197

Leu Thr Val Glu Glu Met Phe Ala Val Ser Asn Asn Pro Arg Gln Asn
1               5                   10                  15

Ser Tyr Asp Leu Gln Gln Trp Tyr His Met Gln Gln Gln His Gln Ala
            20                  25                  30

Gln Gln Gln Ala Tyr Gln Glu Gln Leu Gln Gln Gln Gly Phe Val Lys
        35                  40                  45

Lys Lys Gly Cys Asn Cys Gly Lys Lys Lys Ser Thr Ile Lys His Tyr
    50                  55                  60

Glu Glu
65

<210> SEQ ID NO 198
<211> LENGTH: 156
<212> TYPE: PRT
<213> ORGANISM: Bacillus cereus

<400> SEQUENCE: 198

Met Ser Cys Asn Cys Asn Glu Asp His His His His Asp Cys Asp Phe
1               5                   10                  15

Asn Cys Val Ser Asn Val Val Arg Phe Ile His Glu Leu Gln Glu Cys
            20                  25                  30

Ala Thr Thr Thr Cys Gly Ser Gly Cys Glu Val Pro Phe Leu Gly Ala
        35                  40                  45

His Asn Ser Ala Ser Val Ala Asn Thr Arg Pro Phe Ile Leu Tyr Thr
    50                  55                  60

Lys Ala Gly Ala Pro Phe Glu Ala Phe Ala Pro Ser Ala Asn Leu Thr
65                  70                  75                  80

Ser Cys Arg Ser Pro Ile Phe Arg Val Glu Ser Ile Asp Asp Asp Asp
                85                  90                  95

Cys Ala Val Leu Arg Val Leu Ser Val Val Leu Gly Asp Thr Ser Pro
            100                 105                 110

Val Pro Pro Thr Asp Asp Pro Ile Cys Thr Phe Leu Ala Val Pro Asn
        115                 120                 125

Ala Arg Leu Ile Ser Thr Asn Thr Cys Leu Thr Val Asp Leu Ser Cys
    130                 135                 140

Phe Cys Ala Ile Gln Cys Leu Arg Asp Val Thr Ile
145                 150                 155

<210> SEQ ID NO 199
<211> LENGTH: 182
<212> TYPE: PRT
<213> ORGANISM: Bacillus anthracis

<400> SEQUENCE: 199

Met Glu Val Gly Gly Thr Ser Val Lys Asn Lys Asn Lys Ser Ser Thr
1               5                   10                  15

Val Gly Lys Pro Leu Leu Tyr Ile Ala Gln Val Ser Leu Glu Leu Ala
            20                  25                  30

Ala Pro Lys Thr Lys Arg Ile Ile Leu Thr Asn Phe Glu Asn Glu Asp
        35                  40                  45

Arg Lys Glu Glu Ser Asn Arg Asn Glu Asn Val Val Ser Ser Ala Val
    50                  55                  60

Glu Glu Val Ile Glu Gln Glu Glu Gln Gln Gln Glu Gln Glu Gln Glu

```
65                  70                  75                  80

Gln Glu Glu Gln Val Glu Glu Lys Thr Glu Glu Glu Glu Gln Val Gln
                85                  90                  95

Glu Gln Gln Glu Pro Val Arg Thr Val Pro Tyr Asn Lys Ser Phe Lys
            100                 105                 110

Asp Met Asn Asn Glu Glu Lys Ile His Phe Leu Leu Asn Arg Pro His
        115                 120                 125

Tyr Ile Pro Lys Val Arg Cys Arg Ile Lys Thr Ala Thr Ile Ser Tyr
    130                 135                 140

Val Gly Ser Ile Ile Ser Tyr Arg Asn Gly Ile Val Ala Ile Met Pro
145                 150                 155                 160

Pro Asn Ser Met Arg Asp Ile Arg Leu Ser Ile Glu Glu Ile Lys Ser
                165                 170                 175

Ile Asp Met Ala Gly Phe
            180


<210> SEQ ID NO 200
<211> LENGTH: 36
<212> TYPE: DNA
<213> ORGANISM: Gallus gallus

<400> SEQUENCE: 200

gcagctgcgg cagctggctc catcggcgca gcaagc                              36


<210> SEQ ID NO 201
<211> LENGTH: 36
<212> TYPE: DNA
<213> ORGANISM: Gallus gallus

<400> SEQUENCE: 201

ctgcagttac tcgagctgca gttaagggga aacaca                              36


<210> SEQ ID NO 202
<211> LENGTH: 38
<212> TYPE: DNA
<213> ORGANISM: Bacillus anthracis

<400> SEQUENCE: 202

gcagctgcgg cagctatgaa aaaacgaaaa gtgttaat                            38


<210> SEQ ID NO 203
<211> LENGTH: 36
<212> TYPE: DNA
<213> ORGANISM: Bacillus anthracis

<400> SEQUENCE: 203

ctgcagttac tcgagttatc ctatctcata gccttt                              36


<210> SEQ ID NO 204
<211> LENGTH: 426
<212> TYPE: PRT
<213> ORGANISM: Solanum tuberosum

<400> SEQUENCE: 204

Asn Ala Gln Ile Pro Leu Arg Arg His Leu Leu Ser His Glu Ser Glu
1               5                   10                  15

His Tyr Ala Val Ile Phe Asp Ala Gly Ser Thr Gly Ser Arg Val His
            20                  25                  30

Val Phe Arg Phe Asp Glu Lys Leu Gly Leu Leu Pro Ile Gly Asn Asn
        35                  40                  45
```

```
Ile Glu Tyr Phe Met Ala Thr Glu Pro Gly Leu Ser Ser Tyr Ala Glu
    50                  55                  60

Asp Pro Lys Ala Ala Ala Asn Ser Leu Glu Pro Leu Leu Asp Gly Ala
65                  70                  75                  80

Glu Gly Val Val Pro Gln Glu Leu Gln Ser Glu Thr Pro Leu Glu Leu
                85                  90                  95

Gly Ala Thr Ala Gly Leu Arg Met Leu Lys Gly Asp Ala Ala Glu Lys
            100                 105                 110

Ile Leu Gln Ala Val Arg Asn Leu Val Lys Asn Gln Ser Thr Phe His
        115                 120                 125

Ser Lys Asp Gln Trp Val Thr Ile Leu Asp Gly Thr Gln Glu Gly Ser
    130                 135                 140

Tyr Met Trp Ala Ala Ile Asn Tyr Leu Leu Gly Asn Leu Gly Lys Asp
145                 150                 155                 160

Tyr Lys Ser Thr Thr Ala Thr Ile Asp Leu Gly Gly Gly Ser Val Gln
                165                 170                 175

Met Ala Tyr Ala Ile Ser Asn Glu Gln Phe Ala Lys Ala Pro Gln Asn
            180                 185                 190

Glu Asp Gly Glu Pro Tyr Val Gln Gln Lys His Leu Met Ser Lys Asp
        195                 200                 205

Tyr Asn Leu Tyr Val His Ser Tyr Leu Asn Tyr Gly Gln Leu Ala Gly
    210                 215                 220

Arg Ala Glu Ile Phe Lys Ala Ser Arg Asn Glu Ser Asn Pro Cys Ala
225                 230                 235                 240

Leu Glu Gly Cys Asp Gly Tyr Tyr Ser Tyr Gly Gly Val Asp Tyr Lys
                245                 250                 255

Val Lys Ala Pro Lys Lys Gly Ser Ser Trp Lys Arg Cys Arg Arg Leu
            260                 265                 270

Thr Arg His Ala Leu Lys Ile Asn Ala Lys Cys Asn Ile Glu Glu Cys
        275                 280                 285

Thr Phe Asn Gly Val Trp Asn Gly Gly Gly Gly Asp Gly Gln Lys Asn
    290                 295                 300

Ile His Ala Ser Ser Phe Phe Tyr Asp Ile Gly Ala Gln Val Gly Ile
305                 310                 315                 320

Val Asp Thr Lys Phe Pro Ser Ala Leu Ala Lys Pro Ile Gln Tyr Leu
                325                 330                 335

Asn Ala Ala Lys Val Ala Cys Gln Thr Asn Val Ala Asp Ile Lys Ser
            340                 345                 350

Ile Phe Pro Lys Thr Gln Asp Arg Asn Ile Pro Tyr Leu Cys Met Asp
        355                 360                 365

Leu Ile Tyr Glu Tyr Thr Leu Leu Val Asp Gly Phe Gly Leu Asn Pro
    370                 375                 380

His Lys Glu Ile Thr Val Ile His Asp Val Gln Tyr Lys Asn Tyr Leu
385                 390                 395                 400

Val Gly Ala Ala Trp Pro Leu Gly Cys Ala Ile Asp Leu Val Ser Ser
                405                 410                 415

Thr Thr Asn Lys Ile Arg Val Ala Ser Ser
            420                 425
```

<210> SEQ ID NO 205
<211> LENGTH: 158
<212> TYPE: PRT
<213> ORGANISM: Bacillus subtilis

<400> SEQUENCE: 205

Met Tyr Glu Phe Lys Asp Tyr Tyr Gln Asn Thr Val Gln Leu Ser Phe
1               5                   10                  15

Asp Asp Gln Pro Phe Ser Asp Ser Pro Lys His Val Trp Val Ile Cys
            20                  25                  30

Arg Phe Gly Gly Lys Trp Leu Leu Thr Glu His Glu Asp Arg Gly Tyr
        35                  40                  45

Glu Phe Pro Gly Gly Lys Val Glu Pro Met Glu Cys Ala Glu Glu Ala
    50                  55                  60

Ala Leu Arg Glu Val Lys Glu Glu Thr Gly Ala Arg Val Lys Ser Leu
65                  70                  75                  80

Lys Tyr Leu Gly Gln Tyr Lys Val Leu Gly Lys Glu Lys Val Ile Val
                85                  90                  95

Lys Asn Ile Tyr Phe Ala Asp Ile Glu Lys Leu Glu Lys Gln Ala Asp
            100                 105                 110

Tyr Phe Glu Thr Lys Gly Pro Val Leu Phe His Glu Leu Pro Glu Asn
        115                 120                 125

Leu Ser Arg Asn Lys Lys Phe Ser Phe Ile Met Lys Asp Ser Val Leu
    130                 135                 140

Pro Ile Ser Leu Lys Lys Leu Lys Glu Ser Gly Trp Ile Glu
145                 150                 155

<210> SEQ ID NO 206
<211> LENGTH: 642
<212> TYPE: PRT
<213> ORGANISM: Bacillus thuringiensis

<400> SEQUENCE: 206

Asp Ser Pro Lys Gln Ser Gln Lys Ile Val Gly Tyr Phe Pro Ser Trp
1               5                   10                  15

Gly Val Tyr Gly Arg Asn Tyr Gln Val Ala Asp Ile Asp Ala Ser Lys
            20                  25                  30

Leu Thr His Leu Asn Tyr Ala Phe Ala Asp Ile Cys Trp Lys Gly Lys
        35                  40                  45

His Gly Asn Pro Ser Thr His Pro Asp Asn Pro Asn Lys Gln Thr Trp
    50                  55                  60

Asn Cys Lys Glu Ser Gly Val Pro Leu Gln Asn Lys Glu Val Pro Asn
65                  70                  75                  80

Gly Thr Leu Val Leu Gly Glu Pro Trp Ala Asp Val Thr Lys Ser Tyr
                85                  90                  95

Pro Gly Ser Gly Thr Thr Trp Glu Asp Cys Asp Lys Tyr Ala Arg Cys
            100                 105                 110

Gly Asn Phe Gly Glu Leu Lys Arg Leu Lys Ala Lys Tyr Pro His Leu
        115                 120                 125

Lys Thr Ile Ile Ser Val Gly Gly Trp Thr Trp Ser Asn Arg Phe Ser
    130                 135                 140

Asp Met Ala Ala Asp Glu Lys Thr Arg Lys Val Phe Ala Glu Ser Thr
145                 150                 155                 160

Val Ala Phe Leu Arg Ala Tyr Gly Phe Asp Gly Val Asp Leu Asp Trp
                165                 170                 175

Glu Tyr Pro Gly Val Glu Thr Ile Pro Gly Gly Ser Tyr Arg Pro Glu
            180                 185                 190

Asp Lys Gln Asn Phe Thr Leu Leu Leu Gln Asp Val Arg Asn Ala Leu
        195                 200                 205

Asn Lys Ala Gly Ala Glu Asp Gly Lys Gln Tyr Leu Leu Thr Ile Ala
    210                 215                 220

Ser Gly Ala Ser Gln Arg Tyr Ala Asp His Thr Glu Leu Lys Lys Ile
225                 230                 235                 240

Ser Gln Ile Leu Asp Trp Ile Asn Ile Met Thr Tyr Asp Phe His Gly
                245                 250                 255

Gly Trp Glu Ala Thr Ser Asn His Asn Ala Ala Leu Tyr Lys Asp Pro
            260                 265                 270

Asn Asp Pro Ala Ala Asn Thr Asn Phe Tyr Val Asp Gly Ala Ile Asp
        275                 280                 285

Val Tyr Thr Asn Glu Gly Val Pro Val Asp Lys Leu Val Leu Gly Val
    290                 295                 300

Pro Phe Tyr Gly Arg Gly Trp Lys Ser Cys Gly Lys Glu Asn Asn Gly
305                 310                 315                 320

Gln Tyr Gln Pro Cys Lys Pro Gly Ser Asp Gly Lys Leu Ala Ser Lys
                325                 330                 335

Gly Thr Trp Asp Asp Tyr Ser Thr Gly Asp Thr Gly Val Tyr Asp Tyr
            340                 345                 350

Gly Asp Leu Thr Ala Asn Tyr Val Asn Lys Asn Gly Phe Val Arg Tyr
        355                 360                 365

Trp Asn Asp Thr Ala Lys Val Pro Tyr Leu Tyr Asn Ala Thr Thr Gly
    370                 375                 380

Thr Phe Ile Ser Tyr Asp Asp Asn Glu Ser Met Lys Tyr Lys Thr Asp
385                 390                 395                 400

Tyr Ile Lys Thr Lys Gly Leu Ser Gly Ala Met Phe Trp Glu Leu Ser
                405                 410                 415

Gly Asp Cys Arg Thr Ser Pro Lys Tyr Ser Cys Ser Gly Pro Lys Leu
            420                 425                 430

Leu Asp Thr Leu Val Lys Glu Leu Leu Gly Gly Pro Ile Asn Gln Lys
        435                 440                 445

Asp Thr Glu Pro Pro Thr Asn Val Lys Asn Ile Ile Val Thr Asn Lys
    450                 455                 460

Thr Ser Ser Ser Val Gln Leu Ser Trp Thr Ala Ser Thr Asp Asn Val
465                 470                 475                 480

Gly Val Thr Glu Tyr Glu Ile Thr Ala Gly Glu Glu Lys Trp Ser Ala
                485                 490                 495

Thr Thr Asn Ser Ile Thr Ile Lys Asn Leu Lys Pro Asn Thr Glu Tyr
            500                 505                 510

Thr Phe Ser Val Ile Ala Lys Asp Ala Ser Gly Asn Lys Ser His Pro
        515                 520                 525

Thr Ala Leu Thr Val Lys Thr Asp Glu Ala Asn Thr Thr Pro Pro Asp
    530                 535                 540

Gly Asn Gly Thr Ala Thr Phe Ser Val Thr Ser Asn Trp Gly Ser Gly
545                 550                 555                 560

Tyr Asn Phe Ser Ile Ile Ile Lys Asn Asn Gly Thr Ile Pro Ile Lys
                565                 570                 575

Asn Trp Lys Leu Glu Phe Asp Tyr Ser Gly Asn Leu Thr Gln Val Trp
            580                 585                 590

Asp Ser Lys Ile Ser Ser Lys Thr Asn Asn His Tyr Val Ile Thr Asn
        595                 600                 605

Ala Gly Trp Asn Gly Glu Ile Pro Pro Gly Gly Ser Ile Thr Ile Gly
    610                 615                 620

Gly Ala Gly Thr Gly Asn Pro Ala Glu Leu Leu Asn Ala Val Ile Ser 625 630 635 640

Glu Asn

<210> SEQ ID NO 207
<211> LENGTH: 250
<212> TYPE: PRT
<213> ORGANISM: Bacillus thuringiensis

<400> SEQUENCE: 207

Met Thr Val Lys Lys Leu Tyr Phe Ile Pro Ala Gly Arg Cys Met Leu
1 5 10 15

Asp His Ser Ser Val Asn Ser Thr Leu Thr Pro Gly Asn Leu Leu Asn
20 25 30

Leu Pro Val Trp Cys Tyr Leu Leu Glu Thr Glu Glu Gly Pro Ile Leu
35 40 45

Val Asp Thr Gly Met Pro Glu Ile Ala Val Asn Asn Glu Gly Leu Phe
50 55 60

Asn Gly Thr Phe Val Glu Gly Gln Ile Leu Pro Lys Met Thr Glu Glu
65 70 75 80

Asp Arg Ile Ile Thr Ile Leu Lys Arg Ala Gly Tyr Glu Pro Asp Asp
85 90 95

Leu Leu Tyr Ile Ile Ser Ser His Leu His Phe Asp His Ala Gly Gly
100 105 110

Asn Gly Ala Phe Ser Asn Thr Pro Ile Ile Ile Gln Arg Ala Glu Tyr
115 120 125

Glu Ala Ala Gln Tyr Arg Glu Glu Tyr Leu Lys Glu Cys Ile Leu Pro
130 135 140

His Leu Asn Tyr Lys Ile Ile Glu Gly Asp Tyr Glu Val Val Pro Gly
145 150 155 160

Val Arg Leu Leu Tyr Thr Pro Gly His Ser Pro Gly His Gln Ser Leu
165 170 175

Leu Ile Glu Thr Glu Lys Ser Gly Pro Ile Leu Leu Thr Ile Asp Ala
180 185 190

Ser Tyr Thr Lys Glu Asn Phe Glu Asp Glu Val Pro Phe Ala Gly Phe
195 200 205

Asp Ser Glu Leu Ala Leu Ser Ser Ile Lys Arg Leu Lys Glu Val Val
210 215 220

Ala Lys Glu Lys Pro Ile Ile Phe Phe Gly His Asp Ile Glu Gln Glu
225 230 235 240

Lys Gly Cys Lys Val Phe Pro Glu Tyr Ile
245 250

<210> SEQ ID NO 208
<211> LENGTH: 250
<212> TYPE: PRT
<213> ORGANISM: Bacillus pseudomycoides

<400> SEQUENCE: 208

Met Thr Val Lys Lys Leu Tyr Phe Leu Pro Ala Gly Arg Cys Met Leu
1 5 10 15

Asp His Ser Ser Ile Asn Ser Thr Leu Thr Pro Gly Lys Leu Leu Asp
20 25 30

Leu Pro Val Trp Cys Tyr Leu Leu Glu Thr Thr Glu Gly Pro Ile Leu
35 40 45

Ile Asp Thr Gly Met Pro Glu Ser Ala Val Asp Asn Glu Asn Leu Phe
50 55 60

Lys Gly Thr Phe Val Glu Gly Gln Ile Phe Pro Lys Met Lys Pro Asp
65 70 75 80

Asp Ser Ile Val Asn Ile Leu Lys Arg Val Gly Tyr Ala Pro Glu Asp
85 90 95

Leu Leu Cys Val Ile Ser Ser His Phe His Phe Asp His Ala Gly Gly
100 105 110

Asn Gly Ser Phe Ser His Thr Pro Ile Ile Val Gln Arg Thr Glu Tyr
115 120 125

Asp Ala Ala Leu His Arg Glu Glu Tyr Leu Lys Glu Cys Ile Leu Pro
130 135 140

Asp Leu Asn Tyr Gln Ile Ile Glu Gly Asp Tyr Glu Val Met Pro Gly
145 150 155 160

Val Gln Leu Leu Tyr Thr Pro Gly His Ser Pro Gly His Gln Ser Ile
165 170 175

Phe Val Glu Thr Glu Lys Ser Gly Pro Val Leu Leu Thr Ile Asp Ala
180 185 190

Ala Tyr Thr Gln Glu Asn Phe Glu Gln Gly Val Pro Phe Ala Gly Phe
195 200 205

Asn Ser Glu Met Ala Ser Gln Ser Ile Asn Arg Leu Lys Glu Ile Val
210 215 220

Leu Asp Glu Lys Pro Ile Ile Phe Phe Gly His Asp Met Glu Gln Glu
225 230 235 240

Lys Arg Cys Lys Thr Phe Pro Glu Phe Leu
245 250

<210> SEQ ID NO 209
<211> LENGTH: 442
<212> TYPE: PRT
<213> ORGANISM: Bacillus subtilis

<400> SEQUENCE: 209

Met Phe Gly Tyr Ser Met Val Gln Met Val Arg Ala Asn Ala His Lys
1 5 10 15

Leu Asp Trp Pro Leu Arg Glu Thr Val Leu Gln Leu Tyr Lys Pro Phe
20 25 30

Lys Trp Thr Pro Cys Phe Leu His Lys Phe Phe Glu Thr Lys Leu Gln
35 40 45

Asn Arg Lys Lys Met Ser Val Ile Ile Glu Phe Glu Glu Gly Cys His
50 55 60

Glu Thr Gly Phe Gln Met Ala Gly Glu Val Leu Gln Lys Glu Lys Arg
65 70 75 80

Ser Lys Leu Lys Ser Arg Phe Asn Lys Ile Asn Cys Cys Ser Ala Glu
85 90 95

Val Thr Pro Ser Ala Leu His Ser Leu Leu Ser Glu Cys Ser Asn Ile
100 105 110

Arg Lys Val Tyr Leu Asn Arg Glu Val Lys Ala Leu Leu Asp Thr Ala
115 120 125

Thr Glu Ala Ser His Ala Lys Glu Val Val Arg Asn Gly Gln Thr Leu
130 135 140

Thr Gly Lys Gly Val Thr Val Ala Val Val Asp Thr Gly Ile Tyr Pro
145 150 155 160

His Pro Asp Leu Glu Gly Arg Ile Ile Gly Phe Ala Asp Met Val Asn
165 170 175

Gln Lys Thr Glu Pro Tyr Asp Asp Asn Gly His Gly Thr His Cys Ala

```
            180                 185                 190

Gly Asp Val Ala Ser Ser Gly Ala Ser Ser Ser Gly Gln Tyr Arg Gly
        195                 200                 205

Pro Ala Pro Glu Ala Asn Leu Ile Gly Val Lys Val Leu Asn Lys Gln
    210                 215                 220

Gly Ser Gly Thr Leu Ala Asp Ile Ile Glu Gly Val Glu Trp Cys Ile
225                 230                 235                 240

Gln Tyr Asn Glu Asp Asn Pro Asp Glu Pro Ile Asp Ile Met Ser Met
                245                 250                 255

Ser Leu Gly Gly Asp Ala Leu Arg Tyr Asp His Glu Gln Glu Asp Pro
            260                 265                 270

Leu Val Arg Ala Val Glu Glu Ala Trp Ser Ala Gly Ile Val Val Cys
        275                 280                 285

Val Ala Ala Gly Asn Ser Gly Pro Asp Ser Gln Thr Ile Ala Ser Pro
    290                 295                 300

Gly Val Ser Glu Lys Val Ile Thr Val Gly Ala Leu Asp Asp Asn Asn
305                 310                 315                 320

Thr Ala Ser Ser Asp Asp Asp Thr Val Ala Ser Phe Ser Ser Arg Gly
                325                 330                 335

Pro Thr Val Tyr Gly Lys Glu Lys Pro Asp Ile Leu Ala Pro Gly Val
            340                 345                 350

Asn Ile Ile Ser Leu Arg Ser Pro Asn Ser Tyr Ile Asp Lys Leu Gln
        355                 360                 365

Lys Ser Ser Arg Val Gly Ser Gln Tyr Phe Thr Met Ser Gly Thr Ser
    370                 375                 380

Met Ala Thr Pro Ile Cys Ala Gly Ile Ala Ala Leu Ile Leu Gln Gln
385                 390                 395                 400

Asn Pro Asp Leu Thr Pro Asp Glu Val Lys Glu Leu Leu Lys Asn Gly
                405                 410                 415

Thr Asp Lys Trp Lys Asp Glu Asp Pro Asn Ile Tyr Gly Ala Gly Ala
            420                 425                 430

Val Asn Ala Glu Asn Ser Val Pro Gly Gln
        435                 440


<210> SEQ ID NO 210
<211> LENGTH: 775
<212> TYPE: PRT
<213> ORGANISM: Bacillus subtilis

<400> SEQUENCE: 210

Ser Ser Lys Thr Ser Ala Asp Leu Glu Lys Ala Glu Val Phe Gly Asp
1               5                   10                  15

Ile Asp Met Thr Thr Ser Lys Lys Thr Thr Val Ile Val Glu Leu Lys
            20                  25                  30

Glu Lys Ser Leu Ala Glu Ala Lys Glu Ala Gly Glu Ser Gln Ser Lys
        35                  40                  45

Ser Lys Leu Lys Thr Ala Arg Thr Lys Ala Lys Asn Lys Ala Ile Lys
    50                  55                  60

Ala Val Lys Asn Gly Lys Val Asn Arg Glu Tyr Glu Gln Val Phe Ser
65                  70                  75                  80

Gly Phe Ser Met Lys Leu Pro Ala Asn Glu Ile Pro Lys Leu Leu Ala
                85                  90                  95

Val Lys Asp Val Lys Ala Val Tyr Pro Asn Val Thr Tyr Lys Thr Asp
            100                 105                 110
```

```
Asn Met Lys Asp Lys Asp Val Thr Ile Ser Glu Asp Ala Val Ser Pro
        115                 120                 125

Gln Met Asp Asp Ser Ala Pro Tyr Ile Gly Ala Asn Asp Ala Trp Asp
    130                 135                 140

Leu Gly Tyr Thr Gly Lys Gly Ile Lys Val Ala Ile Ile Asp Thr Gly
145                 150                 155                 160

Val Glu Tyr Asn His Pro Asp Leu Lys Lys Asn Phe Gly Gln Tyr Lys
                165                 170                 175

Gly Tyr Asp Phe Val Asp Asn Asp Tyr Asp Pro Lys Glu Thr Pro Thr
            180                 185                 190

Gly Asp Pro Arg Gly Glu Ala Thr Asp His Gly Thr His Val Ala Gly
        195                 200                 205

Thr Val Ala Ala Asn Gly Thr Ile Lys Gly Val Ala Pro Asp Ala Thr
    210                 215                 220

Leu Leu Ala Tyr Arg Val Leu Gly Pro Gly Gly Ser Gly Thr Thr Glu
225                 230                 235                 240

Asn Val Ile Ala Gly Val Glu Arg Ala Val Gln Asp Gly Ala Asp Val
                245                 250                 255

Met Asn Leu Ser Leu Gly Asn Ser Leu Asn Asn Pro Asp Trp Ala Thr
            260                 265                 270

Ser Thr Ala Leu Asp Trp Ala Met Ser Glu Gly Val Val Ala Val Thr
        275                 280                 285

Ser Asn Gly Asn Ser Gly Pro Asn Gly Trp Thr Val Gly Ser Pro Gly
    290                 295                 300

Thr Ser Arg Glu Ala Ile Ser Val Gly Ala Thr Gln Leu Pro Leu Asn
305                 310                 315                 320

Glu Tyr Ala Val Thr Phe Gly Ser Tyr Ser Ser Ala Lys Val Met Gly
                325                 330                 335

Tyr Asn Lys Glu Asp Asp Val Lys Ala Leu Asn Asn Lys Glu Val Glu
            340                 345                 350

Leu Val Glu Ala Gly Ile Gly Glu Ala Lys Asp Phe Glu Gly Lys Asp
        355                 360                 365

Leu Thr Gly Lys Val Ala Val Val Lys Arg Gly Ser Ile Ala Phe Val
    370                 375                 380

Asp Lys Ala Asp Asn Ala Lys Lys Ala Gly Ala Ile Gly Met Val Val
385                 390                 395                 400

Tyr Asn Asn Leu Ser Gly Glu Ile Glu Ala Asn Val Pro Gly Met Ser
                405                 410                 415

Val Pro Thr Ile Lys Leu Ser Leu Glu Asp Gly Glu Lys Leu Val Ser
            420                 425                 430

Ala Leu Lys Ala Gly Glu Thr Lys Thr Thr Phe Lys Leu Thr Val Ser
        435                 440                 445

Lys Ala Leu Gly Glu Gln Val Ala Asp Phe Ser Ser Arg Gly Pro Val
    450                 455                 460

Met Asp Thr Trp Met Ile Lys Pro Asp Ile Ser Ala Pro Gly Val Asn
465                 470                 475                 480

Ile Val Ser Thr Ile Pro Thr His Asp Pro Asp His Pro Tyr Gly Tyr
                485                 490                 495

Gly Ser Lys Gln Gly Thr Ser Met Ala Ser Pro His Ile Ala Gly Ala
            500                 505                 510

Val Ala Val Ile Lys Gln Ala Lys Pro Lys Trp Ser Val Glu Gln Ile
        515                 520                 525

Lys Ala Ala Ile Met Asn Thr Ala Val Thr Leu Lys Asp Ser Asp Gly
```

```
    530                 535                 540

Glu Val Tyr Pro His Asn Ala Gln Gly Ala Gly Ser Ala Arg Ile Met
545                 550                 555                 560

Asn Ala Ile Lys Ala Asp Ser Leu Val Ser Pro Gly Ser Tyr Ser Tyr
                565                 570                 575

Gly Thr Phe Leu Lys Glu Asn Gly Asn Glu Thr Lys Asn Glu Thr Phe
            580                 585                 590

Thr Ile Glu Asn Gln Ser Ser Ile Arg Lys Ser Tyr Thr Leu Glu Tyr
        595                 600                 605

Ser Phe Asn Gly Ser Gly Ile Ser Thr Ser Gly Thr Ser Arg Val Val
    610                 615                 620

Ile Pro Ala His Gln Thr Gly Lys Ala Thr Ala Lys Val Lys Val Asn
625                 630                 635                 640

Thr Lys Lys Thr Lys Ala Gly Thr Tyr Glu Gly Thr Val Ile Val Arg
                645                 650                 655

Glu Gly Gly Lys Thr Val Ala Lys Val Pro Thr Leu Leu Ile Val Lys
            660                 665                 670

Glu Pro Asp Tyr Pro Arg Val Thr Ser Val Ser Val Ser Glu Gly Ser
        675                 680                 685

Val Gln Gly Thr Tyr Gln Ile Glu Thr Tyr Leu Pro Ala Gly Ala Glu
    690                 695                 700

Glu Leu Ala Phe Leu Val Tyr Asp Ser Asn Leu Asp Phe Ala Gly Gln
705                 710                 715                 720

Ala Gly Ile Tyr Lys Asn Gln Asp Lys Gly Tyr Gln Tyr Phe Asp Trp
                725                 730                 735

Asp Gly Thr Ile Asn Gly Gly Thr Lys Leu Pro Ala Gly Glu Tyr Tyr
            740                 745                 750

Leu Leu Ala Tyr Ala Ala Asn Lys Gly Lys Ser Ser Gln Val Leu Thr
        755                 760                 765

Glu Glu Pro Phe Thr Val Glu
    770                 775


<210> SEQ ID NO 211
<211> LENGTH: 870
<212> TYPE: PRT
<213> ORGANISM: Bacillus sphaericus

<400> SEQUENCE: 211

Met Ala Ile Lys Lys Val Leu Lys Ile Ile Leu Ala Ile Ile Ile Ile
1               5                   10                  15

Ile Ser Cys Gln Leu Pro Leu Asn Gln Lys Thr Val Tyr Ala Ser Pro
            20                  25                  30

Asn Ser Pro Lys Asp Asn Thr Trp Ile Gln Ala Ala Ser Leu Thr Trp
        35                  40                  45

Leu Met Asp Met Ser Ser Leu Leu Tyr Gln Leu Ile Ser Thr Arg Ile
    50                  55                  60

Pro Ser Phe Ala Ser Pro Asn Gly Leu His Met Arg Glu Gln Thr Ile
65                  70                  75                  80

Asp Ser Asn Thr Gly Gln Ile Gln Ile Asp Asn Glu His Arg Leu Leu
                85                  90                  95

Arg Trp Asp Arg Arg Pro Pro Asn Asp Ile Phe Leu Asn Gly Phe Ile
            100                 105                 110

Pro Arg Val Thr Asn Gln Asn Leu Ser Pro Val Glu Asp Thr His Leu
        115                 120                 125
```

```
Leu Asn Tyr Leu Arg Thr Asn Ser Pro Ser Ile Phe Val Ser Thr Thr
    130                 135                 140

Arg Ala Arg Tyr Asn Asn Leu Gly Leu Glu Ile Thr Pro Trp Thr Pro
145                 150                 155                 160

His Ser Ala Asn Asn Asn Ile Ile Tyr Arg Tyr Glu Ile Phe Ala Pro
                165                 170                 175

Gly Gly Ile Asp Ile Asn Ala Ser Phe Ser Arg Asn His Asn Pro Phe
            180                 185                 190

Pro Asn Glu Asp Glu Ile Thr Phe Pro Gly Gly Ile Arg Pro Glu Phe
        195                 200                 205

Ile Arg Ser Thr Tyr Glu Tyr His Asn Gly Glu Ile Val Arg Ile Trp
    210                 215                 220

Ile Asn Pro Asn Phe Ile Asn Pro Ser Thr Leu Asn Asp Val Ser Gly
225                 230                 235                 240

Pro Ser Asn Ile Ser Lys Val Phe Trp His Glu Asn His Ser Glu Gly
                245                 250                 255

Asn Asn Met Asp Ser Lys Gly Phe Ile Leu Asp Leu Asp Tyr Asn Gln
            260                 265                 270

Asp Phe Asp Met Phe Ala Pro Asn Gly Glu Ile Pro Asn Asn Asn Leu
        275                 280                 285

Phe Asn Asn Asn Ser Leu Asn Val Ile Gln Asn Ser Glu Tyr Gln Ile
    290                 295                 300

Lys Asn Lys Lys Asp Arg Asn Ile Val Val Thr Leu Asp Ser Asp Tyr
305                 310                 315                 320

Gly Gly Ser Pro Val Glu Ser Tyr Lys Asn Phe Gly Phe Glu Asn Gln
                325                 330                 335

Lys Trp Asn Ile Lys Tyr Asp Ser Lys Lys Asn Ala Tyr Lys Ile Tyr
            340                 345                 350

Asn Arg Glu Thr Pro Thr Leu Leu Leu Ser Trp Asn Ser Asn Ser Ser
        355                 360                 365

Asn Gly Glu Gln Val Ile Arg Gly Tyr Thr Glu Ser Gly Ser Asn Asn
    370                 375                 380

Gln Tyr Trp Thr Ile Glu Lys Asn Val Asn Gly Phe Tyr Lys Phe Arg
385                 390                 395                 400

Asn Leu Ser Asp Pro Ser Lys Ile Leu Asp Leu Lys Asp Gly Asn Thr
                405                 410                 415

Leu Asn Lys Thr Pro Leu Val Val Ser Ser Glu Asn Ser Ser Ser Ser
            420                 425                 430

Gln Glu Trp Leu Ile Glu Lys Thr Asn Tyr Gln Thr Val Lys Asp Gly
        435                 440                 445

Thr Tyr Gln Val Ser Ser Lys Leu Asn Glu Asn Lys Val Ile Glu Gln
    450                 455                 460

Ile Ser Thr Asn Lys Val His Ile Phe Ser Asn Ser Asp Lys Glu Asn
465                 470                 475                 480

Gln Val Trp Asn Leu Ile Tyr Asn Pro Ile Leu Lys Ala Tyr Lys Ile
                485                 490                 495

Lys Ser Leu Lys Tyr Pro Asn Tyr Ser Leu Ala Trp Asp Ser Asn Asn
            500                 505                 510

Thr Arg Thr Ile Val Ala Ala Thr Gly Asp Tyr Asn Asp Gln Tyr Trp
        515                 520                 525

Leu Ile Glu Arg Asn Glu Asp Asn Thr Tyr Ile Ile Arg Asn Tyr Glu
    530                 535                 540

Asn Arg Lys Ile Val Leu Asp Leu Ser Asn Gly Ser Thr Thr Asp Gly
```

```
545                 550                 555                 560

Asn Gly Leu Leu Gly Phe Glu Phe His Gly Gly Ile Asn Gln Arg Trp
                565                 570                 575

Ile Ile Lys Pro Phe Ser Phe Asn Ser Ile Gln Asp Gly Ile Tyr Gln
            580                 585                 590

Phe Met Thr Val Ile Asn Gln Asp Leu Ile Ala Asp Leu Thr Thr Asn
        595                 600                 605

Asn Tyr Thr Ile Ala Thr Lys Thr Asn Asn Tyr Ser Ser Asn Gln Lys
    610                 615                 620

Trp Thr Val Thr Tyr Asn Asp Lys Lys Arg Ala Tyr Lys Ile Arg Asn
625                 630                 635                 640

Leu Gln His Ala His Leu Ser Leu Ala Trp Asp Ser Asn His Ser Asp
                645                 650                 655

Lys Ile Phe Gly Ala Thr Gly Asp Tyr Asp Asp Gln Tyr Trp Ile Pro
            660                 665                 670

Ile Leu Gln Thr Asp Gly Ser Phe Ile Phe Arg Asn Tyr Lys Asn Pro
        675                 680                 685

Asn Lys Ile Phe Gly Thr Asn Gly Gln Pro Ile Asn Asp Ile Pro Leu
    690                 695                 700

Lys Ala Gln Asp Val Thr Gly Gln Asn Asn Gln Lys Trp Tyr Leu Arg
705                 710                 715                 720

His Leu Asn Ser Ser Asn Asn Phe Thr Gly Tyr Phe Asn Ile Ser Ser
                725                 730                 735

Lys Lys Asn Phe Asn Lys Ile Ile Thr Met Asn Ser Asn Lys Thr Gln
            740                 745                 750

Ala Val Ile Phe Asp Asn Ile Gly Ile Asn Asn Gln Ser Trp Lys Leu
        755                 760                 765

Lys Tyr Asn Asp Asn Lys Asn Ala Tyr Gln Ile His Ile Leu Asp Asn
    770                 775                 780

Phe Leu Tyr Phe Gln Gly Gly His Asn Ile Val Ala Thr Met Arg Asn
785                 790                 795                 800

Val Thr Asn Asp Asp Leu Arg Ser Tyr Trp Tyr Val Glu Tyr Asn Phe
                805                 810                 815

Asn Lys Asp Gly Phe Ile Ile Arg Asn Ala Phe Asp Thr Ser Tyr Val
            820                 825                 830

Leu Asp Val Phe Gln Gly Asn Phe Ala Asn Asn Thr Pro Ile Ile Thr
        835                 840                 845

Tyr Gln Asn Tyr Leu Asn Asp Asn Gln Leu Trp Asn Phe Ile Pro Ser
    850                 855                 860

Leu Gly Val Glu Pro Arg
865                 870


<210> SEQ ID NO 212
<211> LENGTH: 25
<212> TYPE: PRT
<213> ORGANISM: Bos taurus

<400> SEQUENCE: 212

Phe Lys Cys Arg Arg Trp Gln Trp Arg Met Lys Lys Phe Gly Ala Pro
1               5                   10                  15

Thr Ile Thr Cys Val Arg Arg Ala Phe
            20                  25


<210> SEQ ID NO 213
<211> LENGTH: 15
```

<212> TYPE: PRT
<213> ORGANISM: Gallus gallus

<400> SEQUENCE: 213

Ile Val Thr Asp Gly Asn Gly Met Arg Ala Trp Val Ala Trp Arg
1 5 10 15

<210> SEQ ID NO 214
<211> LENGTH: 306
<212> TYPE: PRT
<213> ORGANISM: Hordeum vulgare

<400> SEQUENCE: 214

Ile Gly Val Cys Tyr Gly Val Ile Gly Asn Asn Leu Pro Ser Arg Ser
1 5 10 15

Asp Val Val Gln Leu Tyr Arg Ser Lys Gly Ile Asn Gly Met Arg Ile
20 25 30

Tyr Phe Ala Asp Gly Gln Ala Leu Ser Ala Leu Arg Asn Ser Gly Ile
35 40 45

Gly Leu Ile Leu Asp Ile Gly Asn Asp Gln Leu Ala Asn Ile Ala Ala
50 55 60

Ser Thr Ser Asn Ala Ala Ser Trp Val Gln Asn Asn Val Arg Pro Tyr
65 70 75 80

Tyr Pro Ala Val Asn Ile Lys Tyr Ile Ala Ala Gly Asn Glu Val Gln
85 90 95

Gly Gly Ala Thr Gln Ser Ile Leu Pro Ala Met Arg Asn Leu Asn Ala
100 105 110

Ala Leu Ser Ala Ala Gly Leu Gly Ala Ile Lys Val Ser Thr Ser Ile
115 120 125

Arg Phe Asp Glu Val Ala Asn Ser Phe Pro Pro Ser Ala Gly Val Phe
130 135 140

Lys Asn Ala Tyr Met Thr Asp Val Ala Arg Leu Leu Ala Ser Thr Gly
145 150 155 160

Ala Pro Leu Leu Ala Asn Val Tyr Pro Tyr Phe Ala Tyr Arg Asp Asn
165 170 175

Pro Gly Ser Ile Ser Leu Asn Tyr Ala Thr Phe Gln Pro Gly Thr Thr
180 185 190

Val Arg Asp Gln Asn Asn Gly Leu Thr Tyr Thr Ser Leu Phe Asp Ala
195 200 205

Met Val Asp Ala Val Tyr Ala Ala Leu Glu Lys Ala Gly Ala Pro Ala
210 215 220

Val Lys Val Val Val Ser Glu Ser Gly Trp Pro Ser Ala Gly Gly Phe
225 230 235 240

Ala Ala Ser Ala Gly Asn Ala Arg Thr Tyr Asn Gln Gly Leu Ile Asn
245 250 255

His Val Gly Gly Gly Thr Pro Lys Lys Arg Glu Ala Leu Glu Thr Tyr
260 265 270

Ile Phe Ala Met Phe Asn Glu Asn Gln Lys Thr Gly Asp Ala Thr Glu
275 280 285

Arg Ser Phe Gly Leu Phe Asn Pro Asp Lys Ser Pro Ala Tyr Asn Ile
290 295 300

Gln Phe
305

<210> SEQ ID NO 215
<211> LENGTH: 1167

<212> TYPE: PRT
<213> ORGANISM: Bacillus thuringiensis

<400> SEQUENCE: 215

```
Met Thr Asn Pro Thr Ile Leu Tyr Pro Ser Tyr His Asn Val Leu Ala
1               5                   10                  15

His Pro Ile Arg Leu Asp Ser Phe Phe Asp Pro Phe Val Glu Thr Phe
            20                  25                  30

Lys Asp Leu Lys Gly Ala Trp Glu Glu Phe Gly Lys Thr Gly Tyr Met
        35                  40                  45

Asp Pro Leu Lys Gln His Leu Gln Ile Ala Trp Asp Thr Ser Gln Asn
    50                  55                  60

Gly Thr Val Asp Tyr Leu Ala Leu Thr Lys Ala Ser Ile Ser Leu Ile
65                  70                  75                  80

Gly Leu Ile Pro Gly Ala Asp Ala Val Val Pro Phe Ile Asn Met Phe
                85                  90                  95

Val Asp Phe Ile Phe Pro Lys Leu Phe Gly Arg Gly Ser Gln Gln Asn
            100                 105                 110

Ala Gln Ala Gln Phe Phe Glu Leu Ile Ile Glu Lys Val Lys Glu Leu
        115                 120                 125

Val Asp Glu Asp Phe Arg Asn Phe Thr Leu Asn Asn Leu Leu Asn Tyr
    130                 135                 140

Leu Asp Gly Met Gln Thr Ala Leu Ser His Phe Gln Asn Asp Val Gln
145                 150                 155                 160

Ile Ala Ile Cys Gln Gly Glu Gln Pro Gly Leu Met Leu Asp Gln Thr
                165                 170                 175

Pro Thr Ala Cys Thr Pro Thr Thr Asp His Leu Ile Ser Val Arg Glu
            180                 185                 190

Ser Phe Lys Asp Ala Arg Thr Thr Ile Glu Thr Ala Leu Pro His Phe
        195                 200                 205

Lys Asn Pro Met Leu Ser Thr Asn Asp Asn Thr Pro Asp Phe Asn Ser
    210                 215                 220

Asp Thr Val Leu Leu Thr Leu Pro Met Tyr Thr Thr Gly Ala Thr Leu
225                 230                 235                 240

Asn Leu Ile Leu His Gln Gly Tyr Ile Gln Phe Ala Glu Arg Trp Lys
                245                 250                 255

Ser Val Asn Tyr Asp Glu Ser Phe Ile Asn Gln Thr Lys Val Asp Leu
            260                 265                 270

Gln Arg Arg Ile Gln Asp Tyr Ser Thr Thr Val Ser Thr Thr Phe Glu
        275                 280                 285

Lys Phe Lys Pro Thr Leu Asn Pro Ser Asn Lys Glu Ser Val Asn Lys
    290                 295                 300

Tyr Asn Arg Tyr Val Arg Ser Met Thr Leu Gln Ser Leu Asp Ile Ala
305                 310                 315                 320

Ala Thr Trp Pro Thr Leu Asp Asn Val Asn Tyr Pro Ser Asn Val Asp
                325                 330                 335

Ile Gln Leu Asp Gln Thr Arg Leu Val Phe Ser Asp Val Ala Gly Pro
            340                 345                 350

Trp Glu Gly Asn Asp Asn Ile Thr Ser Asn Ile Ile Asp Val Leu Thr
        355                 360                 365

Pro Ile Asn Thr Gly Ile Gly Phe Gln Glu Ser Ser Asp Leu Arg Lys
    370                 375                 380

Phe Thr Tyr Pro Arg Ile Glu Leu Gln Ser Met Gln Phe His Gly Gln
385                 390                 395                 400
```

```
Tyr Val Asn Ser Lys Ser Val Glu His Cys Tyr Ser Asp Gly Leu Lys
                405                 410                 415

Leu Asn Tyr Lys Asn Lys Thr Ile Thr Ala Gly Val Ser Asn Ile Asp
            420                 425                 430

Glu Ser Asn Gln Asn Asn Lys His Asn Tyr Gly Pro Val Ile Asn Ser
        435                 440                 445

Pro Ile Thr Asp Ile Asn Val Asn Ser Gln Asn Ser Gln Tyr Leu Asp
    450                 455                 460

Leu Asn Ser Val Met Val Asn Gly Gly Gln Lys Val Ala Gly Cys Ser
465                 470                 475                 480

Pro Leu Ser Ser Asn Gly Asn Ser Asn Asn Ala Ala Leu Pro Asn Gln
                485                 490                 495

Lys Ile Asn Val Ile Tyr Ser Val Gln Ser Asn Asp Lys Pro Glu Lys
            500                 505                 510

His Ala Asp Thr Tyr Arg Lys Trp Gly Tyr Met Ser Ser His Ile Pro
        515                 520                 525

Tyr Asp Leu Val Pro Glu Asn Val Ile Gly Asp Ile Asp Pro Asp Thr
    530                 535                 540

Lys Gln Pro Ser Leu Leu Leu Lys Gly Phe Pro Ala Glu Lys Gly Tyr
545                 550                 555                 560

Gly Asp Ser Ile Ala Tyr Val Ser Glu Pro Leu Asn Gly Ala Asn Ala
                565                 570                 575

Val Lys Leu Thr Ser Tyr Gln Val Leu Lys Met Glu Val Thr Asn Gln
            580                 585                 590

Thr Thr Gln Lys Tyr Arg Ile Arg Ile Arg Tyr Ala Thr Gly Gly Asp
        595                 600                 605

Thr Ala Ala Ser Ile Trp Phe His Ile Ile Gly Pro Ser Gly Asn Asp
    610                 615                 620

Leu Thr Asn Glu Gly His Asn Phe Ser Ser Val Ser Ser Arg Asn Lys
625                 630                 635                 640

Met Phe Val Gln Gly Asn Asn Gly Lys Tyr Val Leu Asn Ile Leu Thr
                645                 650                 655

Asp Ser Ile Glu Leu Pro Ser Gly Gln Gln Thr Ile Leu Ile Gln Asn
            660                 665                 670

Thr Asn Ser Gln Asp Leu Phe Leu Asp Arg Ile Glu Phe Ile Ser Leu
        675                 680                 685

Pro Ser Thr Ser Thr Pro Thr Ser Thr Asn Phe Val Glu Pro Glu Ser
    690                 695                 700

Leu Glu Lys Ile Ile Asn Gln Val Asn Gln Leu Phe Ser Ser Ser Ser
705                 710                 715                 720

Gln Thr Glu Leu Ala His Thr Val Ser Asp Tyr Lys Ile Asp Gln Val
                725                 730                 735

Val Leu Lys Val Asn Ala Leu Ser Asp Asp Val Phe Gly Val Glu Lys
            740                 745                 750

Lys Ala Leu Arg Lys Leu Val Asn Gln Ala Lys Gln Leu Ser Lys Ala
        755                 760                 765

Arg Asn Val Leu Val Gly Gly Asn Phe Glu Lys Gly His Glu Trp Ala
    770                 775                 780

Leu Ser Arg Glu Ala Thr Met Val Ala Asn His Glu Leu Phe Lys Gly
785                 790                 795                 800

Asp His Leu Leu Leu Pro Pro Pro Thr Leu Tyr Pro Ser Tyr Ala Tyr
                805                 810                 815
```

```
Gln Lys Ile Asp Glu Ser Lys Leu Lys Ser Asn Thr Arg Tyr Thr Val
            820                 825                 830

Ser Gly Phe Ile Ala Gln Ser Glu His Leu Glu Val Val Val Ser Arg
        835                 840                 845

Tyr Gly Lys Glu Val His Asp Met Leu Asp Ile Pro Tyr Glu Glu Ala
    850                 855                 860

Leu Pro Ile Ser Ser Asp Glu Ser Pro Asn Cys Cys Lys Pro Ala Ala
865                 870                 875                 880

Cys Gln Cys Ser Ser Cys Asp Gly Ser Gln Ser Asp Ser His Phe Phe
                885                 890                 895

Ser Tyr Ser Ile Asp Val Gly Ser Leu Gln Ser Asp Val Asn Leu Gly
            900                 905                 910

Ile Glu Phe Gly Leu Arg Ile Ala Lys Pro Asn Gly Phe Ala Lys Ile
        915                 920                 925

Ser Asn Leu Glu Ile Lys Glu Asp Arg Pro Leu Thr Glu Lys Glu Ile
    930                 935                 940

Lys Lys Val Gln Arg Lys Glu Gln Lys Trp Lys Lys Ala Phe Asn Gln
945                 950                 955                 960

Glu Gln Ala Glu Val Ala Thr Thr Leu Gln Pro Thr Leu Asp Gln Ile
                965                 970                 975

Asn Ala Leu Tyr Gln Asn Glu Asp Trp Asn Gly Ser Val His Pro His
            980                 985                 990

Val Thr Tyr Gln His Leu Ser Ala  Val Val Val Pro Thr  Leu Pro Lys
        995                 1000                 1005

Gln Arg  His Trp Phe Met Glu  Asp Arg Glu Gly Glu  His Val Val
    1010                 1015                 1020

Leu Thr  Gln Gln Phe Gln Gln  Ala Leu Asp Arg Ala  Phe Gln Gln
    1025                 1030                 1035

Ile Glu  Glu Gln Asn Leu Ile  His Asn Gly Asn Phe  Ala Asn Gly
    1040                 1045                 1050

Leu Thr  Asp Trp Thr Val Thr  Gly Asp Ala Gln Leu  Thr Ile Phe
    1055                 1060                 1065

Asp Glu  Asp Pro Val Leu Glu  Leu Ala His Trp Asp  Ala Ser Ile
    1070                 1075                 1080

Ser Gln  Thr Ile Glu Ile Met  Asp Phe Glu Glu Asp  Thr Glu Tyr
    1085                 1090                 1095

Lys Leu  Arg Val Arg Gly Lys  Gly Lys Gly Thr Val  Thr Val Gln
    1100                 1105                 1110

His Gly  Glu Glu Glu Leu Glu  Thr Met Thr Phe Asn  Thr Thr Ser
    1115                 1120                 1125

Phe Thr  Thr Gln Glu Gln Thr  Phe Tyr Phe Glu Gly  Asp Thr Val
    1130                 1135                 1140

Asp Val  His Val Gln Ser Glu  Asn Asn Thr Phe Leu  Ile Asp Ser
    1145                 1150                 1155

Val Glu  Leu Ile Glu Ile Ile  Glu Glu
    1160                 1165


<210> SEQ ID NO 216
<211> LENGTH: 839
<212> TYPE: PRT
<213> ORGANISM: Bacillus circulans

<400> SEQUENCE: 216

Ala Glu Thr Ala Gly Thr Thr Ile Thr Ser Met Ser Tyr Phe Ser Thr
1               5                   10                  15
```

```
Ala Asp Gly Pro Ile Ile Thr Lys Ser Gly Val Gly Gln Ala Ser Tyr
            20                  25                  30

Gly Phe Val Met Pro Ile Phe Asn Gly Gly Ser Ala Thr Trp Asn Asp
        35                  40                  45

Val Ala Gln Asp Leu Gly Val Lys Val Lys Val Asn Gly Ser Trp Val
    50                  55                  60

Asp Ile Asp Ser Val Ser Ser Phe Val Tyr Asn Gln Asn Trp Gly His
65                  70                  75                  80

Trp Asn Asp Gly Gly Phe Thr Gly Tyr Trp Phe Thr Leu Ser Ala Thr
                85                  90                  95

Thr Glu Ile Gln Leu Tyr Ser Lys Ala Asn Glu Val Thr Leu Glu Tyr
            100                 105                 110

Ser Leu Val Phe Gln Asn Ile Asn Lys Thr Thr Ile Thr Ala Met Thr
        115                 120                 125

Pro Thr Gln Gly Pro Gln Ile Thr Ala Gly Phe Thr Gly Gly Ala Gly
    130                 135                 140

Phe Thr Tyr Pro Ile Phe Asn His Asp Pro Ala Ile Thr Tyr Ala Ala
145                 150                 155                 160

Val Ala Asp Asp Leu Lys Val Tyr Val Lys Pro Val Asn Ser Ser Gln
                165                 170                 175

Trp Ile Asp Ile Asp Asn Asn Ala Ala Ser Gly Trp Ile Tyr Asp Gln
            180                 185                 190

Asn Phe Gly Gln Phe Thr Asp Gly Gly Gly Gly Tyr Trp Phe Asn Val
        195                 200                 205

Thr Glu Ser Ile Asn Val Lys Leu Glu Ser Lys Thr Ser Ser Thr Asn
    210                 215                 220

Ile Val Tyr Thr Ile Ser Phe Asn Glu Pro Val Arg Asn Ser Tyr Val
225                 230                 235                 240

Leu Thr Pro Tyr Glu Gly Thr Thr Phe Thr Ala Asp Ala Ser Gly Ala
                245                 250                 255

Ile Gly Ile Pro Leu Pro Lys Ile Asp Gly Gly Ala Pro Ile Gly Thr
            260                 265                 270

Glu Leu Gly Asn Phe Val Tyr Gln Ile Asn Ile Asn Gly Gln Trp Val
        275                 280                 285

Asp Leu Asp Asn Ser Ser Gln Ser Gly Phe Val Tyr Ser Ala Asn Gly
    290                 295                 300

Tyr Asn Asn Met Ser Ala Ala Asn Gln Trp Gly Tyr Trp Ala Asp His
305                 310                 315                 320

Ile Tyr Gly Leu Trp Phe Gln Pro Ile Gln Val Asp Met Gln Ile Arg
                325                 330                 335

Ile Gly Tyr Pro Leu Asn Gly Gln Ala Gly Gly Ser Val Gly Ser Asn
            340                 345                 350

Phe Val Asn Tyr Thr Leu Ile Gly Asn Pro Asp Ala Pro Arg Pro Asp
        355                 360                 365

Val Asn Asp Gln Glu Asp Ile Pro Ile Gly Thr Pro Asn Asp Ser Ala
    370                 375                 380

Ile Glu Gly Met Asn Leu Ile Trp Gln Asp Glu Phe Asn Gly Thr Ala
385                 390                 395                 400

Leu Asp Gln Ser Lys Trp Asn Tyr Glu Thr Gly Tyr Tyr Leu Asn Asp
                405                 410                 415

Asp Pro Asn Thr Trp Gly Trp Gly Asn Ser Glu Leu Gln His Tyr Thr
            420                 425                 430
```

```
Asp Arg Ala Gln Asn Val Phe Val Gln Asp Gly Lys Leu Asn Ile Lys
        435                 440                 445

Ala Leu Asn Glu Pro Lys Ser Phe Pro Gln Asp Pro Ser Arg Tyr Ala
    450                 455                 460

Gln Tyr Ser Ser Gly Lys Ile Asn Thr Lys Asp His Phe Ser Leu Lys
465                 470                 475                 480

Tyr Gly Arg Val Asp Phe Arg Ala Lys Leu Pro Thr Gly Asn Gly Ile
                485                 490                 495

Trp Pro Ala Leu Trp Met Leu Pro Gln Asp Asn Val Tyr Gly Thr Trp
            500                 505                 510

Ala Ser Ser Gly Glu Ile Asp Val Met Glu Ala Lys Gly Arg Leu Pro
        515                 520                 525

Gly Ser Thr Ser Gly Ala Val His Phe Gly Gly Gln Trp Pro Thr Asn
    530                 535                 540

Arg Tyr Leu Ser Gly Glu Tyr His Phe Pro Glu Gly Gln Thr Phe Ala
545                 550                 555                 560

Asn Asp Tyr His Val Tyr Ser Val Val Trp Glu Glu Asp Asn Ile Lys
                565                 570                 575

Trp Tyr Val Asp Gly Lys Phe Phe Phe Lys Val Thr Arg Asp Gln Trp
            580                 585                 590

Tyr Ser Ala Ala Ala Pro Asn Asn Pro Asn Ala Pro Phe Asp Gln Pro
        595                 600                 605

Phe Tyr Leu Ile Met Asn Leu Ala Ile Gly Gly Thr Phe Asp Gly Gly
    610                 615                 620

Arg Thr Pro Asp Pro Ser Asp Ile Pro Ala Thr Met Gln Val Asp Tyr
625                 630                 635                 640

Val Arg Val Tyr Lys Glu Gly Glu Gly Gly Gly Gln Asn Pro Gly Asn
                645                 650                 655

Val Pro Val Thr Gly Val Thr Val Asn Pro Thr Thr Ala Gln Val Glu
            660                 665                 670

Val Gly Gln Ser Val Gln Leu Asn Ala Ser Val Ala Pro Ser Asn Ala
        675                 680                 685

Thr Asn Lys Gln Val Thr Trp Ser Val Ser Gly Ser Ser Ile Ala Ser
    690                 695                 700

Val Ser Pro Asn Gly Leu Val Thr Gly Leu Ala Gln Gly Thr Thr Thr
705                 710                 715                 720

Val Thr Ala Thr Thr Ala Asp Gly Asn Lys Ala Ala Ser Ala Thr Ile
                725                 730                 735

Thr Val Ala Pro Ala Pro Ser Thr Val Ile Val Ile Gly Asp Glu Val
            740                 745                 750

Lys Gly Leu Lys Lys Ile Gly Asp Asp Leu Leu Phe Tyr Val Asn Gly
        755                 760                 765

Ala Thr Phe Ala Asp Leu His Tyr Lys Val Asn Asn Gly Gly Gln Leu
    770                 775                 780

Asn Val Ala Met Ala Pro Thr Gly Asn Gly Asn Tyr Thr Tyr Pro Val
785                 790                 795                 800

His Asn Leu Lys His Gly Asp Thr Val Glu Tyr Phe Phe Thr Tyr Asn
                805                 810                 815

Pro Gly Gln Gly Ala Leu Asp Thr Pro Trp Gln Thr Tyr Val His Gly
            820                 825                 830

Val Thr Gln Gly Thr Pro Glu
        835
```

<210> SEQ ID NO 217
<211> LENGTH: 385
<212> TYPE: PRT
<213> ORGANISM: Gallus gallus

<400> SEQUENCE: 217

```
Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Thr Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
                245                 250                 255

Ser Ile Ile Asn Phe Glu Lys Leu Thr Glu Trp Thr Ser Ser Asn Val
            260                 265                 270

Met Glu Glu Arg Lys Ile Lys Val Tyr Leu Pro Arg Met Lys Met Glu
        275                 280                 285

Glu Lys Tyr Asn Leu Thr Ser Val Leu Met Ala Met Gly Ile Thr Asp
    290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
                325                 330                 335

Ala Gly Arg Glu Val Val Gly Ser Ala Glu Ala Gly Val Asp Ala Ala
            340                 345                 350

Ser Val Ser Glu Glu Phe Arg Ala Asp His Pro Phe Leu Phe Cys Ile
        355                 360                 365

Lys His Ile Ala Thr Asn Ala Val Leu Phe Phe Gly Arg Cys Val Ser
    370                 375                 380
```

Pro
385

<210> SEQ ID NO 218
<211> LENGTH: 764
<212> TYPE: PRT
<213> ORGANISM: Bacillus anthracis

<400> SEQUENCE: 218

Met Lys Lys Arg Lys Val Leu Ile Pro Leu Met Ala Leu Ser Thr Ile
1 5 10 15

Leu Val Ser Ser Thr Gly Asn Leu Glu Val Ile Gln Ala Glu Val Lys
20 25 30

Gln Glu Asn Arg Leu Leu Asn Glu Ser Glu Ser Ser Ser Gln Gly Leu
35 40 45

Leu Gly Tyr Tyr Phe Ser Asp Leu Asn Phe Gln Ala Pro Met Val Val
50 55 60

Thr Ser Ser Thr Thr Gly Asp Leu Ser Ile Pro Ser Ser Glu Leu Glu
65 70 75 80

Asn Ile Pro Ser Glu Asn Gln Tyr Phe Gln Ser Ala Ile Trp Ser Gly
85 90 95

Phe Ile Lys Val Lys Lys Ser Asp Glu Tyr Thr Phe Ala Thr Ser Ala
100 105 110

Asp Asn His Val Thr Met Trp Val Asp Asp Gln Glu Val Ile Asn Lys
115 120 125

Ala Ser Asn Ser Asn Lys Ile Arg Leu Glu Lys Gly Arg Leu Tyr Gln
130 135 140

Ile Lys Ile Gln Tyr Gln Arg Glu Asn Pro Thr Glu Lys Gly Leu Asp
145 150 155 160

Phe Lys Leu Tyr Trp Thr Asp Ser Gln Asn Lys Lys Glu Val Ile Ser
165 170 175

Ser Asp Asn Leu Gln Leu Pro Glu Leu Lys Gln Lys Ser Ser Asn Ser
180 185 190

Arg Lys Lys Arg Ser Thr Ser Ala Gly Pro Thr Val Pro Asp Arg Asp
195 200 205

Asn Asp Gly Ile Pro Asp Ser Leu Glu Val Glu Gly Tyr Thr Val Asp
210 215 220

Val Lys Asn Lys Arg Thr Phe Leu Ser Pro Trp Ile Ser Asn Ile His
225 230 235 240

Glu Lys Lys Gly Leu Thr Lys Tyr Lys Ser Ser Pro Glu Lys Trp Ser
245 250 255

Thr Ala Ser Asp Pro Tyr Ser Asp Phe Glu Lys Val Thr Gly Arg Ile
260 265 270

Asp Lys Asn Val Ser Pro Glu Ala Arg His Pro Leu Val Ala Ala Tyr
275 280 285

Pro Ile Val His Val Asp Met Glu Asn Ile Ile Leu Ser Lys Asn Glu
290 295 300

Asp Gln Ser Thr Gln Asn Thr Asp Ser Glu Thr Arg Thr Ile Ser Lys
305 310 315 320

Asn Thr Ser Thr Ser Arg Thr His Thr Ser Glu Val His Gly Asn Ala
325 330 335

Glu Val His Ala Ser Phe Phe Asp Ile Gly Gly Ser Val Ser Ala Gly
340 345 350

Phe Ser Asn Ser Asn Ser Ser Thr Val Ala Ile Asp His Ser Leu Ser
355 360 365

```
Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760
```